(12) United States Patent
Prieve et al.

(10) Patent No.: US 11,219,634 B2
(45) Date of Patent: Jan. 11, 2022

(54) METHODS, COMPOSITIONS, AND SYSTEMS FOR DELIVERING THERAPEUTIC AND DIAGNOSTIC AGENTS INTO CELLS

(71) Applicant: GENEVANT SCIENCES GMBH, Basel (CH)

(72) Inventors: Mary G. Prieve, Lake Forest Park, WA (US); Michael E. Houston, Jr., Kirkland, WA (US); Pierrot Harvie, Seattle, WA (US); Sean D. Monahan, Lake Forest Park, WA (US)

(73) Assignee: Genevant Sciences GmbH, Basel (CH)

( * ) Notice: Subject to any disclaimer, the term of this patent is extended or adjusted under 35 U.S.C. 154(b) by 293 days.

(21) Appl. No.: 15/545,302

(22) PCT Filed: Jan. 21, 2016

(86) PCT No.: PCT/US2016/014232
§ 371 (c)(1),
(2) Date: Jul. 20, 2017

(87) PCT Pub. No.: WO2016/118697
PCT Pub. Date: Jul. 28, 2016

(65) Prior Publication Data
US 2018/0221402 A1  Aug. 9, 2018

Related U.S. Application Data

(60) Provisional application No. 62/106,024, filed on Jan. 21, 2015, provisional application No. 62/173,847, filed on Jun. 10, 2015, provisional application No. 62/233,568, filed on Sep. 28, 2015.

(51) Int. Cl.
| A61K 31/7105 | (2006.01) |
| A61K 9/00 | (2006.01) |
| A61K 47/18 | (2017.01) |
| A61K 47/32 | (2006.01) |
| A61K 9/127 | (2006.01) |
| A61K 9/51 | (2006.01) |
| C08F 293/00 | (2006.01) |
| A61K 48/00 | (2006.01) |
| A61K 31/407 | (2006.01) |
| A61K 31/5365 | (2006.01) |
| A61K 31/704 | (2006.01) |
| A61K 31/7048 | (2006.01) |
| A61K 31/4745 | (2006.01) |
| A61K 31/47 | (2006.01) |
| A61K 31/475 | (2006.01) |
| A61K 31/40 | (2006.01) |
| A61K 9/107 | (2006.01) |

(52) U.S. Cl.
CPC ........ *A61K 31/7105* (2013.01); *A61K 9/0019* (2013.01); *A61K 9/1075* (2013.01); *A61K 9/1272* (2013.01); *A61K 9/5123* (2013.01); *A61K 31/40* (2013.01); *A61K 31/407* (2013.01); *A61K 31/47* (2013.01); *A61K 31/475* (2013.01); *A61K 31/4745* (2013.01); *A61K 31/5365* (2013.01); *A61K 31/704* (2013.01); *A61K 31/7048* (2013.01); *A61K 47/186* (2013.01); *A61K 47/32* (2013.01); *A61K 48/0041* (2013.01); *C08F 293/00* (2013.01)

(58) Field of Classification Search
CPC .. A61K 31/7105; A61K 47/186; A61K 47/32; A61K 48/0041; A61K 9/0019; A61K 9/1272; A61K 9/5123; A61K 31/40; A61K 31/407; A61K 31/47; A61K 31/4745; A61K 31/475; A61K 31/5365; A61K 31/704; A61K 31/7048; A61K 33/24; C08F 293/00
USPC ....................................... 424/450
See application file for complete search history.

(56) References Cited

U.S. PATENT DOCUMENTS

| 4,603,044 A | 7/1986 | Geho et al. |
| 4,699,784 A | 10/1987 | Shih et al. |
| 5,057,313 A | 10/1991 | Shih et al. |
| 5,844,107 A | 12/1998 | Hanson et al. |
| 6,306,994 B1 | 10/2001 | Donald et al. |
| 6,359,054 B1 | 3/2002 | Lemieux et al. |
| 6,383,811 B2 | 5/2002 | Wolff et al. |
| 6,410,057 B1 | 6/2002 | Kweon-Choi et al. |
| 6,780,428 B2 | 8/2004 | Ranger et al. |
| 6,835,393 B2 | 12/2004 | Hoffman et al. |
| 6,939,564 B2 | 6/2005 | Ranger et al. |

(Continued)

FOREIGN PATENT DOCUMENTS

| EP | 0321233 A1 | 6/1989 |
| EP | 2180004 A1 | 4/2010 |

(Continued)

OTHER PUBLICATIONS

PCT International Search Report & Written Opinion for PCT/US2016/014232, dated Jun. 16, 2016, 18 Pages.

(Continued)

*Primary Examiner* — Janet L Epps-Smith
(74) *Attorney, Agent, or Firm* — Sterne, Kessler, Goldstein & Fox P.L.L.C.

(57) ABSTRACT

Disclosed are methods for delivering a therapeutic or diagnostic agent to the cytosol of a cell in a subject. The disclosed methods generally include administering to the subject an effective amount of a lipid nanoparticle comprising the therapeutic or diagnostic agent and an effective amount of a membrane-destabilizing polymer. Also disclosed are related compositions and delivery systems.

12 Claims, 5 Drawing Sheets

Specification includes a Sequence Listing.

(56) References Cited

U.S. PATENT DOCUMENTS

| | | |
|---|---|---|
| 6,916,488 B1 | 7/2005 | Meier et al. |
| 6,919,091 B2 | 7/2005 | Trubetskoy et al. |
| 7,033,607 B2 | 4/2006 | Trubetskoy et al. |
| 7,094,810 B2 | 8/2006 | Sant et al. |
| 7,098,032 B2 | 8/2006 | Trubetskoy et al. |
| 7,217,776 B1 | 5/2007 | Mallapragada et al. |
| 7,374,778 B2 | 5/2008 | Hoffman et al. |
| 7,510,731 B2 | 3/2009 | Ranger et al. |
| 7,524,680 B2 | 4/2009 | Wolff et al. |
| 7,718,193 B2 | 5/2010 | Stayton et al. |
| 7,737,108 B1 | 6/2010 | Hoffman et al. |
| 8,058,069 B2 | 11/2011 | Yaworski et al. |
| 8,323,698 B2 | 12/2012 | Gu et al. |
| 8,367,113 B2 | 2/2013 | Gu et al. |
| 8,367,628 B2 | 2/2013 | Goodwin et al. |
| 8,399,657 B2 | 3/2013 | Zhu |
| 8,754,062 B2 | 6/2014 | de Fougerolles et al. |
| 8,822,213 B2 | 9/2014 | Stayton et al. |
| 8,962,757 B2 | 2/2015 | Devore et al. |
| 9,006,193 B2 | 4/2015 | Stayton et al. |
| 9,061,021 B2 | 6/2015 | Guild et al. |
| 9,211,250 B2 | 12/2015 | Johnson et al. |
| 9,220,791 B2 | 12/2015 | Stayton et al. |
| 9,404,127 B2 | 8/2016 | Yaworski et al. |
| 9,464,300 B2 | 10/2016 | Prieve et al. |
| 9,476,063 B2 | 10/2016 | Stayton et al. |
| 9,522,176 B2 | 12/2016 | DeRosa et al. |
| 9,629,804 B2 | 4/2017 | Heartlein et al. |
| 9,867,885 B2 | 1/2018 | Monahan et al. |
| 10,646,582 B2 | 5/2020 | Monahan et al. |
| 10,660,970 B2 | 5/2020 | Monahan et al. |
| 2001/0007666 A1 | 7/2001 | Hoffman et al. |
| 2003/0008009 A1 | 1/2003 | Trubetskoy et al. |
| 2003/0134420 A1 | 7/2003 | Lollo et al. |
| 2003/0143204 A1 | 7/2003 | Lewis et al. |
| 2003/0191081 A1 | 10/2003 | Lemieux et al. |
| 2003/0211167 A1 | 11/2003 | Gustavsson et al. |
| 2004/0054127 A1 | 3/2004 | Uin et al. |
| 2004/0072784 A1 | 4/2004 | Sant et al. |
| 2004/0016223 A1 | 8/2004 | Trubetskoy et al. |
| 2004/0151775 A1 | 8/2004 | Rozema et al. |
| 2005/0070721 A1 | 3/2005 | Bae et al. |
| 2005/0154165 A1 | 7/2005 | Petereit et al. |
| 2005/0220880 A1 | 10/2005 | Lewis et al. |
| 2005/0260276 A1 | 11/2005 | Yang et al. |
| 2006/0000891 A1 | 1/2006 | MacLachlan et al. |
| 2006/0030685 A1 | 2/2006 | Boupat et al. |
| 2006/0134221 A1 | 6/2006 | Geall |
| 2006/0165810 A1 | 7/2006 | Discher et al. |
| 2006/0171980 A1 | 8/2006 | Helmus et al. |
| 2006/0217285 A1 | 9/2006 | Destarac |
| 2006/0235161 A1 | 10/2006 | Heller et al. |
| 2007/0003609 A1 | 1/2007 | Collin-Djangone et al. |
| 2007/0010632 A1 | 1/2007 | Kaplan et al. |
| 2007/0037891 A1 | 2/2007 | Esfand et al. |
| 2007/0059271 A1 | 3/2007 | Kataoka et al. |
| 2007/0110709 A1 | 5/2007 | Ranger et al. |
| 2007/0134188 A1 | 6/2007 | Collin-Djangone et al. |
| 2007/0224241 A1 | 9/2007 | Stayton et al. |
| 2008/0069902 A1 | 3/2008 | Zhao et al. |
| 2008/0081075 A1 | 4/2008 | Hsiue et al. |
| 2008/0171067 A1 | 7/2008 | Govindan et al. |
| 2008/0243049 A1 | 10/2008 | Hardy |
| 2009/0036625 A1 | 2/2009 | Chang et al. |
| 2010/0150952 A1 | 6/2010 | Stayton et al. |
| 2010/0159019 A1 | 6/2010 | Yang et al. |
| 2011/0123636 A1 | 5/2011 | Stayton et al. |
| 2011/0129921 A1 | 6/2011 | Johnson et al. |
| 2011/0142951 A1 | 6/2011 | Johnson et al. |
| 2011/0143434 A1 | 6/2011 | Stayton et al. |
| 2011/0143435 A1 | 6/2011 | Stayton et al. |
| 2011/0281354 A1 | 11/2011 | Stayton et al. |
| 2011/0281934 A1 | 11/2011 | Johnson et al. |
| 2011/0286957 A1 | 11/2011 | Prieve et al. |
| 2012/0021514 A1* | 1/2012 | Johnson ............... A61K 9/0019 435/375 |
| 2012/0251618 A1 | 10/2012 | Schrum et al. |
| 2013/0011362 A1 | 1/2013 | Monahan et al. |
| 2013/0195967 A1 | 8/2013 | Guild et al. |
| 2014/0155472 A1 | 6/2014 | Bancel et al. |
| 2014/0206753 A1 | 7/2014 | Guild et al. |
| 2014/0228516 A1 | 8/2014 | Stayton et al. |
| 2014/0294940 A1 | 10/2014 | Guild et al. |
| 2015/0238619 A1 | 8/2015 | Stayton et al. |
| 2015/0283254 A1 | 10/2015 | Duvall et al. |
| 2015/0366997 A1 | 12/2015 | Guild et al. |
| 2016/0082121 A1 | 3/2016 | Stayton et al. |
| 2016/0151409 A1 | 6/2016 | Derosa et al. |
| 2016/0206750 A1 | 7/2016 | Monahan et al. |
| 2017/0049801 A1 | 2/2017 | Prieve et al. |
| 2018/0243433 A1 | 8/2018 | Monahan et al. |
| 2018/0311381 A1 | 11/2018 | Bancel et al. |
| 2019/0030129 A1 | 1/2019 | Schrum et al. |
| 2020/0078313 A1 | 3/2020 | Roy et al. |
| 2021/0023235 A1 | 1/2021 | Monahan et al. |

FOREIGN PATENT DOCUMENTS

| | | | |
|---|---|---|---|
| FR | 2767829 A1 | 3/1999 | |
| WO | WO 99/19303 A1 | 4/1999 | |
| WO | WO 9929303 A1 | 6/1999 | |
| WO | WO 01/87227 A2 | 11/2001 | |
| WO | WO 03/87188 A1 | 10/2003 | |
| WO | WO 2005/108614 A2 | 11/2005 | |
| WO | WO 2006/016166 A1 | 2/2006 | |
| WO | WO 2007/008300 A2 | 1/2007 | |
| WO | WO 2007/109584 A1 | 9/2007 | |
| WO | WO 2008/004978 A1 | 1/2008 | |
| WO | WO 2008/022309 A2 | 2/2008 | |
| WO | WO 2008/071009 A1 | 6/2008 | |
| WO | WO 2008/085556 A2 | 7/2008 | |
| WO | WO 2008/148174 A1 | 12/2008 | |
| WO | WO 2008/153940 A1 | 12/2008 | |
| WO | WO 2009/009025 A1 | 1/2009 | |
| WO | WO 2009/021728 A2 | 2/2009 | |
| WO | WO 2009016166 A1 | 2/2009 | |
| WO | WO 2009/127060 A1 | 10/2009 | |
| WO | WO 2009/140421 A2 | 11/2009 | |
| WO | WO 2009/140423 A2 | 11/2009 | |
| WO | WO 2009/140427 A2 | 11/2009 | |
| WO | WO 2009/140429 A2 | 11/2009 | |
| WO | WO 2009140429 A2 | 11/2009 | |
| WO | WO-2009140429 A2 * | 11/2009 | ........... A61K 9/1075 |
| WO | WO 2009140432 A2 | 11/2009 | |
| WO | WO 2010/021770 A1 | 2/2010 | |
| WO | WO 2010/053596 A1 | 5/2010 | |
| WO | WO 2010/053597 A1 | 5/2010 | |
| WO | WO 2010/054266 A2 | 5/2010 | |
| WO | WO 2010/077678 A2 | 7/2010 | |
| WO | WO 2011060281 A1 | 5/2011 | |
| WO | WO 2011062965 A2 | 5/2011 | |
| WO | WO 2011/068810 A1 | 6/2011 | |
| WO | WO 2012019168 A2 | 2/2012 | |
| WO | WO 2013071047 A1 | 5/2013 | |
| WO | WO 2014081507 A1 | 5/2015 | |
| WO | WO 2015138348 A1 | 9/2015 | |
| WO | WO 2015138357 A2 | 9/2015 | |
| WO | WO 2015/138348 A1 | 9/2017 | |
| WO | WO 2017201349 A1 | 11/2017 | |
| WO | WO 2018129586 A1 | 7/2018 | |
| WO | WO 2018183808 A1 | 10/2018 | |
| WO | WO 2019089818 A1 | 5/2019 | |
| WO | WO 2019104152 A1 | 5/2019 | |
| WO | WO 2019104195 A1 | 5/2019 | |

OTHER PUBLICATIONS

Chen, Q.-R., et al., "Co-polymer of histidine and lysine markedly enhances transfection efficiency of liposomes," Gene Therapy, 2000, pp. 1698-1705, vol. 7.

(56) References Cited

OTHER PUBLICATIONS

Chen, Q-R., et al., "Branched co-polymers of histidine and lysine are efficient carriers of plasmids," Nucleic Acids Research, 2001, pp. 1334-1340, vol. 29, No. 6.

Cheung, C. Y., et al., "A pH-Sensitive Polymers That Enhances Cationic Lipid-Mediated Gene Transfer," Bioconjugate Chem., 2001, pp. 906-910, vol. 12.

Kyriakides, T.R., et al., "pH-Sensitive polymers that enhance intracellular drug delivery in vivo," Journal of Controlled Release, 2002, pp. 295-303, vol. 78.

Wooddell, Christine I., et al., "Hepatocyte-targeted RNAi Therapeutics for the Treatment of Chronic Hepatitis B Virus Infection," Molecular Therapy, 2013, pp. 973-985, vol. 21, No. 5.

Abra, R.M. et al., "The Next Generation of Liposome Delivery Systems: Recent Experience with Tumor-Targeted, Sterically Stabilized Immunoliposomes and Active Loading Gradients," Journal of Liposome Research, 2002, pp. 1-3, vol. 12, No. 1-2.

Adami, R.C. et al., "An Amino Acid-based Amphoteric Liposomal Delivery System for Systemic Administration of siRNA," Molecular Therapy 19:1141-1151, 2011, published online Apr. 19, 2011, DOI:10.1038/mt.2011.56.

Akinc, A. et al., "A Combinatorial Library of Lipid-Like Materials for Delivery of RNAi Therapeutics," Nature Biotechnology, May 2008, pp. 561-569, vol. 26, No. 5, published online Apr. 27, 2008, DGI:10.1038/nbt1402.

Allen, T.M. et al., "Pharmacokinetics of Stealth Versus Conventional Liposomes: Effect of Dose," Biochimica et Biophysica Acta, 1991, pp. 133-141, vol. 1068.

Allen, T.M. et al., "Subcutaneous Administration of Liposomes: a Comparison with the Intravenous and Intraperitoneal Routes of Injection," Biochimica et Biophysica Acta, Jul. 25, 1993, pp. 9-16, vol. 1150.

Anderson et al., "Stability of mRNA/cationic Lipid Lipoplexes in Human and Rat Cerebrospinal Rluid: Methods and Evidence for Nonviral mRNA Gene Delivery to the Central Nervous System," Human Gene Therapy, Feb. 10, 2003, pp. 191-202, vol. 14.

Asai, T. et al., "Systemic Delivery of Small RNA Using Lipid Nanoparticles," Biol. Pharm. Bull., 2014, pp. 201-205, vol. 37, No. 2.

Biessen et al., "Synthesis of Cluster Galactosides with High Affinity for the Hepatic Asialoglycoprotein Receptor," J. Med. Chem., 1995, pp. 1538-1546, vol. 38.

Carrillo-Carrasco, N. et al., "Liver-Directed Recombinant Adeno-Associated Viral Gene Delivery Rescues a Lethal Mouse Model of Methylmalonic Acidemia and Provides Long-Term Phenotypic Correction," Human Gene Therapy, Sep. 2010, pp. 1147-1154, vol. 21, published online Jul. 30, 2010, DOI:10.1089/hum.2010.008.

Chandler, R.J. et al., "Adeno-Associated Virus Serotype 8 Gene Transfer Rescues a Neonatal Lethal Murine Model of Propionic Academia," Human Gene Therapy, Apr. 2011, pp. 477-481, vol. 22, published online Oct. 15, 2010, DOI:10.1089/hum.2010.164.

Chandler, R.J. et al., "Liver-Directed Adeno-Associated Virus Serotype 8 Gene Transfer Rescues a Lethal Murine Model of Citrullinemia type 1," Gene Therapy, 2013, pp. 1188-1191, vol. 20, DOI:10.1038/gt.2013.53.

Chen, T. et al., "Proton-induced Permeability and Fusion of Large Unilamellar Vesicles by Covalently Conjugated Poly(2-Ethylacrylic Acid)," Journal of Liposome Research, 1999, pp. 387-405, vol. 9, No. 3.

Chen, Q-R. et al., "Co-Polymer of Histidine and Lysine Markedly Enhances Transfection Efficiency of Liposomes," Gene Therapy, 2000, p. 1698-1705, vol. 7.

Cheung, C.Y. et al., "A pH-Sensitive Polymer that Enhances Lipid-Mediated Gene Transfer," Bioconjugate Chem., 2001, pp. 906-910, vol. 12, published online Oct. 27, 2001.

Claassen, E. et al., "The Effect of Elimination of Macrophages on the Tissue Distribution of Liposomes Containing [3H]methotrexate," Biochimica et Biophysica Acta, Dec. 20, 1984, pp. 428-434, vol. 802.

Crawford, M. et al., "Peptide Aptamers: Tools for Biology and Drug Discovery," Briefings in Functional Genomics and Proteomics, Apr. 2003, pp. 72-79, vol. 2, No. 1.

Cunningham, S.C. et al., "Induction and Prevention of Severe Hyperammonemia in the Spf$^{ash}$ Mouse Model of Ornithine Transcarbamylase Deficiency Using shRNA and rAAV-Mediated Gene Delivery," Molecular Therapy, May 2011, pp. 854-859, vol. 19, No. 5, DOI:10.1038/mt.2011.32.

Dabkowska, A.P. et al., "The Effect of Neutral Helper Lipids on the Structure of Cationic Lipid Monolayers," Journal of the Royal Society Interface, 2012, pp. 548-561, vol. 9, published online Aug. 10, 2011, DOI:10.1098/rsif.2011.0356.

Dominska, M. et al., "Breaking Down the Barriers: siRNA Delivery and Endosome Escape," Journal of Cell Science, 2010, pp. 1183-1189, vol. 123, No. 8.

Dong, Y. et al., "Lipopeptide Nanoparticles for Potent and Selective siRNA Delivery in Rodents and Nonhuman Primates," Proc. Natl. Acad. Sci. USA, Mar. 18, 2014, pp. 3955-3960, vol. 111, No. 11.

Dwarki, V.J. et al., "Cationic Liposome-Mediated RNA Transfection," Methods in Enzymology, 1993, pp. 644-654, vol. 217.

Erez, A. et al., "Requirement of Argininosuccinate Lyase for Systemic Nitric Oxide Production," Nature Medicine, Dec. 2011, pp. 1619-1626, vol. 17, No. 12, published online Nov. 13, 2011, DOI:10.1038/nm.2544.

Gubernator, J., "Active Methods of Drug Loading into Liposomes: Recent Strategies for Stable Drug Entrapment and Increased in Vivo Activity," Expert Opinion on Drug Delivery, May 2011, pp. 565-580, vol. 8, published online Apr. 15, 2011, DOI:10.1517/17425247. 2011.566552.

Guenzel, A.J. et al., "Generation of a Hypomorphic Model of Propionic Acidemia Amenable to Gene Therapy Testing," Molecular Therapy, Jul. 2013, pp. 1316-1323, vol. 21, No. 7, published online May 7, 2013, DOI:10.1038/mt.2013.68.

Hafez, I.M. et al., "Tunable pH-Sensitive Liposomes Composed of Mixtures of Cationic and Anionic Lipids," Biophysical Journal, Sep. 2000, pp. 438-1446, vol. 79.

Hanson et al., "Antigen Delivery by Lipid-Enveloped PLGA Microparticle Vaccines Mediated by in Situ Vesicle Shedding," Biomacromolecules, Jun. 4, 2014, pp. 2475-2481, vol. 15, DOI:10.1021/bm500337r.

Hanson, M.C. et al., "Nanoparticulate STING Agonists are Potent Lymph Node-Targeted Vaccine Adjuvants," The Journal of Clinical Investion, Jun. 2015, pp. 2532-2546, vol. 125, No. 6, DOI:10.1172/JCI79915.

Harasym, T.O. et al., "Clearance Properties of Liposomes Involving Conjugated Proteins for Targeting," Advanced Drug Delivery Reviews, 1998, pp. 99-118, vol. 32.

Heyes et al., "Cationic Lipid Saturation Influences Intracellular Delivery of Encapsulated Nucleic Acids," Journal of Controlled Release, Oct. 3, 2005, pp. 276-287, vol. 107.

Hodges et al., "The spf$^{ash}$ Mouse—A Missense Mutation in the Ornithine Transcarbamylase Gene also Causes Aberrant mRNA Splicing," Proc. Natl. Acad. Sci. USA, Jun. 1989, pp. 4142-4146, vol. 86.

Hong, C.A. et al., "Functional Nanostructures for Effective Delivery of Small Interfering RNA Therapeutics," Theranostics, Sep. 19, 2014, pp. 1211-1232, vol. 4, Issue 12, DOI:10.7150/thno.8491.

Irvine, D.J. et al., "Synthetic Nanoparticles for Vaccines and Immunotherapy," Chemical Reviews, Jul. 8, 2015, pp. 11109-11146, vol. 115, DOI:10.1021/acs.chemrev.5b00109.

Jayaraman, M. et al., "Maximizing the Potency of siRNA Lipid Nanoparticles for Hepatic Gene Silencing In Vivo," Angewandte Chemie Int. Ed., 2012, pp. 8529-8533, vol. 51.

Kariko, K. et al., "Incorporation of Pseudouridine Into mRNA Yields Superior Nonimmunogenic Vector With Increased Translational Capacity and Biological Stability," Molecular Therapy, Nov. 2008, pp. 1833-1840, vol. 16.

Kariko, K. et al., "Generating the Optimal mRNA for Therapy: HLPC Purification Eliminates Immune Activation and Improves Translation of Nucleoside-Modified, Protein-Encoding mRNA," Nucleic Acids Researcg, Sep. 2, 2011, pp. 1-10, published online Sep. 2, 2011, DOI 10.1093/nar/gkr695.

(56) References Cited

OTHER PUBLICATIONS

Kato, Y. et al., "Modification of Liposomes by Addition of HCO60. I. Targeting of Liposomes to Liver by Addition of HCO60 to Liposomes," Biol. Pharm. Bull., 1993, pp. 960-964, vol. 16, No. 10.

Kato, Y. et al., "Targeted Delivery of Peptides, Protein, and Genes by Receptor-mediated Endocytosis," Critical Reviews in Therapeutic Drug Carrier Systems, 1997, pp. 287-331, vol. 14, No. 3.

Khorev, O. et al., "Trivalent, Gal/Gal/VAc-Containing Ligands Designed for the Asialoglycoprotein Receptor," Bioorganic & Medicinal Chemistry, 2008, pp. 5216-5231, vol. 16.

Kim, J-Y. et al., "The Use of PEGylated Liposomes to Prolong Circulation Lifetimes of Tissue Plasminogen Activator," Biomaterials, Oct. 2009, pp. 5751-5756, vol. 30, published online Aug. 4, 2009, DOI:10.1016/j.biomaterials.2009.07.021.

Lechardeur, D. et al., "Metabolic Instability of Plasmid DNA in the Cytosol: a Potential Barrier to Gene Transfer," Gene Therapy, 1999, pp. 482-497, vol. 6.

Lee, Y.C. et al., "Chapter 33: Interactions of Oligosaccharides and Glycopeptides with Hepatic Carbohydrate Receptors," Carbohydrates and Chemistry and Biology (B. Ernst, G.W. Hart, & P. Sinay, Eds., Wiley-WCH: Weinheim), 2000, pp. 549-561, vol. 4.

Lee, J-M. et al., "Recent Developments in Nanoparticle-Based siRNA Delivery for Cancer Therapy," BioMed Research International, vol. 2013, Article ID 782041, 10 pages, http://dx.doi.org/10.1155/2013/782041.

Li, X-J. et al., "Theory of Tunable pH-Sensitive Vesicles of Anionic and Cationic Lipids or Anionic and Neutral Lipids," Biophysical Journal, Apr. 2001, pp. 1703-1711, vol. 80.

Li, T. et al., "TAL nucleases (TALNs): Hybrid Proteins Composed of TAL Effectors and FokI DNA-Cleavage Domain," Nucleic Acids Research, Jan. 2011, pp. 359-372, vol. 39, No. 1, published online Aug. 10, 2010, DOI:10.1093/nar/gkq704.

Love, K.T. et al., "Lipid-like Materials for Low-Dose, in Vivo Gene Silencing," Proc. Natl. Acad. Sci. USA, Feb. 2, 2010, pp. 1864-1869, vol. 107, No. 5, DOI:10.1073/pnas.0910603106.

Lu, D. et al., "Optimization of Methods to Achieve mRNA-Mediated Transfection of Tumor Cells in Vtro and in Vivo Employing Cationic Liposome Vectors," Cancer Gene Therapy, 1994, pp. 245-252, vol. 1, No. 4.

Martin, B. et al., "The Design of Cationic Lipids for Gene Delivery," Current Pharmaceutical Design, 2005, pp. 375-394, vol. 11.

Miyazaki, T. et al., "Fatal Propionic Acidemia in Mice Lacking Propionyl-CoA Carboxylase and Its Rescue by Postnatal, Liver-Specific Supplementation via a Transgene," The Journal of Biological Chemistry, Sep. 21, 2001, pp. 35995-35999, vol. 276, No. 38, published, JBC Papers in Press, Jul. 18, 2001, DOI:10.1074/jbc.M105467200.

Murahashi, N. et al., "Hepatic Accumulation of Glutamic Acid Branched Neogalactosyllipid Modified Liposomes," Biol. Pharm. Bull., 1997, pp. 259-266, vol. 20, No. 3.

Nagamani, S.C.S. et al., "Nitric Oxide Supplementation for Treatment of Long Term Complications in Argininosuccinic Aciduria," The American Journal of Human Genetics, May 4, 2012, pp. 836-846, vol. 90, DOI:10.1016/j.ajhg.2012.03.018.

Oberle, V. et al., "Efficient Transfer of Chromosome-Based DNA Constructs into Mammalian Cells," Biochimica et Biophysica Acta, 2004, pp. 223-230, vol. 1676.

Okumura, K. et al., "Bax mRNA Therapy Using Cationic Liposomes for Human Malignant Melanoma," The Journal of Gene Medicine, 2008, pp. 910-917, vol. 10.

Pejawar-Gaddy, S. et al., "Design of Lipid Nanocapsule Delivery Vehicles for Multivalent Display of Recombinant Env Trimers in HIV Vaccination," Bioconjugate Chemistry, Jul. 14, 2014, pp. 1470-1478, vol. 25, DOI:10.1021/bc5002246.

Perez, C.J. et al., "Two Hypomorphic Alleles of Mouse Ass1 as a New Animal Model of Citrullinemia Type I and Other Hyperammonemic Syndromes," The American Journal of Pathology, Oct. 2010, pp. 1958-1968, vol. 177, No. 4, DOI:10.2353/ajpath.2010.100118.

Ren, T. et al., "Structural Basis of DOTMA for its High Intravenous Transfection Activity in Mouse," Gene Therapy, 2000, pp. 764-768, vol. 7.

Rensen, P.C.N. et al., "Design and Synthesis of Novel N-acetylgalactosamine-Terminated Glycolipids for Targeting of Lipoproteins to the Hepatic asialoglycoprotein Receptor," J. Med. Chem., Oct. 6, 2004, pp. 5798-5808, vol. 47, DOI:10.1021/jm049481d.

Richter, H. et al., "Exploiting CRISPR/Cas: Interference Mechanisms and Applications," Int. J. Mol. Sci., 2013, pp. 14518-14531, vol. 14, DOI:10.3390/ijms140714518.

Robbins, M. et al., "siRNA and Innate Immunity," Oligonucleotides, 2009, pp. 89-102, vol. 19, No. 2.

Rosenberg, L.E. et al., "Biogenesis of Ornithine Transcarbamylase in spfash Mutant Mice: Two Cytoplasmic Precursors, One Mitochondrial Enzyme," Science, Oct. 1983, pp. 426-428, vol. 222, No. 4622.

Samad, A. et al., "Liposomal Drug Delivery Systems: An Update Review," Current Drug Delivery, Oct. 2007, pp. 297-305, vol. 4.

Sapra, P. et al., "Ligand-Targeted Liposomal Anticancer Drugs," Progress in Lipid Research, Sep. 2003, pp. 439-462, vol. 42.

Scherphof, G.L. et al., "Uptake and Intracellular Processing of Targeted and Nontargeted Liposomes by Rat Kupffer Cells in Vivo and in Vitro," Ann. N.Y. Acad. Sci., Jun. 1985, pp. 368-384, vol. 446.

Semple, S.C. et al., "Immunogenicity and Rapid Blood Clearance of Liposomes Containing Polyethylene Glycol-Lipid Conjugates and Nucleic Acid," The Journal of Pharmacology and Experimental Therapeutics, 2005, pp. 1020-1026, vol. 312, No. 3, DOI:10.1124/jpet.104.078113.

Semple, S.C. et al., "Rational Design of Cationic Lipids for siRNA Delivery," Nature Biotechnology, 2010, pp. 172-176, vol. 28, published online Jan. 17, 2010, DOI:10.1038/nbt.1602.

Shimizu, K. et al., "Formulation of Liposomes with a Soybean-Derived Sterylglucoside Mixture and Cholesterol for Liver Targeting," Biol. Pharm. Bull., 1997, pp. 881-886, vol. 20.

Silva, G. et al., "Meganucleases and Other Tools for Targeted Genome Engineering: Perspectives and Challenges for Gene Therapy," Current Gene Therapy, Feb. 2011, pp. 11-27, vol. 11.

Sliedregt, L.A.J.M. et al., "Design and Synthesis of Novel Amphiphilic Dendritic Galactosides for Selective Targeting of Liposomes to the Hepatic Asialoglycoprotein Receptor," J. Med. Chem., Feb. 5, 1999, pp. 609-618, vol. 42, DOI:10.1021/jm981078h.

Smith, J. et al., "Requirements for Double-Strand Cleavage by Chimeric Restriction enzymes with zinc finger DNA-recognition domains," Nucleic Acids Research, Sep. 1, 2000, pp. 3361-3369, vol. 28, No. 17.

Soutschek, J. et al., "Therapeutic Silencing of an Endogenous Gene by Systemic administration of modified siRNAs," Nature, Nov. 2004, pp. 173-178, vol. 432.

Su, X. et al., "In Vitro and in Vivo mRNA Delivery Using Lipid-Enveloped pH-Responsive Polymer Nanoparticles," Mol Pharm., 2011, pp. 774-787, vol. 8, No. 3.

Tam, Y.Y.C. et al., "Advances in Lipid Nanoparticles for siRNA Delivery," Pharmaceutics, 2013, pp. 498-507, vol. 5; doi:10.3390/pharmaceutics5030498.

Tsui, N.B.Y. et al., "Stability of Endogenous and Added RNA in Blood Specimens, Serum, and Plasma," Clinical Chemistry, 2002, pp. 1647-1653, vol. 48, No. 10.

Wan, C. et al., "Lipid Nanoparticle Delivery Systems for siRNA-Based Therapeutics," Drug Deliv. and Transl. Res., 2013, 10 pages, DOI 10.1007/s13346-013-0161-z.

Wang, J. et al., "Delivery of siRNA Therapeutics: Barriers and Carriers," The AAPS Journal, Dec. 2010, pp. 492-503, vol. 12, No. 4; DOI: 10.1208/s12248-010-9210-4.

Watts, J.K. et al., "Chemically Modified siRNA: Tools and Applications," Drug Discovery Today, Oct. 2008, pp. 842-855, vol. 13, No. 19/20.

Whitehead, K.A. et al., "Degradable Lipid Nanoparticles with Predictable in Vivo siRNA Delivery Activity," Nature Communications, 2014, 10 pages, vol. 5, published online Jun. 27, 2014, DOI:10.1038/ncomms5277.

(56) References Cited

OTHER PUBLICATIONS

Wong, S.C. et al., "Co-Injection of a Targeted, Reversibly Masked Endosomolytic Polymer Dramatically Improves the Efficacy of Cholesterol-Conjugated Small Interfering RNAs In Vivo," Nucleic Acid Therapeutics, 2012, pp. 380-390, vol. 22, No. 6; DOI: 10.1089/nat.2012.0389.

Wooddell, C.I. et al., "Hepatocyte-Targeted RNAi Therapeutics for the Treatment of Chronic Hepatitis B Virus Infection," Molecular Therapy, May 2013, pp. 973-985, vol. 21, No. 5.

Yamamoto, A. et al., "Current Prospects for mRNA Gene Delivery," European Journal of Pharmaceutics and Biopharmaceutics, 2009, pp. 484-489, vol. 71, doi: 10.1016/j.ejpb.2008.09.016, published online Oct. 10, 2008.

Ye, X. et al., "Prolonged Metabolic Correction in Adult Ornithine Transcarbamylase-deficient Mice with Adenoviral Vectors," The Journal of Biological Chemistry, Feb. 16, 1996, pp. 3639-3646, vol. 271, No. 7.

Zimmermann, T.S. et al., "RNAi-Mediated Gene Silencing in Non-Human Primates," Nature, May 4, 2006, pp. 111-114, vol. 441, published online Mar. 26, 2006, DOI:10.1038/nature04688.

International Search Report and Written Opinion dated Jun. 16, 2016, issued in corresponding International Application No. PCT/US2016/014232, filed Jan. 21, 2016.

Invitation to Pay Additional Fees and Communication Relating to Results of the Partial International Search dated Apr. 8, 2016, issued in corresponding International Application No. PCT/US2016/014232, filed Jan. 21, 2016.

Abstract of Japanese Patent No. JPH04244018 to Hayakawa et al., Sep. 1, 1992.

Midoux, P. et al., "Chemical Vectors for Gene Delivery: a Current Review on Polymers, Peptides and Lipids Containing Histidine or Imidazole as Nucleic Acids Carriers," British Journal of Pharmacology, 2009, pp. 166-178, vol. 157.

Agarwal, A., et al., "Dual-Role Self-Assembling Nanoplexes for Efficient Gene Transfection and Sustained Gene Delivery," Biomaterials 29(5):607-617, Feb. 2008.

Alvarez-Lorenzo, C., et al., "Biophysical Characterization of Complexation of DNA With Block Copolymers of Poly(2-dimethylaminoethyl) Methacrylate, Poly(ethylene oxide), and Poly(propylene oxide)," Langmuir 21(11):5142-5148, May 2005.

Benoit, D.SW., et al., "Resensitizing Multidrug Resistant Cells to Doxorubicin Through Plk1 Knockdown Using a Novel pH-Responsive Micelle siRNA Delivery System," Abstracts of Society for Biomaterials Meeting, Apr. 22, 2009, 1 page.

Boeckle, S., et al., "Purification of Polyethylenimine Polyplexes Highlights the Role of Free Polycations in Gene Transfer," Journal of Gene Medicine 6(10):1102-1111, Oct. 2004.

Bulmus, V., et al., "A New pH-Responsive and Glutathione-Reactive, Endosomal Membrane-Disruptive Polymeric Carrier for Intracellular Delivery of Biomolecular Drugs," Journal of Controlled Release 93(2):105—120, Dec. 2003.

Cai, Y., et al., "A Zwitterionic ABC Triblock Copolymer That Forms a 'Trinity' of Micellar Aggregates in Aqueous Solution," Macromolecules 37(19):7116-7122, Sep. 2004.

Cheng, Z., et al., "Brush-Type Amphiphilic Diblock Copolymers From 'Living'/Controlled Radical Polymerizations and Their Aggregation Behavior," Langmuir 21(16):7180-7185, Jul. 2005.

Chiefari, J., et al. "Living Free-Radical Polymerization by Reversible Addition-Fragmentation Chain Transfer: The RAFT Process," Macromolecules, vol. 31, pp. 5559-5562, 1998.

Chiu, H.-C., et al., "Synthesis and Characterization of Amphiphilic Poly( ethylene glycol) Graft Copolymers and their Potential Application as Drug Carriers," Polymer 39(8-9):1609-1616, 1998.

Cho, Y.W., et al., "Polycation Gene Delivery Systems: Escape From Endosomes to Cytosol," Journal of Pharmacy and Pharmacology 55(6):721-734, Jun. 2003.

Convertine, A.J., et al., "Development of a Novel Endosomolytic Diblock Copolymer for siRNA Delivery," Journal of Controlled Release 133(3):221-229, Feb. 2009.

Dufresne, M.-H., et al., "Characterization of Polyion Complex Micelles Designed to Address the Challenges of oligonucleotide Delivery," Pharmaceutical Research 25(9):2083-2093, Sep. 2008.

Duvall, C.L., et al., "Polymer Enhanced Intracellular Delivery of a Pro-Apoptotic Peptide for Cancer Therapy," abstracts of Society for Biomaterials Meeting, Apr. 22, 2009, 1 page.

Eliyahu, H., et al., "Novel Dextran-Spermine Conjugates as Transfecting Agents: Comparing Water-Soluble and Micellar Polymers," Gene Therapy 12(6):494-503, Mar. 2005.

El-Sayed, M.E.H., et al., "Rational Design of Composition and Activity Correlations for pH-Sensitive and Glutathione-Reactive Polymer Therapeutics," Journal of Controlled Release 101 (1-3):47-58, Jan. 2005.

El-Sayed, M.E.H., et al., "Smart Polymeric Carriers for Enhanced Intracellular Delivery of Therapeutic Macromolecules," Expert Opinion on Biological Therapy 5(1):23-32, Jan. 2005.

Finne-Wistrand, A., and A.-C. Albertson, "The Use of Polymer Design in Resorbable Colloids," Annual Review of Materials Research 36:369-395, Aug. 2006.

Fishbein, I., et al., "Local Delivery of Gene Vectors From Bare-Metal Stents by Use of a Biodegradable Synthetic complex Inhibits In-Stent Restenosis in Rat Carotid Arteries," Circulation 117(16):2096-2103, Apr. 2008.

Funhoff, A.M., et al., "Endosomal Escape of Polymeric Gene Delivery Complexes Is Not Always Enhanced by Polymers Buffering at Low pH," Biomacromolecules 5(1):32-39, Jan.-Feb. 2004.

Gary, D.J., et al., "Polymer-Based siRNA Delivery: Perspectives on the Fundamental and Phenomenological Distinctions From Polymer-Based DNA Delivery," Journal of Controlled Release 121(1-2):64-73, Aug. 2007.

Gaucher, G., et al., "Block Copolymer Micelles: Preparation, Characterization and Application in Drug Delivery," Journal of Controlled Release 109(1-3):169-188, Dec. 2005.

Georgiou, T.K., and C.S. Patrickios, "Synthesis, Characterization, and DNA Adsorption Studies of Ampholytic Model Conetworks Based on Cross-Linked Star Copolymers," Biomacromolecules 9(2):574-582, Feb. 2008.

Germershaus, O., et al., "Gene Delivery Using Chitosan, Trimethyl Chitosan or Polyethylenglycol-grafl-trimethyl Chitosan Block Copolymers: Establishment of Structure-Activity Relationships In Vitro," Journal of Controlled Release 125(2):145—154, Jan. 2008.

Guo, Y., et al., "Capillary Electrophoresis Analysis of Poly( ethylene glycol) and Ligand-Modified Polylysine Gene Delivery Vectors," Analytical Biochemistry 363(2):204-209, Apr. 2007.

Gyda, M., et al. (2012) "The Tumor Suppressor Gene retinoblastorna-1 Is Required for Retinotectal Development and Visual Function in Zebrafish", PLoS Genetics, 8(11) article e1003106, 11 pages.

Henry, S.M., et al., "pH-Responsive Poly(styrene-alt-maleic anhydride) Alkylamide Copolymers for Intracellular Drug Delivery," Biomacromolecules 7(8):2407-2414, Aug. 2006.

Heredia, K.L., et al., "Reversible siRNA-Polymer Conjugates by RAFT Polymerization," Chemical Communications 28(28):3245-3247, Jul. 2008.

Hood, J.D., et al., "Tumor Regression by Targeted Gene Delivery to the Neovasculature," Science 296(5577):2404-2407, Jun. 2002.

Inoue, T., et al., "An AB Block Copolymer of Oligo(methyl methacrylate) and Poly(acrylic acid) for Micellar Delivery of Hydrophobic Drugs," Journal of Controlled Release 51(2-3):221-229, Feb. 1998.

Jensen, K.D., et al., "Antisense Oligonucleotides Delivered to the Lysosome Escape and Actively Inhibit the Hepatitis B Virus," Bioconjugate Chemistry 13{5):975-984, Sep.-Oct. 2002.

Jeong, J.H., et al., "siRNA Conjugate Delivery Systems," Bioconjugate Chemistry 20(1):5-14, Jan. 2009.

Jeong, Y.-l., et al., "Cellular Recognition of Paclitaxei-Loaded Polymeric Nanoparticles Composed of Poly ($\gamma$-benzyl $_L$-glutamate) and Poly {ethylene glycol) Diblock Copolymer Endcapped With Galactose Moiety," International Journal of Pharmaceutics 296{1-2):151-161, May 2005.

Jiang, T., et al., "Adsorption of Plasmid DNA Onto N,N'-{Dimethylamino)ethyl-methacrylate Graft-Polymerized Poly-L-Lactic Acid Film Surface for Promotion of In-Situ Gene Delivery," Biomacromolecules 8{6):1951-1957, Jun. 2007.

(56) References Cited

OTHER PUBLICATIONS

Joralemon, M.J., et al., "Synthesis, Characterization, and Bioavailability of Mannosylated Shell Cross-Linked Nanoparticles," Biomacromolecules 5{3}:903-913, May-Jun. 2004.

Kabanov, A.V., et al., "Piuronic Micelles as a Tool for Low-Molecular Compound Vector Delivery Into a Cell: Effect of *Staphylococcus aureus* Enterotoxin Bon Cell Loading With Micelle Incorporated Fluorescent Dye," Biochemistry International 26{6}: 1035-1042, May 1992.

Kariko, et al. (2012) "Increased Erythropoiesis in Mice Injected With Subrnicrograrn Quantities of Pseudouridine-Containing mRNA Encoding Erythropoietin", Molecular Therapy, 20(5): 948-953.

Kataoka, K., et al., "Smart Polymeric Micelles as Nanocarriers for Oligonucleotides and siRNA Delivery," Nucleic Acids Symposium Series 49{1}: 17-18, Sep. 2005.

Kim, E.-M., et al., "Asialoglycoprotein receptor targeted gene delivery using galactosylated polyethylenimine-graft-poly(ethylene glycol): in vitro and in vivo studies," Journal of Controlled Release 108:557-67 (2005).

Kim, E.-M., et al., "Monitoring the Effect of PEGylation on Polyethylenimine In Vivo Using Nuclear Imaging Technique," Nuclear Medicine and Biology 31(6):781-784, Aug. 2004.

Kono, K., et al., "Transfection Activity of Polyamidoamine Dendrimers Having Hydrophobic Amino Acid Residues in the Periphery," Bioconjugate Chemistry 16(1):208-214, Jan. 2005.

Kulkarni, S., et al, "Controlling the Aggregation of Conjugates of Streptavidin With Smart Block Copolymers Prepared via the RAFT Copolymerization Technique," Biomacromolecules 7(10):2736-2741, Oct. 2006.

Kurisawa, M., et al., "Transfection Efficiency Increases by Incorporating Hydrophobic Monomer Units Into Polymeric Gene Carriers," Journal of Controlled Release 68(1):1-8, Jul. 2000.

Lam, J.K.W., et al., "Phosphocoline-Polycation Diblock Copolymers as Synthetic Vectors for Gene Delivery," Journal of Controlled Release 100(2):293-312, Nov. 2004.

Le Garrec, D., et al., "Micelles in Anticancer Drug Delivery," American Journal of Drug Delivery 2(1):15-42, Mar. 2004.

Lee, E.S., et al., "Poly{L-histidine)-PEG Block Copolymer Micelles and pH-Induced Destabilization," Journal of Controlled Release 90(3):363-374, Jul. 2003.

Lee, E.S., et al.,"Super pH-Sensitive Multifunctional Polymeric Micelle," Nano Letters 5(2):325-329, Feb. 2005.

Lomas, H., et al., "Biomimetic pH Sensitive Polymersomes for Efficient DNA Encapsulation and Delivery," Advanced Materials 19(23):4238-4243( 2007).

Lowe, A.B., and C.L. McCormick, "Stimuli Responsive Water-Soluble and Amphiphilic {Co)polymers,"Chap. 1, in C.L. McCormick {ed.), "Stimuli-Responsive Water Soluble and Amphiphilic Polymers," ACS Symposium Series, American Chemical Society, Washington, D.C., 2000, vol. 780, pp. 1-13.

Meyer, M., et al., "Synthesis and Biological Evaluation of a Bioresponsive and Endosomolytic siRNA-Polymer conjugate," Molecular Pharmaceutics 6{3}:752-762, May-Jun. 2009.

Meyer, O., et al., "Copolymers of N-lsopropylacrylamide Can Trigger pH Sensitivity to Stable Liposomes,"FEBS Letters 421 {1 ):61-64, Jan. 1998.

Mian, A., et al. (2004) "Long-term correction of ornithine transcarbarnylase deficiency by WPRE-rnediated overexpression using a helper-dependent adenovirus", Molecular Therapy, 10(3): 492-499.

Mountrichas, G., and S. Pispas, "Synthesis and pH Responsive Self-Assembly of New Double Hydrophilic Block Copolymers," Macromolecules 39{14}:4767-4774, Jul. 2006.

Murthy, N., et al., "Bioinspired pH-Responsive Polymers for the Intracellular Delivery of Biomolecular Drugs," Bioconjugate Chemistry 14{2}:412-419, Mar.-Apr. 2003.

Murthy, N., et al., "The Design and Synthesis of Polymers for Eukaryotic Membrane Disruption," Journal of Controlled Release 61{ 1-2):137-143, Aug. 1999.

Nagasaki, Y., et al., "Sugar-Installed Block Copolymer Micelles: Their Preparation and Specific Interaction with Lectin Molecules," Biomacromolecules 2{4}:1067-1070, Winter 2001.

Neu, M., et al., "Recent Advances in Rational Gene Transfer Vector Design Based on Poly (ethylene imine) and Its Derivatives," Journal of Gene Medicine 7(8):992-1009, Aug. 2005.

Ogris, M., et al., "PEGylated DNA/Transferrin-PE1 Complexes: Reduced Interaction With Blood Components, extended Circulation in Blood and Potential for Systemic Gene Delivery," Gene Therapy 6(4):595-605, Apr. 1999.

Oishi, M., et al., "Lactosylated Poly(ethylene glycol)-siRNA Conjugate Through Acid-Labile B-Thiopropionate linkage to Construct pH-Sensitive Polyion Complex Micelles Achieving Enhanced Gene Silencing in Hepatoma Cells," Journal of the American Chemical Society 127(6):1624-1625, Feb. 2005.

Oishi, M., et al., "pH-Responsive Oligodeoxynucleotide (ODN}-Poly(Ethylene Glycol) Conjugate Through acid-Labile JB-Thiopropionate Linkage: Preparation and Polyion Complex Micelle Formation," Biomacromolecules (5):1426-1432, Aug. 2003.

Oupicky, D., et al., "DNA Delivery Systems Based on Complexes of DNA With Synthetic Polycations and their Copolymers,"Journal of Controlled Release 65( 1-2):149-171, Mar. 2000.

Patrickios, C.S., et al., "Diblock, ABC Triblock, and Random Methacrylic Polyampholytes: Synthesis by Group Transfer Polymerization and Solution Behavior," Macromolecules 27(4):930-937, Feb. 1994.

Peppas, N.A., "Is There a Future in Glucose-Sensitive, Responsive Insulin Delivery Systems?" Drug Delivery Science and Technology 14(4):247-256, Sep. 2004.

Raso, V., "Intracellular Targeting Using Bispecific Antibodies," Methods in Molecular Medicine 25:37-50, Jan. 2000.

Read, M.L., et al., "Physicochemical and Biological Characterisation of an Antisense Oligonucleotide Targeted gains the Bcl-2 mRNA Complexed With Cationic-Hydrophilic Copolymers," European Journal of Pharmaceutical Sciences 10(3):169-177, May 2000.

Rozema, D.B., et al., "Dynamic PolyConjugates for Targeted In Vivo Delivery of siRNA to Hepatocytes," Proceedings of the National Academy of Sciences (PNAS) 1 04(32): 12982-12987, Aug. 2007.

Satturwar, P., et al., "pH-Responsive Polymeric Micelles of Poly-(ethylene glycol)-b-poly(alkyl(meth)acrylate-co-methacrylic acid): influence of the Copolymer Composition on Self-Assembling Properties and Release of Candesartan Cilexetil," European Journal of Pharmaceutics and Biopharmaceutics 65(3):379-387, Mar. 2007.

Sawant, R.M., et al., "'SMART' Drug Delivery Systems: Double-Targeted pH-Responsive Pharmaceutical Nanocarriers," Bioconjugate Chemistry 17(4):943-949, Jul.-Aug. 2006.

Scales, C.W., et al., "Corona-Stabilized Interpolyelectrolyte Complexes of SiRNA With Nonimmunogenic, Hydrophilic/Cationic Block Copolymers Prepared by Aqueous RAFT Polymerization," Macromolecules 9(20):6871-6881, Oct. 2006.

Segura, T., and J.A. Hubbell, "Synthesis and In Vitro Characterization of an ABC Triblock Copolymer or siRNA Delivery," Bioconjugate Chemistry 18(3):736-745, May 2007.

Stayton, P.S., and A.S. Hoffman, "'Smart' pH-Responsive Carriers for Intracellular Delivery of Biomolecular Drugs," in V. Torchilin (ed.), "Fundamental Biomedical Technologies: Multifunctional Pharmaceutical Nanocarriers," Springer Science+Business Media, LLC, New York, May 2008, vol. 4, pp. 143-160.

Stayton, P.S., et al., "Intelligent Biohybrid Materials for Therapeutic and Imaging Agent Delivery," Proceedings of the IEEE 93(4):726-736, Apr. 2005.

Takeda, N., et al., "Temperature-Responsive Polymeric Carriers Incorporating Hydrophobic Monomers for Effective Transfection in Small Doses," Journal of Controlled Release 95(2):343-355, Mar. 2004.

Taton, D., et al., "Direct Synthesis of Double Hydrophilic Statistical Di- and Triblock Copolymers Comprised of Acrylamide and Acrylic Acid Units via the MADIX Process," Macromolecular Rapid Communications 2(18):1497-1503, Dec. 2001.

Teoh, S.K., et al., "Self-Assembly of Stimuli-Responsive Water-Soluble [60]Fullerene End-Capped Ampholytic Block Copolymer, "Journal of Physical Chemistry B 109(10):4431-4438, Feb. 2005.

(56) References Cited

OTHER PUBLICATIONS

Torchilin, V. P., "Micellar Nanocarriers: Pharmaceutical Perspectives," Pharmaceutical Research 24(1):1-16, Jan. 2007.

Turk, M. J., et al., "Characterization of a Novel pH-Sensitive Peptide That Enhances Drug Release From Folate-Targeted Liposomes at Endosomal pHs," Biochimica et Biophysica Acta 1559(1)56-68, Feb. 2002.

Varghese, O. P., et al., "In Situ Cross-Linkable High Molecular Weight Hyaluronan-Bisphosphonate Conjugate or Localized Delivery and Cell-Specific Targeting: A Hydrogel Linked Prodrug Approach," Journal of the American Chemical Society 131(25):8781-8783, Jul. 2009.

Veron, L., et al., "Hydrolyzable p(DMAPEMA) Polymers for Gene Delivery," Macromolecular Bioscience 6(7):540-554, Jul. 2006.

Wakebayashi, D., et al., "Lactose-Conjugated Polyion Complex Micelles Incorporating Plasmid DNA as a Targetable Gene Vector System: Their Preparation and Gene Transfecting Efficiency Against Cultured HepG2 Cells," Journal of Controlled Release 95(3):653-664, Mar. 2004.

Wang, L., et al., "Delivery of Antisense Oligonucleotides Using HPMA Polymer: Synthesis of a Thiol Polymer and Is Conjugation to Water-Soluble Molecules," Bioconjugate Chemistry 9(6):749-757, Nov.-Dec. 1998.

Wei, J.-S., et al., "Temperature- and pH-Sensitive Core-Shell Nanoparticles Self-Assembled From Poly(N-isopropylacrylamide-co-acrylic acid-co-cholesteryl acrylate) for Intracellular Delivery of Anticancer Drugs," Frontiers in Bioscience 10:3058-3067, Sep. 2005.

Yamamoto, S.-l, et al., "Temperature- and pH-Responsive Dense Copolymer Brushes Prepared by ATRP," Macromolecules 41 (19): 7013-7020, Oct. 2008.

Yasugi, K., et al., "Sugar-Installed Polymer Micelles: Synthesis and Micellization of Poly(ethylene glycol)-poly(D,L-lactide) Block Copolymers Having Sugar Groups at the PEG Chain End," Macromolecules 2(24):8024-8032, Nov. 1999.

Yessine, M.-A., et al., "Proton-Actuated Membrane-Destabilizing Polyion Complex Micelles," Bioconjugate Chemistry 18(3):1010-1014, May-Jun. 2007.

Yoo, H.S., and T. G. Park, "Folate Receptor Targeted Biodegradable Polymeric Doxorubicin Micelles," Journal of Controlled Release 96(2):273-283, Apr. 2004.

York, A.W., et al., "Advances in the Synthesis of Amphiphilic Block Copolymers via RAFT Polymerization: Stimuli-Responsive Drug and Gene Delivery," Advanced Drug Delivery Reviews 60(9):1018-1036, Jun. 2008.

Yu, H., et al., "A Novel Amphiphilic Double-[60]Fullerene-Capped Triblock Copolymer," Macromolecules 38(23):9889-9893, Nov. 2005.

Zhao, X., et al.,"Nanostructure of Polyplexes Formed Between Cationic Diblock Copolymer and Antisense Oligodeoxynucleotide and Its influence on Cell Transfection Efficiency," Biomacromolecules 8(11 ):3493-3502, Nov. 2007.

Cheung, C.Y., et al., "A pH-Sensitive Polymer That Enhances Cationic Lipid-Mediated Gene Transfer," Bioconjugate Chemistry 12(6):906-910, Oct. 2001.

Glinel, K. et al., "Responsive Polyelectrolyte Multilayers," Colloids and Surfaces A: Physiochemical and Engineering Aspects, 303:3-13, (Aug. 2007).

Kyriakides, T.R., et al., "pH-Sensitive Polymers That Enhance Intracellular Drug Delivery In Vivo," Journal of Controlled Release 78(1-3):295-303, (Jan. 2002).

Lundy, B. B. et al., "Neutral Polymeric Micelles for RNA Delivery," Bioconjugate Chemistry, 24(3):398-407, (Mar. 20, 2013).

Nelson, C.E. et al., "Balancing Cationic and Hydrophobic Content of PEGylated siRNA Polyplexes Enhances Endosome Escape, Stability, Blood Circulation Time, and Bioactivity in Vivo," ACS Nano, 7(10):8870-8880 (2013).

Schellinger, J.G. et al., "Melittin-Grafted HPMA-Oligolysine Based Copolymers for Gene Delivery," Biomaterials, 34(9):2318-2326 (Mar. 2013).

Shi, J. et al., "Influence of Histidine Incorporation on Buffer Capacity and Gene Transfection Efficiency of HPMA-co-oligolysine Brush Polymers," Biomacromolecules, 14(6):1961-1970 (Jun. 10, 2013).

Wilson, J.T. et al., "pH-Responsive Nanoparticle Vaccines for Dual-Delivery of Antigens and Immunostimulatory Oligonucleotides," ACS Nano, 7(5):3912-3925, (May 28, 2013).

Wooddell, C.I. et al., "Hepatocyte-targeted RNAi Therapeutics for the Treatment of Chronic Hepatitis B Virus Infection," Molecular Therapy 21(5):973-985, American Society of Gene & Cell Therapy, United States (May 2013).

\* cited by examiner

METHODS, COMPOSITIONS, AND SYSTEMS FOR DELIVERING THERAPEUTIC AND DIAGNOSTIC AGENTS INTO CELLS

The instant application contains a Sequence Listing which has been submitted in ASCII format via EFS-Web and is hereby incorporated by reference in its entirety. Said ASCII Copy, created on Jan. 13, 2016, is named "3900_PCT1_Seq_Listing_ST25" and is 66,448 bytes in size.

BACKGROUND OF THE INVENTION

Lipid nanoparticles (LNPs) are effective drug delivery systems for biologically active compounds such as therapeutic nucleic acids, proteins, and peptides, which are otherwise cell impermeable. Liposomal formulations have also been developed for small molecule drugs, generally with the aim to enrich the drug in certain tissues as well as to mitigate toxicity.

Drugs based on nucleic acids, which include large nucleic acid molecules such as, e.g., in vitro transcribed messenger RNA (mRNA) as well as smaller polynucleotides that interact with a messenger RNA or a gene, have to be delivered to the proper cellular compartment in order to be effective. For example, double-stranded nucleic acids such as double-stranded RNA molecules (dsRNA), including, e.g., siRNAs, suffer from their physico-chemical properties that render them impermeable to cells. Upon delivery into the proper compartment, siRNAs block gene expression through a highly conserved regulatory mechanism known as RNA interference (RNAi). Typically, siRNAs are large in size with a molecular weight ranging from 12-17 kDa, and are highly anionic due to their phosphate backbone with up to 50 negative charges. In addition, the two complementary RNA strands result in a rigid helix. These features contribute to the siRNA's poor "drug-like" properties. When administered intravenously, the siRNA is rapidly excreted from the body with a typical half-life in the range of only 10 minutes. Additionally, siRNAs are rapidly degraded by nucleases present in blood and other fluids or in tissues, and have been shown to stimulate strong immune responses in vitro and in vivo. See, e.g., Robbins et al., *Oligonucleotides* 19:89-102, 2009. mRNA molecules suffer from similar issues of impermeability, fragility, and immunogenicity.

By introduction of appropriate chemical modifications, stability towards nucleases can be increased and at the same time immune stimulation can be suppressed. Conjugation of lipophilic small molecules to the siRNAs improves the pharmacokinetic characteristics of the double-stranded RNA molecule. It has been demonstrated that these small molecule siRNA conjugates are efficacious in a specific down regulation of a gene expressed in hepatocytes of rodents. However, in order to elicit the desired biologic effect, a large dose was needed. See Soutschek et al., *Nature* 432:173-178, 2004.

Lipid nanoparticle formulations have improved nucleic acid delivery in vivo. For example, such formulations have significantly reduced siRNA doses necessary to achieve target knockdown in vivo. See Zimmermann et al., *Nature* 441:111-114, 2006. Typically, such lipid nanoparticle drug delivery systems are multi-component formulations comprising cationic lipids, helper lipids, and lipids containing polyethylene glycol. The positively charged cationic lipids bind to the anionic nucleic acid, while the other components support a stable self-assembly of the lipid nanoparticles.

Efforts have been directed toward improving delivery efficacy of lipid nanoparticle formulations. Many such efforts have been aimed toward developing more appropriate cationic lipids. See, e.g., Akinc et al., *Nature Biotechnology* 26:561-569, 2008; Love et al., *Proc. Natl. Acad. Sci. USA* 107:1864-1869, 2010; Baigude et al., *Journal of Controlled Release* 107:276-287, 2005; Semple et al., *Nature Biotechnology* 28:172-176, 2010. Despites these efforts, improvements in terms of increased efficacy and/or decreased toxicity are still needed, especially for lipid nanoparticle based drug delivery systems intended for therapeutic uses.

SUMMARY OF THE INVENTION

In one aspect, the present invention provides a method for delivering a therapeutic or diagnostic agent to the cytosol of a target cell within a subject. The method generally includes administering to the subject (a) an effective amount of a lipid nanoparticle comprising the therapeutic or diagnostic agent and (b) an effective amount of a membrane-destabilizing polymer, where the therapeutic or diagnostic agent is delivered to the cytosol of the target cell. The lipid nanoparticle and membrane-destabilizing polymer can be administered separately (e.g., the membrane-destabilizing polymer administered after administration of the lipid nanoparticle) or, alternatively, together within a single composition. Typically, the lipid nanoparticle is less than about 200 nm in size. In certain variations, the lipid nanoparticle and the membrane-destabilizing polymer are administered in a repeat dosage regime (e.g., a weekly or bi-weekly repeated administration protocol).

In some embodiments, the lipid nanoparticle comprises a cationic lipid. Particularly suitable cationic lipids include N-[1-(2,3-dioleyloxy)propyl]-N,N,N-trimethylammonium chloride (DOTMA); N-[1-(2,3-dioleoyloxy)propyl]-N,N,N-trimethylammonium chloride (DOTAP); 1,2-dioleoyl-sn-glycero-3-ethylphosphocholine (DOEPC); 1,2-dilauroyl-sn-glycero-3-ethylphosphocholine (DLEPC); 1,2-dimyristoyl-sn-glycero-3-ethylphosphocholine (DMEPC); 1,2-dimyristoleoyl-sn-glycero-3-ethylphosphocholine (14:1), N1-[2-((1S)-1-[(3-aminopropyl)amino]-4-[di(3-amino-propyl)amino]butylcarboxamido)ethyl]-3,4-di[oleyloxy]-benzamide (MVL5); Dioctadecylamido-glycylspermine (DOGS); 3b-[N—(N',N'-dimethylaminoethyl)carbamoyl] cholesterol (DC-Chol); Dioctadecyldimethylammonium Bromide (DDAB); a Saint lipid (e.g., SAINT-2, N-methyl-4-(dioleyl)methylpyridinium); 1,2-dimyristyloxypropyl-3-dimethylhydroxyethylammonium bromide (DMRIE); 1,2-dioleoyl-3-dimethyl-hydroxyethyl ammonium bromide (DORIE); 1,2-dioleoyloxypropyl-3-dimethylhydroxyethyl ammonium chloride (DORI); Di-alkylated Amino Acid (DILA$^2$) (e.g., C18:1-norArg-C16); Dioleyldimethylammonium chloride (DODAC); 1-palmitoyl-2-oleoyl-sn-glycero-3-ethylphosphocholine (POEPC); and 1,2-dimyristoleoyl-sn-glycero-3-ethylphosphocholine (MOEPC). In some variations, the cationic lipid is an ionizable cationic lipid such as, e.g., Dioctadecyldimethylammonium bromide (DDAB), 1,2-dilinoleyloxy-3-dimethylaminopropane (DLinDMA), 2,2-dilinoleyl-4-(2dimethylaminoethyl)-[1,3]-dioxolane (DLin-KC2-DMA), heptatriaconta-6,9,28,31-tetraen-19-yl 4-(dimethylamino)butanoate (DLin-MC3-DMA), 1,2-Dioleoyloxy-3-dimethylaminopropane (DODAP), 1,2-Dioleyloxy-3-dimethylaminopropane (DODMA), Morpholinocholesterol (Mo-CHOL), (R)-5-(dimethylamino)pentane-1,2-diyl dioleate hydrochloride (DODAPen-C1), (R)-5-guanidinopentane-1,2-diyl dioleate hydrochloride (DOPen-G), (R)-N,N,N-trimethyl-4,5-bis (oleoyloxy)pentan-1-aminium chloride (DOTAPen). In certain embodiments, a lipid nanoparticle includes a combination or two or more cationic lipids (e.g., two or more cationic lipids as above).

In some embodiments of a method as above, the lipid nanoparticle includes an ionizable anionic lipid such as, e.g., cholesteryl hemisuccinate (CHEMS), phosphatidylserine, palmitoylhomoserine, or α-tocopherol hemisuccinate. In certain variations, a lipid nanoparticle includes a combination or two or more ionizable anionic lipids (e.g., two or more ionizable anionic lipids as above).

In some variations of a method as above, the lipid nanoparticle includes a helper lipid. Particularly suitable helper lipids includes cholesterol (CHOL); 1,2-distearoyl-sn-glycero-3-phosphocholine (DSPC); 1,2-dipalmitoyl-sn-glycero-3-phosphocholine (DPPC); 1,2-dimyristoyl-sn-glycero-3-phosphocholine (DMPC); 1,2-dioleoyl-sn-glycero-3-phosphoethanolamine (DOPE); 1,2-dilauroyl-sn-glycero-3-phosphoethanolamine (DLPE); 1,2-dimyristoyl-sn-glycero-3-phosphoethanolamine (DMPE); and 1,2-diphytanoyl-sn-glycero-3-phosphoethanolamine (DPHyPE). In certain embodiments, a lipid nanoparticle includes a combination or two or more helper lipids (e.g., two or more helper lipids as above).

In certain embodiments of a method as above, the lipid nanoparticle includes a polyethylenegycol-lipid conjugate (PEG-lipid) such as, e.g., N-(Carbonyl-methoxypolyethyleneglycol$_n$)-1,2-dimyristoyl-sn-glycero-3-phosphoethanolamine (DMPE-PEG$_n$ where n is 350, 500, 750, 1000 or 2000), N-(Carbonyl-methoxypolyethyleneglycol$_n$)-1,2-distearoyl-sn-glycero-3-phosphoethanolamine (DSPE-PEG$_n$ where n is 350, 500, 750, 1000 or 2000), DSPE-polyglycelin-cyclohexyl-carboxylic acid, DSPE-polyglycelin-2-methylglutar-carboxylic acid, polyethylene glycol-dimyristolglycerol (PEG-DMG), polyethylene glycol-distearoyl glycerol (PEG-DSG), or N-octanoyl-sphingosine-1-{(succinyl[methoxy(polyethylene glycol)2000]} (C8 PEG2000 Ceramide). In some variations of DMPE-PEG$_n$ where n is 350, 500, 750, 1000 or 2000, the PEG-lipid is N-(Carbonyl-methoxypolyethyleneglycol 2000)-1,2-dimyristoyl-sn-glycero-3-phosphoethanolamine (DMPE-PEG 2,000). In some variations of DSPE-PEG$_n$ where n is 350, 500, 750, 1000 or 2000, the PEG-lipid is N-(Carbonyl-methoxypolyethyleneglycol 2000)-1,2-distearoyl-sn-glycero-3-phosphoethanolamine (DSPE-PEG 2,000). In certain embodiments, a lipid nanoparticle includes a combination or two or more PEG-lipids (e.g., two or more PEG-lipids as above).

In some embodiments of a method as above, at least one of the lipid nanoparticle and membrane-destabilizing polymer includes a first targeting ligand that specifically binds to a molecule on the surface of the target cell. The membrane-destabilizing polymer, the lipid nanoparticle, or both the membrane-destabilizing polymer and lipid nanoparticle may include the first targeting ligand. In some embodiments, one of the lipid nanoparticle and membrane-destabilizing polymer includes the first targeting ligand, and the other of the lipid nanoparticle and membrane-destabilizing polymer includes a second targeting ligand that is different from the first targeting ligand and either (i) specifically binds to the same cell surface molecule recognized by the first targeting ligand or (ii) specifically binds to a different cell surface molecule on the surface of the target cell. In particular variations, either the first targeting ligand, the second targeting ligand, or both the first and second targeting ligands specifically bind(s) to a cell surface molecule selected from transferrin receptor type 1, transferrin receptor type 2, the EGF receptor, HER2/Neu, a VEGF receptor, a PDGF receptor, an integrin, an NGF receptor, CD2, CD3, CD4, CD8, CD19, CD20, CD22, CD33, CD43, CD38, CD56, CD69, the asialoglycoprotein receptor (ASGPR), prostate-specific membrane antigen (PSMA), a folate receptor, and a sigma receptor.

In certain embodiments of a method as above in which at least one of the lipid nanoparticle and membrane-destabilizing polymer includes a first targeting ligand (and the other of the lipid nanoparticle and membrane-destabilizing polymer optionally includes a second targeting ligand), the first and/or second targeting ligand includes a small molecule targeting moiety. In specific variations, the small molecule targeting moiety is a sugar (e.g., lactose, galactose, N-acetyl galactosamine (NAG, also referred to as GalNAc), mannose, and mannose-6-phosphate (M6P)), a vitamin (e.g., folate), a bisphosphonate, or an analogue thereof. In other embodiments, the first and/or second targeting ligand is a protein such as, e.g., an antibody, a peptide aptamer, or a protein derived from a natural ligand of the cell surface molecule. In yet other embodiments, the first and/or second targeting ligand is a peptide such as, e.g., an integrin-binding peptide, a LOX-1-binding peptide, and epidermal growth factor (EGF) peptide, a neurotensin peptide, an NL4 peptide, or a YIGSR laminin peptide.

In certain embodiments of a method as above, target cell is selected from a secretory cell, a chondrocyte, an epithelial cell, a nerve cell, a muscle cell, a blood cell, an endothelial cell, a pericyte, a fibroblast, a glial cell, and a dendritic cell. Other suitable target cells include cancer cells, immune cells, bacterially-infected cells, virally-infected cells, or cells having an abnormal metabolic activity.

In a particular variation where the target cell is a secretory cell, the target secretory cell is a hepatocyte. In some such embodiments, at least one of the lipid nanoparticle and membrane-destabilizing polymer includes a first targeting ligand that specifically binds to a molecule on the surface of the hepatocyte. In certain embodiments, the first targeting ligand specifically binds to the asialoglycoprotein receptor (ASGPR); for example, in particular variations, the first targeting ligand includes an N-acetylgalactosamine (NAG) residue. In some embodiments as above comprising a first targeting ligand that binds to a molecule on the surface of hepatocytes, both the lipid nanoparticle and the membrane-destabilizing polymer include the first targeting ligand. In other embodiments one of the lipid nanoparticle and membrane-destabilizing polymer includes the first targeting ligand, and the other of the lipid nanoparticle and membrane destabilizing polymer includes a second targeting ligand that is different from the first targeting ligand and either (i) specifically binds to the asialoglycoprotein receptor (ASGPR) or (ii) specifically binds to a different cell surface molecule on the surface of the hepatocyte; in some such embodiments, the second targeting ligand includes an N-acetylgalactosamine (NAG) residue.

In some embodiments of a method as above, the membrane-destabilizing polymer is a copolymer, a synthetic peptide, a membrane-destabilizing toxin or derivative thereof, or a viral fusogenic peptide or derivative thereof. In a particular variation, the membrane-destabilizing polymer is a pH-sensitive polymer such as, e.g., a pH-sensitive copolymer. The copolymer may be a block copolymer such as, for example, a diblock copolymer. In some variations, the block copolymer includes a hydrophobic, membrane-destabilizing block and a hydrophilic block. In some such embodiments, the hydrophilic block is polymerized from both hydrophilic monomers and hydrophobic monomers such that there are more hydrophilic monomeric residues than hydrophobic monomeric residues in the hydrophilic block. The hydrophilic block may be cleavably linked to the hydrophobic block, such as through a disulfide bond or a pH-sensitive bond. In some embodiments, the hydrophilic block includes monomeric residues linked to a pendant shielding moiety such as, e.g., a polyethylene glycol (PEG) moiety. The shielding moiety may be cleavably linked to the hydrophilic block, such as through a disulfide bond or a pH-sensitive bond. Particularly suitable pH-sensitive bonds (for linkage of the hydrophilic and hydrophobic blocks or linkage of the shielding moiety to the hydrophilic block) include hydrazone, acetal, ketal, imine, orthoester, carbonate, and maleamic acid linkages.

The pH-sensitive polymer may include monomeric residues having a carboxylic acid functional group, monomeric residues having an amine functional group, and/or monomeric residues having a hydrophobic functional group. In some variations, the pH-sensitive polymer includes monomeric residues derived from polymerization of a ($C_2$-$C_8$) alkylacrylic acid (e.g., propylacrylic acid); monomeric residues derived from polymerization of a ($C_2$-$C_8$) alkyl-ethacrylate, a ($C_2$-$C_8$) alkyl-methacrylate, or a ($C_2$-$C_8$) alkyl-acrylate; and/or monomeric residues derived from polymerization of (N,N-di($C_1$-$C_6$)alkyl-amino($C_1$-$C_6$)alkyl-ethacrylate, (N,N-di($C_1$-$C_6$)alkyl-amino($C_1$-$C_6$)alkyl-methacrylate, or (N,N-di($C_1$-$C_6$)alkyl-amino($C_1$-$C_6$)alkyl-acrylate. In a specific variation, the pH-sensitive polymer includes a random copolymer chain having monomeric residues derived from polymerization of propyl acrylic acid, N,N-dimethylaminoethylmethacrylate, and butyl methacrylate; in some such embodiments, the pH-sensitive polymer is a block copolymer comprising the random copolymer chain as a membrane disrupting polymer block, and further including one or more additional blocks.

In certain embodiments, the pH-sensitive membrane-destabilizing polymer is a diblock copolymer having a hydrophilic random copolymer block and a hydrophobic random copolymer block, where (i) the hydrophilic block is an amphiphilic block comprising both hydrophilic monomeric residues and hydrophobic monomeric residues, where the number of hydrophilic monomeric residues in the hydrophilic block is greater than the number of hydrophobic monomeric residues, (ii) the hydrophobic block is an amphiphilic, membrane-destabilizing block comprising both hydrophobic monomeric residues and hydrophilic monomeric residues and having an overall hydrophobic character at a pH of about 7.4; and (iii) each of the hydrophilic monomeric residues of the hydrophilic and hydrophobic blocks is independently selected from the group consisting of monomeric residues that are ionic at a pH of about 7.4, monomeric residues that are neutral at a pH of about 7.4, and monomeric residues that are zwitterionic at a pH of about 7.4.

In yet other variations, the pH-sensitive polymer is covalently linked to a membrane-destabilizing peptide. In some such embodiments, the pH-sensitive polymer includes a plurality of pendant linking groups, and a plurality of membrane-destabilizing peptides are linked to the pH-sensitive polymer via the plurality of pendant linking groups.

In some embodiments, the pH-sensitive polymer includes a random block copolymer of formula I:

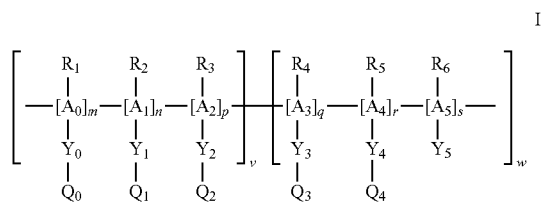

I where $A_0$, $A_1$, $A_2$, $A_3$, $A_4$ and $A_5$ are each independently selected from the group consisting of —C—C—, —C(O)(C)$_a$C(O)O—, —O(C)$_a$C(O)—, —O(C)$_b$—, and —CR$_8$—CR$_9$; where tetravalent carbon atoms of $A_0$-$A_5$ that are not fully substituted with $R_1$-$R_6$ and $Y_0$-$Y_5$ are completed with an appropriate number of hydrogen atoms; wherein a and b are each independently 1-4; and where $R_8$ and $R_9$ are each independently selected from the group consisting of —C(O)OH, —C(O)Oalkyl, and —C(O)NR$_{10}$, where $R_8$ and $R_9$ are optionally covalently linked together to form a ring structure (e.g., a cyclic anhydride or cyclic imide);

$Y_5$ is hydrogen or is selected from the group consisting of -(1C-10C)alkyl, -(3C-6C)cycloalkyl, —O-(1C-10C)alkyl, —C(O)O(1C-10C)alkyl, —C(O)NR$_{11}$(1C-10C)alkyl, and -(6C-10C)aryl, any of which is optionally substituted with one or more fluorine atoms;

$Y_0$, $Y_3$, and $Y_4$ are each independently selected from the group consisting of a covalent bond, -(1C-10C)alkyl-, —C(O)O(2C-10C)alkyl-, —OC(O)(1C-10C)alkyl-, —O(2C-10C)alkyl-, —S(2C-10C)alkyl-, and —C(O)NR$_{12}$(2C-10C)alkyl-;

$Y_1$ and $Y_2$ are each independently selected from the group consisting of a covalent bond, -(1C-18C)alkyl-, -(3C-18C)branched alkyl, —C(O)O(2C-18C)alkyl-, —C(O)O(2C-18C)branched alkyl, —OC(O)(1C-18C)alkyl-, —OC(O)(1C-18C)branched alkyl-, —O(2C-18C)alkyl-, —O(2C-18C)branched alkyl-, —S(2C-18C)alkyl-, —S(2C-18C)branched alkyl-, —C(O)NR$_{12}$(2C-18C)alkyl-, and —C(O)NR$_{12}$(2C-18C)branched alkyl-, where any alkyl or branched alkyl group of $Y_1$ or $Y_2$ is optionally substituted with one or more fluorine atoms;

$R_1$, $R_2$, $R_3$, $R_4$, $R_5$, $R_6$, $R_8$, $R_9$, $R_{10}$, $R_{11}$, and $R_{12}$ are each independently hydrogen, —CN, or selected from the group consisting of alkyl, alkynyl, heteroalkyl, cycloalkyl, heterocycloalkyl, aryl and heteroaryl, any of which is optionally substituted with one or more fluorine atoms;

$Q_0$ is a residue selected from the group consisting of residues which are hydrophilic at physiologic pH; O—[(C)$_{2-3}$—O]$_x$—R$_7$; and O—[(C)$_{2-3}$—O]$_x$—C(O)—NR$_{13}$R$_{14}$; where x is 1-48; $R_7$ is —CH$_3$ or —CO$_2$H; and $R_{13}$ and $R_{14}$ are each independently hydrogen, —CN, or selected from the group consisting of alkyl, alkynyl, heteroalkyl, cycloalkyl, heterocycloalkyl, aryl and heteroaryl, any of which is optionally substituted with one or more fluorine atoms;

$Q_1$ and $Q_2$ are each independently absent or selected from a residue which is hydrophilic at normal physiological pH; a conjugatable or functionalizable residue; a residue which is hydrophobic at normal physiological pH; an alkyl group optionally substituted with one or more fluorine atoms; and a branched alkyl group optionally substituted with one or more fluorine atoms;

$Q_3$ is a residue which is positively charged at normal physiological pH;

$Q_4$ is a residue which is negatively charged at normal physiological pH, but undergoes protonation at lower pH;

m is a mole fraction of greater than 0 to 1.0;

n is a mole fraction of 0 to less than 1.0;

p is a mole fraction of 0 to less than 1.0; wherein m+n+p=1;

q is a mole fraction of 0.1 to 0.9;

r is a mole fraction of 0.05 to 0.9;

s is present up to a mole fraction of 0.85; wherein q+r+s=1;
v is from 1 to 25 kDa; and
w is from 1 to 50 kDa.

In some embodiments comprising a pH-sensitive polymer of formula I as above, m is greater than n+p. In some such variations, p is 0.

In some embodiments comprising a pH-sensitive polymer of formula I as above, n is greater than 0. In some such variations, at least one of $Y_1$ and $Q_1$ contains the alkyl or branched alkyl group substituted with the one or more fluorine atoms. In more particular variations, p is 0 and/or m is greater than n.

In certain embodiments comprising a pH-sensitive polymer of formula I, the pH-sensitive polymer is a polymer of formula II:

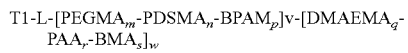

where
PEGMA is polyethyleneglycol methacrylate residue with 2-20 ethylene glycol units;
PDSMA is pyridyl disulfide methacrylate residue;
BPAM is 2-[2-Boc amino ethoxy]ethyl methacrylate residue;
BMA is butyl methacrylate residue;
PAA is propyl acrylic acid residue;
DMAEMA is dimethylaminoethyl methacrylate residue;
m is a mole fraction of 0.6 to 1;
n is a mole fraction of 0 to 0.4 (e.g., 0 to 0.2);
p is a mole fraction of 0 to 0.4 (e.g., 0 to 0.2);
m+n+p=1;
q is a mole fraction of 0.2 to 0.75;
r is a mole fraction of 0.05 to 0.6;
s is a mole fraction of 0.2 to 0.75;
q+r+s=1;
v is 1 to 25 kDa;
w is 1 to 25 kDa;
T1 is absent or is the first targeting ligand; and
L is absent or is a linking moiety.

In other embodiments comprising a pH-sensitive polymer of formula I, the pH-sensitive polymer is a polymer of formula V:

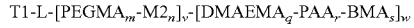

where
PEGMA is polyethyleneglycol methacrylate residue with 2-20 ethylene glycol units;
M2 is a methacrylate residue selected from the group consisting of
  a (C4-C18)alkyl-methacrylate residue;
  a (C4-C18)branched alkyl-methacrylate residue;
  a cholesteryl methacrylate residue;
  a (C4-C18)alkyl-methacrylate residue substituted with one or more fluorine atoms; and
  a (C4-C18)branched alkyl-methacrylate residue substituted with one or more fluorine atoms;
BMA is butyl methacrylate residue;
PAA is propyl acrylic acid residue;
DMAEMA is dimethylaminoethyl methacrylate residue;
m and n are each a mole fraction greater than 0, wherein m is greater than n and m+n=1;
q is a mole fraction of 0.2 to 0.75;
r is a mole fraction of 0.05 to 0.6;
s is a mole fraction of 0.2 to 0.75;
q+r+s=1;
v is 1 to 25 kDa;
w is 1 to 25 kDa;
T1 is absent or is the first targeting ligand; and
L is absent or is a linking moiety.

In some specific embodiments of a polymer of formula V, M2 is selected from 2,2,3,3,4,4,4-heptafluorobutyl methacrylate residue; 3,3,4,4,5,6,6,6-octafluoro-5-(trifluoromethyl)hexyl methacrylate residue; 2,2,3,3,4,4,5,5,6,6,7,7,8,8,8-pentadecafluorooctyl 2-methylacrylate residue; 3,3,4,4,5,5,6,6,6-nonafluorohexyl methacrylate residue (also referred to as 2-propenoic acid, 2-methyl-, 3,3,4,4,5,5,6,6,6-nonafluorohexyl ester residue); 3,3,4,4,5,5,6,6,7,7,8,8,8-tridecafluorooctyl methacrylate residue; 1,1,1-trifluoro-2-(trifluoromethyl)-2-hydroxy-4-methyl-5-pentyl methacrylate residue; 2-[(1',1',1'-trifluoro-2'-(trifluoromethyl)-2'-hydroxy)propyl]-3-norbornyl methacrylate residue; 2-ethylhexyl methacrylate residue; butyl methacrylate residue; hexyl methacrylate residue; octyl methacrylate residue; n-decyl methacrylate residue; lauryl methacrylate residue; myristyl methacrylate residue; stearyl methacrylate residue; cholesteryl methacrylate residue; ethylene glycol phenyl ether methacrylate residue; 2-propenoic acid, 2-methyl-, 2-phenylethyl ester residue; 2-propenoic acid, 2-methyl-, 2-[[(1,1-dimethylethoxy)carbonyl]amino]ethyl ester residue; 2-propenoic acid, 2-methyl-, 2-(1H-imidazol-1-yl)ethyl ester residue; 2-propenoic acid, 2-methyl-, cyclohexyl ester residue; 2-propenoic acid, 2-methyl-, 2-[bis(1-methylethyl)amino]ethyl ester residue; 2-propenoic acid, 2-methyl-, 3-methylbutyl ester residue; neopentyl methacrylate residue; tert-butyl methacrylate residue; 3,3,5-trimethyl cyclohexyl methacrylate residue; 2-hydroxypropyl methacrylate residue; 5-nonyl methacrylate residue; 2-butyl-1-octyl methacrylate residue; 2-hexyl-1-decyl methacrylate residue; and 2-(tert-butyl amino)ethyl methacrylate residue.

In particular variations of a method as above comprising a pH-sensitive polymer of formula II or formula V, PEGMA has 4-5 ethylene glycol units or 7-8 ethylene glycol units; T1 and L are present and T1 includes an N-acetylgalactosamine (NAG) residue; and/or L includes a polyethylene glycol (PEG) moiety having 2-20 ethylene glycol units.

In certain embodiments, the lipid nanoparticle includes the therapeutic agent. The therapeutic agent may be an anti-cancer agent, an anti-viral agent, an immunomodulatory agent, an anti-inflammatory agent, or an agent that modulates a cellular metabolic activity. Suitable therapeutic agents may be selected from polynucleotides, proteins, peptides, and small molecules.

In some embodiments, the therapeutic agent is a polynucleotide. In some such variations, the lipid nanoparticle has an N:P (nitrogen to phosphate) ratio of about 1 to about 30. In certain embodiments, the polynucleotide is an mRNA, such as, for example, an mRNA encoding a functional protein associated with a protein deficiency disease. In particular variations, the target cell is a hepatocyte and the mRNA encodes a protein selected from the group consisting of alpha-1-antitrypsin (A1AT), carbamoyl phosphate synthetase I (CPS1), fumarylacetoacetase (FAH) enzyme, alanine:glyoxylate-aminotransferase (AGT), methylmalonyl CoA mutase (MUT), propionyl CoA carboxylase alpha subunit (PCCA), propionyl CoA carboxylase beta subunit (PCCB), a subunit of branched-chain ketoacid dehydrogenase (BCKDH), ornithine transcarbamylase (OTC), copper-transporting ATPase Atp7B, bilirubin uridinediphosphate glucuronyltransferase (BGT) enzyme, hepcidin, glucose-6-phosphatase (G6Pase), glucose 6-phosphate translocase, lysosomal glucocerebrosidase (GB), Niemann-Pick C1 protein (NPC1), Niemann-Pick C2 protein (NPC2), acid sphingomyelinase (ASM), Factor IX, galactose-1-phosphate uridylyltransferase, galactokinase, UDP-galactose 4-epimerase, transthyretin, a complement regulatory protein, phenylalanine hydroxylase (PAH), homogentisate 1,2-dioxygenase, porphobilinogen deaminase, hypoxanthine-guanine phosphoribosyltransferase (HGPRT), argininosuccinate lyase (ASL), argininosuccinate synthetase (ASS1), P-type ATPase protein FIC-1, alpha-galactosidase A, acid ceramidase, acid α-L-fucosidase, acid f-galactosidase, iduronate-2-sulfatase, alpha-L-iduronidase, galactocerebrosidase, acid α-mannosidase, β-mannosidase, arylsulfatase B, arylsulfatase A, N-acetylgalactosamine-6-sulfate sulfatase, acid f-galactosidase, acid α-glucosidase, β-hexosaminidase B, heparan-N-sulfatase, alpha-N-acetylglucosaminidase, acetyl-CoA:α-glucosaminide N-acetyltransferase, N-acetylglucosamine-6-sulfate sulfatase, alpha-N-acetylgalactosaminidase, sialidase, β-glucuronidase, β-hexosaminidase A. In some embodiments, the polynucleotide is a DNA, such as, for example, a DNA encoding a functional protein associated with a protein deficiency disease (e.g., a protein selected from the proteins listed above).

In certain embodiments, the therapeutic agent is an mRNA encoding a secreted protein. Suitable secreted proteins include hormones, cytokines, growth factors, clotting factors, anti-protease proteins, angiogenic proteins, antiangiogenic proteins, chemokines, and antibodies. In particular variations, the secreted protein is selected from erythropoietin (EPO), thrombopoietin (TPO), granulocyte-colony stimulating factor (G-CSF), granulocyte macrophage-colony stimulating factor, (GM-CSF), leptin, a platelet-derived growth factor (e.g., platelet-derived growth factor B (PDGF-B)), keratinocyte growth factor (KGF), bone morphogenic protein 2 (BMP-2), bone morphogenic protein 7 (BMP-7), insulin, glucagon-like peptide-1 (GLP-1), human growth hormone (HGF), Factor VII, Factor VIII, Factor IX, a relaxin (e.g., relaxin-2), an interferon (e.g., interferon-α (IFN-α), interferon-f (IFN-f), interferon-γ (IFN-γ)), interleukin-2 (IL-2), interleukin-4 (IL-4), interleukin-10 (IL-10), interleukin-11 (IL-11), interleukin-12 (IL-12), interleukin-18 (IL-18), interleukin-21 (IL-21), a CC subfamily chemokine, a CXC subfamily chemokine, a C subfamily chemokine, and a CX3C subfamily chemokine. In some embodiments where the secreted protein is an antibody, the antibody is a genetically engineered antibody selected from a chimeric antibody, a humanized antibody, a single-chain antibody (e.g., a single-chain Fv (scFv)), and a bispecific antibody.

In other embodiments where the therapeutic agent is a polynucleotide, the polynucleotide is an oligonucleotide. Suitable oligonucleotide therapeutic agents include siRNAs, antisense oligonucleotides, anti-miRs (also known as antagomiRs), locked nucleic acid (LNA)-based oligonucleotides, dicer substrates, miRNAs, aiRNAs, shRNAs, ribozymes, and nucleic acid aptamers.

In certain embodiments, the therapeutic agent is a protein, such as, e.g., an antibody or a peptide aptamer. Particular variations of antibody therapeutic agents include single chain antibodies and a bispecific antibodies.

In some embodiments, the therapeutic agent is a peptide. Exemplary peptide therapeutic agents include peptide vaccines comprising one or more short or long amino acid sequences from disease-associated antigens (e.g., tumor antigens).

In other embodiments, the therapeutic agent is a small molecule. In specific variations, the small molecule is selected from an anti-tubulin agent, a DNA minor groove binding agent, and a DNA replication inhibitor. In other variations, the small molecule is selected from an anthracycline, an auristatin, a camptothecin, a duocarmycin, an etoposide, a maytansinoid, a vinca alkaloid, and a platinum (II) compound.

In other embodiments, the therapeutic agent is a component of a gene editing system that disrupts or corrects a gene associated with a disease. In some embodiments, the component of the gene editing system is a polynucleotide (e.g., an mRNA) encoding a nuclease. Particularly suitable nucleases include zinc finger nucleases (ZFNs), transcription activator-like effector nucleases (TALENs), CRISPR-associated protein 9 (Cas9), and engineered meganucleases. In particular variations in which the nuclease is Cas9, the lipid nanoparticle further includes a guide RNA that targets the nuclease to a specific site in the target cell genome. In some variations directed to gene editing as above, the lipid nanoparticle further includes a polynucleotide containing a DNA donor sequence for correcting a disease-associated gene by homologous recombination. In other variations, the method further includes administering to the subject an effective amount of a second lipid nanoparticle that includes a polynucleotide containing a DNA donor sequence for correcting a disease-associated gene by homologous recombination.

In some embodiments, the therapeutic agent is an immunogen. Suitable immunogens include peptides, proteins, mRNAs, short RNAs, DNAs, and simple or complex carbohydrates. In certain variations, the immunogen is derived from an infectious agent (e.g., a virus or bacteria) or a cancer cell. In some such embodiments, the membrane destabilizing polymer is also associated with an immunogen, which may be the same or different than the immunogen of the lipid nanoparticle.

In certain embodiments of a method as above where the therapeutic agent is a polynucleotide, the lipid nanoparticle includes a mixture of lipid components comprising (i) a cationic lipid that is permanently charged at physiological pH, where the cationic lipid is present in the mixture from about 35 mole % to about 55 mole %; (ii) an ionizable anionic lipid, where the anionic lipid is optionally absent and, if present, is present in the mixture from about 25 mole % to about 40 mole %; (iii) a helper lipid, where if the ionizable anionic lipid is absent, then the helper lipid is present in the mixture from about 40 mole % to about 50 mole %, and if the ionizable anionic lipid is present, then the helper lipid is present in the mixture from about 5 mole % to about 20 mole %; and (iv) a PEG-lipid, where the PEG-lipid is present in the mixture from about 2 mole % to about 15 mole %. In some such embodiments, the cationic lipid is DOTAP, the ionizable anionic lipid is CHEMS, the helper lipid is CHOL, and/or the PEG-lipid is DSPE-PEG2k or DMPE-PEG2k. In some variations of a method comprising a lipid nanoparticle as above, the ionizable anionic lipid is absent, the cationic lipid is present from about 35 mole % to about 45 mole %, and the PEG-lipid is present from about 5% mole % to about 15 mole %. In other variations, the ionizable anionic lipid is present, and the cationic lipid is present from about 40 mole % to about 55 mole %; in some such variations, the PEG-lipid is present from about 5 mole % to about 15 mole %. In more specific embodiments, (a) the cationic lipid is DOTAP, the ionizable anionic lipid is absent, the helper lipid is CHOL, the PEG-lipid is DSPE-PEG2k, and the molar ratio of DOTAP:CHOL:DSPE-PEG2k is about 40:50:10; (b) the cationic lipid is DOTAP, the ionizable anionic lipid is CHEMS, the helper lipid is CHOL, the PEG-lipid is DMPE-PEG2k, and the molar ratio of DOTAP:CHEMS:CHOL:DMPE-PEG2k is about 50:32:16:2; (c) the cationic lipid is DOTAP, the ionizable anionic lipid is CHEMS, the helper lipid is CHOL, the PEG-lipid is DSPE-PEG2k, and the molar ratio of DOTAP:CHEMS:CHOL:DSPE-PEG2k is about 50:32:8:10; or (d) the cationic lipid is DOTAP, the ionizable anionic lipid is CHEMS, the helper lipid is CHOL, the PEG-lipid is DMPE-PEG2k, and the molar ratio of DOTAP:CHEMS:CHOL:DMPE-PEG2k is about 50:32:8:10.

In another aspect, the present invention provides a composition for delivering a therapeutic or diagnostic agent to the cytosol of a target cell within a subject. The composition generally includes (a) a lipid nanoparticle comprising the therapeutic or diagnostic agent and (b) a membrane-destabilizing polymer. In some embodiments, at least one of the lipid nanoparticle and membrane-destabilizing polymer includes a first targeting ligand that specifically binds to a molecule on the surface of the target cell. The lipid nanoparticle, membrane-destabilizing polymer, therapeutic agent, and/or targeting ligand(s) of the composition include the various embodiments described above with respect to a method for delivering a therapeutic or diagnostic agent to a cell.

In yet another aspect, the present invention provides a delivery system for delivering a therapeutic or diagnostic agent to the cytosol of a target cell within a subject. The system generally includes (a) a carrier composition comprising a lipid nanoparticle, wherein the lipid nanoparticle comprises the therapeutic or diagnostic agent, and (b) an enhancer composition comprising a membrane-destabilizing polymer. In some embodiments, at least one of the lipid nanoparticle and membrane-destabilizing polymer includes a first targeting ligand that specifically binds to a molecule on the surface of the target cell. The lipid nanoparticle, membrane-destabilizing polymer, therapeutic agent, and/or targeting ligand(s) of the composition include the various embodiments described above with respect to a method for delivering a therapeutic or diagnostic agent to a cell.

In still another aspect, the present invention provides a method for treating a disease characterized by a genetic defect that results in a deficiency of a functional protein. The method generally includes administering to a subject having the disease (a) an effective amount of a lipid nanoparticle comprising an mRNA that encodes the functional protein or a protein having the same biological activity as the functional protein and (b) an effective amount of a membrane-destabilizing polymer, where the mRNA is delivered to the cytosol of target cells of a target tissue associated with the disease, and where the mRNA is translated during protein synthesis so as to produce the encoded protein within the target tissue, thereby treating the disease. In some embodiments, at least one of the lipid nanoparticle and membrane-destabilizing polymer comprises a first targeting ligand that specifically binds to a molecule on the surface of the target cells of the target tissue. The lipid nanoparticle and membrane-destabilizing polymer can be administered separately (e.g., the membrane-destabilizing polymer administered after administration of the lipid nanoparticle) or, alternatively, together within a single composition. The lipid nanoparticle and membrane-destabilizing polymer include the various embodiments described above with respect to a method for delivering a therapeutic or diagnostic agent to a cell, provided that the therapeutic agent is the mRNA, the lipid nanoparticle includes a cationic lipid (e.g., an ionizable cationic lipid), and the targeting ligand, if present, is selected to bind to the target cells of the target tissue exhibiting the protein deficiency. In certain variations, the lipid nanoparticle and the membrane-destabilizing polymer are administered in a repeat dosage regime (e.g., a weekly or bi-weekly repeated administration protocol).

In certain embodiments, the disease is a protein deficiency disease of the liver. In some such embodiments, the mRNA encodes a functional protein selected from alpha-1-antitrypsin (A1AT), carbamoyl phosphate synthetase I (CPS1), fumarylacetoacetase (FAH) enzyme, alanine:glyoxylate-aminotransferase (AGT), methylmalonyl CoA mutase (MUT), propionyl CoA carboxylase alpha subunit (PCCA), propionyl CoA carboxylase beta subunit (PCCB), a subunit of branched-chain ketoacid dehydrogenase (BCKDH), ornithine transcarbamylase (OTC), copper-transporting ATPase Atp7B, bilirubin uridinediphosphate glucuronyltransferase (BGT) enzyme, hepcidin, glucose-6-phosphatase (G6Pase), glucose 6-phosphate translocase, lysosomal glucocerebrosidase (GB), Niemann-Pick C1 protein (NPC1), Niemann-Pick C2 protein (NPC2), acid sphingomyelinase (ASM), Factor IX, galactose-1-phosphate uridylyltransferase, galactokinase, UDP-galactose 4-epimerase, transthyretin, a complement regulatory protein, phenylalanine hydroxylase (PAH), homogentisate 1,2-dioxygenase, porphobilinogen deaminase, hypoxanthine-guanine phosphoribosyltransferase (HGPRT), argininosuccinate lyase (ASL), argininosuccinate synthetase (ASS1), P-type ATPase protein FIC-1, alpha-galactosidase A, acid ceramidase, acid α-L-fucosidase, acid β-galactosidase, iduronate-2-sulfatase, alpha-L-iduronidase, galactocerebrosidase, acid α-mannosidase, β-mannosidase, arylsulfatase B, arylsulfatase A, N-acetylgalactosamine-6-sulfate sulfatase, acid β-galactosidase, acid α-glucosidase, β-hexosaminidase B, heparan-N-sulfatase, alpha-N-acetylglucosaminidase, acetyl-CoA:α-glucosaminide N-acetyltransferase, N-acetylglucosamine-6-sulfate sulfatase, alpha-N-acetylgalactosaminidase, sialidase, β-glucuronidase, and β-hexosaminidase A.

In other embodiments in which the disease is a protein deficiency disease of the liver, the disease is a urea cycle disorder. In some such embodiments, the urea cycle disorder is selected from ornithine transcarbamylase (OTC) deficiency, carbamoyl phosphate synthetase I (CPS1) deficiency, argininosuccinic aciduria (argininosuccinate lyase (ASL) deficiency), and citrullinemia (argininosuccinate synthetase (ASS1) deficiency). In certain variations where the urea cycle disorder is ornithine transcarbamylase (OTC) deficiency, the mRNA encodes a functional OTC protein comprising an amino acid sequence having at least 90% or at least 95% sequence identity with residues 35-354 of SEQ ID NO:1. In certain variations where the urea cycle disorder is argininosuccinic aciduria (argininosuccinate lyase (ASL) deficiency), the mRNA encodes a functional ASL protein comprising an amino acid sequence having at least 90% or at least 95% sequence identity with SEQ ID NO:48. In certain variations where the urea cycle disorder is citrullinemia (argininosuccinate synthetase (ASS1) deficiency), the mRNA encodes a functional ASS1 protein comprising an amino acid sequence having at least 90% or at least 95% sequence identity with SEQ ID NO:50.

In certain embodiments for treating a protein deficiency disease of the liver as above, at least one of the membrane-destabilizing polymer and the lipid nanoparticle comprises a targeting ligand that specifically binds to the asialoglycoprotein receptor (ASGPR). Particularly suitable ASGPR-specific targeting ligands comprise an N-acetylgalactosamine (NAG) residue.

In another aspect, the present invention provides a pH-sensitive, membrane-destabilizing polymer. In some embodiments, the pH-sensitive, membrane-destabilizing polymer comprises a random block copolymer of formula Ia:

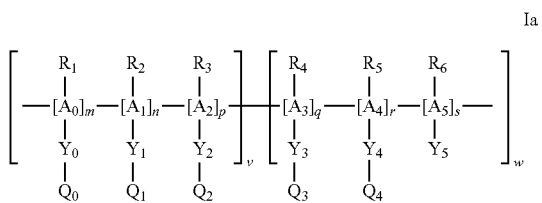

$$\left[\begin{array}{ccc} R_1 & R_2 & R_3 \\ | & | & | \\ -[A_0]_m-[A_1]_n-[A_2]_p- \\ | & | & | \\ Y_0 & Y_1 & Y_2 \\ | & | & | \\ Q_0 & Q_1 & Q_2 \end{array}\right]_v \left[\begin{array}{ccc} R_4 & R_5 & R_6 \\ | & | & | \\ -[A_3]_q-[A_4]_r-[A_5]_s- \\ | & | & | \\ Y_3 & Y_4 & Y_5 \\ | & | & | \\ Q_3 & Q_4 \end{array}\right]_w \quad \text{Ia}$$

wherein $A_0$, $A_1$, $A_2$, $A_3$, $A_4$ and $A_5$ are each independently selected from the group consisting of —C—C—, —C(O)(C)$_a$C(O)O—, —O(C)$_a$C(O)—, —O(C)$_b$—, and —CR$_8$—CR$_9$—; where tetravalent carbon atoms of $A_0$-$A_5$ that are not fully substituted with $R_1$-$R_6$ and $Y_0$-$Y_5$ are completed with an appropriate number of hydrogen atoms; wherein a and b are each independently 1-4; and where $R_8$ and $R_9$ are each independently selected from the group consisting of —C(O)OH, —C(O)Oalkyl, and —C(O)NR$_{10}$, where $R_8$ and $R_9$ are optionally covalently linked together to form a ring structure;

$Y_5$ is hydrogen or is selected from the group consisting of -(1C-10C)alkyl, -(3C-6C)cycloalkyl, —O-(1C-10C)alkyl, —C(O)O(1C-10C)alkyl, —C(O)NR$_{11}$(1C-10C)alkyl, and -(6C-10C)aryl, any of which is optionally substituted with one or more fluorine atoms;

$Y_0$, $Y_3$, and $Y_4$ are each independently selected from the group consisting of a covalent bond, -(1C-10C)alkyl-, —C(O)O(2C-10C)alkyl-, —OC(O)(1C-10C)alkyl-, —O(2C-10C)alkyl-, —S(2C-10C)alkyl-, and —C(O)NR$_{12}$(2C-10C) alkyl-;

$Y_1$ and $Y_2$ are each independently selected from the group consisting of a covalent bond, -(1C-18C)alkyl-, -(3C-18C)branched alkyl, —C(O)O(2C-18C)alkyl-, —C(O)O(2C-18C)branched alkyl, —OC(O)(1C-18C)alkyl-, —OC(O)(1C-18C)branched alkyl-, —O(2C-18C)alkyl-, —O(2C-18C)branched alkyl-, —S(2C-18C)alkyl-, —S(2C-18C)branched alkyl-, —C(O)NR$_{12}$(2C-18C)alkyl-, and —C(O)NR$_{12}$(2C-18C)branched alkyl-, where any alkyl or branched alkyl group of $Y_1$ or $Y_2$ is optionally substituted with one or more fluorine atoms;

$R_1$, $R_2$, $R_3$, $R_4$, $R_5$, $R_6$, $R_8$, $R_9$, $R_{10}$, $R_{11}$, and $R_{12}$ are each independently hydrogen, —CN, or selected from the group consisting of alkyl, alkynyl, heteroalkyl, cycloalkyl, heterocycloalkyl, aryl and heteroaryl, any of which is optionally substituted with one or more fluorine atoms;

$Q_0$ is a residue selected from the group consisting of residues which are hydrophilic at physiologic pH; O—[(C)$_{2-3}$—O]$_x$—R$_7$; and O—[(C)$_{2-3}$—O]$_x$—C(O)—NR$_{13}$R$_{14}$; where x is 1-48; R$_7$ is —CH$_3$ or —CO$_2$H; and R$_{13}$ and R$_{14}$ are each independently hydrogen, —CN, or selected from the group consisting of alkyl, alkynyl, heteroalkyl, cycloalkyl, heterocycloalkyl, aryl and heteroaryl, any of which is optionally substituted with one or more fluorine atoms;

$Q_1$ and $Q_2$ are each independently absent or selected from a residue which is hydrophilic at normal physiological pH; a conjugatable or functionalizable residue; a residue which is hydrophobic at normal physiological pH; an alkyl group optionally substituted with one or more fluorine atoms; and a branched alkyl group optionally substituted with one or more fluorine atoms;

$Q_3$ is a residue which is positively charged at normal physiological pH;

$Q_4$ is a residue which is negatively charged at normal physiological pH, but undergoes protonation at lower pH;

m is a mole fraction of greater than 0.5 to less than 1.0;
n is a mole fraction of greater than 0 to less than 0.5;
p is a mole fraction of 0 to less than 0.5; wherein m+n+p=1;
q is a mole fraction of 0.1 to 0.9;
r is a mole fraction of 0.05 to 0.9;
s is present up to a mole fraction of 0.85; wherein q+r+s=1;
v is from 1 to 25 kDa;
w is from 1 to 50 kDa; and
at least one of $Y_1$ and $Q_1$ contains the alkyl or branched alkyl group substituted with the one or more fluorine atoms.

In some embodiments of a pH-sensitive polymer comprising a copolymer of formula Ia as above, p is 0.

In some embodiments of a pH-sensitive polymer comprising a copolymer of formula Ia as above, $R_2$-$A_1$-$Y_1$-$Q_1$ taken together is a methacrylate residue selected from the group consisting of 2,2,3,3,4,4,4-heptafluorobutyl methacrylate residue; 3,3,4,4,5,6,6,6-octafluoro-5(trifluoromethyl)hexyl methacrylate residue; 2,2,3,3,4,4,5,5,6,6,7,7,8,8,8-pentadecafluorooctyl 2-methylacrylate residue; 3,3,4,4,5,5,6,6,6-nonafluorohexyl methacrylate residue (also referred to as 2-propenoic acid, 2-methyl-, 3,3,4,4,5,5,6,6,6-nonafluorohexyl ester residue); 3,3,4,4,5,5,6,6,7,7,8,8,8-tridecafluorooctyl methacrylate residue; 1,1,1-trifluoro-2-(trifluoromethyl)-2-hydroxy-4-methyl-5-pentyl methacrylate residue; and 2-[(1',1',1'-trifluoro-2'-(trifluoromethyl)-2'-hydroxy)propyl]-3-norbornyl methacrylate residue.

In some embodiments of a pH-sensitive polymer comprising a copolymer of formula Ia as above,
(a) $Y_3$ is —C(O)OCH$_2$CH$_2$, $Q_3$ is dimethylamino, and/or $R_4$ is —CH$_3$;
(b) $Y_4$ is a covalent bond, $Q_4$ is a carboxyl residue, and/or $R_5$ is —CH$_2$CH$_2$CH$_3$;
(c) $Y_5$ is —C(O)O(CH$_2$)$_3$CH$_3$ and/or $R_6$ is —CH$_3$; and/or
(d) $Y_0$ is —C(O)O(2C-10C)alkyl-, $Q_0$ is O—[(C)$_{2-3}$—O]$_x$—R$_7$ (where x is 1-48 and R$_7$ is —CH$_3$), and/or $R_1$ is —CH$_3$.

In certain embodiments of a pH-sensitive polymer comprising a copolymer of formula Ia as above, the pH-sensitive polymer is a polymer of formula Va:

T1-L-[PEGMA$_m$-M2$_n$]$_v$-[DMAEMA$_q$-PAA$_r$-BMA$_s$]$_w$     Va where
PEGMA is polyethyleneglycol methacrylate residue with 2-20 ethylene glycol units;
M2 is a methacrylate residue selected from the group consisting of
  a (C4-C18)alkyl-methacrylate residue substituted with one or more fluorine atoms, and
  a (C4-C18)branched alkyl-methacrylate residue substituted with one or more fluorine atoms,
BMA is butyl methacrylate residue;
PAA is propyl acrylic acid residue;
DMAEMA is dimethylaminoethyl methacrylate residue;
m and n are each a mole fraction greater than 0, where m is greater than n and m+n=1;
q is a mole fraction of 0.2 to 0.75;
r is a mole fraction of 0.05 to 0.6;
s is a mole fraction of 0.2 to 0.75;
q+r+s=1;
v is 1 to 25 kDa;
w is 1 to 25 kDa;
T1 is absent or is the first targeting ligand; and
L is absent or is a linking moiety.

In certain variations of a pH-sensitive polymer of formula Va as above, M2 is a methacrylate residue selected from the group consisting of 2,2,3,3,4,4,4-heptafluorobutyl methacrylate residue; 3,3,4,4,5,6,6,6-octafluoro-5(trifluoromethyl)hexyl methacrylate residue; 2,2,3,3,4,4,5,5,6,6,7,7,8,8,8-pentadecafluorooctyl 2-methylacrylate residue; 3,3,4,4,5,5,6,6,6-nonafluorohexyl methacrylate residue; and 3,3,4,4,5,5,6,6,7,7,8,8,8-tridecafluorooctyl methacrylate residue; 1,1,1-trifluoro-2-(trifluoromethyl)-2-hydroxy-4-methyl-5-pentyl methacrylate residue; and 2-[(1',1',1'-trifluoro-2'-(trifluoromethyl)-2'-hydroxy)propyl]-3-norbornyl methacrylate residue.

In other embodiments, a pH-sensitive, membrane-destabilizing polymer is a polymer of formula V:

$$T1-L-[PEGMA_m-M2n]_v-[DMAEMA_q-PAA_r-BMA_s]_w \quad V$$

where
PEGMA is polyethyleneglycol methacrylate residue with 2-20 ethylene glycol units;
M2 is a methacrylate residue selected from the group consisting of
   a (C4-C18)alkyl-methacrylate residue;
   a (C4-C18)branched alkyl-methacrylate residue;
   a cholesteryl methacrylate residue;
   a (C4-C18)alkyl-methacrylate residue substituted with one or more fluorine atoms; and
   a (C4-C18)branched alkyl-methacrylate residue substituted with one or more fluorine atoms;
BMA is butyl methacrylate residue;
PAA is propyl acrylic acid residue;
DMAEMA is dimethylaminoethyl methacrylate residue;
m and n are each a mole fraction greater than 0, wherein m is greater than n and m+n=1;
q is a mole fraction of 0.2 to 0.75;
r is a mole fraction of 0.05 to 0.6;
s is a mole fraction of 0.2 to 0.75;
q+r+s=1;
v is 1 to 25 kDa;
w is 1 to 25 kDa;
T1 is absent or is the first targeting ligand; and
L is absent or is a linking moiety.

In certain variations of a pH-sensitive polymer of formula V as above, M2 is a methacrylate residue selected from the group consisting of 2,2,3,3,4,4,4-heptafluorobutyl methacrylate residue; 3,3,4,4,5,6,6,6-octafluoro-5(trifluoromethyl)hexyl methacrylate residue; 2,2,3,3,4,4,5,5,6,6,7,7,8,8,8-pentadecafluorooctyl 2-methylacrylate residue; 3,3,4,4,5,5,6,6,6-nonafluorohexyl methacrylate residue; 3,3,4,4,5,5,6,6,7,7,8,8,8-tridecafluorooctyl methacrylate residue; 1,1,1-trifluoro-2-(trifluoromethyl)-2-hydroxy-4-methyl-5-pentyl methacrylate residue; 2-[(1',1',1'-trifluoro-2'-(trifluoromethyl)-2'-hydroxy)propyl]-3-norbornyl methacrylate residue; 2-ethylhexyl methacrylate residue; butyl methacrylate residue; hexyl methacrylate residue; octyl methacrylate residue, n-decyl methacrylate residue; lauryl methacrylate residue; myristyl methacrylate residue; stearyl methacrylate residue; cholesteryl methacrylate residue; ethylene glycol phenyl ether methacrylate residue; 2-propenoic acid, 2-methyl-, 2-phenylethyl ester residue; 2-propenoic acid, 2-methyl-, 2-[[(1,1-dimethylethoxy)carbonyl]amino]ethyl ester residue; 2-propenoic acid, 2-methyl-, 2-(1H-imidazol-1-yl)ethyl ester residue; 2-propenoic acid, 2-methyl-, cyclohexyl ester residue; 2-propenoic acid, 2-methyl-, 2-[bis(1-methylethyl)amino]ethyl ester residue; 2-propenoic acid, 2-methyl-, 3-methylbutyl ester residue; neopentyl methacrylate residue; tert-butyl methacrylate residue; 3,3,5-trimethyl cyclohexyl methacrylate residue; 2-hydroxypropyl methacrylate residue; 5-nonyl methacrylate residue; 2-butyl-1-octyl methacrylate residue; 2-hexyl-1-decyl methacrylate residue; and 2-(tert-butyl amino)ethyl methacrylate residue.

In yet another aspect, the present invention provides a lipid nanoparticle. In some embodiments, the lipid nanoparticle comprises (a) a polynucleotide, and (b) a mixture of lipid components comprising (i) a cationic lipid that is permanently charged at physiological pH, where the cationic lipid is present in the mixture from about 35 mole % to about 55 mole %; (ii) an ionizable anionic lipid, where the anionic lipid is optionally absent and, if present, is present in the mixture from about 25 mole % to about 40 mole %; (iii) a helper lipid, where if the ionizable anionic lipid is absent, then the helper lipid is present in the mixture from about 40 mole % to about 50 mole %, and if the ionizable anionic lipid is present, then the helper lipid is present in the mixture from about 5 mole % to about 20 mole %; and (iv) a PEG-lipid, where the PEG-lipid is present in the mixture from about 5 mole % to about 15 mole %. In some such embodiments, the cationic lipid is DOTAP, the ionizable anionic lipid is CHEMS, the helper lipid is CHOL, and/or the PEG-lipid is DSPE-PEG2k or DMPE-PEG2k. In some variations of a lipid nanoparticle as above, the ionizable anionic lipid is absent and the cationic lipid is present from about 35 mole % to about 45 mole %. In other variations, the ionizable anionic lipid is present, and the cationic lipid is present from about 40 mole % to about 55 mole %. In more specific embodiments, (a) the cationic lipid is DOTAP, the ionizable anionic lipid is absent, the helper lipid is CHOL, the PEG-lipid is DSPE-PEG2k, and the molar ratio of DOTAP:CHOL:DSPE-PEG2k is about 40:50:10; (b) the cationic lipid is DOTAP, the ionizable anionic lipid is CHEMS, the helper lipid is CHOL, the PEG-lipid is DSPE-PEG2k, and the molar ratio of DOTAP:CHEMS:CHOL:DSPE-PEG2k is about 50:32:8:10; or (c) the cationic lipid is DOTAP, the ionizable anionic lipid is CHEMS, the helper lipid is CHOL, the PEG-lipid is DMPE-PEG2k, and the molar ratio of DOTAP:CHEMS:CHOL:DMPE-PEG2k is about 50:32:8:10. In certain embodiments of a lipid nanoparticle as above, the polynucleotide is an mRNA.

These and other aspects of the invention will become evident upon reference to the following detailed description of the invention.

DEFINITIONS

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

As used herein, the term "lipid nanoparticle" or "LNP" refers to a particle of less than about 1,000 nm, typically less than about 200 nm, that is formulated with at least one lipid molecular species. Lipid nanoparticles include (but are not limited to) liposomes, irrespective of their lamellarity, shape, or structure. As used herein, a "liposome" is a structure having lipid-containing membranes enclosing an aqueous interior. Liposomes may have one or more lipid membranes. Single-layered liposomes are referred to as "unilamellar," and multi-layered liposomes are referred to as "multilamellar." Lipid nanoparticles may further include one or more additional lipids and/or other components, which may be included in the liposome compositions for a variety of purposes, such as to stabilize a lipid membrane, to prevent lipid oxidation, or to attach ligands on the liposome surface. Any number of lipids may be present, including amphipathic, neutral, cationic, and anionic lipids. Lipid nanoparticles can be complexed with therapeutic or diagnostic agents, including polynucleotides, proteins, peptides, or small molecules, and are useful as in vivo delivery vehicles.

The term "cationic lipid" refers to any of a number of lipid species which carry a net positive charge at physiological pH. Such lipids include, but are not limited to, DODAC, DOTMA, DOTAP, DC-Chol, DMRIE, DOEPC, DLEPC, DMEPC, 14:1, MVL5, DOGS, DORIE, DORI, and DILA$^2$.

The term "neutral lipid" refers to any of a number of lipid species that exist either in an uncharged or neutral zwitterionic form at physiological pH. Such lipids include, for example cholesterol, DOPE, DLPE, DLPC, phosphatidylcholines, phosphatidylethanolamines, phosphatidylserines, ceramide, sphingomyelin, cephalin, and cerebrosides.

The term "non-cationic lipid" refers to any neutral lipid as described above as well as anionic lipids (i.e., lipid species that carry a net negative charge at physiological pH). Examples of anionic lipids include, but are not limited to, cardiolipin, phosphatidylserine and phosphatidic acid.

An "ionizable anionic lipid" means an anionic lipid that undergoes protonation as the pH is reduced toward the $pK_a$ of the lipid. At the $pK_a$ of the ionizable anionic lipid, half of the lipid is in the anionic form and half of the lipid is in the protonated form. In the context of lipid nanoparticles, at pH values above the $pK_a$ of the ionizable anionic lipid, more of the lipid is negatively charged, and the negatively charged form of the lipid can stabilize other lipids in a bilayer organization, allowing the formation of bilayer vesicles. These vesicles then fuse as the pH is reduced toward the $pK_a$ of the ionizable anionic lipid, such as in the endosomal environment, and more of the ionizable anionic lipid becomes protonated. Examples of ionizable anionic lipids include cholesteryl hemisuccinate (CHEMS), phosphatidylserine, palmitoylhomoserine, and α-tocopherol hemisuccinate.

An "ionizable cationic lipid" means a cationic lipid that undergoes protonation as the pH is reduced toward the $pK_a$ of the lipid. At the $pK_a$ of the ionizable cationic lipid, half of the lipid in in the protonated form and half of the lipid is in the neutral form. In the context of lipid nanoparticles, at pH values below the $pK_a$ of the ionizable cationic lipid, the positively charged form of the lipid can interact with negatively charged oligonucleotides, allowing for encapsulation of the oligonucleotides inside of vesicles and nanoparticles. At pH values above the $pK_a$, more of the cationic lipid is neutral and this lack of charge can affect the surface potential of lipid nanoparticles as well as affect release of oligonucleotides from these lipids. Additionally, appropriately designed cationic lipids with unsaturated tails can mediate fusion events with other membranes by undergoing lamellar to inverse hexagonal phase transitions. Such fusion events can result in endosomolysis which can enable delivery of material into the cytosol. Examples of ionizable anionic lipids include DDAB, DlinDMA, DLin-KC2-DMA, MC3 lipid (DLin-MC3-DMA), DODAP, DODMA, and Mo-CHOL.

An "exchangeable PEG-lipid" means a PEG-lipid that is not stable in a lipid nanoparticle (LNP) membrane at physiologic temperature, such that PEG-lipid molecules in the LNP leave the LNP membrane over time. Exchangeable PEG-lipids leaving the LNP membrane typically move into a biological membrane (e.g., blood cell membranes) or may form micelles by themselves. The rate of release of a PEG-lipid from an LNP is mainly a function of the length of the alkyl chain and the level of unsaturation in the alkyl chain (i.e., the number of carbon-to-carbon double bonds). Typically, a PEG-lipid having a saturated chain of 14 carbons or less will be exchangeable. A C18 chain with one or more double bonds (e.g., 18:1, 18:2) will also be exchangeable. Generally, a PEG-lipid having an alkyl chain of greater than 18 carbons will not be exchangeable or exchanges at a much lower rate than a PEG-lipid having an alkyl chain of 14 carbons or less. Other factors that can increase the rate of release of a PEG-lipid include asymmetry in the alkyl chain (e.g., PEG-Ceramides with different alkyl chain lengths (e.g., cerC8)) as well as the size of the PEG moiety, with larger molecular weight PEG moieties contributing to exchangeability of the lipid.

As used herein, "amphipathic" or "amphiphilic" compounds have both hydrophilic (water-soluble) and hydrophobic (water-insoluble) parts.

As used herein, the term "therapeutic agent" refers to any molecular species (e.g., polynucleotide, protein, peptide, or small molecule) that may have a therapeutic effect upon delivery into a cell. In the case of a polynucleotide, this effect can be mediated by the nucleic acid itself (e.g., anti-sense polynucleotide), following transcription (e.g., anti-sense RNA, ribozymes, interfering dsRNA, mRNA), or following expression into a protein. A "therapeutic" effect of an expressed protein in attenuating or preventing the disease state can be accomplished by the protein either staying within the cell, remaining attached to the cell in the membrane, or being secreted and dissociated from the cell where it can enter the general circulation and blood. Secreted proteins that can be therapeutic include hormones, cytokines, growth factors, clotting factors, anti-protease proteins (e.g., alpha1-antitrypsin), angiogenic proteins (e.g., vascular endothelial growth factor, fibroblast growth factors), anti-angiogenic proteins (e.g., endostatin, angiostatin), and other proteins that are present in the blood. Proteins on the membrane can have a therapeutic effect by providing a receptor for the cell to take up a protein or lipoprotein. Therapeutic proteins that stay within the cell (intracellular proteins) can be enzymes that clear a circulating toxic metabolite as in phenylketonuria. They can also cause a cancer cell to be less proliferative or cancerous (e.g., less metastatic), or interfere with the replication of a virus. Intracellular proteins can be part of the cytoskeleton (e.g., actin, dystrophin, myosins, sarcoglycans, and dystroglycans) and thus have a therapeutic effect in cardiomyopathies and musculoskeletal diseases (e.g., Duchenne muscular dystrophy, limb-girdle disease). Protein agents may also be delivered directly into a cell (i.e., in protein form, rather than as an encoding polynucleotide to be expressed). Other therapeutic proteins of particular interest to treating heart disease include polypeptides affecting cardiac contractility (e.g., calcium and sodium channels), inhibitors of restenosis (e.g., nitric oxide synthetase), angiogenic factors, and anti-angiogenic factors. Protein agents may also include antibodies (e.g., small single-chain antibodies or bispecific antibodies) directed at intracellular targets. Other exemplary "therapeutic agents" include small molecules, such as, for example, small molecule inhibitors or agonists of intracellular target molecules (e.g., kinase inhibitors, inhibitors of DNA synthesis pathways) or small molecules having a cytotoxic or cytostatic effect on a cell (such as chemotherapeutic agents for cancer treatment); anti-infective agents (e.g., anti-viral agents or anti-bacterial agents); or vaccines (which may include proteins, peptides, DNA, or RNA). In some embodiments, a "therapeutic agent" is a component of a gene editing system that disrupts or corrects genes that cause disease (e.g., a polynucleotide encoding a nuclease; a guide RNA that may be formulated with a polynucleotide encoding a nuclease; or a donor DNA sequence for correcting a gene by homologous recombination).

As used herein, the term "diagnostic agent" refers to a component that can be detected in a subject or test sample from a subject. Exemplary diagnostic agents include radioactive agents, fluorescent agents, contrast agents (e.g., an MRI or X-ray contrast agent), and other imaging reagents. Diagnostic reagents also include, for example, immunodiagnostic reagents (e.g., antibodies directed to intracellular targets) as well as other specific binding agents. A diagnostic agent may consist of, for example, a diagnostically detectable label that is complexed with a lipid nanoparticle, or may comprise a diagnostically detectable label conjugated to another molecule (e.g., a specific binding molecule, such as, e.g., a peptide, protein, or polynucleotide). Many different labels exist in the art and methods of labeling are well-known by the skilled artisan. General classes of labels that can be used in the present invention include, but are not limited to, radioactive isotopes, paramagnetic isotopes, compounds that can be imaged by positron emission tomography (PET), fluorescent or colored compounds, compounds which can be imaged by magnetic resonance, chemiluminescent compounds, bioluminescent compounds, and the like. Particularly suitable detectable labels include, but are not limited to, radioactive, fluorescent, fluorogenic, or chromogenic labels. Useful radiolabels (radionuclides), which are detected simply by $\gamma$ counter, scintillation counter or autoradiography include, but are not limited to, $^{3}H$, $^{125}I$, $^{131}I$, $^{35}S$, and $^{14}C$.

As used herein, the term "membrane-destabilizing polymer" refers to a polymer that is capable of inducing one or more of the following effects upon a biological membrane: an alteration or disruption that allows small molecule permeability, pore formation in the membrane, a fusion and/or fission of membranes, an alteration or disruption that allows large molecule permeability, a dissolving of the membrane, or causing membrane perturbation that opens tight junctions and enables paracellular transport. This alteration can be functionally defined by the compound's activity in at least one the following assays: red blood cell lysis (hemolysis), liposome leakage, liposome fusion, cell fusion, cell lysis, and release of endosomal contents. Typically, a membrane-destabilizing polymer allows for the transport of molecules with a molecular weight greater than 50 atomic mass units to cross a membrane. This transport may be accomplished by either the loss of membrane structure or the formation of holes or pores in the membrane. In particular variations, a membrane-destabilizing polymer is a copolymer (e.g., an amphipathic copolymer), a synthetic amphipathic peptide, a membrane active toxin (e.g., pardaxin, melittin, cecropin, magainin, PGLa, indolicidin, dermaseptin, or a derivative thereof), or a viral fusogenic peptide (e.g., the influenza virus hemagglutinin subunit HA-2 peptide).

As used herein, a "block copolymer" refers to a structure comprising one or more sub-combination of constitutional or monomeric units. In some embodiments, the block copolymer is a diblock copolymer, a tri-block copolymer or a higher-ordered block copolymer. For example, a diblock copolymer can comprise two blocks; a schematic generalization of such a polymer is represented by the following: $[A_a\text{-}B_b\text{-}C_c\text{-} \ldots ]_m\text{-}[X_x\text{-}Y_y\text{-}Z_z\text{-} \ldots ]$, or $[A_a\text{-}B_b\text{-}C_c\text{-} \ldots ]_m\text{-}b\text{-}[X_x\text{-}Y_y\text{-}Z_z\text{-} \ldots ]_n$, wherein each letter stands for a constitutional or monomeric unit, and wherein each subscript to a constitutional unit represents the mole fraction of that unit in the particular block, the three dots indicate that there may be more (there may also be fewer) constitutional units in each block, and m and n indicate the molecular weight (or weight fraction) of each block in the diblock copolymer. As suggested by such schematic representation, in some instances, the number and the nature of each constitutional unit is separately controlled for each block. The schematic is not meant to, and should not be construed to, infer any relationship whatsoever between the number of constitutional units or between the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the form: x-x-y-z-x-y-y-z-y-z-z-z . . . . An exemplary alternating random configuration may have the form: x-y-x-z-y-x-y-z-y-x-z . . . , and an exemplary regular alternating configuration may have the form: x-y-z-x-y-z-x-y-z . . . . An exemplary regular block configuration may have the following general configuration: . . . x-x-x-y-y-y-z-z-z-x-x-x . . . , while an exemplary random block configuration may have the general configuration: . . . x-x-x-z-z-x-x-y-y-y-y-z-z-z-x-x-z-z-z- . . . . In a gradient polymer, the content of one or more monomeric units increases or decreases in a gradient manner from the $\alpha$ end of the polymer to the $\omega$ end. In none of the preceding generic examples is the particular juxtaposition of individual constitutional units or blocks or the number of constitutional units in a block or the number of blocks meant nor should they be construed as in any manner bearing on or limiting the actual structure of block copolymers forming the polymeric carrier of this invention.

As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers.

As used herein, the term "molecular weight" for a polymer or polymer block is the number average molecular weight. It is understood in the art that a population of polymer molecules will have a distribution of different molecular weights. This distribution of molecular weights can be described by the term dispersity index or polydispersity index (PI or PDI), which is the weight average molecular weight/number average molecular weight.

As used herein the term "polynucleotide" refers to a polymer comprising two or more nucleotide monomeric units ("nucleotides"). Typical polynucleotides in accordance with certain embodiments of the present invention include those comprising 7-20,000 nucleotide monomeric units, 7-15,000 nucleotide monomeric units, 7-10,000 nucleotide monomeric units, 7-5,000 nucleotide monomeric units and 7-1000 nucleotide monomeric units. Polynucleotides of less than 200 nucleotides are generally referred to as "oligonucleotides." Polynucleotides include deoxyribonucleic acid (DNA) and ribonucleic acid (RNA), or their derivatives, and combinations of DNA, RNA. DNA may be in form of cDNA, in vitro polymerized DNA, plasmid DNA, parts of a plasmid DNA, genetic material derived from a virus, linear DNA, vectors (Pl, PAC, BAC, YAC, and artificial chromosomes), expression vectors, expression cassettes, chimeric sequences, recombinant DNA, chromosomal DNA, antisense DNA, or derivatives of these groups. RNA may be in the form of messenger RNA (mRNA), in vitro polymerized RNA, recombinant RNA, transfer RNA (tRNA), small nuclear RNA (snRNA), ribosomal RNA (rRNA), chimeric sequences, dicer substrate and the precursors thereof, locked nucleic acids, anti-sense RNA, interfering RNA (RNAi), asymmetric interfering RNA (aiRNA), small interfering RNA (siRNA), microRNA (miRNA), ribozymes, external guide sequences, small non-messenger RNAs (snmRNA), untranslatedRNA (utRNA), snoRNAs (24-mers, modified snmRNA that act by an anti-sense mechanism), tiny non-coding RNAs (tncRNAs), small hairpin RNA (shRNA), or their derivatives. In addition, DNA and RNA may be single, double, triple, or quadruple stranded. Double stranded RNA (dsRNA) and siRNA are of interest particularly in connection with the phenomenon of RNA interference. Examples of oligonucleotides as used herein include, but are not limited to, siRNA, an antisense oligonucleotide, a dicer substrate, a miRNA, an aiRNA or an shRNA. Further examples of oligonucleotides as used herein include, but are not limited to dsRNA having a length of from 17 to 29 nucleotides, or from 19 to 25 nucleotides, and being at least 90 percent, or 95 percent or 100 percent (of the nucleotides of a dsRNA) complementary to a coding or a non-coding section of the nucleic acid sequence of a therapeutically relevant protein or antigen. Ninety percent complementary means that a 20 nucleotide length of a dsRNA contains not more than 2 nucleotides without a corresponding complementarity with the corresponding section of the mRNA. Yet further examples of polynucleotides as used herein include, but are not limited to single stranded mRNA which can be modified or unmodified. Modified mRNA includes at least one modification and a translatable region. Modification(s) may be located on the backbone, a nucleoside of the nucleic acid molecule, and/or a 5' cap structure. For example, a modification may be located on a nucleoside (e.g., substitution of uridine residues with pseudouridine), or modifications may be located on both a nucleoside and a backbone linkage. Typically, mRNAs in accordance with certain compositions and methods of the present invention include those comprising 300-20,000 nucleotide monomeric units, 300-15,000 nucleotide monomeric units, 300-10,000 nucleotide monomeric units, 300-5,000 nucleotide monomeric units, 300-2000 nucleotide monomeric units, 300-1,500 nucleotide monomeric units, and 300-1000 nucleotide monomeric units. In some variations, an mRNA in accordance with compositions and methods of the present disclosure is at least 500, at least 1,000, at least 1,200, or at least 1,500 nucleotide monomeric units.

Polynucleotides may include nucleotides that have been modified relative to naturally occurring nucleotides. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleotide monomeric units can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "polynucleotide" also includes so-called "peptide nucleic acids," which comprise naturally-occurring or modified nucleic acid bases attached to a polyamide backbone.

A "polypeptide" is a polymer of amino acid residues joined by peptide bonds, whether produced naturally or synthetically. Polypeptides of less than about 50 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

With regard to proteins as described herein, reference to amino acid residues corresponding to those specified by SEQ ID NO includes post-translational modifications of such residues.

As used herein, the term "antibody" refers to any immunoglobulin protein that specifically binds to an antigen, as well as antigen-binding fragments thereof and engineered variants thereof. Hence, the term "antibody" includes, for example, polyclonal antibodies, monoclonal antibodies, and antigen-binding antibody fragments that contain the paratope of an intact antibody, such as Fab, Fab', F(ab')$_2$ and F(v) fragments. Genetically engineered intact antibodies and fragments, such as chimeric antibodies, humanized antibodies, single-chain Fv fragments, single-chain antibodies, diabodies, minibodies, linear antibodies, multivalent or multispecific hybrid antibodies, and the like are also included. Thus, the term "antibody" is used expansively to include any protein that comprises an antigen binding site of an antibody and is capable of binding to its antigen. In some embodiments, an antibody has affinity to a cell surface molecule.

The term "genetically engineered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with cells and other effector functions. Typically, changes in the variable region will be made in order to improve the antigen binding characteristics, improve variable region stability, or reduce the risk of immunogenicity.

An "antigen-binding site of an antibody" is that portion of an antibody that is sufficient to bind to its antigen. The minimum such region is typically a variable domain or a genetically engineered variant thereof. Single-domain binding sites can be generated from camelid antibodies (see Muyldermans and Lauwereys, J. Mol. Recog. 12:131-140, 1999; Nguyen et al., EMBO J. 19:921-930, 2000) or from $V_H$ domains of other species to produce single-domain antibodies ("dAbs"; see Ward et al., Nature 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see, e.g., Pessi et al., *Nature* 362: 367-369, 1993; Qiu et al., *Nature Biotechnol.* 25:921-929, 2007). More commonly, an antigen-binding site of an antibody comprises both a heavy chain variable domain and a light chain variable domain that bind to a common epitope. Examples of molecules comprising an antigen-binding site of an antibody are known in the art and include, for example, Fv fragments, single-chain Fv fragments (scFv), Fab fragments, diabodies, minibodies, Fab-scFv fusions, bispecific (scFv)$_4$-IgG, and bispecific (scFv)$_2$-Fab. (See, e.g., Hu et al., *Cancer Res.* 56:3055-3061, 1996; Atwell et al., *Molecular Immunology* 33:1301-1312, 1996; Carter and Merchant, *Curr. Opin. Biotechnol.* 8:449-454, 1997; Zuo et al., *Protein Engineering* 13:361-367, 2000; and Lu et al., *J. Immunol. Methods* 267:213-226, 2002.)

As used herein, the terms "single-chain Fv" and "single-chain antibody" refer to antibody fragments that comprise, within a single polypeptide chain, the variable regions from both heavy and light chains, but lack constant regions. In general, a single-chain antibody further comprises a polypeptide linker between the $V_H$ and $V_L$ domains, which enables it to form the desired structure that allows for antigen binding. Single-chain antibodies are discussed in detail by, for example, Pluckthun in *The Pharmacology of Monoclonal Antibodies*, vol. 113 (Rosenburg and Moore eds., Springer-Verlag, New York, 1994), pp. 269-315. (See also WIPO Publication WO 88/01649; U.S. Pat. Nos. 4,946,778 and 5,260,203; Bird et al., *Science* 242:423-426, 1988.) Single-chain antibodies can also be bi-specific and/or humanized.

A "bispecific antibody" is a hybrid antibody having two different heavy/light chain pairs and two different binding sites. Bispecific antibodies are well-established in the art as a standard technique to create a single protein that binds to two different determinants. See, e.g., Kufer et al., *Trends Biotechnol.* 22:238-244, 2004. Bispecific antibodies may be made in many different formats, including but not limited to quadroma, F(ab')2, tetravalent, heterodimeric scFv, bispecific scFv, tandem scFv, diabody and minibody formats, or scFvs appended to or recombinantly fused with whole antibodies. See e.g., Kufer et al., 2004; Holliger and Hudson *Nature Biotechnology* 23:1126-1136, 2005; Morrison and Coloma, WO 95/09917.

As used herein, an "immunogen" is an entity (e.g., a peptide, protein, a nucleic acid, or a carbohydrate) that induces an immune response, which may include an innate or an adaptive immune response (e.g., that protects a subject from an infection or cancer). An adaptive immune response can be a humoral and/or cell-mediated immune response. In certain embodiments, an immunogen in the context of the present disclosure is used as a vaccine.

As used herein the term "sugar" refers to saccharides such as monosaccharides, disaccharides, oligosaccharides, and polysaccharides for example. Typically, sugars as used herein target or deliver copolymers to target cells or tissues, or specific cells types and enhance the association of molecules with the target cells. For example, liver hepatocytes contain asialoglycoprotein (ASGP) receptors. Therefore, galactose-containing targeting groups may be used to target hepatocytes. Examples of galactose containing targeting groups include, but are not limited to, galactose or galactose derivatives such as its protected analogs, N-acetylgalactosamine (NAG, also referred to as GalNAc) or N-acetylgalactosamine derivatives such as its protected analogs, oligosaccharides, and saccharide clusters such as Tyr-Glu-Glu-(aminohexyl GalNAc)3, lysine-based galactose clusters, and cholane-based galactose clusters. Other examples of sugars include, but are not limited to, mannose and mannose derivatives such as its protected analogs. In some variations, a sugar is a multivalent structure comprising two or more sugar moieties (e.g., three or four moieties). In some such multivalent sugar embodiments, each moiety is connected to a common branching point via a linker. An exemplary multivalent sugar is a tri-N-acetylgalactosamine (tri-NAG) structure having three NAG moieties. Tri-NAG structures are generally known in the art and are described, for example, in Lee et al., *Carbohydrates and Chemistry and Biology* (B. Ernst, G. W. Hart, & P. Sinay, Eds., Wiley-WCH: Weinheim, 2000), Vol. 4, p 459 (and references cited therein); Biessen et al. *J. Med. Chem.* 38:1538, 1995; Sliedregt et al., *J. Med. Chem.* 42:609, 1999; Rensen et al., *J. Med. Chem.* 47:5798, 2004; Khorev et al., *Bioorg. Med. Chem.* 16:5216, 2008. Another exemplary multivalent sugar is a bis-mannose-6-phosphate (bis-M6P) structure having two mannose-6-phosphate moieties (see, e.g., U.S. Pat. No. 8,399,657 to Zhu et al.).

As used herein the term "vitamin" refers any of various fat-soluble or water-soluble organic substances that are essential in minute amounts for normal growth and activity of living organisms. Exemplary vitamins include Vitamin A (Retinol), Vitamin B1 (Thiamine), Vitamin C (Ascorbic acid), Vitamin D (Calciferol), Vitamin B2 (Riboflavin), Vitamin E (Tocopherol), Vitamin B12 (Cobalamins), Vitamin K1 (Phylloquinone), Vitamin B5 (Pantothenic acid), Vitamin B7 (Biotin), Vitamin B6 (Pyridoxine), Vitamin B3 (Niacin), Vitamin B9 (Folic acid) and their derivatives. Typically, vitamins as used herein target or deliver lipid nanoparticles and/or membrane-destabilizing polymers to target cells or tissues, or specific cells types and enhance the association of molecules with the target cells. An example of a vitamin as used herein includes Vitamin $B_9$, including folic acid, folate and their derivatives.

As used herein, a "targeting ligand" refers to a moiety that is capable of specifically binding to a molecule on the surface of a target cell, such as a cell within a target tissue of a subject. A molecule (e.g., cell surface molecule) that specifically binds to a targeting moiety is also referred to herein as a "binding partner."

As used herein, "alkyl" refers to a straight or branched chain fully saturated (no double or triple bonds) hydrocarbon (carbon and hydrogen only) group, optionally having a cycloalkyl group as part of the hydrocarbon chain (either at a terminal position or non-terminal position in the chain). An alkyl group herein contains from one to ten carbon atoms in the principal chain and up to 20 carbon atoms, and may be linear or branched. Examples of alkyl groups include, but are not limited to, methyl, ethyl, propyl, isopropyl, butyl, isobutyl, sec-butyl, tertiary butyl, pentyl and hexyl. As used herein, "alkyl" includes "alkylene" groups, which refer to straight or branched fully saturated hydrocarbon groups having two rather than one open valences for bonding to other groups. Examples of alkylene groups include, but are not limited to methylene (—CH$_2$—), ethylene (—CH$_2$CH$_2$—), propylene (—CH$_2$CH$_2$CH$_2$—), n-butylene (—CH$_2$CH$_2$CH$_2$CH$_2$—), sec-butylene (—CH$_2$CH$_2$CH (CH$_3$)—), and the like. An alkyl group of this disclosure may optionally be substituted with one or more fluorine groups.

As used herein, "mC to nC," "Cm to Cn," or "Cm to C$_n$," wherein m and n are integers, refers to the number of possible carbon atoms in the indicated group. That is, the group can contain from "m" to "n", inclusive, carbon atoms. An alkyl group of this disclosure may comprise from 1 to 18 carbon atoms, that is, m is 1 and n is 18. Of course, a particular alkyl group may be more limited. For instance without limitation, an alkyl group of this disclosure may consist of 3 to 8 carbon atoms, in which case it would be designated as a (3C-8C)alkyl group. The numbers are inclusive and incorporate all straight or branched chain structures having the indicated number of carbon atoms. For example without limitation, a "1C to 4C alkyl" or "(1C-4C)alkyl" group refers to all alkyl groups having from 1 to 4 carbons, that is, $CH_3$—, $CH_3CH_2$—, $CH_3CH_2CH_2$—, $CH_3CH(CH_3)$—, $CH_3CH_2CH_2CH_2$—, $CH_3CH_2CH(CH_3)$—, $(CH_3)_2CHCH_2$— and $(CH_3)_3CH$—.

As used herein, the term "aryl" or "aryl group" refers to optionally substituted monocyclic, bicyclic, and tricyclic ring systems having a total of five to fourteen ring members, wherein at least one ring in the system is aromatic and wherein each ring in the system contains three to seven ring members. The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

As used herein, the term "heteroalkyl" means an alkyl group wherein at least one of the backbone carbon atoms is replaced with a heteroatom.

As used herein, the term "heteroaryl" means an aryl group wherein at least one of the ring members is a heteroatom, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbonyl, substituted hydrocarbonyl, keto (i.e., =O), hydroxy, protected hydroxy, acyl, acyloxy, alkoxy, alkenoxy, alkynoxy, aryloxy, halogen, amido, amino, nitro, cyano, thiol, ketals, acetals, esters and ethers.

As use herein, "cycloalkyl" refers to an alkyl group in which the end carbon atoms of the alkyl chain are covalently bonded to one another. The numbers "m" and "n" refer to the number of carbon atoms in the ring formed. Thus for instance, a (3C-8C) cycloalkyl group refers to a three, four, five, six, seven or eight member ring, that is, cyclopropane, cyclobutane, cyclopentane, cyclohexane, cycloheptane and cyclooctane. A cycloalkyl group of this invention may optionally be substituted with one or more fluorine groups and/or one or more alkyl groups.

As used herein, the term "heterocycloalkyl" means a cycloalkyl group wherein at least one of the backbone carbon atoms is replaced with a heteroatom.

As used herein, the term "alkynyl" refers to an unsaturated, straight chain hydrocarbon group having from two to ten carbon atoms therein and in which at least two carbon atoms are bonded together by a triple bond.

As used herein, the term "alkenyl" refers to an unsaturated, straight chain hydrocarbon group having from two to ten carbon atoms therein and in which at least two carbon atoms are bonded together by a double bond.

When a functional group, such as an amine, is termed "protected," this means that the group is in modified form to preclude undesired side reactions at the protected site. Suitable protecting groups for the copolymers of the present disclosure will be recognized from the present application taking into account the level of skill in the art, and with reference to standard textbooks, such as Greene, T. W. et al., Protective Groups in Organic Synthesis Wiley, New York (1991). Carboxy groups can be protected as esters thereof, for example methyl, ethyl, tert-butyl, benzyl, and 4-nitrobenzyl esters. Hydroxy groups can be protected as ethers or esters thereof, for example methoxymethyl ethers, tetrahydropyranyl ethers, benzyl ethers, acetates or benzoates. Mercapto groups can be protected as thioethers or thioesters, for example pyridyl thioethers, maleimide thioethers, tert-butyl thioethers, thioacetates or thiobenzoates. Amino groups can be protected as carbamates, such as tert-butoxycarbonyl derivatives, or as amides, such as acetamides and benzamides.

As is well-known in the art, nomenclature of PEG molecular weight can use the overall molecular weight (including the PEG end groups) or the number of repeat units. For example $PEG_{12}$ is also known as $PEG_{0.6kDa}$ or $PEG_{0.6k}$. $PEG_{36}$ is also known as $PEG_{1.6kDa}$ or $PEG_{1.6k}$. $PEG_{48}$ is also known as $PEG_{2.2kDa}$ or $PEG_{2.2k}$. A particular form of $PEG_{48}$ is also known as $PEG_{24}$-amido-$PEG_{24}$, but has also been generally described as $PEG_{2.2kDa}$ or $PEG_{2.2k}$.

$PEGMA_{4-5}$ (Poly(ethylene glycol) methyl ether methacrylate, average Mn=300) is also known as $PEGMA_{0.3kDA}$ or $PEGMA_{0.3k}$ or $PEGMA_{300}$, which is the average molecular weight of a mixture of $PEGMA_4$ and $PEGMA_5$. Similarly, $PEGMA_{7-9}$ (Poly(ethylene glycol) methyl ether methacrylate, average Mn=500) is also known as $PEGMA_{0.5kDA}$ or $PEGMA_{0.5k}$ or $PEGMA_{500}$, which is the average molecular weight of a mixture of $PEG_7$ and $PEG_9$. Similarly, $PEGMA_{17-19}$ (Poly(ethylene glycol) methyl ether methacrylate, average Mn=1000) is also known as $PEGMA_{1kDA}$ or $PEGMA_{1k}$ or $PEGMA_{1000}$, which is the average molecular weight of a mixture of $PEGMA_{17}$ and $PEGMA_{19}$.

As used herein, a "labile bond" is a covalent bond that is capable of being selectively broken. That is, the labile bond may be broken in the presence of other covalent bonds without the breakage of the other covalent bonds. For example, a disulfide bond is capable of being broken in the presence of thiols without cleavage of other bonds, such as carbon-carbon, carbon-oxygen, carbon-sulfur, carbon-nitrogen bonds, which may also be present in the molecule. Labile also means "cleavable."

As used herein, a "labile linkage" is a chemical compound that contains a labile bond and provides a link or spacer between two other groups. The groups that are linked may be chosen from compounds such as biologically active compounds, membrane active compounds, compounds that inhibit membrane activity, functional reactive groups, monomers, and cell targeting signals. The spacer group may contain chemical moieties chosen from a group that includes alkanes, alkenes, esters, ethers, glycerol, amide, saccharides, polysaccharides, and heteroatoms such as oxygen, sulfur, or nitrogen. The spacer may be electronically neutral, may bear a positive or negative charge, or may bear both positive and negative charges with an overall charge of neutral, positive or negative.

As used herein, "pH-labile" or "pH-sensitive" refers to the selective breakage of a covalent bond under acidic conditions (pH<7), or that the covalent bond is broken more rapidly under acidic conditions (pH<7) than under neutral conditions. That is, the pH-labile bond may be broken under acidic conditions in the presence of other covalent bonds that are not broken.

As used herein, a "micelle" includes a particle comprising a core and a hydrophilic shell, wherein the core is held together at least partially, predominantly or substantially through hydrophobic interactions. In certain instances, as used herein, a "micelle" is a multi-component, nanoparticle comprising at least two domains, the inner domain or core, and the outer domain or shell. The core is at least partially, predominantly or substantially held together by hydrophobic interactions, and is present in the center of the micelle. As used herein, the "shell of a micelle" is defined as non-core portion of the micelle.

As used herein, a particle or assembly is "micelle-like" if it substantially behaves like a micelle: (1) it is formed by spontaneous self association of block copolymers to form organized assemblies (e.g., micelles) upon dilution from a water-miscible solvent (such as but not limited to ethanol) to aqueous solvents (for example phosphate-buffered saline, pH 7.4); (2) it is stable to dilution (e.g., down to a polymer concentration of 100 µg/ml, 50 µg/ml, 10 µg/ml, 5 ug/ml or 1 µg/ml, which constitutes the critical stability concentration or the critical micelle concentration (CMC)); and/or (3) it has an increasing instability as the concentration of organic solvent increases, such organic solvents including, but not limited to dimethylformamide (DMF), dimethylsulfoxide (DMS), and dioxane.

The term "effective amount," in the context of methods as described herein for delivering a therapeutic or diagnostic agent intracellularly by administering to a subject a lipid nanoparticle and a membrane-destabilizing polymer, refers to an amount the lipid nanoparticle and an amount of the membrane-destabilizing polymer that together is sufficient to achieve detectable delivery of the therapeutic or diagnostic agent to the cytosol of a target cell or target tissue. Reference herein to delivery of a therapeutic or diagnostic agent to the "cytosol" includes delivery of such a therapeutic or diagnostic agent that may ultimately be targeted to the nucleus of a cell subsequent to its delivery to the cytosol.

The term "effective amount" or "therapeutically effective amount," in the context of treatment of a disease by administering to a subject a lipid nanoparticle and membrane-destabilizing polymer as described herein, refers to an amount the lipid nanoparticle (comprising the therapeutic agent) and an amount of the membrane-destabilizing polymer that together is sufficient to inhibit the occurrence or ameliorate one or more symptoms of the disease in the subject. An effective amount of an agent-containing lipid nanoparticle and membrane-destabilizing polymer is administered according to the present methods in an "effective regime." The term "effective regime" refers to a combination of agent-containing lipid nanoparticle being administered, membrane-destabilizing polymer being administered, and dosage frequency adequate to accomplish treatment or prevention of the disease.

The term "patient" or "subject," in the context of therapeutic or diagnostic agent delivery in vivo as described herein, includes human and other mammalian subjects.

Percent sequence identity is determined by conventional methods. See, e.g., Altschul et al., *Bull. Math. Bio.* 48:603, 1986, and Henikoff and Henikoff, *Proc. Natl. Acad. Sci. USA* 89:10915, 1992. For example, two amino acid sequences can be aligned to optimize the alignment scores using a gap opening penalty of 10, a gap extension penalty of 1, and the "BLOSUM62" scoring matrix of Henikoff and Henikoff, supra. The percent identity is then calculated as: ([Total number of identical matches]/[length of the longer sequence plus the number of gaps introduced into the longer sequence in order to align the two sequences])(100). Those skilled in the art appreciate that there are many established algorithms available to align two amino acid sequences. The "FASTA" similarity search algorithm of Pearson and Lipman (*Proc. Nat'l Acad. Sci. USA* 85:2444, 1988, and by Pearson, *Meth. Enzymol.* 183:63, 1990) is a suitable protein alignment method for examining the level of identity shared by an amino acid sequence disclosed herein and a second amino acid sequence.

When such a value is expressed as "about" X or "approximately" X, the stated value of X will be understood to be accurate to ±10%.

DESCRIPTION OF THE INVENTION

Figure 1A:
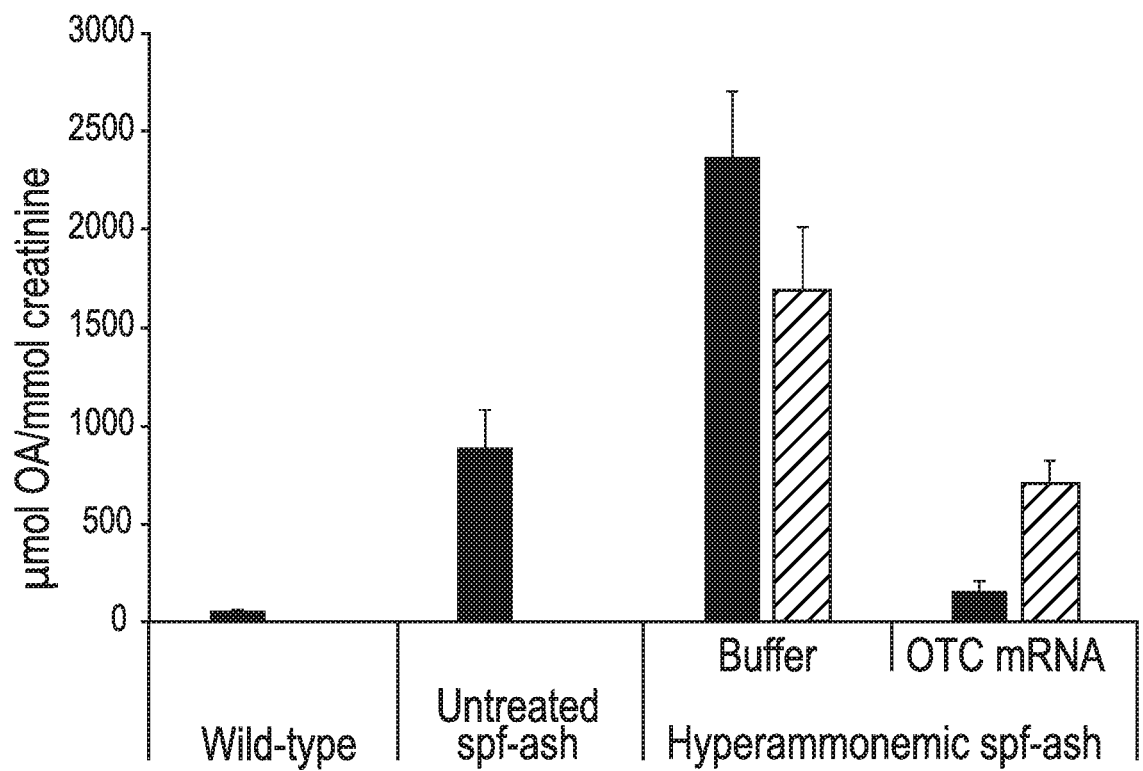
FIGS. 1A and 1B show reduction in orotic acid (OA) and plasma ammonia levels in hyperammonemic OTC-spf$^{ash}$ mice treated with mRNA encoding ornithine transcarbamylase (OTC). Hyperammonemia was induced in OTC-spf$^{ash}$ mice by treatment with AAV2/8 vector/OTC shRNA, and four days after AAV dosing, mice were treated twice per week with 1 mg/kg of OTC mRNA formulated in DOTAP:CHEMS:CHOL:DMPE-PEG$_{2k}$ (50:32:16:2) at N:P 7+co-injection of 50 mg/kg P67. See Example 21. Urine collected at day 6 and day 13 (post-AAV treatment) was analyzed for OA levels that were normalized to creatine levels, and plasma collected at day 13 was analyzed for ammonia levels. Orotic acid levels are shown in FIG. 1A (black fill=day 6; crosshatch fill=day 13). Plasma ammonia levels are shown in FIG. 1B.

The present invention is directed to methods, compositions, and delivery systems for in vivo delivery of a therapeutic or diagnostic agent to the cytosol of a target cell (e.g., in vivo cytosolic delivery of the agent to a plurality of target cells within a target tissue). The methods, compositions, and delivery systems may be used for intracellular delivery of a wide variety of molecular agents, including polynucleotides, peptide, proteins, and small molecules, and thus have a variety of diagnostic and therapeutic applications, including, e.g., the treatment of cancer, infectious disease, and diseases characterized by protein deficiencies.

The present invention relates, inter alia, to formulations used for delivery of the therapeutic or diagnostic agent. Generally, the therapeutic or diagnostic agent is formulated in a lipid nanoparticle ("LNP"; e.g., a liposome) and either a membrane-destabilizing polymer is added to the formulation (a co-formulation for co-injection of LNP and polymer) or the LNP "carrier" formulation and the membrane-destabilizing polymer are used separately via separate (e.g., sequential) injections into a subject. Either one or both of the LNP and membrane-destabilizing polymer may include a targeting ligand that binds to a molecule on the surface of the desired cell target. In certain other embodiments, neither the LNP nor the membrane-destabilizing polymer have a targeting ligand. The function of the lipid nanoparticle is to encapsulate the therapeutic or diagnostic agent, preventing its interaction with various components of the systemic circulation and facilitating delivery to and uptake into the desired tissues and cells. The lipid nanoparticle may also participate in lysis of endosomes. While not intending to be bound by theory, it is believed that the membrane-destabilizing polymer functions as an agent to elicit or enhance the delivery of the therapeutic or diagnostic agent into the cytosol of target cells, possibly by improving endosomal escape of the LNP from the endosome. For example, the lipid nanoparticle and the membrane-destabilizing polymer may co-localize to an intracellular vesicle within the target cell, where the membrane-destabilizing polymer may facilitate release of the therapeutic or diagnostic agent by disrupting the vesicle membrane. As shown in the working examples herein, the combination of LNP and membrane-destabilizing polymer demonstrated enhanced activity of the delivered agent (either using co-injection or sequential injections) as compared to the use of LNPs alone. See Examples 1, 2, 18, and 20, infra. Again without intending to be bound by theory, this result is believed to be due to enhanced delivery of the agent into the target cells when polymer is used in combination with an LNP carrier.

Accordingly, in one aspect, the present invention provides a method for delivering a therapeutic or diagnostic agent to the cytosol of a target cell. The method generally includes administering to the subject (a) an effective amount of a lipid nanoparticle comprising the therapeutic or diagnostic agent and (b) an effective amount of a membrane-destabilizing polymer, where the therapeutic or diagnostic agent is delivered to the cytosol of the target cell. In some embodiments of the method, at least one of the lipid nanoparticle and membrane-destabilizing polymer includes a first targeting ligand that specifically binds to a molecule on the surface of the target cell.

In another aspect, the present invention provides a composition for delivering a therapeutic or diagnostic agent to the cytosol of a target cell. The composition generally includes (a) a lipid nanoparticle comprising the therapeutic or diagnostic agent and (b) a membrane-destabilizing polymer. In some embodiments of the composition, at least one of the lipid nanoparticle and membrane-destabilizing polymer includes a first targeting ligand that specifically binds to a molecule on the surface of the target cell. Such compositions may be used in certain embodiments of the delivery methods described herein, particularly embodiments comprising co-injection of a membrane-destabilizing polymer and a lipid nanoparticle comprising the therapeutic or diagnostic agent.

In another aspect, the present invention provides a delivery system for delivering a therapeutic or diagnostic agent to the cytosol of a target cell. The delivery system generally includes (a) a carrier composition comprising a lipid nanoparticle, where the lipid nanoparticle comprises the therapeutic or diagnostic agent and (b) an enhancer composition comprising a membrane-destabilizing polymer. In some embodiments of the delivery system, at least one of the lipid nanoparticle and membrane-destabilizing polymer includes a first targeting ligand that specifically binds to a molecule on the surface of the target cell. Such delivery systems may be used in certain embodiments of the delivery methods described herein, particularly embodiments comprising separate (e.g., sequential) injection of a membrane-destabilizing polymer and a lipid nanoparticle comprising the therapeutic or diagnostic agent.

In another aspect, the present invention provides a membrane-destabilizing polymer as described herein.

In another aspect, the present invention provides a lipid nanoparticle as described herein.

Typically, where a membrane-destabilizing polymer is added to a lipid nanoparticle formulation in accordance with the present disclosure (e.g., for making a composition comprising (a) a lipid nanoparticle comprising a therapeutic or diagnostic agent and (b) a membrane-destabilizing polymer), the polymer is not contained within the lipid nanoparticle. In certain embodiments of the various aspects disclosed herein, the membrane-destabilizing polymer forms a nanoparticle that is compositionally distinct from the lipid nanoparticle. For example, where the membrane-destabilizing polymer is a polymer comprising hydrophilic and hydrophobic segments, the polymer may form a micelle or micelle-like particle in aqueous solution.

A wide variety of therapeutic and diagnostic agents are generally known and may be used in accordance with the present methods, compositions, and delivery systems. The therapeutic or diagnostic agent to be delivered can be, for example, a polynucleotide, a protein, a peptide, or a small molecule. Suitable classes of therapeutic agents include, for example, anti-cancer agents, anti-infective agents (e.g., anti-viral or anti-bacterial agents), immunomodulatory agents (e.g., immunosuppressive or immunostimulatory agents), anti-inflammatory agents, or agents that modulate a cellular metabolic activity. Suitable diagnostic agents include, e.g., a variety of detectable agents, which may be used alone or as a conjugate (label) to another molecule (e.g., a polynucleotide, a protein, a peptide, or a small molecule) having a desired property useful in a diagnostic method (e.g., a binding specificity for a desired intracellular target). General classes of labels that can be used in the present invention include, but are not limited to, radioactive isotopes, paramagnetic isotopes, compounds that can be imaged by positron emission tomography (PET), fluorescent or colored compounds, compounds which can be imaged by magnetic resonance, chemiluminescent compounds, bioluminescent compounds, and other imaging reagents.

Methods for formulating lipid nanoparticles for drug delivery are generally known in the art and may be adapted for use in the context of the present invention. For example, lipid nanoparticle formulations for delivery of small RNAs are discussed in, e.g., Hong and Nam, *Theranostics* 4:1211-1232, 2014; Asai and Oku, *Biol. Pharm. Bull.* 37:201-205, 2014; and Tam et al., *Pharmaceutics* 5:498-507, 2013. Lipid particle formulations and lipid design for drug delivery are also discussed in, e.g., Samad et al., *Current Drug Delivery* 4:297-305, 2007; Martin et al., *Current Pharmaceutical Design* 11:375-394, 2005; Hafez et al., *Biophysical Journal* 79:1438-1446, 2000; Jayaraman et al., *Angew. Chem. Int. Ed.* 51:8529-8533, 2012; Li and Schick, *Biophysical Jour-* nal 80:1703-1711, 2001; Adami et al., *Molecular Therapy* 19:1141-1151, 2011); Dabkowska et al., *J. R. Soc. Interface* 9:548-561, 2012; Gubernator, *Expert Opinion on Drug Delivery* 8:565-80, 2011; Whitehead et al., *Nat. Commun.* 5:4277, 2014; and Dong et al., *Proc. Natl. Acad. Sci. USA* 111:3955-60, 2014.

For LNP formulations comprising a polynucleotide agent, a lipid nanoparticle includes one or more cationic lipids, which are useful, inter alia, in complexing with the polynucleotide via electrostatic interactions. The lipid nanoparticle may further include additional lipids, which may serve various purposes such as aiding manufacturing and storage stability as well as modulation of the biodistribution. Biodistribution may also be modulated by incorporation of targeting ligands conjugated to the lipids part of the lipid nanoparticle. Lipid nanoparticles comprising polynucleotides are typically formulated with a N:P ratio ranging from about 1 to about 30. In more specific variations, the N:P ratio is from about 1 to about 14, from 1 to about 7, or from about 3 to about 7 (e.g., an N:P ratio of about 3, about 3.5, or about 7).

In certain embodiments, a cationic lipid for forming the lipid nanoparticle comprises a quaternary amine and is consequently permanently positively charged. Particularly suitable, permanently charged cationic lipids that may be used in polynucleotide LNP formulations include, for example, N-[1-(2,3-dioleyloxy)propyl]-N,N,N-trimethylammonium chloride (DOTMA), N-[1-(2,3-dioleoyloxy)propyl]-N,N,N-trimethylammonium chloride (DOTAP), 1,2-dioleoyl-sn-glycero-3-ethylphosphocholine (DOEPC), 1,2-dilauroyl-sn-glycero-3-ethylphosphocholine (DLEPC), 1,2-dimyristoyl-sn-glycero-3-ethylphosphocholine (DMEPC), 1,2-dimyristoleoyl-sn-glycero-3-ethylphosphocholine (14:1), N1-[2-((1S)-1-[(3-aminopropyl)amino]-4-[di(3-aminopropyl)amino]butylcarboxamido)ethyl]-3,4-di[oleyloxy]-benzamide (MVL5), Dioctadecylamido-glycylspermine (DOGS), 3b-[N—(N',N'-dimethylaminoethyl)carbamoyl]cholesterol (DC-Chol), Dioctadecyldimethylammonium Bromide (DDAB), Saint lipids such as SAINT-2, N-methyl-4-(dioleyl)methylpyridinium, 1,2-dimyristyloxypropyl-3-dimethylhydroxyethylammonium bromide (DMRIE), 1,2-dioleoyl-3-dimethyl-hydroxyethyl ammonium bromide (DORIE), 1,2-dioleoyloxypropyl-3-dimethylhydroxyethyl ammonium chloride (DORI), Di-alkylated Amino Acid (DILA$^2$) (e.g., C18:1-norArg-C16), Dioleyldimethylammonium chloride (DODAC), 1-palmitoyl-2-oleoyl-sn-glycero-3-ethylphosphocholine (POEPC), 1,2-dimyristoleoyl-sn-glycero-3-ethylphosphocholine (MOEPC), and (R)-N,N,N-trimethyl-4,5-bis(oleoyloxy)pentan-1-aminium chloride (DOTAPen). Also suitable are cationic lipids with headgroups that are charged at physiological pH, such as primary amines (e.g., DODAG N',N'-dioctadecyl-N-4,8-diaza-10-aminodecanoylglycine amide) and guanidinium head groups (e.g., bis-guanidinium-spermidine-cholesterol (BGSC), bis-guanidiniumtren-cholesterol (BGTC), PONA, and (R)-5-guanidinopentane-1,2-diyl dioleate hydrochloride (DOPen-G)). Yet another suitable cationic lipid is (R)-5-(dimethylamino)pentane-1,2-diyl dioleate hydrochloride (DODAPen-C1). In certain embodiments, the cationic lipid is a particular enantiomer or the racemic form, and includes the various salt forms of a cationic lipid as above (e.g., chloride or sulfate). For example, in some embodiments, the cationic lipid is N-[1-(2,3-dioleoyloxy)propyl]-N,N,N-trimethylammonium chloride (DOTAP-C1) or N-[1-(2,3-dioleoyloxy)propyl]-N,N,N-trimethylammonium sulfate (DOTAP-Sulfate).

In certain variations, a cationic lipid for forming the lipid nanoparticle utilizes side chains of amino acids as the head groups, where the α-amino and α-carboxyl groups serve as attachment sites for the hydrophobic tails (also referred to as a "DiLA$^2$" architecture; see Adami et al., *Molecular Therapy* 19:1141-1151, 2011). A particular variant of a cationic lipid having a DiLA$^2$ structure is C18:1-norArg-C16. See Adami et al., supra.

Typically, a lipid nanoparticle comprising a cationic lipid as above includes one or more additional lipids. Additional lipids suitable to be incorporated into the lipid nanoparticles may include one or more of an anionic lipid, a neutral helper lipid, and a PEG-conjugated lipid (also referred to herein as a "PEG-lipid"). Hence in certain embodiments, lipid nanoparticles are provided that comprise a cationic lipid as above and one or more additional lipids selected from the group of an anionic lipid, a helper lipid and a PEG-lipid.

Anionic lipids for use in cationic lipid-containing LNP formulations are typically ionizable anionic lipids. While negatively charged at pH values above the pK$_a$ of the anionic lipid, an ionizable anionic lipid will generally stabilize other lipids in the LNP and allow the formation of bilayer vesicles, but will facilitate fusion of these vesicles as the pH is reduced toward the pK$_a$, such as in the acidic endosomal environment of a cell. Suitable ionizable anionic lipids include cholesteryl hemisuccinate (CHEMS), phosphatidylserine, palmitoylhomoserine, and α-tocopherol hemisuccinate.

Helper lipids are neutral lipids that help make a stable liposome dispersion and may also enhance the effectiveness of cationic lipid-based delivery formulations. Cholesterol (CHOL) is one particularly suitable helper lipid for used in lipid nanoparticle formulations. Suitable helper lipids also include neutral zwitterionic lipids such as, for example, 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), or any related phosphatidylcholine such as natural sphingomyelin (SM) and synthetic derivatives thereof such as 1-oleoyl-2-cholesteryl-hemisuccinoyl-sn-glycero-3-phosphocholine (OChemsPC). Other suitable helper lipids include 1,2-dioleoyl-sn-glycero-3-phosphoethanolamine (DOPE), 1,2-dilauroyl-sn-glycero-3-phosphoethanolamine (DLPE), 1,2-dimyristoyl-sn-glycero-3-phosphoethanolamine (DMPE), and 1,2-diphytanoyl-sn-glycero-3-phosphoethanolamine (DPHyPE).

In some embodiments, LNPs contain uncharged lipids modified with hydrophilic polymers such as, e.g., polyethylene glycol (also referred to herein as "PEG-lipids"). Such PEG-lipids generally serve to help with assembly of the nanoparticle during its manufacture, stabilize the lipid nanoparticle, avoid its aggregation, and prevent its interaction with serum proteins, opsonins, and RBCs. The polyethylene glycol (PEG) size can vary from approximately 1 to 5 approximately kDa. Depending on the relative amounts of these molecules in the formulation and the length of the hydrocarbon chain, the PEG-lipid can influence the pharmacokinetic characteristics, biodistribution, and efficacy of a formulation. PEG-lipids having relatively short lipid hydrocarbon chains of about 14 carbons dissociate from the LNP in vivo in plasma with a half-life of less than 1 h. In contrast, a PEG-lipid with a relatively long lipid hydrocarbon chain length of about 18 carbons circulates fully associated with the formulation for several days. Hence, in typical embodiments, the PEG-lipid comprises a lipid hydrocarbon chain of 12 to 20 carbon atoms, 14 to 18 carbon atoms, or of 14 carbon atoms. Typically, the concentration of the PEG-lipid is about 0.5 to 10 mol %. Examples of suitable PEG modified lipids include PEGylated ceramide conjugates and PEGylated distearoylphosphatidyl-ethanolamine (PEG-DSPE). Other compounds that can be used to stabilize lipid nanoparticles include gangliosides ($GM_1$, GM3, and the like). Preferred PEG-lipids have a PEG size ranging from about 1 to about 5 kDa, with a preferred size range of about 2 to about 5 kDa. Specific examples are methoxy-polyethyleneglycol-carbamoyl-dimyristyloxy-propylamine (PEG2000-c-DMA), α-(3'-(1,2-dimyristoyl-3-propanoxy)-carboxamide-propyl]-ω-me-thoxy-polyoxyethylene (PEG2000-c-DOMG), N-(Carbonyl-methoxypolyethyleneglycol 2000)-1,2-dimyristoyl-sn-glycero-3-phosphoethanolamine (DMPE-PEG 2,000), polyethylene gycol-dimyristolglycerol (PEG-DMG), and N-octanoyl-sphingosine-1-{succinyl[methoxy(polyethylene glycol) 2000]} (C8 PEG2000Ceramide). In some variations of DMPE-$PEG_n$ where n is 350, 500, 750, 1000 or 2000, the PEG-lipid is N-(Carbonyl-methoxypolyethyleneglycol 2000)-1,2-dimyristoyl-sn-glycero-3-phosphoethanolamine (DMPE-PEG 2,000). In some variations of DSPE-$PEG_n$ where n is 350, 500, 750, 1000 or 2000, the PEG-lipid is N-(Carbonyl-methoxypolyethyleneglycol 2000)-1,2-distearoyl-sn-glycero-3-phosphoethanolamine (DSPE-PEG 2,000). In some embodiments, a PEG-lipid is conjugated to a targeting ligand that specifically binds to molecule on the surface of a target cell (e.g., an N-acetylgalactosamine (NAG) sugar residue); such PEG-lipids are particularly useful for formulating lipid nanoparticles that include a targeting ligand as further described herein. An exemplary PEG-lipid comprising a NAG moiety is DSPE-PEG2k-NAG (see, e.g., Examples 19 and 22, infra).

In certain embodiments, a lipid nanoparticle as above comprises an ionizable cationic lipid, typically in lieu of any permanently charged cationic lipid. The ionizable cationic lipid will have at least one protonatable or deprotonatable group, typically such that the lipid is positively charged at a pH at or below physiological pH (e.g., pH 7.4), and neutral at a second pH, preferably at or above physiological pH. It will be understood that the addition or removal of protons as a function of pH is an equilibrium process, and that the reference to a charged or a neutral lipid refers to the nature of the predominant species and does not require that all of the lipid be present in the charged or neutral form. In certain embodiments, ionizable cationic lipids have a $pK_a$ of the protonatable group in the range of about 4 to about 11. Most preferred is a $pK_a$ of about 4 to about 7, because these lipids will be cationic at a lower pH formulation stage, while particles will be largely (though not completely) surface neutralized at physiological pH around pH 7.4. One of the benefits of this $pK_a$ is that at least some nucleic acid associated with the outside surface of the particle will lose its electrostatic interaction at physiological pH and be removed by simple dialysis; thus greatly reducing the particle's susceptibility to clearance. Suitable ionizable cationic lipids for use in accordance with the present invention include, for example, Dioctadecyldimethylammonium bromide (DDAB), 1,2-dilinoleyloxy-3-dimethylaminopropane (DLinDMA), 2,2-dilinoleyl-4-(2dimethylaminoethyl)-[1,3]-dioxolane (DLin-KC2-DMA), heptatriaconta-6,9,28,31-tetraen-19-yl 4-(dimethylamino)butanoate (DLin-MC3-DMA), 1,2-Dioleoyloxy-3-dimethylaminopropane (DODAP), 1,2-Dioleyloxy-3-dimethylaminopropane (DODMA), Morpholinocholesterol (Mo-CHOL), lipidoids such as C12-200 (see Love et al., *Proc. Natl. Acad. Sci. USA* 107:1864-9, 2010), lipopeptide type compounds such as cKK-E12 (Dong et al., *Proc. Natl. Acad. Sci. USA* 111:3955-60, 2014), and lipids such as AIC-0217 and AIC-0218 (Acuitas Therapeutics, Vancouver, BC). Other suitable ionizable cationic lipids may, for example, be derived from cationic lipid structures previously described herein.

In some embodiments, a lipid nanoparticle composition contains one or more cationic lipids that are from about 0.5% to about 70% (mol %) of the total amount of lipid and delivery-enhancing components, including any polymeric (e.g., PEG) component, but not including the polynucleotide (e.g., RNA) component. In more particular variations, a lipid nanoparticle composition contains one or more cationic lipids from about 10% to about 55%, one or more cationic lipids from about 15% to about 35%, or one or more cationic lipids from about 35% to about 55%.

In certain embodiments, a lipid nanoparticle composition contains one or more non-cationic lipids, where the non-cationic lipids are from about 2% to about 95% (mol %) of the total amount of lipid and delivery-enhancing components, including any polymeric (e.g., PEG) component, but not including the polynucleotide (e.g., RNA) component. In some embodiments, a lipid nanoparticle composition contains one or more non-cationic lipids from about 20% to about 75%, or from about 45% to about 75%, or from about 45% to about 55%. In other variations, a lipid nanoparticle composition contains one or more non-cationic lipids from about 10% to about 50%.

In some embodiments, a lipid nanoparticle composition contains one or more polymeric lipids (e.g., PEG-lipid), where the polymeric lipids are from about 0.2% to about 20% (mol %) of the total amount of lipid and delivery-enhancing components, including any polymeric (e.g., PEG) component, but not including the polynucleotide (e.g., RNA) component. In some embodiments, a lipid nanoparticle composition contains one or more polymeric lipids from about 0.5% to about 10%, or one or more polymeric lipids from about 1% to about 5% of the composition.

Lipid nanoparticle formulations comprising small molecule agents are also known. See, e.g., Gubernator, *Expert Opinion on Drug Delivery* 8:565-80, 2011. For example, small molecules can be encapsulated in, e.g., a DSPC:CHOL:DSPE-PEG (50:45:5 mol %) liposome using a passive or an active loading method. Basically, for a passive loading method, the lipids are solubilized in organic solvent, then the solvent is evaporated to form a thin lipid film which is hydrated with an aqueous solution containing a hydrophilic or hydrophobic drug to be encapsulated. The liposome mixture is then typically homogenized by vortex and extruded through polycarbonate membrane in order to reduce the particle size (e.g., to ~100 nm). Non-encapsulated drug can be removed using dialysis or column filtration.

Ionizable small molecules can be actively trapped into liposomes (remote loading method). Typically, in this particular case, the drug is protonated or precipitated inside the preformed liposomes thus remaining entrapped in the liposome core. Typically, a pH gradient (acetate, citrate or ammonium sulfate) where there is a 1 to 3 pH unit difference between the liposome inner and outer compartment is used to encapsulate the ionizable small molecules. A metal gradient ($Cu^{2+}$, $Mn^{2+}$ or $Mg^{2+}$ gradient) can also be used to actively load a drug into liposomes. Ionophores such as A23187 can also be used generate a pH gradient in the liposome using $K^+$, $Mn^{2+}$ or $Mg^{2+}$. An EDTA gradient method can also be used to actively trap small molecules inside a liposome. In the remote loading method, the liposomes typically are formed by a simple lipid-film hydration technique (e.g., as described above for the passive entrapment method with the exception that the hydration buffer contain the solute required to generate the gradient across the lipid bilayer). The non-encapsulated solute is typically removed by dialysis or column filtration. Following the liposome formation and establishment of a gradient across the liposomal bilayers, an unprotonated drug is added in the loading buffer outside the liposome and can cross the lipid bilayer and becomes protonated inside the liposome, and then become stabilized by the anions present in the internal aqueous compartment of the liposome. The suspension may need to be incubated above the phase transition temperature of the liposomal lipids to accelerate the drug loading. The non-encapsulated free drug can be removed, by dialysis or by ion exchange chromatography.

Lipid nanoparticle formulations for protein or peptide therapeutics are also generally known. In some embodiments, proteinaceous agents are incorporated into liposomes by a lipid film hydration method. For example, a protein may be incorporated into PEGylated liposomes composed of, e.g., egg phosphatidylcholine (EPC), cholesterol, sodium cholesterol-3-sulfate and distearolyphosphatidyl ethanolamine-N-PEG 2000 (DSPE-PEG [2000]). Such a formulation method was shown to increase pharmacokinetics substantially for tPA incorporated into a liposome. See Kim et al., Biomaterials 30:5751-5756, 2009.

In some embodiments, a lipid nanoparticle composition includes a cationic lipid, an anionic lipid, a helper lipid, and a PEG-lipid. Such a mixture of LNP lipid components can be represented by the formula [cationic lipid]$_w$:[anionic lipid]$_x$:[helper lipid]$_y$: [PEG-lipid]$_z$, where the subscripts w, x, y, and z represent the mole % of each lipid component within the mixture (not including the therapeutic or diagnostic agent component (e.g., polynucleotide) of the LNP). This formula can be alternatively expressed as [cationic lipid]:[anionic lipid]:[helper lipid]:[PEG-lipid](w:x:y:z), where w, x, y, and z represent the mole % of the cationic lipid, anionic lipid, helper lipid, and PEG-lipid, respectively. In various embodiments, each of the cationic lipid, anionic lipid, helper lipid, and PEG-lipid are selected from the exemplary lipids disclosed herein. In some embodiments, w is from about 10 to about 70, from about 30 to about 60, or from about 35 to about 55; x is from 0 to about 60, from 0 to about 50, from about 10 to about 50, or from about 20 to about 45; y is from about 5 to about 40, from about 5 to about 30, or from about 5 to about 20; and z is from about 1 to about 20, from about 2 to about 20, or from about 5 to about 15. For example, a lipid mixture having the cationic lipid DOTAP present at about 50 mole %, the anionic lipid CHEMS present at about 32 mole %, the helper lipid CHOL present at about 8 mole %, and the PEG-lipid DMPE-PEG2k present at about 10 mole % can be expressed as DOTAP$_{50}$: CHEMS$_{32}$:CHOL$_8$:DMPE-PEG2k$_{10}$ or as DOTAP: CHEMS:CHOL:DMPE-PEG2k (50:32:8:10).

In particular embodiments, a lipid nanoparticle for use in accordance with the present invention includes a mixture of lipid components comprising (i) a cationic lipid from about 30 mole % to about 60 mole %; (ii) an anionic lipid from 0 mole % to about 50 mole %; (iii) a helper lipid from about 1 mole % to about 50 mole %; and (iv) a PEG-lipid from about 1 mole % to about 20 mole %. Typically, the cationic lipid is a cationic lipid that is permanently charged at physiological pH (e.g., DOTAP). If present, the anionic lipid is typically an ionizable anionic lipid such as, for example, CHEMS. A particularly suitable helper lipid for use such embodiments is cholesterol (CHOL), and particularly suitable PEG-lipids include DSPE-PEG2k and DMPE-PEG2k. An excess of cationic lipid to anionic lipid, if present, is preferred. In some variations, (i) the cationic lipid (e.g., DOTAP) is present in the lipid mixture from about 35 mole % to about 55 mole %, from about 40 mole % to about 55 mole %, from about 45 mole % to about 55 mole %, or from about 40 mole % to about 50 mole %; (ii) the anionic lipid (e.g., CHEMS) is present in the lipid mixture from 0 mole % to about 45 mole %, from about 10 mole % to about 45 mole %, from about 20 mole % to about 45 mole %, from about 30 mole % to about 45 mole %, or from about 30 mole % to about 40 mole %; (iii) the helper lipid (e.g., CHOL) is present in the lipid mixture from about 5 mole % to about 50 mole %, from about 5 mole % to about 40 mole %, from about 5 mole % to about 30 mole %, from about 5 mole % to about 20 mole %, or from about 5 mole % to about 10 mole %; and (iv), the PEG-lipid (e.g., DSPE-PEG2k or DMPE-PEG2k) is present in the lipid mixture from about 1 mole % to about 5 mole %, from about 2 mole % to about 20 mole %, from about 2% mole % to about 15 mole %, from about 2 mole % to about 10 mole %, from about 5 mole % to about 20 mole %, from about 5 mole % to about 15 mole %, or from about 5 mole % to about 10 mole %. In some preferred embodiments, the PEG-lipid is present in the lipid mixture at a mole % greater than 5 (e.g., from a mole % greater than 5 to about 20 mole %, to about 15 mole %, or to about 10 mole %); in some such embodiments, the PEG-lipid is present at mole % of at least about 6, at least about 7, at least about 8, at least about 9, or least about 10. In some embodiments of an LNP composition as above wherein an anionic lipid is absent, the cationic lipid (e.g., DOTAP) is present in the lipid mixture from about 35 mole % to about 45 mole %; the helper lipid (e.g., CHOL) is present in the lipid mixture from about 40 mole % to about 50 mole %; and the PEG-lipid (e.g., DSPE-PEG2k or DMPE-PEG2k) is present in the lipid mixture from about 5 mole % to about 15 mole %; in some such embodiments, the molar ratio of [cationic lipid]:[helper lipid]:[PEG-lipid] is about 40:50:10. In other embodiments of an LNP composition as above wherein an anionic lipid is present, the cationic lipid (e.g., DOTAP) is present in the lipid mixture from about 40 mole % to about 55 mole %; the anionic lipid (e.g., CHEMS) is present in the lipid mixture from about 25 mole % to about 40 mole %; the helper lipid (e.g., CHOL) is present in the lipid mixture from about 5 mole % to about 20 mole %; and the PEG-lipid (e.g., DSPE-PEG2k or DMPE-PEG2k) is present in the lipid mixture from about 2 mole % to about 15 mole %, from about 2 mole % to about 10 mole %, or from about 5 mole % to about 15 mole %; in some such embodiments, the molar ratio of [cationic lipid]:[anionic lipid]:[helper lipid]:[PEG-lipid] is about 50:32:16:2 or about 50:32:8:10. In more specific variations, the LNP composition includes a mixture of lipid components (with the molar ratio of components specified in parentheses) selected from (a) DOTAP:CHEMS:CHOL:DMPE-PEG2k (50:32:16:2); (b) DOTAP:CHEMS:CHOL:DSPE-PEG2k (50:32:8:10); (c) DOTAP:CHEMS:CHOL:DMPE-PEG2k (50:32:8:10); and (d) DOTAP:CHOL:DSPE-PEG2k (40:50: 10). Mixtures of lipid components as described above are particularly suitable for lipid nanoparticle compositions comprising a polynucleotide such as, for example, an mRNA. LNPs comprising a high PEG-lipid content (for example, a mole % of greater than 5, such as, e.g., about 10%) represent some preferred embodiments for polynucleotide (e.g., mRNA) delivery, and as shown by studies described herein, higher PEG-lipid content was particularly efficacious in methods for delivery of polynucleotides to cells in vivo. See, e.g., Example 20.

In some embodiments, a lipid nanoparticle is less than about 200 nm in size. For example, the lipid nanoparticle may be from about 30 nm to about 150 nm in size. In certain variations, the size of the lipid nanoparticle (e.g., between about 30 nm and about 150 nm) facilitates delivery to the liver by an enhanced permeation and retention effect. The lipid nanoparticle may further include a targeting ligand to target the particle to a desired tissue. The lipid nanoparticle may have a positive or negative zeta potential; in some variations, the zeta potential of the lipid nanoparticle is substantially neutral.

In accordance with the present invention, a membrane-destabilizing polymer is either co-formulated with the lipid nanoparticle containing the therapeutic or diagnostic agent, for co-injection into a subject, or is separately formulated for separate injection (e.g., sequential injection) of the LNP and membrane-destabilizing polymer. Typically, for co-injection variations, the lipid nanoparticle and membrane-destabilizing polymer are initially formulated as separate compositions and then mixed together into a single composition prior to administration (typically within one hour prior to administration, more typically within 30 minutes prior to administration, and preferably within 15 minutes or within five minutes prior to administration). The membrane-destabilizing polymer elicits a permeability change in a cellular membrane structure (e.g., an endosomal membrane) so as to permit macromolecules or biomolecules, or small molecules, to enter a cell or to exit a cellular vesicle (e.g., an endosome or lysosome). A variety of membrane-destabilizing polymers are generally known in the art and may be used in accordance with the present methods described herein. Known types of membrane-destabilizing polymers include, for example, copolymers such as amphipathic copolymers, polycationic or amphipathic peptides, membrane active toxins, and viral fusogenic peptides. Certain types of particularly suitable membrane-destabilizing polymers are described, e.g., in International PCT Application Publication Nos. WO 2009/140427 and WO 2009/140429, each incorporated by reference herein in its entirety.

In some embodiments, a membrane-destabilizing polymer is or comprises a membrane-destabilizing peptide. In particular variations, a membrane-destabilizing peptide is selected from

```
GALA
(e.g., WEAALAEALAEALAEHLAEALAEALEALAA (SEQ ID NO: 15));

truncated GALA
(e.g., CAEALAEALAEALAEALA (SEQ ID NO: 16));

melittin
(e.g., GIGAVLKVLTTGLPALISWIKRKRQQ (SEQ ID NO: 17)
or

CGIGAVLKVLTTGLPALISWIKRKRQQ (SEQ ID NO: 18));

HPH-1
(e.g., FIIDIIAFLLMGGFIVYVKNL (SEQ ID NO: 19)
or

CAAFIIDHAFLLMGGFIVYVKNL (SEQ ID NO: 20));

sHGP
(e.g., CARGWEVLKYWWNLLQY (SEQ ID NO: 21));

bPrPp
(e.g., MVKSKIGSWILVLFVAMWSDVGLCKKRPKP (SEQ ID NO: 22));

MAP
(e.g., KLALKLALKALKAALKLA (SEQ ID NO: 23));

PTD4
(e.g., YARAAARQARA (SEQ ID NO: 24));

Maurocalcine
(e.g., GDCLPHLKLCKENKDCCSKKCKRRGTNIE (SEQ ID NO: 25));

SynB3
(e.g., RRLSYSRRRF (SEQ ID NO: 26));

SynB1
(e.g., RGGRLSYSRRRFSTSTGR (SEQ ID NO: 27));

YTA4
(e.g., IAWVKAFIRKLRKGPLG (SEQ ID NO: 28));

YTA2
(e.g., YTAIAWVKAFIRKLRK (SEQ ID NO: 29));

CADY
(e.g., GLWRALWRLLRSLWRLLWRA (SEQ ID NO: 30));

Pep-3
(e.g., KWFETWFTEWPKKRK (SEQ ID NO: 31));

Pep-1
(e.g., KETWWETWWTEWSQPKKKRKV (SEQ ID NO: 32));
```

```
PepFect
(e.g., AGYLLGK(eNHa)INLKALAALAKKIL (SEQ ID NO: 33));

PepFect-3
(e.g., AGYLLGKINLKALAALAKKIL (SEQ ID NO: 34));

Penetratin
(e.g., RQIKIWFQNRRMKWKK (SEQ ID NO: 35));

KALA
(e.g., WEAKLAKALAKALAKHLAKALAKALKACEA (SEQ ID NO: 36));

pVEC
(e.g., LLIILRRRIRKQAHAHSK (SEQ ID NO: 37));

RVG
(e.g., YTIWMPENPRPGTPCDIFTNSRGKRASNG (SEQ ID NO: 38));

MPS
(e.g., AAVALLPAVLLALLAK (SEQ ID NO: 39));

Transportan
(e.g., GWTLNSAGYLLGKINLKALAALAKKIL (SEQ ID NO: 40));

TAT
(e.g., GRKKRRQRRPPQ (SEQ ID NO: 41));

BMV Gag-(7-25)
(e.g., KMTRAQRRAAARRNRRWTAR (SEQ ID NO: 42));

hCT(18-32)-k7
(e.g., KKRKAPKKKRKFA-KFHTFPQTAIGVGAP (SEQ ID NO: 43));

M1073
(e.g., MVTVLFRRLRIRRASGPPRVRV (SEQ ID NO: 44));

EB1
(e.g., LIRLWSHLIHIWFQNRRLKWKKK (SEQ ID NO: 45))
and

MPG-β
(e.g., GALFLGFLGAAGSTMGAWSQPKKKRKV (SEQ ID NO: 46)
or

GALFLAFLAAALSLMGLWSQPKKKRKV (SEQ ID NO: 47)).
```

The membrane-destabilizing polymer can be a pH sensitive polymer having membrane-destabilizing activity at a desired pH. In some embodiments, membrane-destabilizing polymers (e.g., copolymers such as block copolymers) provided herein are membrane destabilizing (e.g., in an aqueous medium) at an endosomal pH. In some embodiments, the membrane-destabilizing polymers are membrane destabilizing (e.g., in an aqueous medium) at a pH of about 6.5 or lower, preferably at a pH ranging from about 5.0 to about 6.5, or at a pH of about 6.2 or lower, preferably at a pH ranging from about 5.0 to about 6.2, or at a pH of about 6.0 or lower, preferably at a pH ranging from about 5.0 to about 6.0.

Typically, in each case, the membrane-destabilizing polymer can have membrane destabilizing activity at a desired quantity (e.g., concentration) of polymer. A membrane-destabilizing characteristic of a polymer can be determined by suitable assays known in the art. For example, membrane-destabilizing activity of a polymer can be determined in an in vitro cell assay such as the red blood cell hemolysis assay or a liposomal leakage assay. An endosomolytic polymer activity can be determined in an in vitro cell assay.

In general, the membrane-destabilizing polymer is composed of monomeric residues with particular properties. For example, the polymer may have amines that are primary, secondary, tertiary, or quaternary and which drive interactions of the polymer with membranes. These amines may be permanently charged or have $pK_a$s ranging from 4 to 14. In particular, these $pK_a$s may be between 4.5 and 7.5 such that they can undergo acid-base reactions in endosome. The polymers may also have hydrophobic groups to further enhance interaction with membranes. The polymer may also have carboxylic functional groups with $pK_a$s in the range of 4.0 to 7.5.

In certain embodiments, a membrane-destabilizing polymer includes one or more monomeric species selected from anionic, cationic, hydrophobic, and hydrophilic monomeric residues. Anionic monomeric residues comprise a species charged or chargeable to an anion, including a protonatable anionic species. Anionic monomeric residues can be anionic at an approximately neutral pH of 7.2-7.4. Cationic monomeric residues comprise a species charged or chargeable to a cation, including a deprotonatable cationic species. Cationic monomeric residues can be cationic at an approximately neutral pH of 7.2-7.4. Hydrophobic monomeric residues comprise a hydrophobic species. Hydrophilic monomeric residues comprise a hydrophilic species.

In some variations, a membrane-destabilizing polymer is or comprises at least one polymer chain that is hydrophobic. In some such embodiments, the polymer is or comprises at least one polymer chain that includes a plurality of anionic monomeric residues. In this regard, for example, the polymer may be or comprise at least one polymer chain that includes (i) a plurality of hydrophobic monomeric residues having a hydrophobic species, and (ii) a plurality of anionic monomeric residues that are preferably anionic at approximately neutral pH, and substantially neutral or non-charged at an endosomal pH or weakly acidic pH.

In such aforementioned embodiments, the polymer can further include a plurality of cationic species. Accordingly, for example, the polymer can be or comprise at least one polymer chain that includes a plurality of anionic monomeric residues (e.g., having species that are anionic at about neutral pH), and a plurality of hydrophobic monomeric residues (e.g., having hydrophobic species), and optionally a plurality of cationic monomeric residues (e.g., having species that are cationic at about neutral pH). In such embodiments, and as discussed further below, the polymer can be or comprise at least one polymer chain that is charge modulated, and preferably charge balanced—being substantially overall neutral in charge.

In some embodiments, membrane-destabilizing polymer is a block copolymer comprising a membrane-destabilizing segment (e.g., as a block or region of the polymer). The membrane-destabilizing segment can comprise a plurality of anionic monomeric residues (e.g., having species that are anionic at about neutral pH), and a plurality of hydrophobic monomeric residues (e.g., having hydrophobic species), and optionally a plurality of cationic monomeric residues (e.g., having species that are cationic at about neutral pH). In such embodiments, the segment (e.g., block or region) can be hydrophobic considered in the aggregate. In such embodiments, the block copolymer may further comprise a hydrophilic segment.

In some embodiments of a block copolymer comprising a membrane-destabilizing block, the block copolymer includes a first polymer chain defining a first block A of the copolymer and a second, membrane-destabilizing polymer chain defining a second block B of the copolymer. For example, the block copolymer can comprise a first polymer chain defining a first block A of the copolymer, which is hydrophilic, and a second polymer chain defining a second block B of the copolymer that includes (i) a plurality of hydrophobic monomeric residues and (ii) a plurality of anionic monomeric residues being anionic at serum physiological pH and substantially neutral or non-charged at an endosomal pH.

In some embodiments, the membrane-destabilizing polymer is or comprises at least one polymer chain that includes a plurality of anionic monomeric residues, a plurality of hydrophobic monomeric residues, and optionally a plurality of cationic monomeric residues in ratios adapted to enhance membrane destabilizing or membrane destabilizing activity of the polymer chain. For example and without limitation, in such embodiments at pH 7.4, the ratio of hydrophobic:(anionic+cationic) species ranges from about 1:2 to about 3:1, and the ratio of anionic:cationic species ranges from about 1:0 to about 1:5. In other such embodiments, at pH 7.4, the ratio of hydrophobic:(anionic+cationic) species ranges from about 1:1 to about 2:1, and the ratio of anionic:cationic species ranges from about 4:1 to about 1:5.

In some embodiments, the membrane-destabilizing polymer is or comprises at least one polymer chain that includes a plurality of cationic monomeric residues, a plurality of hydrophobic monomeric residues, and optionally a plurality of anionic monomeric residues in ratios adapted to enhance membrane destabilizing or membrane destabilizing activity of the polymer chain. For example and without limitation, in such embodiments at pH 7.4, the ratio of hydrophobic:(cationic+anionic) species ranges from about 1:2 to about 3:1, and the ratio of cationic:anionic species ranges from about 1:0 to about 1:20. In other such embodiments, at pH 7.4, the ratio of hydrophobic:(cationic+anionic) species ranges from about 1:1 to about 2:1, and the ratio of cationic: anionic species ranges from about 1:0 to about 1:5.

In some embodiments, the membrane-destabilizing polymer is or comprises at least one polymer chain that includes a plurality of cationic monomeric residues, and optionally a plurality of hydrophobic monomeric residues in ratios adapted to enhance membrane destabilizing or membrane destabilizing activity of the polymer chain. For example and without limitation, in such embodiments at pH 7.4, the ratio of hydrophobic:cationic species ranges from about 0:1 to about 5:1. In other such embodiments, at pH 7.4, the ratio of hydrophobic:cationic species ranges from about 0:1 to about 2:1.

Generally, the membrane-destabilizing polymer can be or comprise at least one polymer chain that is charge modulated, for example including hydrophobic monomeric residues together with both anionic monomeric residues and cationic monomeric residues. The relative ratio of anionic monomeric residues and cationic monomeric residues can be controlled to achieve a desired overall charge characteristic. In typical embodiments, for example, such polymer or polymer chain can be charge balanced—having a substantially neutral overall charge in an aqueous medium at physiological pH (e.g., pH 7.2 to 7.4).

Embodiments comprising a block copolymer, in which at least one block is or comprises a membrane-destabilizing polymer, such as a hydrophobic membrane-destabilizing polymer, can comprise one or more further polymer chains as additional blocks of the block copolymer. Generally, such further polymer blocks are not narrowly critical, and can be or comprise a polymer chain which is hydrophilic, hydrophobic, amphiphilic, and in each case, which is neutral, anionic or cationic in overall charge characteristics.

In some embodiments, the membrane-destabilizing polymer is or comprises a polymer chain that is adapted to facilitate one or more additional constituent components and/or functional features. For example, such polymer chain can comprise an end functional group (e.g., on the alpha end or omega end of the polymer chain) adapted for covalently linking, directly or indirectly, to a targeting ligand (affinity reagent) or a shielding agent. Additionally or alternatively, such polymer chain can comprise one or more monomeric residues having a pendant functional group adapted for conjugating to an agent. Such conjugatable monomeric residues can be effected for covalently linking, directly or indirectly, to an affinity reagent, a shielding agent, or other biomolecular agent. Additionally or alternatively, such polymer chain can comprise one or more monomeric residues having a shielding species. For example, shielding monomeric residues can be derived directly from a polymerization reaction which includes polymerizable monomers comprising a shielding moiety. Shielding agents include poly ethylene glycol monomers and/or polymers. Additionally or alternatively, such polymer chain can comprise one or more monomeric residues having a two or more pendant functional groups suitable for cross-linking between polymer chains. Such cross-linking monomeric residues can be a constituent moiety of a cross-linked polymer or polymer chain, as derived directly from a polymerization reaction that includes one or more polymerizable monomers comprising a multi-functional (e.g., bis-functional) cross-linking monomer.

Generally, one or more blocks of a block copolymer can be a random copolymer block which comprises two or more compositionally distinct monomeric residues.

Generally, a single monomeric residue can include multiple moieties having different functionality—e.g., can comprise hydrophobic species as well as anionic species, can comprise hydrophobic species as well as cationic species, or can comprise anionic species as well as cationic species. Hence, in any embodiment, the polymer can be or can comprise a polymer comprising a monomeric residue such as an anionic hydrophobic monomeric residue—which includes hydrophobic species and anionic species (e.g., species that are anionic at about neutral pH).

In typical variations, anionic monomeric residues comprise a protonatable anionic species. Considered in the aggregate, as incorporated into a polymer chain, such anionic monomeric residues can be substantially anionic at a pH of or greater than 7.0 and substantially neutral (non-charged) at pH of or less than 6.0. Preferably, such anionic monomeric residues have a $pK_a$ ranging from about 4 to about 6.8, (e.g., from about 4 to about 6, from about 4 to about 5, from about 5 to about 6, from about 5 to about 6.8, or from about 5.5 to about 6.8). Anionic monomeric residues can independently comprise a plurality of monomeric residues having a protonatable anionic species selected from carboxylic acid, sulfonamide, boronic acid, sulfonic acid, sulfinic acid, sulfuric acid, phosphoric acid, phosphinic acid, and phosphorous acid groups, and combinations thereof. Particularly suitable anionic monomeric residues may be derived from polymerization of a ($C_2$-$C_8$) alkylacrylic acid.

Hydrophobic monomeric residues can be charged or noncharged, generally. Some embodiments include neutral (non-charged) hydrophobic monomeric residues. In some embodiments, polymer chains can independently comprise a plurality of monomeric residues having a hydrophobic species selected from ($C_1$-$C_{18}$) alkyl (e.g., ($C_2$-$C_8$) alkyl), ($C_1$-$C_{18}$) alkenyl (e.g., ($C_2$-$C_8$) alkenyl), ($C_1$-$C_{18}$) alkynyl (e.g., ($C_2$-$C_8$) alkynyl), aryl, heteroaryl, and cholesterol (each of which may be optionally substituted). In certain embodiments, the plurality of monomeric residues can be derived from polymerization of ($C_1$-$C_{18}$) alkyl-ethacrylate (e.g., ($C_2$-$C_8$) alkyl-ethacrylate), a ($C_1$-$C_{18}$) alkyl-methacrylate (e.g., ($C_2$-$C_8$) alkyl-methacrylate), or a ($C_1$-$C_{18}$) alkyl-acrylate (e.g., ($C_2$-$C_8$) alkyl-acrylate) (each of which may be optionally substituted).

Cationic monomeric residues can preferably comprise a deprotonatable cationic species. Considered in the aggregate, as incorporated into a polymer chain, such cationic monomeric residues can be substantially cationic at a pH of or greater than 7.0. Preferably, such cationic monomeric residues have a $pK_a$ ranging from about 5.5 to about 9.0 (e.g., from about 6.5 to about 9.0). Cationic monomeric residues can independently comprise a plurality of monomeric residues having a deprotonatable cationic species selected from the group consisting of acyclic amine, acyclic imine, cyclic amine, cyclic imine, and nitrogen-containing heteroaryl. Preferred cationic monomeric residues can be derived from polymerization of, in each case optionally substituted, (N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, or N,N-di($C_1$-$C_6$)alkyl-amino ($C_1$-$C_6$)alkyl-acrylate.

In some embodiments, a pH-sensitive membrane-destabilizing polymer includes a random copolymer chain, such as, e.g., a random copolymer chain comprising two or more monomeric residue species as described above. For example, in particular variations, the random copolymer chain has monomeric residues derived from polymerization of propyl acrylic acid, N,N-dimethylaminoethylmethacrylate, and butyl methacrylate. In particular embodiments, the pH-sensitive polymer is a block copolymer comprising the random copolymer chain as a membrane-destabilizing polymer block, and further comprising one or more additional blocks (e.g., a hydrophilic block). For example, in some embodiments, the polymer is a diblock copolymer comprising a membrane-destabilizing random copolymer block and a second block, which can be represented by the schematic $[A]_v$-$[B]_w$, where [B] represents the membrane-destabilizing block, [A] represents the second block (e.g., a hydrophilic block or an amphiphilic block), and the letters v and w represent the molecular weight (number average) of the respective blocks in the copolymer. In certain variations of a block copolymer comprising a membrane-destabilizing polymer block and a hydrophilic block, the hydrophilic block is polymerized from both hydrophilic monomers and hydrophobic monomers such that there are more hydrophilic monomeric residues than hydrophobic monomeric residues in the hydrophilic block.

In some variations, a pH-sensitive membrane-destabilizing polymer is a diblock copolymer having a hydrophilic random copolymer block and a hydrophobic random copolymer block, where (i) the hydrophilic block is an amphiphilic block comprising both hydrophilic monomeric residues and hydrophobic monomeric residues, where the number of hydrophilic monomeric residues in the hydrophilic block is greater than the number of hydrophobic monomeric residues, (ii) the hydrophobic block is an amphiphilic, membrane-destabilizing block comprising both hydrophobic monomeric residues and hydrophilic monomeric residues and having an overall hydrophobic character at a pH of about 7.4, and (iii) each of the hydrophilic monomeric residues of the hydrophilic and hydrophobic blocks is independently selected from monomeric residues that are ionic at a pH of about 7.4, monomeric residues that are neutral at a pH of about 7.4, and monomeric residues that are zwitterionic at a pH of about 7.4. In some such embodiments, the monomers used to prepare the diblock copolymer comprise acrylate(s), methacrylate(s), acrylamide(s), and/or methacrylamide(s). In particular variations, the hydrophilic block comprises hydrophilic monomeric residues that are neutral at a pH of about 7.4, and/or the hydrophobic block comprises both hydrophilic monomeric residues that are cationic at a pH of about 7.4 and hydrophilic monomeric residues that are anionic at a pH of about 7.4. Suitable hydrophilic and hydrophobic monomeric residues for use in a diblock copolymer as above are further described herein. In some embodiments, a diblock copolymer as above is a random block copolymer of formula I as set forth herein.

In some variations, a pH-sensitive membrane-destabilizing polymer is a diblock copolymer having a hydrophilic random copolymer block and a hydrophobic random copolymer block, where (i) the hydrophilic block is an amphiphilic block comprising both hydrophilic monomeric residues and hydrophobic monomeric residues and having an overall hydrophilic character at a pH of about 7.4, (ii) the hydrophobic block is an amphiphilic, membrane-destabilizing block comprising both hydrophobic monomeric residues and hydrophilic monomeric residues and having an overall hydrophobic character at a pH of about 7.4, and (iii) each of the hydrophilic monomeric residues of the hydrophilic and hydrophobic blocks is independently selected from monomeric residues that are ionic at a pH of about 7.4, monomeric residues that are neutral at a pH of about 7.4, and monomeric residues that are zwitterionic at a pH of about 7.4. In some such embodiments, the monomers used to prepare the diblock copolymer comprise acrylate(s), methacrylate(s), acrylamide(s), and/or methacrylamide(s).

In certain embodiments, a pH-sensitive polymer is covalently linked to a membrane-destabilizing peptide. For example, the pH-sensitive polymer may include a plurality of pendant linking groups, and a plurality of membrane-destabilizing peptides may be linked to the pH-sensitive polymer via the plurality of pendant linking groups. In some variations, a peptide comprising a cysteine residue at either the amino or carboxyl terminus is conjugated to a monomer containing a disulfide moiety through the cysteine thiol to form a disulfide bridge. Exemplary membrane-destabilizing peptides that may be linked to a polymer include, for example,

```
GALA
(e.g., WEAALAEALAEALAEHLAEALAEALEALAA (SEQ ID NO: 15));

truncated GALA
(e.g., CAEALAEALAEALAEALA (SEQ ID NO: 16));

melittin
(e.g., GIGAVLKVLTTGLPALISWIKRKRQQ (SEQ ID NO: 17)
or

CGIGAVLKVLTTGLPALISWIKRKRQQ (SEQ ID NO: 18));

HPH-1
(e.g., FIIDIIAFLLMGGFIVYVKNL (SEQ ID NO: 19)
or

CAAFIIDHAFLLMGGFIVYVKNL (SEQ ID NO: 20));

sHGP
(e.g., CARGWEVLKYWWNLLQY (SEQ ID NO: 21));

bPrPp
(e.g., MVKSKIGSWILVLFVAMWSDVGLCKKRPKP (SEQ ID NO: 22));

MAP
(e.g., KLALKLALKALKAALKLA (SEQ ID NO: 23));

PTD4
(e.g., YARAAARQARA (SEQ ID NO: 24));

Maurocalcine
(e.g., GDCLPHLKLCKENKDCCSKKCKRRGTNIE (SEQ ID NO: 25));

SynB3
(e.g., RRLSYSRRRF (SEQ ID NO: 26));

SynB1
(e.g., RGGRLSYSRRRFSTSTGR (SEQ ID NO: 27));

YTA4
(e.g., IAWVKAFIRKLRKGPLG (SEQ ID NO: 28));

YTA2
(e.g., YTAIAWVKAFIRKLRK (SEQ ID NO: 29));

CADY
(e.g., GLWRALWRLLRSLWRLLWRA (SEQ ID NO: 30));

Pep-3
(e.g., KWFETWFTEWPKKRK (SEQ ID NO: 31));

Pep-1
(e.g., KETWWETWWTEWSQPKKKRKV (SEQ ID NO: 32));

PepFect
(e.g., AGYLLGK(eNHa)INLKALAALAKKIL (SEQ ID NO: 33));

PepFect-3
(e.g., AGYLLGKINLKALAALAKKIL (SEQ ID NO: 34));

Penetratin
(e.g., RQIKIWFQNRRMKWKK (SEQ ID NO: 35));

KALA
(e.g., WEAKLAKALAKALAKHLAKALAKALKACEA (SEQ ID NO: 36));

pVEC
(e.g., LLIILRRRIRKQAHAHSK (SEQ ID NO: 37));

RVG
(e.g., YTIWMPENPRPGTPCDIFTNSRGKRASNG (SEQ ID NO: 38));

MPS
(e.g., AAVALLPAVLLALLAK (SEQ ID NO: 39));
```

-continued

Transportan
(e.g., GWTLNSAGYLLGKINLKALAALAKKIL (SEQ ID NO: 40));

TAT
(e.g., GRKKRRQRRPPQ (SEQ ID NO: 41));

BMV Gag-(7-25)
(e.g., KMTRAQRRAAARRNRRWTAR (SEQ ID NO: 42));

hCT(18-32)-k7
(e.g., KKRKAPKKKRKFA-KFHTFPQTAIGVGAP (SEQ ID NO: 43));

M1073
(e.g., MVTVLFRRLRIRRASGPPRVRV (SEQ ID NO: 44));

EB1
(e.g., LIRLWSHLIHIWFQNRRLKWKKK (SEQ ID NO: 45))
and

MPG-β
(e.g., GALFLGFLGAAGSTMGAWSQPKKKRKV (SEQ ID NO: 46)
or

GALFLAFLAAALSLMGLWSQPKKKRKV (SEQ ID NO: 47)).

In some embodiments, a pH-sensitive polymer includes a random block copolymer of formula I:

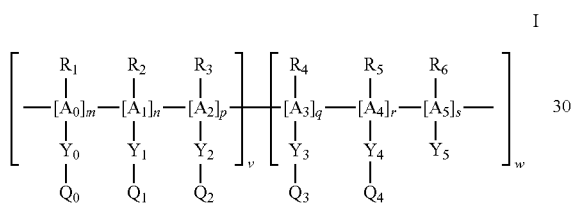

where
- $A_0$, $A_1$, $A_2$, $A_3$, $A_4$ and $A_5$ are each independently selected from the group consisting of —C—C—, —C(O)(C)$_a$C(O)O—, —O(C)$_a$C(O)—, —O(C)$_b$—, and —CR$_8$—CR$_9$; where tetravalent carbon atoms of $A_0$-$A_5$ that are not fully substituted with $R_1$-$R_6$ and $Y_0$-$Y_5$ are completed with an appropriate number of hydrogen atoms; wherein a and b are each independently 1-4; and where $R_8$ and $R_9$ are each independently selected from the group consisting of —C(O)OH, —C(O)Oalkyl, and —C(O)NR$_{10}$, where $R_8$ and $R_9$ are optionally covalently linked together to form a ring structure (e.g., a cyclic anhydride or cyclic imide);
- $Y_5$ is hydrogen or is selected from the group consisting of -(1C-10C)alkyl, -(3C-6C)cycloalkyl, —O-(1C-10C)alkyl, —C(O)O(1C-10C)alkyl, —C(O)NR$_{11}$(1C-10C)alkyl, and -(6C-10C)aryl, any of which is optionally substituted with one or more fluorine atoms;
- $Y_0$, $Y_3$, and $Y_4$ are each independently selected from the group consisting of a covalent bond, -(1C-10C)alkyl-, —C(O)O(2C-10C)alkyl-, —OC(O)(1C-10C)alkyl-, —O(2C-10C)alkyl-, —S(2C-10C)alkyl-, and —C(O)NR$_{12}$(2C-10C)alkyl-;
- $Y_1$ and $Y_2$ are each independently selected from the group consisting of a covalent bond, -(1C-18C)alkyl-, -(3C-18C)branched alkyl, —C(O)O(2C-18C)alkyl-, —C(O)O(2C-18C)branched alkyl, —OC(O)(1C-18C)alkyl-, —OC(O)(1C-18C)branched alkyl, —O(2C-18C)alkyl-, —O(2C-18C)branched alkyl-, —S(2C-18C)alkyl-, —S(2C-18C)branched alkyl-, —C(O)NR$_{12}$(2C-18C)alkyl-, and —C(O)NR$_{12}$(2C-18C)branched alkyl-, where any alkyl or branched alkyl group of $Y_1$ or $Y_2$ is optionally substituted with one or more fluorine atoms;
- $R_1$, $R_2$, $R_3$, $R_4$, $R_5$, $R_6$, $R_8$, $R_9$, $R_{10}$, $R_{11}$, and $R_{12}$ are each independently hydrogen, —CN, or selected from the group consisting of alkyl, alkynyl, heteroalkyl, cycloalkyl, heterocycloalkyl, aryl and heteroaryl, any of which is optionally substituted with one or more fluorine atoms;
- $Q_0$ is a residue selected from the group consisting of residues which are hydrophilic at physiologic pH; O—[(C)$_{2-3}$—O]$_x$—R$_7$; and O—[(C)$_{2-3}$—O]$_x$—C(O)—NR$_{13}$R$_{14}$; where x is 1-48; R$_7$ is —CH$_3$ or —CO$_2$H; and $R_{13}$ and $R_{14}$ are each independently hydrogen, —CN, or selected from the group consisting of alkyl, alkynyl, heteroalkyl, cycloalkyl, heterocycloalkyl, aryl and heteroaryl, any of which is optionally substituted with one or more fluorine atoms;
- $Q_1$ and $Q_2$ are each independently absent or selected from a residue which is hydrophilic at normal physiological pH; a conjugatable or functionalizable residue; a residue which is hydrophobic at normal physiological pH; an alkyl group optionally substituted with one or more fluorine atoms; and a branched alkyl group optionally substituted with one or more fluorine atoms;
- $Q_3$ is a residue which is positively charged at normal physiological pH;
- $Q_4$ is a residue which is negatively charged at normal physiological pH, but undergoes protonation at lower pH;
- m is a mole fraction of greater than 0 to 1.0;
- n is a mole fraction of 0 to less than 1.0;
- p is a mole fraction of 0 to less than 1.0; wherein m+n+p=1;
- q is a mole fraction of 0.1 to 0.9;
- r is a mole fraction of 0.05 to 0.9;
- s is present up to a mole fraction of 0.85; wherein q+r+s=1;
- v is from 1 to 25 kDa; and
- w is from 1 to 50 kDa.

In certain embodiments of a polymer of formula I as above, m is greater than n+p. In some such variations, p is 0.

In certain embodiments of a polymer of formula I as above, n is greater than 0. Particularly suitable polymers of formula I where n is greater than 0 include polymers where R$_2$-A$_1$-Y$_1$-Q$_1$ taken together is a monomeric residue having an overall hydrophobic character. In some such variations, the hydrophobic monomer contains an alkyl or branched alkyl group substituted with one or more fluorine atoms (e.g., at least one of Y$_1$ and Q$_1$ contains the alkyl or branched alkyl group as specified in formula I for Y$_1$ and Q$_1$, and where the alkyl or branched alkyl group is substituted with the one or more fluorine atoms).

In some variations of a polymer of formula I where n is greater than 0, p is 0. In some such embodiments, m is greater than n. For example, m is typically greater than n where R$_2$-A$_1$-Y$_1$-Q$_1$ taken together is a monomeric residue having an overall hydrophobic character.

In some specific embodiments of a polymer of formula I, the ratio of w:v ranges from about 1:1 to about 5:1, or from about 1:1 to about 2:1.

Exemplary but non-limiting membrane-destabilizing polymers can be or comprise a polymer chain which is a random copolymer represented as formula 1, optionally with one or more counterions.

In certain embodiments, the constitutional units of the second block of formula 1 are derived from the polymerizable monomers N,N-dimethylaminoethylmethacrylate (DMAEMA), propylacrylic acid (PAA) and butyl methacrylate (BMA).

In certain embodiments comprising a pH-sensitive polymer of formula I, the pH-sensitive polymer is a polymer of formula II:

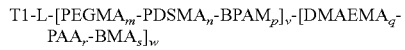
T1-L-[PEGMA$_m$-PDSMA$_n$-BPAM$_p$]$_v$-[DMAEMA$_q$-PAA$_r$-BMA$_s$]$_w$    II where
PEGMA is polyethyleneglycol methacrylate residue with 2-20 ethylene glycol units;
PDSMA is pyridyl disulfide methacrylate residue;
BPAM is 2-[2-Boc amino ethoxy]ethyl methacrylate residue;
BMA is butyl methacrylate residue;
PAA is propyl acrylic acid residue;
DMAEMA is dimethylaminoethyl methacrylate residue;
m is a mole fraction of 0.6 to 1;
n is a mole fraction of 0 to 0.4 (e.g., 0 to 0.2);
p is a mole fraction of 0 to 0.4 (e.g., 0 to 0.2);
m+n+p=1;
q is a mole fraction of 0.2 to 0.75;
r is a mole fraction of 0.05 to 0.6;
s is a mole fraction of 0.2 to 0.75;
q+r+s=1;
v is 1 to 25 kDa;
w is 1 to 25 kDa;
T1 is absent or is the first targeting ligand; and
L is absent or is a linking moiety.

In other embodiments comprising a pH-sensitive polymer of formula I, the pH-sensitive polymer is a polymer of formula V:

T1-L-[PEGMA$_m$-M2n]$_v$-[DMAEMA$_q$-PAA$_r$-BMA$_s$]$_w$    V where
PEGMA is polyethyleneglycol methacrylate residue with 2-20 ethylene glycol units;
M2 is a methacrylate residue selected from the group consisting of
a (C4-C18)alkyl-methacrylate residue;
a (C4-C18)branched alkyl-methacrylate residue;
a cholesteryl methacrylate residue;
a (C4-C18)alkyl-methacrylate residue substituted with one or more fluorine atoms; and a (C4-C18)branched alkyl-methacrylate residue substituted with one or more fluorine atoms;
BMA is butyl methacrylate residue;
PAA is propyl acrylic acid residue;
DMAEMA is dimethylaminoethyl methacrylate residue;
m and n are each a mole fraction greater than 0, wherein m is greater than n and m+n=1;
q is a mole fraction of 0.2 to 0.75;
r is a mole fraction of 0.05 to 0.6;
s is a mole fraction of 0.2 to 0.75;
q+r+s=1;
v is 1 to 25 kDa;
w is 1 to 25 kDa;
T1 is absent or is the first targeting ligand; and
L is absent or is a linking moiety.

Particularly suitable M2 methacrylate residues for use in a polymer of formula V include 2,2,3,3,4,4,4-heptafluorobutyl methacrylate residue; 3,3,4,4,5,6,6,6-octafluoro-5-(trifluoromethyl)hexyl methacrylate residue; 2,2,3,3,4,4,5,5,6,6,7,7,8,8,8-pentadecafluorooctyl 2-methylacrylate residue; 3,3,4,4,5,5,6,6,6-nonafluorohexyl methacrylate residue (also referred to as 2-propenoic acid, 2-methyl-, 3,3,4,4,5,5,6,6,6-nonafluorohexyl ester residue); 3,3,4,4,5,5,6,6,7,7,8,8,8-tridecafluorooctyl methacrylate residue; 1,1,1-trifluoro-2-(trifluoromethyl)-2-hydroxy-4-methyl-5-pentyl methacrylate residue; 2-[(1',1',1'-trifluoro-2'-(trifluoromethyl)-2'-hydroxy)propyl]-3-norbornyl methacrylate residue; 2-ethylhexyl methacrylate residue; butyl methacrylate residue; hexyl methacrylate residue; octyl methacrylate residue; n-decyl methacrylate residue; lauryl methacrylate residue; myristyl methacrylate residue; stearyl methacrylate residue; cholesteryl methacrylate residue; ethylene glycol phenyl ether methacrylate residue; 2-propenoic acid, 2-methyl-, 2-phenylethyl ester residue; 2-propenoic acid, 2-methyl-, 2-[[(1,1-dimethylethoxy)carbonyl]amino]ethyl ester residue; 2-propenoic acid, 2-methyl-, 2-(1H-imidazol-1-yl)ethyl ester residue; 2-propenoic acid, 2-methyl-, cyclohexyl ester residue; 2-propenoic acid, 2-methyl-, 2-[bis(1-methylethyl)amino]ethyl ester residue; 2-propenoic acid, 2-methyl-, 3-methylbutyl ester residue; neopentyl methacrylate residue; tert-butyl methacrylate residue; 3,3,5-trimethyl cyclohexyl methacrylate residue; 2-hydroxypropyl methacrylate residue; 5-nonyl methacrylate residue; 2-butyl-1-octyl methacrylate residue; 2-hexyl-1-decyl methacrylate residue; and 2-(tert-butyl amino)ethyl methacrylate residue.

In particular variations of a pH-sensitive polymer of formula II or formula V, PEGMA has 4-5 ethylene glycol units or 7-8 ethylene glycol units. In some embodiments, T1 and L are present. T1 may include, for example, an N-acetylgalactosamine (NAG) residue, such as, e.g., a tri-NAG moiety as described further herein. L may be a hydrophilic moiety such as, for example, a moiety comprising one or more PEG chains. In some embodiments, L is a hydrophilic moiety comprising from 2 to 240 ethylene glycol units (e.g., a polyethylene glycol (PEG) moiety having 2-20 ethylene glycol units).

In specific embodiments, a pH-sensitive polymer of formula II is selected from the group consisting of

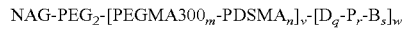
NAG-PEG$_2$-[PEGMA300$_m$-PDSMA$_n$]$_v$-[D$_q$-P$_r$-B$_s$]$_w$    IIa

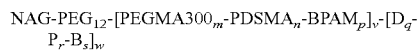
NAG-PEG$_{12}$-[PEGMA300$_m$-PDSMA$_n$-BPAM$_p$]$_v$-[D$_q$-P$_r$-B$_s$]$_w$    IIb where "D" is DMAEMA as defined above for formula II, "P" is PAA as defined above for formula II, "B" is BMA as defined above for formula II, "NAG" is an N-acetylgalactosamine residue, "PEG$_{12}$" is polyethylene glycol having 12 ethylene glycol units and functionalized at each end for attachment to the NAG residue and chain transfer agent, "PEGMA," "PDSMA," and "BPAM" are as defined above for formula II, and the values for m, n, p, q, r, s, v, and w are as defined above for formula II. In particular variations of a polymer of formula IIa, m is from 0.85 to 0.9, n is from 0.1 to 0.15, q is from 0.33 to 0.37, r is from 0.07 to 0.15, s is from 0.52 to 0.57, v is from 3 kDa to 4.5 kDa, and/or w is from 5.5 kDa to 7 kDa. In particular variations of a polymer of formula IIb, m is from 0.75 to 0.8, n is from 0.1 to 0.13, p is from 0.1 to 0.12, q is from 0.25 to 0.37, r is from 0.07 to 0.25, s is from 0.5 to 0.57, v is from 3 kDa to 4.5 kDa, and w is from 5.5 kDa to 7 kDa. In some specific embodiments, the ratio of w:v ranges from about 1:1 to about 5:1, or from about 1:1 to about 2:1.

In specific embodiments, a pH-sensitive polymer of formula V is selected from the group consisting of NAG-PEG$_{12}$-[PEGMA300$_m$-(Fl-BMA)$_n$]$_v$-[D$_q$-P$_r$-B$_s$]$_w$  Vb NAG-PEG$_{12}$-[PEGMA300$_m$-(OFl-5TFM-HMA)$_n$]$_v$-[D$_q$-P$_r$-B$_s$]$_w$  Vc NAG-PEG$_{12}$-[PEGMA300$_m$-(Fl15-OMA$_n$)]$_v$-[D$_q$-P$_r$-B$_s$]$_w$  Vd NAG-PEG$_{12}$-[PEGMA300$_m$-(B-Fl-HMA)$_n$]$_v$-[D$_q$-P$_r$-B$_s$]$_w$  Ve NAG-PEG$_{12}$-[PEGMA300$_m$-(B-Fl-OMA)$_n$]$_v$-[D$_q$-P$_r$-B$_s$]$_w$  Vf NAG-PEG$_{12}$-[PEGMA300$_m$-EHMA$_n$]$_v$-[D$_q$-P$_r$-B$_s$]$_w$  Vg NAG-PEG$_2$-[PEGMA300$_m$-B$_n$]$_v$-[D$_q$-P$_r$-B$_s$]$_w$  Vh NAG-PEG$_2$-[PEGMA300$_m$-HMA$_n$]$_v$-[D$_q$-P$_r$-B$_s$]$_w$  Vi NAG-PEG$_2$-[PEGMA300$_m$-C8MA$_n$]$_v$-[D$_q$-P$_r$-B$_s$]$_w$  Vj NAG-PEG$_{12}$-[PEGMA300$_m$-C12MA$_n$]$_v$-[D$_q$-P$_r$-B$_s$]$_w$  Vk NAG-PEG$_{12}$-[PEGMA300$_m$-Bu1-OMA$_n$]$_v$-[D$_q$-P$_r$-B$_s$]$_w$  Vl NAG-PEG$_{12}$-[PEGMA300$_m$-NMA$_n$]$_v$-[D$_q$-P$_r$-B$_s$]$_w$  Vm where "D" is DMAEMA as defined above for formula V, "P" is PAA as defined above for formula V, "B" is BMA as defined above for formula V, "NAG" is an N-acetylgalactosamine residue, "PEG$_{12}$" is polyethylene glycol having 12 ethylene glycol units and functionalized at each end for attachment to the NAG residue and chain transfer agent, "PEGMA" is as defined above for formula V, "Fl-BMA" is 2,2,3,3,4,4,4-heptafluorobutyl methacrylate residue, "OFl-5TFM-HMA" is 3,3,4,4,5,6,6,6-octafluoro-5(trifluoromethyl)hexyl methacrylate residue, "F115-OMA" is 2,2,3,3,4,4,5,5,6,6,7,7,8,8,8-pentadecafluorooctyl 2-methylacrylate residue, "B-Fl-HMA" is 3,3,4,4,5,5,6,6,6-nonafluorohexyl methacrylate residue, "B-Fl-OMA" is 3,3,4,4,5,5,6,6,7,7,8,8,8-tridecafluorooctyl methacrylate residue, "EHMA" is 2-ethylhexyl methacrylate residue, "HMA" is hexyl methacrylate residue, "C8MA" is octyl methacrylate residue, "C12MA" is lauryl methacrylate residue, "2-Bu1-OMA" is 2-butyl-1-octyl methacrylate residue, "5-NMA" is 5-nonyl methacrylate residue, and the values for m, n, q, r, s, v, and w are as defined above for formula V.

In some embodiments, the pH-sensitive, membrane-destabilizing polymer comprises a random block copolymer of formula Ia:

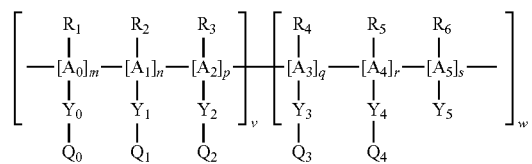

where
A$_0$, A$_1$, A$_2$, A$_3$, A$_4$ and A$_5$ are each independently selected from the group consisting of —C—C—, —C(O)(C)$_a$C(O)O—, —O(C)$_a$C(O)—, —O(C)$_b$—, and —CR$_8$—CR$_9$—; where tetravalent carbon atoms of A$_0$-A$_5$ that are not fully substituted with R$_1$-R$_6$ and Y$_0$-Y$_5$ are completed with an appropriate number of hydrogen atoms; wherein a and b are each independently 1-4; and where R$_8$ and R$_9$ are each independently selected from the group consisting of —C(O)OH, —C(O)Oalkyl, and —C(O)NR$_{10}$, where R$_8$ and R$_9$ are optionally covalently linked together to form a ring structure;

Y$_5$ is hydrogen or is selected from the group consisting of -(1C-10C)alkyl, -(3C-6C)cycloalkyl, —O-(1C-10C)alkyl, —C(O)O(1C-10C)alkyl, —C(O)NR$_{11}$(1C-10C)alkyl, and -(6C-10C)aryl, any of which is optionally substituted with one or more fluorine atoms;

Y$_0$, Y$_3$, and Y$_4$ are each independently selected from the group consisting of a covalent bond, -(1C-10C)alkyl-, —C(O)O(2C-10C)alkyl-, —OC(O)(1C-10C)alkyl-, —O(2C-10C)alkyl-, —S(2C-10C)alkyl-, and —C(O)NR$_{12}$(2C-10C) alkyl-;

Y$_1$ and Y$_2$ are each independently selected from the group consisting of a covalent bond, -(1C-18C)alkyl-, -(3C-18C)branched alkyl, —C(O)O(2C-18C)alkyl-, —C(O)O(2C-18C)branched alkyl, —OC(O)(1C-18C)alkyl-, —OC(O)(1C-18C)branched alkyl-, —O(2C-18C)alkyl-, —O(2C-18C)branched alkyl-, —S(2C-18C)alkyl-, —S(2C-18C)branched alkyl-, —C(O)NR$_{12}$(2C-18C)alkyl-, and —C(O)NR$_{12}$(2C-18C)branched alkyl-, where any alkyl or branched alkyl group of Y$_1$ or Y$_2$ is optionally substituted with one or more fluorine atoms;

R$_1$, R$_2$, R$_3$, R$_4$, R$_5$, R$_6$, R$_8$, R$_9$, R$_{10}$, R$_{11}$, and R$_{12}$ are each independently hydrogen, —CN, or selected from the group consisting of alkyl, alkynyl, heteroalkyl, cycloalkyl, heterocycloalkyl, aryl and heteroaryl, any of which is optionally substituted with one or more fluorine atoms;

Q$_0$ is a residue selected from the group consisting of residues which are hydrophilic at physiologic pH; O—[(C)$_{2-3}$—O]$_x$—R$_7$; and O—[(C)$_{2-3}$—O]$_x$—C(O)—NR$_{13}$R$_{14}$; where x is 1-48; R$_7$ is —CH$_3$ or —CO$_2$H; and R$_{13}$ and R$_{14}$ are each independently hydrogen, —CN, or selected from the group consisting of alkyl, alkynyl, heteroalkyl, cycloalkyl, heterocycloalkyl, aryl and heteroaryl, any of which is optionally substituted with one or more fluorine atoms;

Q$_1$ and Q$_2$ are each independently absent or selected from a residue which is hydrophilic at normal physiological pH; a conjugatable or functionalizable residue; a residue which is hydrophobic at normal physiological pH; an alkyl group optionally substituted with one or more fluorine atoms; and a branched alkyl group optionally substituted with one or more fluorine atoms;

Q$_3$ is a residue which is positively charged at normal physiological pH;

$Q_4$ is a residue which is negatively charged at normal physiological pH, but undergoes protonation at lower pH;

m is a mole fraction of greater than 0.5 to less than 1.0;

n is a mole fraction of greater than 0 to less than 0.5;

p is a mole fraction of 0 to less than 0.5; wherein m+n+p=1;

q is a mole fraction of 0.1 to 0.9;

r is a mole fraction of 0.05 to 0.9;

s is present up to a mole fraction of 0.85; wherein q+r+s=1;

v is from 1 to 25 kDa;

w is from 1 to 50 kDa; and at least one of $Y_1$ and $Q_1$ contains the alkyl or branched alkyl group substituted with the one or more fluorine atoms.

In some embodiments of a pH-sensitive polymer comprising a copolymer of formula Ia as above, p is 0.

Suitable polymers of formula Ia include polymers where $R_2$-$A_1$-$Y_1$-$Q_1$ taken together is a methacrylate residue selected from the group consisting of 2,2,3,3,4,4,4-heptafluorobutyl methacrylate residue; 3,3,4,4,5,6,6,6-octafluoro-5(trifluoromethyl)hexyl methacrylate residue; 2,2,3,3,4,4,5,5,6,6,7,7,8,8,8-pentadecafluorooctyl 2-methylacrylate residue; 3,3,4,4,5,5,6,6,6-nonafluorohexyl methacrylate residue; 3,3,4,4,5,5,6,6,7,7,8,8,8-tridecafluorooctyl methacrylate residue; 1,1,1-trifluoro-2-(trifluoromethyl)-2-hydroxy-4-methyl-5-pentyl methacrylate residue; and 2-[(1',1',1'-trifluoro-2'-(trifluoromethyl)-2'-hydroxy)propyl]-3-norbornyl methacrylate residue.

In various embodiments of a pH-sensitive polymer comprising a copolymer of formula Ia as above, (a) $Y_3$ is —C(O)OCH$_2$CH$_2$, $Q_3$ is dimethylamino, and/or $R_4$ is —CH$_3$; (b) $Y_4$ is a covalent bond, $Q_4$ is a carboxyl residue, and/or $R_5$ is —CH$_2$CH$_2$CH$_3$; (c) $Y_5$ is —C(O)O(CH$_2$)$_3$CH$_3$ and/or $R_6$ is —CH$_3$; and/or (d) $Y_0$ is —C(O)O(2C-10C) alkyl-, $Q_0$ is O—[(C)$_{2-3}$—O]$_x$—$R_7$ (where x is 1-48 and $R_7$ is —CH$_3$), and/or $R_1$ is —CH$_3$. For example, in more specific variations, $R_4$-$A_3$-$Y_3$-$Q_3$ taken together is a dimethylaminoethyl methacrylate residue (DMAEMA); $R_5$-$A_4$-$Y_4$-$Q_4$ taken together is a propyl acrylic acid residue (PAA); $R_6$-$A_5$-$Y_5$ taken together is a butyl methacrylate residue (BMA); and/or $R_1$-$A_0$-$Y_0$-$Q_0$ taken together is a polyethyleneglycol methacrylate residue with 2-20 ethylene glycol units (PEGMA).

In some embodiments of a polymer comprising a copolymer of formula Ia as above, the pH-sensitive polymer is a polymer of formula Va:

$$\text{T1-L-[PEGMA}_m\text{-M2n]v-[DMAEMA}_q\text{-PAA}_r\text{-BMA}_s\text{]}_w \qquad \text{Va}$$

where

PEGMA is polyethyleneglycol methacrylate residue with 2-20 ethylene glycol units;

M2 is a methacrylate residue selected from the group consisting of a (C4-C18)alkyl-methacrylate residue substituted with one or more fluorine atoms, and a (C4-C18)branched alkyl-methacrylate residue substituted with one or more fluorine atoms, BMA is butyl methacrylate residue;

PAA is propyl acrylic acid residue;

DMAEMA is dimethylaminoethyl methacrylate residue;

m and n are each a mole fraction greater than 0, where m is greater than n and m+n=1;

q is a mole fraction of 0.2 to 0.75;

r is a mole fraction of 0.05 to 0.6;

s is a mole fraction of 0.2 to 0.75;

q+r+s=1;

v is 1 to 25 kDa;

w is 1 to 25 kDa;

T1 is absent or is the first targeting ligand; and

L is absent or is a linking moiety.

Particularly suitable M2 methacrylate residues for use in a polymer of formula Va include 2,2,3,3,4,4,4-heptafluorobutyl methacrylate residue; 3,3,4,4,5,6,6,6-octafluoro-5(trifluoromethyl)hexyl methacrylate residue; 2,2,3,3,4,4,5,5,6,6,7,7,8,8,8-pentadecafluorooctyl 2-methylacrylate residue 3,3,4,4,5,5,6,6,6-nonafluorohexyl methacrylate residue; 3,3,4,4,5,5,6,6,7,7,8,8,8-tridecafluorooctyl methacrylate residue; 1,1,1-trifluoro-2-(trifluoromethyl)-2-hydroxy-4-methyl-5-pentyl methacrylate residue; and 2-[(1',1',1'-trifluoro-2'-(trifluoromethyl)-2'-hydroxy)propyl]-3-norbornyl methacrylate residue.

In particular variations of a polymer of formula V, formula Va, or any of formulae Vb-Vm, m is from 0.55 to 0.9 (e.g., from 0.65 to 0.9 or from 0.7 to 0.85), n is from 0.1 to 0.45 (e.g., from 0.1 to 0.35 or from 0.15 to 0.3), q is from 0.25 to 0.4 (e.g., 0.28 to 0.37), r is from 0.07 to 0.15 (e.g., 0.9 to 0.15), s is from 0.5 to 0.65 (e.g., 0.5 to 0.6), v is from 2.5 kDa to 10 kDa (e.g., from 2.5 kDa to 7 kDa, from 2.5 kDa to 5 kDa, from 2.5 kDa to 4.5 kDa, or from 0.29 to 4 kDa), and/or w is from 4 kDa to 9 kDa (e.g., from 4 kDa to 7 kDa, from 4 kDa to 6 kDa, or from 5 kDa to 7 kDa). In some specific embodiments, the ratio of w:v ranges from about 1:0.8 to about 5:1, or from about 1:1 to about 2:1.

Generally, a membrane-destabilizing polymer (or polymer chains included as constituent moieties such as blocks of a block copolymer) can include a shielding agent or solubilizing agent. The shielding agent can be effective for improving solubility of the polymer chain. The shielding agent can also be effective for reducing toxicity of the certain compositions. In some embodiments, the shielding agent can be a polymer comprising a plurality of neutral hydrophilic monomeric residues. The shielding polymer can be covalently coupled to a membrane destabilizing polymer, directly or indirectly, through an end group of the polymer or through a pendant functional group of one or more monomeric residues of the polymer. In some embodiments, a plurality of monomeric residues of the polymer chain can have a shielding species; preferably, such shielding species is a pendant moiety from a polymerizable monomer (from which the shielding monomeric residues are derived). For example, the polymer can comprise a plurality of monomeric residues having a pendant group comprising a shielding oligomer. A shielding/solubilizing species may be conjugated to a polymer via a labile linkage such as, for example, a pH-sensitive bond or linker. Particularly suitable pH-sensitive bonds and linkers include hydrazone, acetal, ketal, imine, orthoester, carbonate, and maleamic acid linkages. Labile linkages may be utilized, e.g., for linkage via a plurality of monomeric residues having pendant linking groups or for linkage of a polymer block comprising the shielding species to another polymer block (e.g., linkage of a shielding block to a membrane-destabilizing block).

A preferred shielding/solubilizing polymer can be a polyethylene glycol (PEG) oligomer (e.g., having 20 or less repeat units) or polymer (e.g., having more than 20 repeat units). PEG can be described as a polyethylene glycol or as a polyethylene oxide, and is understood to be a oligomer or polymer from —CH2-CH2-O— repeat units (which repeat units are also referred to herein as "ethylene glycol units" or "ethylene oxide units"). In certain embodiments, one block of a block copolymer can be or comprises a polyethylene glycol (PEG) oligomer or polymer—for example, covalently coupled to the alpha end or the omega end of the membrane destabilizing block of the copolymer. In another embodiment, a polyethylene glycol (PEG) oligomer or polymer can be covalently coupled to the polymer through a conjugating monomeric residue having a species which includes a functional group suitable for linking, directly or indirectly, to the polyethylene glycol oligomer or polymer. In another embodiment, the monomeric residue can be derived from a polymerizable monomer which includes a polyethylene glycol oligomer pendant to the monomer (e.g., PEGMA as described above).

In one general approach, PEG chains or blocks are covalently coupled to a membrane-destabilizing polymer chain. For such embodiments, for example, PEG chains or blocks can have molecular weights ranging approximately from 1,000 to approximately 30,000. In some embodiments, the PEG is effective as (i.e., is incorporated into) a second block of a block copolymer. For example, PEG can be a second block coupled covalently to a block comprising a membrane destabilizing polymer. In some embodiments, PEG is conjugated to block copolymer ends groups, or to one or more pendant modifiable group present in polymeric compound, such as conjugated to modifiable groups within a hydrophilic segment or block (e.g., a second block) of a polymer (e.g., block copolymer). As an example, a block of a copolymer can be or can be conjugated to a shielding polymer having a repeat unit of formula III

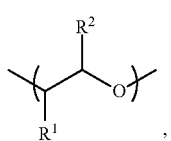

III where $R^1$ and $R^2$ are each independently selected from the group consisting of hydrogen, halogen, hydroxyl, and optionally substituted $C_1$-$C_3$ alkyl, and having a molecular weight ranging from about 1,500 to about 15,000.

In another general approach, a monomeric residue is derived from a polymerizable monomer comprising a PEG oligomer; for example, such monomeric residues can be incorporated into the polymer or into one or more blocks of a block copolymer during polymerization. In preferred embodiments, monomeric residues can be derived from a polymerizable monomer having a pendant group comprising an oligomer of formula IV

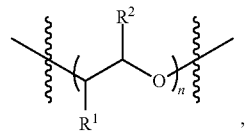

IV where $R^1$ and $R^2$ are each independently selected from the group consisting of hydrogen, halogen, hydroxyl, and optionally substituted $C_1$-$C_3$ alkyl, and n is an integer ranging from 2 to 20.

Generally, a membrane-destabilizing polymer (or polymer chains included as constituent moieties such as blocks of a block copolymer) can be prepared in any suitable manner. Suitable synthetic methods used to produce, for example, a membrane-destabilizing copolymer include, by way of non-limiting example, well-known "living polymerization" methods such as, e.g., cationic, anionic and free radical polymerization.

Using living polymerization, polymers of very low polydispersity or differences in chain length can be obtained. Polydispersity is usually measured by dividing the weight average molecular weight of the polymer chains by their number average molecular weight. The number average molecule weight is sum of individual chain molecular weights divided by the number of chains. The weight average molecular weight is proportional to the square of the molecular weight divided by the number of molecules of that molecular weight. Since the weight average molecular weight is always greater than the number average molecular weight, polydispersity is always greater than or equal to one. As the numbers come closer and closer to being the same, i.e., as the polydispersity approaches a value of one, the polymer becomes closer to being monodisperse in which every chain has exactly the same number of constitutional units. Polydispersity values approaching one are achievable using radical living polymerization. Methods of determining polydispersity such as, without limitation, size exclusion chromatography, dynamic light scattering, matrix-assisted laser desorption/ionization mass spectrometry, and electrospray mass spectrometry are well-known in the art.

Reversible addition-fragmentation chain transfer or RAFT is an exemplary living polymerization technique for use in synthesizing ethylenic backbone polymers. RAFT is well-known to those skilled in the art. RAFT comprises a free radical degenerative chain transfer process. Most RAFT procedures employ thiocarbonylthio compounds such as, without limitation, dithioesters, dithiocarbamates, trithiocarbonates and xanthates to mediate polymerization by a reversible chain transfer mechanism. Reaction of a polymeric radical with the C=S group of any of the preceding compounds leads to the formation of stabilized radical intermediates. These stabilized radical intermediates do not undergo the termination reactions typical of standard radical polymerization but, rather, reintroduce a radical capable of re-initiation or propagation with monomer, reforming the C=S bond in the process. This cycle of addition to the C=S bond followed by fragmentation of the ensuing radical continues until all monomer has been consumed or the reaction is quenched. The low concentration of active radicals at any particular time limits normal termination reactions. In other embodiments, polymers are synthesized by Macromolecular design via reversible addition-fragmentation chain transfer of Xanthates (MADIX) (Direct Synthesis of Double Hydrophilic Statistical Di- and Triblock Copolymers Comprised of Acrylamide and Acrylic Acid Units via the MADIX Process", Daniel Taton et al., *Macromolecular Rapid Communications,* 22:1497-1503, 2001.)

In certain embodiments of the present invention, the lipid nanoparticle and/or the membrane destabilizing polymer includes at least one targeting ligand that specifically binds to a molecule on the surface of the target cell. In some embodiments, the membrane-destabilizing polymer comprises the targeting ligand. In some embodiments, the lipid nanoparticle comprises the targeting ligand. In some embodiments, both the membrane-destabilizing polymer and the lipid nanoparticle comprise a target ligand, which may be the same or different (e.g., different targeting ligand species that bind to the same target cell).

A targeting ligand specifically recognizes a molecule on the surface of the target cell, such as, e.g., a cell surface receptor. Particularly suitable targeting moieties include antibodies, antibody-like molecules, polypeptides, proteins (e.g., insulin-like growth factor II (IGF-II)), peptides (e.g., an integrin-binding peptide such as an RGD-containing peptide), and small molecules such as, for example, sugars (e.g., lactose, galactose, N-acetyl galactosamine (NAG), mannose, mannose-6-phosphate (M6P)) or vitamins (e.g., folate). In some variations, a targeting moiety is a protein derived from a natural ligand of a cell-surface molecule (e.g., derived from a cytokine or from the extracellular domain of a cell-surface receptor that binds to a cell surface counter-receptor). Examples of cell surface molecules that may be targeted by a targeting moiety of a copolymer provided herein include, but are not limited to, the transferrin receptor type 1 and 2, the EGF receptor, HER2/Neu, VEGF receptors, integrins, NGF, CD2, CD3, CD4, CD8, CD19, CD20, CD22, CD33, CD43, CD38, CD56, CD69, the asialoglycoprotein receptor, mannose receptor, the cation-independent mannose-6-phosphate/IGF-II receptor, prostate-specific membrane antigen (PSMA), a folate receptor, and a sigma receptor.

In particular variations, a targeting ligand includes an N-acetylgalactosamine (NAG) sugar residue, which specifically binds to the asialoglycoprotein receptor (ASGPR) on hepatocytes. In some such embodiments, the targeting ligand has the formula

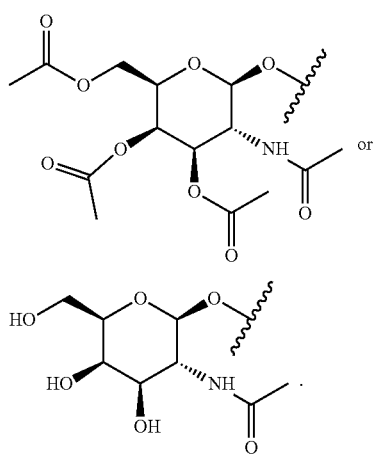

In other embodiments comprising a NAG sugar residue, the targeting ligand comprises multiple NAG sugar residues (e.g., three NAG residues, also referred to herein as a "tri-NAG" structure), which may increase avidity for the asialoglycoprotein receptor relative to a monovalent NAG moiety. In some such embodiments, a tri-NAG structure has the formula

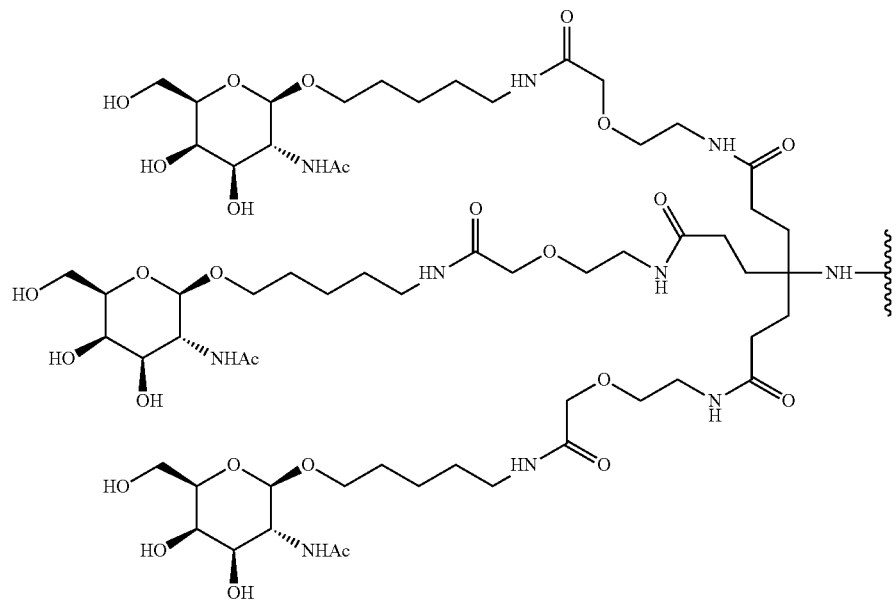 [SMILES: *NC(CCC(=O)NCCOCC(=O)NCCCCCO[C@@H]1O[C@H](CO)[C@H](O)[C@H](O)[C@H]1NC(C)=O)(CCC(=O)NCCOCC(=O)NCCCCCO[C@@H]1O[C@H](CO)[C@H](O)[C@H](O)[C@H]1NC(C)=O)CCC(=O)NCCOCC(=O)NCCCCCO[C@@H]1O[C@H](CO)[C@H](O)[C@H](O)[C@H]1NC(C)=O]

where ~~~ designates a point of attachment.

In various embodiments, a targeting ligand is attached to either end of a membrane-destabilizing polymer (e.g., block copolymer), attached to a side chain of a monomeric unit, incorporated into a polymer block, or attached to a lipid or polymeric component of a lipid nanoparticle. Attachment of a targeting ligand to the membrane-destabilizing polymer or LNP is achieved in any suitable manner, e.g., by any one of a number of conjugation chemistry approaches including, but not limited to, amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In specific embodiments, "click" chemistry is used to attach the targeting ligand to a polymer (for example of "click" reactions, see Wu and Fokin, "Catalytic Azide-Alkyne Cycloaddition: Reactivity and Applications," *Aldrichim. Acta* 40:7-17, 2007). A large variety of conjugation chemistries are optionally utilized (see, e.g., *Bioconjugation*, Aslam and Dent, Eds, Macmillan, 1998 and chapters therein). In some embodiments, targeting ligands are attached to a monomer and the resulting compound is then used in the polymerization synthesis of a polymer (e.g., block copolymer). In some embodiments, targeting moieties are attached to a block of a first block copolymer, or to a block of a second block copolymer in a mixed polymer micellic assembly.

Targeting of lipid particles using a variety of targeting ligands has been previously described. See, e.g., U.S. Pat. Nos. 4,957,773 and 4,603,044. Targeting mechanisms generally require that the targeting ligand be positioned on the surface of the lipid particle in such a manner that the targeting moiety is available for interaction with the target, for example, a cell surface receptor. A variety of different targeting ligands and methods are known and available in the art, including those described above as well as, e.g., in Sapra and Allen, *Prog. Lipid Res.* 42:439-62, 2003, and Abra et al., *J. Liposome Res.* 12:1-3, 2002. Various targeting counter-receptors can be bound to the surface of the liposome, such as antibodies, antibody fragments, carbohydrates, vitamins, and transport proteins. For example, for targeting to the liver, liposomes can be modified with branched type galactosyllipid derivatives to target asialoglycoprotein receptors. See Kato and Sugiyama, *Crit. Rev. Ther. Drug Carrier Syst.* 14:287, 1997; Murahashi et al., *Biol. Pharm. Bull.* 20:259, 1997. In a more general approach to tissue targeting, target cells are prelabeled with biotinylated antibodies specific for a molecule expressed by the target cell. See Harasym et al., *Adv. Drug Deliv. Rev.* 32:99, 1998. After plasma elimination of free antibody, streptavidin-conjugated liposomes are administered. In another approach, targeting antibodies are directly attached to liposomes. See Harasym et al., supra.

In specific variations, a targeting ligand is attached to a polymer using a linker having a formula selected from

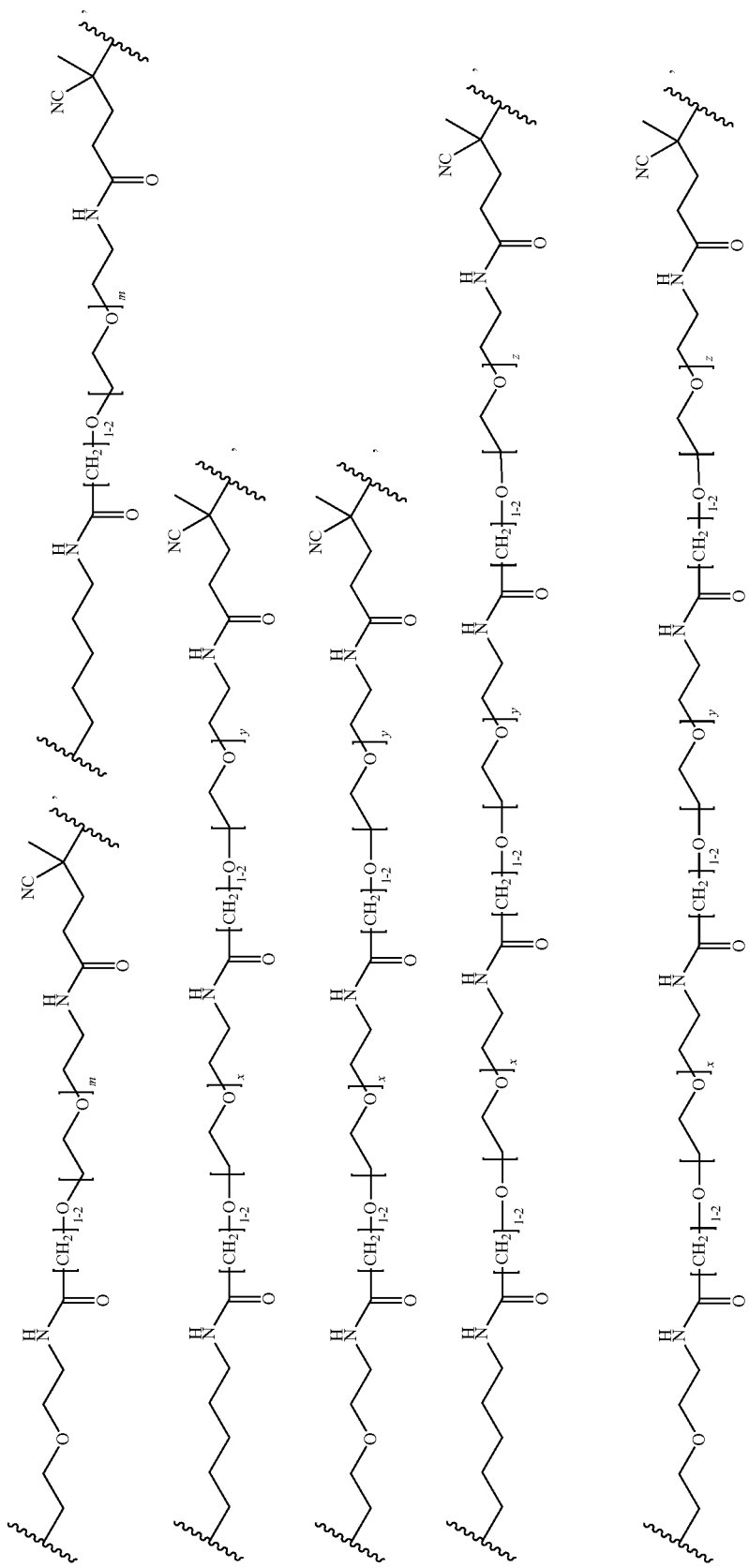

-continued
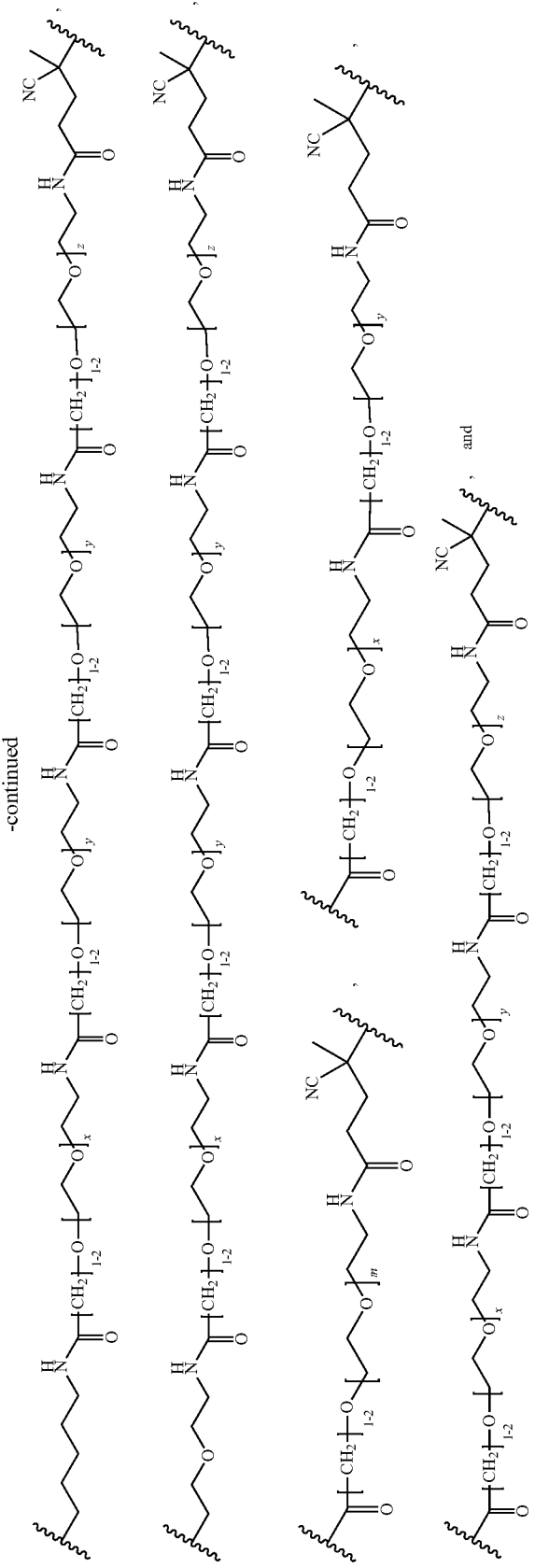

where m is 1-100 or 10-250 and each of w, x, y, and z is independently 1-48. In certain variations of a linker comprising m as above, m is 1-15, 10-20, 20-30, 20-25, 11 or 12. In other variations of a linker comprising m as above, m is 20-60, 25-60, 25-55, 25-50, 25-48, 30-60, 30-55, 30-50, 30-48, 34-60, 34-55, 34-50, 34-48, 36-60, 36-55, 36-50, 36-48, 36, or 48. In yet other embodiments of a linker comprising m as above, m is 60-250, 100-250, 150-250, or 200-250. In certain variations of L1 comprising x and y, x, y and z, or w, x, y and z as above, each of w, x, y, and z is independently 20-30, 20-25, or 23. In other variations of L1 comprising x and y, x, y and z, or w, x, y and z as above, each of w, x, y, and z is independently 1-12, 1-24, 1-36, 8-16, 10-14, 20-28, 22-26, 32-40, 34-38, 8-48, 10-48, 20-48, 22-48, 32-48, 34-48, or 44-48.

Particular embodiments of the present invention are directed at in vivo delivery of therapeutic agents. In some embodiments, the therapeutic agent is a polynucleotide. Suitable polynucleotide therapeutic agents include DNA agents, which may be in the form of cDNA, in vitro polymerized DNA, plasmid DNA, genetic material derived from a virus, linear DNA, vectors, expression vectors, expression cassettes, chimeric sequences, recombinant DNA, anti-sense DNA, or derivatives of these groups. Other suitable polynucleotide therapeutic agents include RNA, which may be in the form of messenger RNA (mRNA), in vitro polymerized RNA, recombinant RNA, transfer RNA (tRNA), small nuclear RNA (snRNA), ribosomal RNA (rRNA), chimeric sequences, dicer substrate and the precursors thereof, locked nucleic acids, anti-sense RNA, interfering RNA (RNAi), asymmetric interfering RNA (aiRNA), small interfering RNA (siRNA), microRNA (miRNA), ribozymes, external guide sequences, small non-messenger RNAs (snmRNA), untranslatedRNA (utRNA), snoRNAs (24-mers, modified snmRNA that act by an anti-sense mechanism), tiny non-coding RNAs (tncRNAs), small hairpin RNA (shRNA), or their derivatives. Double stranded RNA (dsRNA) and siRNA are of interest particularly in connection with the phenomenon of RNA interference. Examples of therapeutic oligonucleotides as used herein include, but are not limited to, siRNA, an antisense oligonucleotide, a dicer substrate, a miRNA, an aiRNA or an shRNA. An example of a large therapeutic polynucleotide as used herein includes, but is not limited to, messenger RNAs (mRNAs) encoding functional proteins for gene replacement therapy. Polynucleotide therapeutic agents may also be nucleic acid aptamers, which are nucleic acid oligomers that specifically bind other macromolecules; such aptamers that bind specifically to other macromolecules can be readily isolated from libraries of such oligomers by known technologies such as SELEX. See, e.g., Stoltenburg et al., *Biomol. Eng.,* 24:381, 2007.

In other embodiments, the therapeutic agent is a protein or a peptide. For example, in certain variations, the agent is an antibody that binds to and either antagonizes or agonizes an intracellular target. Antibodies for use in the present invention may be raised through any known method, such as through injection of immunogen into mice and subsequent fusions of lymphocytes to create hybridomas. Such hybridomas may then be used either (a) to produce antibody directly, or (b) to clone cDNAs encoding antibody fragments for subsequent genetic manipulation. To illustrate one method employing the latter strategy, mRNA is isolated from the hybridoma cells, reverse-transcribed into cDNA using antisense oligo-dT or immunoglobulin gene-specific primers, and cloned into a plasmid vector. Clones are sequenced and characterized. They may then be engineered according to standard protocols to combine the heavy and light chains of the antibody into a bacterial or mammalian expression vector to generate, e.g., a single-chain scFv. A similar approach may be used to generate recombinant bispecific antibodies by combining the heavy and light chains of each of two different antibodies, separated by a short peptide linker, into a bacterial or mammalian expression vector. Recombinant antibodies are then expressed and purified according to well-established protocols in bacteria or mammalian cells. See, e.g., Kufer et al., 2004, supra; *Antibody Engineering: A Practical Approach*, McCafferty, Hoogenboom and Chiswell Eds, IRL Press 1996. Antibodies or other proteinaceous therapeutic molecules such as peptides, may also be created through display technologies that allow selection of interacting affinity reagents through the screening of very large libraries of, for example, immunoglobulin domains or peptides expressed by bacteriophage (*Antibody Engineering: A Practical Approach*, McCafferty, Hoogenboom and Chiswell Eds, IRL Press 1996). Antibodies may also be humanized through grafting of human immunoglobulin domains, or made from transgenic mice or bacteriophage libraries that have human immunoglobulin genes/cDNAs. In some embodiments of the invention, a specific binding protein therapeutic may include structures other than antibodies that are able to bind to targets specifically, including but not limited to avimers (see Silverman et al., *Nature Biotechnology* 23:1556-1561, 2005), ankyrin repeats (see Zahnd et al., *J. Mol. Biol.* 369:1015-1028, 2007) and adnectins (see U.S. Pat. No. 7,115,396), and other such proteins with domains that can be evolved to generate specific affinity for antigens, collectively referred to as "antibody-like molecules". Modifications of protein therapeutics through the incorporation of unnatural amino acids during synthesis may be used to improve their properties (see Datta et al., *J. Am. Chem. Soc.* 124:5652-5653, 2002; and Liu et al., *Nat. Methods* 4:239-244, 2007). Such modifications may have several benefits, including the addition of chemical groups that facilitate subsequent conjugation reactions.

In some embodiments, the therapeutic agent is a peptide. In certain variations, the peptide is a bispecific peptide. Peptides can readily be made and screened to create affinity reagents that recognize and bind to macromolecules such as, e.g., proteins. See, e.g., Johnsson and Ge, *Current Topics in Microbiology and Immunology,* 243:87-105, 1999.

In other embodiments, a protein therapeutic is a peptide aptamer. A peptide aptamer comprises a peptide molecule that specifically binds to a target protein and interferes with the functional ability of that target protein. See, e.g., Kolonin et al., *Proc. Natl. Acad. Sci. USA* 95:14266, 1998. Peptide aptamers consist of a variable peptide loop attached at both ends of a protein scaffold. Such peptide aptamers can often have a binding affinity comparable to that of an antibody (nanomolar range). Due to the highly selective nature of peptide aptamers, they can be used not only to target a specific protein, but also to target specific functions of a given protein (e.g., a signaling function). Further, peptide aptamers can be expressed in a controlled fashion by use of promoters that regulate expression in a temporal, spatial or inducible manner. Peptide aptamers act dominantly, therefore, they can be used to analyze proteins for which loss-of-function mutants are not available. Peptide aptamers are usually prepared by selecting the aptamer for its binding affinity with the specific target from a random pool or library of peptides. Peptide aptamers can be isolated from random peptide libraries by yeast two-hybrid screens. See, e.g., Xu et al., *Proc. Natl. Acad. Sci. USA* 94:12473, 1997. They can also be isolated from phage libraries (see, e.g., Hoogenboom et al., *Immunotechnology* 4:1, 1998) or from chemically generated peptides/libraries.

In yet other embodiments, the therapeutic agent is a small molecule therapeutic. Small molecule therapeutics are generally well-known in the art and may be used in accordance with the present invention. Such molecules include anti-infective (e.g., anti-viral) small molecules, immunomodulatory small molecules, and anti-cancer small molecules, to name a few broad categories. In some variations, the small molecule therapeutic is a hydrophobic small molecule. Small molecule anti-cancer therapeutics include, e.g., a variety of chemotherapeutic drugs such as, for example, tyrosine kinase inhibitors (TKIs), small molecules that influence either DNA or RNA, or small molecules that inhibit cell mitosis by preventing polymerization or depolymerization of microtubules. Particular examples of small molecule chemotherapeutic agents include anti-metabolites (such as Azathioprine, Cytarabine, Fludarabine phosphate, Fludarabine, Gemcitabine, cytarabine, Cladribine, capecitabine 6-mercaptopurine, 6-thioguanine, methotrexate, 5-fluoroouracil and hyroxyurea); alkylating agents (such as Melphalan, Busulfan, Cis-platin, Carboplatin, Cyclophosphamide, Ifosphamide, Dacarabazine, Procarbazine, Chlorambucil, Thiotepa, Lomustine, Temozolamide); anti-mitotic agents (such as Vinorelbine, Vincristine, Vinblastine, Docetaxel, Paclitaxel); topoisomerase inhibitors (such as Doxorubincin, Amsacrine, Irinotecan, Daunorubicin, Epirubicin, Mitomycin, Mitoxantrone, Idarubicin, Teniposide, Etoposide, Topotecan); antibiotics (such as Actinomycin and Bleomycin); Asparaginase; anthracyclines; and taxanes. In certain variations, the small molecule chemotherapeutic is selected from an anti-tubulin agent, a DNA minor groove binding agent, a DNA replication inhibitor, and a tyrosine kinase inhibitor. In other specific variations, the small molecule chemotherapeutic is an anthracycline, an auristatin, a camptothecin, a duocarmycin, an etoposide, a maytansinoid, a vinca alkaloid, or a platinum (II) compound.

In still other embodiments, the therapeutic agent is a component of a gene editing system that disrupts or corrects genes that cause disease. These include, for example, zinc finger nucleases (ZFNs) (see, e.g., Smith et al., *Nucleic Acids Res*. 28:3361-3369, 2000), transcription activator-like effector nucleases (TALENs) (see, e.g., Li et al., *Nucleic Acids Res*. 39:359-372, 2011), the CRISPR/Cas system (see, e.g., Richter et al., *Int. J. Mol. Sci.* 14:14518-14531, 2013), and engineered meganucleases (see, e.g., Silva et al., *Curr. Gene Ther.* 11:11-27, 2011). In such embodiments, the nuclease(s) are encoded by one or more nucleic acids such as mRNA or DNA that are formulated in the lipid nanoparticle. In some variations, multiple mRNAs are formulated in the LNP carrier to deliver two nucleases to the same cell for gene editing to occur (e.g., for a ZFNs or TALENs gene editing system, which typically requires two nucleases to recognize the specific target site within the genome to cause a modification at that site). In the context of the present disclosure, the membrane destabilizing polymer facilitates delivery of the nucleic acid(s) to the cytoplasm, where translation or subsequent nuclear delivery occur. In some variations, one or more additional components of a gene editing system are delivered to a target cell together with the one or more nucleic acids encoding the nuclease(s). For example, in the CRISPR/Cas system, in addition to a nucleic acid encoding the Cas9 protein, a short guide RNA to target the enzyme to a specific site in the genome is typically formulated within the LNP carrier. In certain embodiments, to correct a gene by homologous recombination, a donor DNA sequence may also be delivered and formulated either in the same or a different LNP than with the nucleic acid(s) that encode the nuclease(s). In certain embodiments where the gene editing system corrects a gene associated with a disease, the disease is characterized by deficiency of a functional protein as disclosed herein (see, e.g., discussion of protein deficiency diseases, infra.)

In some embodiments, the therapeutic agent is an immunogen. Using methods as disclosed herein, an immunogen can be effectively delivered to a variety of immune cells to elicit an immune response. In some variations, only the LNP comprises an immunogen. In other embodiments, the membrane destabilizing polymer is also associated with (e.g., covalently coupled to) an immunogen. Suitable immunogens include peptides, proteins, mRNAs, short RNAs, DNAs, simple or complex carbohydrates as well as substances derived from viruses, bacteria, cancer cells, and the like. In some variations, a hapten or adjuvant component is attached (conjugated) or self-associated with the membrane destabilizing polymer or the LNP. In certain embodiments in which both the membrane destabilizing polymer and LNP are associated with an immunogen, the immunogen associated with the polymer is different than that for the LNP; alternatively, both the polymer and LNP have the same immunogenic cargo. For example, in some variations, a immunogenic peptide that is a promiscuous T-cell epitope is attached to the membrane destabilizing polymer or the LNP to enable a more robust immune response. This hapten can be derived from, e.g., the protein sequence encoded by an mRNA component of the LNP or can be from another protein or a combination of more than one T-cell epitope. As another example, the immunogen may be a component of a bacterial cell wall that is attached to the polymer or LNP to enhance the immune response by acting as an adjuvant. In yet other variations, an immmunostimulating oligonucleotide or long nucleic acid is attached or self-associated with the polymer or LNP to activate the innate immune response. Utilizing the dual nature of the delivery system described herein (using both a membrane destabilizing polymer component and an LNP component), one component may be used to initiate a T-cell response while the other component is utilized to initiate a B-cell response. The polymer and LNP components of the hybrid delivery system may be used to elicit an innate immune response, a T-cell response, a B-cell response, or a combination thereof through the attachment or self-association of immunogenic substances. In some embodiments, a first polymer is used to attach and carry an immunogen while a second, membrane destabilizing polymer is used to enable uptake into antigen presenting cells. In certain embodiments for delivering an immunogen to a cell as disclosed herein, at least one of the polymer and the LNP has a targeting ligand to direct the polymer and/or LNP to an immune cell of interest.

For delivery of a therapeutic or diagnostic agent to the cytosol of a target cell (e.g., for delivery to a target tissue comprising the target cells), a membrane-destabilizing polymer and a lipid nanoparticle comprising the therapeutic or diagnostic agent are each administered to a subject in amounts effective to achieve intracellular delivery of the agent. The lipid nanoparticle and membrane-destabilizing polymer may be co-formulated as a single composition for co-injection into a subject. Alternatively, the lipid nanoparticle and membrane-destabilizing polymer may be formulated separately for separate administration. Typically, for separate administration, the lipid nanoparticle and membrane-destabilizing polymer are administered sequentially. For example, in particular embodiments, the membrane-destabilizing polymer is administered after administration of the lipid nanoparticle. In specific variations, the timing between administration of LNP and polymer is about two hours or less, typically about one hour or less, and more typically about 30 minutes or less, about 10 minutes or less, about five minutes or less, or about one minute or less. In some embodiments, the timing between administration of LNP and polymer is about 30 minutes, about 15 minutes, about 10 minutes, about five minutes, or about one minute. Typically, in variations comprising co-injection of the lipid nanoparticle and membrane-destabilizing polymer, the LNP and polymer are initially formulated as separate compositions and then mixed together into a single composition prior to administration.

Any cell type or corresponding tissue may be targeted for agent delivery using the present methods. Suitable target cells include, e.g., chondrocytes, epithelial cells, nerve cells, muscle cells, blood cells (e.g., lymphocytes or myeloid leukocytes), endothelial cells, pericytes, fibroblasts, glial cells, and dendritic cells. Other suitable target cells include cancer cells, immune cells, bacterially-infected cells, virally-infected cells, or cells having an abnormal metabolic activity. In a particular variation where the target cell is a secretory cell, the target secretory cell is a hepatocyte. In some such embodiments, either or both of the LNP and membrane-destabilizing polymer includes a targeting ligand that specifically binds to the asialoglycoprotein receptor (ASGPR); for example, in particular variations, a targeting ligand includes an N-acetylgalactosamine (NAG) residue (e.g., a monovalent NAG moiety or a tri-NAG structure). Target cells further include those where the cell is in a mammalian animal, including, for example, a human, rodent, murine, bovine, canine, feline, sheep, equine, and simian mammal.

In particular embodiments comprising delivery of a polynucleotide, the polynucleotide is an mRNA molecule encoding a functional protein, such as a functional protein associated with a protein deficiency disease, and the method increases the amount of the functional protein within the target cell. For example, in specific variations, the mRNA encodes a protein selected from erythropoietin, thrombopoietin, Factor VII, Factor VIII, LDL receptor, alpha-1-antitrypsin (A1AT), carbamoyl phosphate synthetase I (CPS1), fumarylacetoacetase (FAH) enzyme, alanine:glyoxylate-aminotransferase (AGT), methylmalonyl CoA mutase (MUT), propionyl CoA carboxylase alpha subunit (PCCA), propionyl CoA carboxylase beta subunit (PCCB), a subunit of branched-chain ketoacid dehydrogenase (BCKDH), ornithine transcarbamylase (OTC), copper-transporting ATPase Atp7B, bilirubin uridinediphosphate glucuronyltransferase (BGT) enzyme, hepcidin, glucose-6-phosphatase (G6Pase), glucose 6-phosphate translocase, lysosomal glucocerebrosidase (GB), Niemann-Pick C1 protein (NPC1), Niemann-Pick C2 protein (NPC2), acid sphingomyelinase (ASM), Factor IX, galactose-1-phosphate uridylyltransferase, galactokinase, UDP-galactose 4-epimerase, transthyretin, a complement regulatory protein, phenylalanine hydroxylase (PAH), homogentisate 1,2-dioxygenase, porphobilinogen deaminase, hypoxanthine-guanine phosphoribosyltransferase (HGPRT), argininosuccinate lyase (ASL), argininosuccinate synthetase (ASS1), P-type ATPase protein FIC-1, alpha-galactosidase A, acid ceramidase, acid α-L-fucosidase, acid f-galactosidase, iduronate-2-sulfatase, alpha-L-iduronidase, galactocerebrosidase, acid α-mannosidase, β-mannosidase, arylsulfatase B, arylsulfatase A, N-acetyl-galactosamine-6-sulfate sulfatase, acid f-galactosidase, acid α-glucosidase, β-hexosaminidase B, heparan-N-sulfatase, alpha-N-acetylglucosaminidase, acetyl-CoA:α-glucosaminide N-acetyltransferase, N-acetylglucosamine-6-sulfate sulfatase, alpha-N-acetylgalactosaminidase, sialidase, β-glucuronidase, and β-hexosaminidase A.

In certain embodiments comprising delivery of an mRNA molecule encoding a functional protein, the mRNA encodes a secreted protein. Exemplary secreted proteins include erythropoietin, thrombopoietin, granulocyte-colony stimulating factor, granulocyte macrophage-colony stimulating factor, leptin, platelet-derived growth factors (e.g., platelet-derived growth factor B), keratinocyte growth factor, bone morphogenic protein 2, bone morphogenic protein 7, insulin, glucagon-like peptide-1, human growth hormone, clotting factors (e.g., Factor VII, Factor VIII, Factor IX), relaxins (e.g., relaxin-2), interferons (e.g., interferon-α, interferon-β, interferon-γ), interleukins (e.g., interleukin-2, interleukin-4, interleukin-10, interleukin-11, interleukin-12, interleukin-18, interleukin-21), and chemokines (e.g., CC subfamily chemokines, CXC subfamily chemokines, C subfamily chemokines, CX3C subfamily chemokines). Secreted proteins also include antibodies, which may be selected from various antibody embodiments described herein. Particularly suitable antibodies include genetically engineered antibodies such as, for example, chimeric antibodies, humanized antibodies, single-chain antibodies (e.g., a single-chain Fv (scFv)), and bispecific antibodies. In some variations, the mRNA encodes an antibody that specifically binds and antagonizes a protein selected from vascular endothelial growth factor A (VEGF-A), tumor necrosis factor α (TNFα), interleukin-6 (IL-6), interleukin-17A (IL-17A), interleukin-17F (IL-17F), interleukin-21 (IL-21), interleukin-23 (IL-23), cytotoxic T-lymphocyte-associated protein 4 (CTLA-4), and programmed cell death protein 1 (PD-1).

In certain embodiments comprising increasing the amount of a protein in a cell, the protein is ornithine transcarbamylase (OTC). In such embodiments, an mRNA encoding an OTC protein is formulated into a lipid nanoparticle composition and is administered to a subject with co-injection or separate injection of a membrane-destabilizing polymer as described herein. In particular variations, the mRNA molecule encodes an OTC protein comprising an amino acid sequence having at least 90% or at least 95% sequence identity with residues 35-354 of SEQ ID NO:1 (e.g., at least 96%, at least 97%, at least 98%, at least 99%, at least 99.5%, or 100% sequence identity with residues 35-354 of SEQ ID NO:1). To direct an encoded OTC protein to the mitochondria of the cell, an mRNA molecule encoding the OTC protein includes a sequence encoding a mitochondrial targeting signal peptide (also referred to herein as a "mitochondrial leader sequence"). The mitochondrial leader sequence may be that of a native OTC protein (e.g., residues 1-34 of SEQ ID NO:1 (a native human mitochondrial leader sequence) or residues 1-34 of SEQ ID NO:2 (a native mouse mitochondrial leader sequence)), or may be derived from another protein comprising a mitochondrial targeting signal peptide, or synthesized de novo. An engineered cleavage site may be included at the junction between the mitochondrial leader sequence and the remainder of the polypeptide to optimize proteolytic processing in the cell. The mitochondrial leader sequence is operably linked to the mRNA sequence encoding the mature OTC protein, i.e., the two sequences are joined in the correct reading frame and positioned to direct the newly synthesized polypeptide to the mitochondria of a cell. Mitochondrial leader sequences are commonly positioned at the amino terminus of the protein. In specific variations, the encoded OTC protein with a mitochondrial leader sequence has an amino acid sequence as set forth in SEQ ID NO:1 or SEQ ID NO:2. Suitable mRNA sequences encoding an OTC protein of SEQ ID NO:1, and which may be formulated into a lipid nanoparticle composition, may comprise sequences as shown in SEQ ID NO:6 or SEQ ID NO:8 (coding sequence (CDS) for each corresponding to residues 48-1112). Suitable mRNA sequences encoding an OTC protein of SEQ ID NO:2, and which may be formulated into a lipid nanoparticle composition, may comprise a sequence as shown in SEQ ID NO:7 (coding sequence (CDS) corresponding to residues 48-1112). An OTC-encoding mRNA for formulation with a lipid nanoparticle typically further includes a poly(A) at its 3' end (e.g., a polyA tail of from about 50 to about 500 adenine residues), which may be added to a construct using well-known genetic engineering techniques (e.g., via PCR). Exemplary DNA sequences that may be used for insertion into an appropriate DNA vector for production and preparation of mRNA constructs of SEQ ID NOs. 6-8 are shown in SEQ ID NOs. 3-5, respectively.

In other embodiments comprising increasing the amount of a protein in a cell, the protein is methylmalonyl CoA mutase (MUT), propionyl CoA carboxylase subunit A (PCCA), propionyl CoA carboxylase subunit B (PCCB), or a subunit of branched-chain ketoacid dehydrogenase (BCKDH). In such embodiments, an mRNA encoding a MUT, PCCA, PCCB, or BCKDH subunit protein is formulated into a lipid nanoparticle composition and is administered to a subject with co-injection or separate injection of a membrane-destabilizing polymer as described herein. In particular variations, the mRNA molecule encodes a MUT protein comprising an amino acid sequence having at least 90% or at least 95% sequence identity with residues 33-750 of SEQ ID NO:9 (e.g., at least 96%, at least 97%, at least 98%, at least 99%, at least 99.5%, or 100% sequence identity with residues 33-750 of SEQ ID NO:9). In other variations, the mRNA molecule encodes a PCCA protein comprising an amino acid sequence having at least 90% or at least 95% sequence identity with residues 53-728 of SEQ ID NO:11 (e.g., at least 96%, at least 97%, at least 98%, at least 99%, at least 99.5%, or 100% sequence identity with residues 53-728 of SEQ ID NO:11). In other variations, the mRNA molecule encodes a PCCB protein comprising an amino acid sequence having at least 90% or at least 95% sequence identity with residues 29-539 of SEQ ID NO:13 (e.g., at least 96%, at least 97%, at least 98%, at least 99%, at least 99.5%, or 100% sequence identity with residues 29-539 of SEQ ID NO:13). To direct an encoded MUT, PCCA, PCCB, or BCKDH subunit protein to the mitochondria of the cell, an mRNA molecule encoding the protein includes a sequence encoding a mitochondrial leader sequence. The mitochondrial leader sequence may be that of a native protein (e.g., residues 1-32 of SEQ ID NO:9 (a native human MUT mitochondrial leader sequence), residues 1-52 of SEQ ID NO:11 (a native human PCCA mitochondrial leader sequence), or residues 1-28 of SEQ ID NO:13 (a native human PCCB mitochondrial leader sequence)), or may be derived from another protein comprising a mitochondrial targeting signal peptide, or synthesized de novo. An engineered cleavage site may be included at the junction between the mitochondrial leader sequence and the remainder of the polypeptide to optimize proteolytic processing in the cell. The mitochondrial leader sequence is operably linked to the mRNA sequence encoding the mature MUT, PCCA, PCCB, or BCKDH subunit protein, i.e., the two sequences are joined in the correct reading frame and positioned to direct the newly synthesized polypeptide to the mitochondria of a cell. In specific variations, the encoded MUT protein with a mitochondrial leader sequence has an amino acid sequence as set forth in SEQ ID NO:9, the encoded PCCA protein with a mitochondrial leader sequence has an amino acid sequence as set forth in SEQ ID NO: 11, or the encoded PCCB protein with a mitochondrial leader sequence has an amino acid sequence as set forth in SEQ ID NO:13. A suitable mRNA sequence encoding a MUT protein of SEQ ID NO:9, and which may be formulated into a composition comprising a lipid nanoparticle in accordance with the present disclosure, may comprise the sequence shown in SEQ ID NO:10 (coding sequence corresponding to residues 48-2297). A suitable mRNA sequence encoding a PCCA protein of SEQ ID NO:11, and which may be formulated into a composition comprising a lipid nanoparticle in accordance with the present disclosure, may comprise the sequence shown in SEQ ID NO: 12 (coding sequence corresponding to residues 48-2231). A suitable mRNA sequence encoding a PCCB protein of SEQ ID NO:13, and which may be formulated into a composition comprising a lipid nanoparticle in accordance with the present disclosure, may comprise the sequence shown in SEQ ID NO:14 (coding sequence corresponding to residues 48-1664). A MUT-, PCCA-, PCCB-, or BCKDH-subunit-encoding mRNA for formulation with a lipid nanoparticle typically includes a poly(A) at its 3' end (e.g., a polyA tail of from about 50 to about 500 adenine residues).

In yet other embodiments comprising increasing the amount of a protein in a cell the protein is argininosuccinate lyase (ASL) or argininosuccinate synthetase (ASS1). In such embodiments, an mRNA encoding an ASL or ASS1 protein is formulated into a lipid nanoparticle composition and is administered to a subject with co-injection or separate injection of a membrane-destabilizing polymer as described herein. In particular variations, the mRNA molecule encodes an ASL protein comprising an amino acid sequence having at least 90% or at least 95% sequence identity with SEQ ID NO:48 (e.g., at least 96%, at least 97%, at least 98%, at least 99%, at least 99.5%, or 100% sequence identity with SEQ ID NO:48). In other variations, the mRNA molecule encodes an ASS1 protein comprising an amino acid sequence having at least 90% or at least 95% sequence identity with SEQ ID NO:50 (e.g., at least 96%, at least 97%, at least 98%, at least 99%, at least 99.5%, or 100% sequence identity with SEQ ID NO:50). A suitable mRNA sequence encoding an ASL protein of SEQ ID NO:48, and which may be formulated into a composition comprising a lipid nanoparticle in accordance with the present disclosure, may comprise the sequence shown in SEQ ID NO:49 (coding sequence corresponding to residues 48-1439). A suitable mRNA sequence encoding an ASS1 protein of SEQ ID NO:50, and which may be formulated into a composition comprising a lipid nanoparticle in accordance with the present disclosure, may comprise the sequence shown in SEQ ID NO:51 (coding sequence corresponding to residues 48-1283). An ASL- or ASS1-encoding mRNA for formulation with a lipid nanoparticle typically includes a poly(A) at its 3' end (e.g., a polyA tail of from about 50 to about 500 adenine residues).

Thus, in certain embodiments of the present invention, an mRNA is formulated into a lipid nanoparticle as the mRNA carrier. In some variations, a sequential injection of a membrane-destabilizing polymer nanoparticle is given approximately 1 to 15 minutes following the mRNA/LNP that enhances delivery of the mRNA to the cytoplasm in the target cell. In some embodiments of the present disclosure, the LNP comprises a cationic lipid, a PEG-lipid, cholesterol, and an anionic lipid. The lipids are typically solubilized, e.g., in 100% ethanol, typically from 20 mg/mL to 200 mg/mL individually and then mixed together to obtain, for example, the following lipid ratio ranges: 20-60 mol % cationic lipid, 0-50 mol % anionic lipid, 0-40 mol % cholesterol, and 0-15 mol % PEG-lipid. A lipid mixture in ethanol is typically prepared in a range from 1 mg/mL to 40 mg/mL. The mRNA may be prepared using a standard in vitro transcription reaction according to well-known procedures. The mRNA solution is typically diluted in an aqueous/isotonic buffer at about normal physiological pH (e.g., pH 7.4) at a concentration from 0.01 mg/mL to 1 mg/mL. The lipid mixture in ethanol and mRNA aqueous solution may then be mixed together at a 1:3 ratio of lipid:mRNA using a microfluidic device. Lipid concentrations, mRNA concentrations, and mixing ratio can be adjusted to prepare lipid:mRNA formulations at N:P ratios (nitrogen to phosphorous ratio between the cationic lipid and the mRNA) from 0.5 to 40. After an incubation time, the mRNA/LNP is typically dialyzed overnight in an aqueous/isotonic buffer. The polymer may be solubilized in an aqueous/isotonic buffer at about normal physiological pH (e.g., pH 7.4). Particularly suitable concentrations of solubilized polymer range from 1 mg/mL to 50 mg/mL. The formulations may be used for delivery of the mRNA into target cells (e.g., the formulations may be contacted with cells in vitro or administered to a subject, such as mice, in vivo).

In further variations where an mRNA is formulated into a lipid nanoparticle and delivered in accordance with the present disclosure, the mRNA/LNP is formulated so as to reduce or eliminate an undesired immune response in a subject. For example, RNA transcribed in vitro typically contains multiple contaminants, including short RNAs produced by abortive initiation events, and double-stranded (ds)RNAs generated by self-complementary 3' extension, RNA-primed transcription from RNA templates and RNA-dependent RNA polymerase activity. See Karikó et al., *Nucleic Acids Research*, 2011, 1-10, doi:10.1093/nar/gkr695. These dsRNA contaminants can be immunostimulatory through binding and activating a number of innate immune receptors, including toll-like receptors TLR3, TLR7, TLR8, retinoic acid-inducible gene I (RIG-I), and RNA-dependent protein kinase (PKR). Further, the presence of immunostimulatory nucleic acid encapsulated in lipid nanoparticles containing surface-associated PEG can stimulate an immune response against the carrier. See Semple et al., *J. Pharmacol. Exp. Ther.* 312:1020-1026, 2005. Semple et al. showed this immune response to depend on the presence of non-exchangeable PEG-lipids (DSPE-PEG2000 or PEG ceramide $C_{20}$) in the LNP and to lead to rapid plasma elimination of subsequent repeat administrations of liposome-encapsulated oligodeoxynucleotide (ODN); in contrast, nucleic acid encapsulated in a LNP containing an exchangeable PEG-lipid with a shorter acyl chain (PEG ceramide $C_{14}$) showed no change in circulation levels following repeat administrations. See Semple et al., supra.

To reduce or eliminate a potential immune response against mRNA encapsulated in an LNP, as well as to reduce or eliminate a potential rapid plasma clearance following repeat administrations of the mRNA/LNP, certain variations of the mRNA or mRNA/LNP formulation may be used. For example, the mRNA may be purified (e.g., using HPLC purification) to remove immunostimulatory dsRNA contaminants. HPLC-purified mRNA has been shown to avoid stimulating type I interferon cytokines (IFN-α, IFN-β and TNF-α). See Karikó et al., supra. In some variations, one or more uridines in the mRNA sequence are substituted with pseudouridine or N1-methyl-pseudouridine, which has been shown to avoid activating innate immune receptors (see id.). In other embodiments, the mRNA sequence may be codon optimized to remove or reduce the number of uridines, which can activate the innate immune response. In yet other embodiments, an exchangeable PEG-lipid (e.g., DMPE-PEG2000) in the LNP is used to maintain activity following repeat administration. Any one or more of these variations may be used for in vivo delivery of mRNA and related methods of treatment in accordance with the present disclosure.

Methods for purifying mRNA are generally known in the art and may be used to prepare mRNA for formulation with a lipid nanoparticle in accordance with the present disclosure. For example, after isolation of in vitro-transcribed (IVT) mRNA constructs from transcription mixtures, further purification of the material may be performed using ion-pair/reversed-phase HPLC or anion-exchange HPLC. These techniques may remove length-based sequence variants and other nucleic acid impurities when performed under denaturing conditions. Ion-pair/reversed phase HPLC utilizes a traditional C8 or C18 stationary phase (alternatively, polymeric-based media may be used) and a mobile phase system containing a suitable ion-pairing agent such as triethylammonium acetate. The material is traditionally eluted using an acetonitrile gradient. The purification occurs under denaturing conditions (typically at temperatures >55° C.). Strong or weak anion-exchange HPLC may also be utilized. For example, a strong anion exchange column (utilizing a quaternary ammonium in the stationary phase) may be used with a mobile phase system buffered at neutral to basic pH (e.g., 20 mM sodium phosphate at pH 8.0), with elution modulated by gradient addition of a stronger salt solution (e.g., 1M sodium bromide) to displace interaction of the nucleic acid backbone with the column stationary phase. Because the strong ionic environment increases the stability of the mRNA conformation (and therefore confers a higher Tm relative to the Ion-pair/reversed phase separations), the purification may require a higher temperature and/or pH environment to fully melt out secondary or double-stranded structures.

In certain embodiments of the present invention, a therapeutic agent is delivered intracellularly to cells of a target tissue for treatment of a disease amenable to treatment with the therapeutic agent. In such embodiments, the therapeutic agent is delivered to the target tissue via combined administration of a membrane-destabilizing polymer and lipid nanoparticle comprising the therapeutic agent as described herein, typically in a manner otherwise consistent with conventional methodologies associated with management of the disease or disorder for which treatment is sought. In accordance with the disclosure herein, a therapeutically effective amount of the agent is administered to a subject in need of such treatment for a time and under conditions sufficient to prevent or treat the disease.

Subjects for administration of a therapeutic agent as described herein include patients at high risk for developing a particular disease as well as patients presenting with an existing disease. In certain embodiments, the subject has been diagnosed as having the disease for which treatment is sought. Further, subjects can be monitored during the course of treatment for any change in the disease (e.g., for an increase or decrease in clinical symptoms of the disease).

In prophylactic applications, pharmaceutical compositions are administered to a patient susceptible to, or otherwise at risk of, a particular disease in an amount sufficient to eliminate or reduce the risk or delay the onset of the disease. In therapeutic applications, compositions are administered to a patient suspected of, or already suffering from, such a disease in an amount sufficient to cure, or at least partially arrest, the symptoms of the disease and its complications. An amount adequate to accomplish this is referred to as a therapeutically- or pharmaceutically-effective dose or amount. In both prophylactic and therapeutic regimes, agents are usually administered in several dosages until a sufficient response has been achieved. Typically, the response is monitored and repeated dosages are given if the desired response starts to fade.

To identify subject patients for treatment according to the methods of the invention, accepted screening methods may be employed to determine risk factors associated with specific diseases or to determine the status of an existing disease identified in a subject. Such methods can include, for example, determining whether an individual has relatives who have been diagnosed with a particular disease. Screening methods can also include, for example, blood tests to assay for buildups of metabolites caused by missing or mutated proteins in the liver (for certain liver diseases) or conventional work-ups to determine familial status for a particular disease known to have a heritable component (for example, various cancers and protein deficiency diseases are known to have certain inheritable components). Inheritable components of cancers include, for example, mutations in multiple genes that are transforming (e.g., Ras, Raf, EGFR, cMet and others), the presence or absence of certain HLA and killer inhibitory receptor (KIR) molecules, or mechanisms by which cancer cells are able to modulate immune suppression of cells like NK cells and T cells, either directly or indirectly (see, e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disease of interest. In addition, a wide variety of immunological methods are known in the art that are useful to identify markers for specific diseases. For example, various ELISA immunoassay methods are available and well-known in the art that employ monoclonal antibody probes to detect antigens associated with specific tumors. Screening may be implemented as indicated by known patient symptomology, age factors, related risk factors, etc. These methods allow the clinician to routinely select patients in need of the methods described herein for treatment.

For administration, a lipid nanoparticle and membrane-destabilizing polymer are formulated as a single pharmaceutical composition (for co-injection embodiments; typically mixed together just prior to administration) or as separate pharmaceutical compositions (for separate administration embodiments). A pharmaceutical composition comprising an LNP and/or membrane-destabilizing polymer can be formulated according to known methods to prepare pharmaceutically useful compositions, whereby the LNP and/or polymer component(s) are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), *Remington's Pharmaceutical Sciences* (Mack Publishing Company, 19th ed. 1995).) Formulations may further include one or more excipients, preservatives, solubilizers, buffering agents, etc.

For disease treatment, a pharmaceutical composition is administered to a subject in a therapeutically effective amount. According to the methods of the present invention, the lipid nanoparticle and membrane-destabilizing polymer may be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration. For prevention and treatment purposes, the compositions may be administered to a subject in a single bolus delivery, via continuous delivery (e.g., continuous transdermal delivery) over an extended time period, or in a repeated administration protocol (e.g., on an hourly, daily, weekly, or bi-weekly basis).

Determination of the proper dosage for a particular situation is within the skill in the art. Determination of effective dosages in this context is typically based on animal model studies followed up by human clinical trials and is guided by determining effective dosages and administration protocols that significantly reduce the occurrence or severity of the subject disease in model subjects. Effective doses of the compositions of the present invention vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically or prophylactically effective amount is also one in which any undesired collateral effects are outweighed by beneficial effects. For administration of a therapeutic agent, a dosage typically ranges from about 0.1 μg to about 100 mg/kg or about 1 μg/kg to about 50 mg/kg, and more usually about 1 μg/kg to about 10 mg/kg or about 10 μg to about 5 mg/kg of the subject's body weight, exclusive of other LNP components. In more specific embodiments, an effective amount of the agent is between about 1 μg/kg and about 20 mg/kg, between about 10 μg/kg and about 10 mg/kg, or between about 0.1 mg/kg and about 5 mg/kg, exclusive of other LNP component. The quantity of a membrane-destabilizing polymer may be varied or adjusted, for example, from about 10 μg to about 200 mg/kg, about 10 μg to about 100 mg/kg, about 0.1 mg/kg to about 100 mg/kg, about 0.1 mg/kg to about 50 mg/kg, or about 0.5 mg/kg to about 50 mg/kg. Dosages within this range can be achieved by single or multiple administrations, including, e.g., multiple administrations per day or daily, weekly, bi-weekly, or monthly administrations. For example, in certain variations, a regimen consists of an initial administration followed by multiple, subsequent administrations at weekly or bi-weekly intervals. Another regimen consists of an initial administration followed by multiple, subsequent administrations at monthly or bi-monthly intervals. Alternatively, administrations can be on an irregular basis as indicated by monitoring of physiological correlates of the disease and/or clinical symptoms of the disease.

Lipid nanoparticles can adsorb to virtually any type of cell and then slowly release the encapsulated agent. Alternatively, an absorbed lipid nanoparticle may be endocytosed by cells (e.g., cells that are phagocytic). Endocytosis is typically followed by intralysosomal degradation of LNP lipids and release of the encapsulated agents (see Scherphof et al., *Ann. N.Y. Acad. Sci.* 446:368, 1985). After intravenous administration, lipid nanoparticles (e.g., liposomes of about 0.1 to 1.0 μm) are typically taken up by cells of the reticuloendothelial system, located principally in the liver and spleen. This preferential uptake of smaller liposomes by the cells of the reticuloendothelial system has been used to deliver chemotherapeutic agents to macrophages and to tumors of the liver. As described herein, it is believed the combining administration of a lipid nanoparticle together with administration of a membrane-destabilizing polymer enhances efficiency of delivery of the LNP-associated therapeutic agent to the cytosol of a cell.

The reticuloendothelial system can be circumvented by several methods including saturation with large doses of lipid nanoparticles, or selective macrophage inactivation by pharmacological means (see Claassen et al., *Biochim. Biophys. Acta* 802:428, 1984). In addition, incorporation of glycolipid- or polyethelene glycol-derivatized phospholipids into liposome membranes has been shown to result in a significantly reduced uptake by the reticuloendothelial system (see Allen et al., *Biochim. Biophys. Acta* 1068:133, 1991; Allen et al., *Biochim. Biophys. Acta* 1150:9, 1993).

Lipid nanoparticles can also be prepared to target particular cells or tissues by varying phospholipid composition of the lipid nanoparticles. For example, liposomes prepared with a high content of a nonionic surfactant have been used to target the liver. (See, e.g., Japanese Patent 04-244,018 to Hayakawa et al.; Kato et al., *Biol. Pharm. Bull.* 16:960, 1993.) These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver. (See Shimizu et al., *Biol. Pharm. Bull.* 20:881, 1997.)

Lipid nanoparticles and/or membrane-destabilizing polymers can also be prepared to target particular cells or tissues by using a targeting ligand as discussed herein.

In some embodiments, a lipid nanoparticle and membrane-destabilizing polymer as described herein are used in a method for treating a disease associated with defective gene expression and/or activity in a subject. Such methods of treatment include administering to a subject having the disease associated with defective gene expression and/or activity (a) an effective amount of a lipid nanoparticle comprising a polynucleotide that is homologous to and can silence, for example by cleavage, a gene or that specifies the amino acid sequence of a protein and is translated during protein synthesis, and (b) an effective amount of a membrane-destabilizing polymer, where the polynucleotide is delivered into the cytosol of target cells of a target tissue associated with the disease, thereby treating the disease. In some embodiments, at least one of the lipid nanoparticle and membrane-destabilizing polymer includes a targeting ligand that specifically binds to a molecule on the surface of the target cells of the target tissue within the subject. Examples of a disease associated with defective gene expression and/or activity in a subject treatable by the methods disclosed herein include liver cancer (e.g., hepatocellular carcinoma), hepatitis, hypercholesterolemia, liver fibrosis, and haemochromatosis. In other variations, a disease or condition associated with defective gene expression and/or activity in a subject treatable by the methods disclosed herein is a cancer of the breast, ovaries, pancreas, endometrium, lungs, kidneys, colon, brain (e.g., glioblastoma), or myeloid cells of hematopoietic origin.

In certain embodiments, the disease associated with defective gene expression is a disease characterized by a deficiency in a functional polypeptide (also referred to herein as a "disease associated with a protein deficiency" or a "protein deficiency disease"). Such methods of treatment include administering to a subject having the protein deficiency disease (a) an effective amount of a lipid nanoparticle comprising an mRNA that encodes the functional protein or a protein having the same biological activity as the functional protein and (b) an effective amount of a membrane-destabilizing polymer, where the mRNA is delivered into the cytosol of target cells of a target tissue associated with the protein deficiency, and where the mRNA is translated during protein synthesis so as to produce the encoded protein within the target tissue in an amount sufficient to treat the disease. In some embodiments, at least one of the lipid nanoparticle and membrane-destabilizing polymer comprises a targeting ligand that specifically binds to a molecule on the surface of the target cells of the target tissue. In specific variations, the mRNA encodes a functional erythropoietin, alpha-galactosidase A, LDL receptor, Factor VII, Factor VIII, Factor IX, alpha-L-iduronidase, iduronate-2-sulfatase, heparan-N-sulfatase, alpha-N-acetylglucosaminidase, galactose 6-sulfatase, acid (3-galactosidase, lysosomal acid lipase, ornithine transcarbamylase (OTC), alpha-1-antitrypsin, arylsulfatase A, arylsulfatase B, acid ceramidase, acid α-L-fucosidsase, acid β-glucosidase (also known as glucocerebrosidase), galactocerebrosidase, acid α-mannosidase, acid β-mannosidase, N-acetylgalactosamine-6-sulfate sulfatase, acid sphingomyelinase, acid α-glucosidase, 3-hexosaminidase B, acetyl-CoA:α-glucosaminide N-acetyltransferase, N-acetylglucosamine-6-sulfate sulfatase, alpha-N-acetylgalactosaminidase, sialidase, β-glucuronidase, or β-hexosaminidase A. In other embodiments, the mRNA encodes a functional Retinoblastoma protein (pRb), p53 tumor-suppressor protein, Phosphatase and tensin homolog (PTEN), Von Hippel-Lindau tumor suppressor (pVHL), Adenomatous polyposis coli (APC), FAS receptor (FasR), Suppression of tumorigenicity 5 (ST5), YPEL3, Suppressor of tumorigenicity protein 7 (ST7), or Suppressor of tumorigenicity 14 protein (ST14). In yet other embodiments, the mRNA encodes a functional Galactose-1-phosphate uridylyltransferase, Galactokinase, UDP-galactose 4-epimerase, Transthyretin, complement regulatory protein (e.g., factor H, factor I, or membrane cofactor protein), phenylalanine hydroxylase (PAH), homogentisate 1,2-dioxygenase, Porphobilinogen deaminase, hypoxanthine-guanine phosphoribosyltransferase (HGPRT), argininosuccinate lyase (ASL), argininosuccinate synthetase (ASS1), or P-type ATPase protein, FIC-1.

Further examples of a disease or condition associated with defective gene expression and/or activity in a subject treatable by the methods disclosed herein include protein deficiency diseases associated with single-gene metabolic defects in the liver. Exemplary protein deficiency diseases of the liver include diseases associated with urea cycle defects (e.g., ornithine transcarbamylase (OTC) deficiency, carbamoyl phosphate synthetase I (CPS1) deficiency, argininosuccinic aciduria (argininosuccinate lyase (ASL) deficiency), and citrullinemia (argininosuccinate synthetase (ASS1) deficiency)); tyrosinemia type 1 (fumarylacetoacetase (FAH) enzyme deficiency); primary hyper-oxaluria type 1 (alanine: glyoxylate-aminotransferase (AGT) deficiency); organic acidemia (e.g., methylmalonic acidemia (MMA; deficiency in, for example, methylmalonyl CoA mutase), propionic acidemia (PA; propionyl CoA carboxylase (PCC) deficiency), and maple syrup urine disease (MSUD; branched-chain ketoacid dehydrogenase (BCKDH) deficiency)); Wilson's Disease (deficiency in copper-transporting ATPase, Atp7B); Crigler-Najjar Syndrome Type 1 (bilirubin uridinediphosphate glucuronyltransferase (BGT) enzyme deficiency); hemochromatosis (hepcidin deficiency); glycogen storage disease (GSD) type 1a (glucose-6-phosphatase (G6Pase) deficiency); glycogen storage disease (GSD) type 1b (glucose 6-phosphate translocase deficiency); lysosomal storage diseases (LSDs; deficiencies in lysosomal enzymes) such as, e.g., Gaucher's Disease types 1, 2, and 3 (lysosomal glucocerebrosidase (GB) deficiency), Niemann-Pick Disease Type C (mutation in either the NPC1 or NPC2 gene), and Niemann-Pick Disease Types A and B (acid sphingomyelinase (ASM) deficiency); alpha-1 antitrypsin (A1AT) deficiency; hemophilia B (Factor IX deficiency); galactosemia types 1, 2, and 3 (galactose-1-phosphate uridylyltransferase, galactokinase, and UDP-galactose 4-epimerase deficiencies, respectively); transthyretin-related hereditary amyloidosis (TTR-familial amyloid polyneuropathy; transthyretin deficiency); atypical haemolytic uremic syndrome-1 (deficiencies in complement regulatory proteins, e.g., factor H, factor I, or membrane cofactor protein); phenylketonuria (phenylalanine hydroxylase (PAH) deficiency); alcaptonuria (homogentisate 1,2-dioxygenase deficiency); acute intermittent porphyria (porphobilinogen deaminase deficiency); Lesch-Nyhan syndrome (hypoxanthine-guanine phosphoribosyltransferase (HGPRT) deficiency; and progressive familial intrahepatic cholestasis (PFIC) (P-type ATPase protein, FIC-1 deficiency). Additional examples of protein deficiency diseases that are lysosomal storage diseases (LSDs) include Fabry disease (alpha-galactosidase A deficiency); Farber disease (acid ceramidase deficiency); fucosidosis (acid α-L-fucosidsase deficiency); GM1 gangliosidosis (acid β-galactosidase deficiency); Hunter syndrome (mucopolysaccharidosis type II (MPS II); iduronate-2-sulfatase deficiency); Hurler-Scheie, Hurler, and Scheie syndromes (mucopolysaccharidosis type I (MPS I); alpha-L-iduronidase deficiency); Krabbe disease (galactocerebrosidase deficiency); α-mannosidosis (acid α-mannosidase deficiency); β-mannosidosis (acid β-mannosidase deficiency); Maroteaux-Lamy syndrome (mucopolysaccharidosis type VI (MPS VI); arylsulfatase B deficiency); metachromatic leukodystrophy (arylsulfatase A deficiency); Morquio syndrome type A (mucopolysaccharidosis type IVA (MPS IVA); N-acetylgalactosamine-6-sulfate sulfatase deficiency); Morquio syndrome type B (mucopolysaccharidosis type IVB (MPS IVB); acid f-galactosidase deficiency); Pompe disease (acid α-glucosidase deficiency); Sandhoff disease (β-hexosaminidase B deficiency); Sanfilippo syndrome type A (mucopolysaccharidosis type IIIA (MPS IIIA); heparan-N-sulfatase deficiency); Sanfilippo syndrome type B (mucopolysaccharidosis type IIIB (MPS IIIB); alpha-N-acetylglucosaminidase deficiency); Sanfilippo syndrome type C (mucopolysaccharidosis type IIIC (MPS IIIC); acetyl-CoA:α-glucosaminide N-acetyltransferase deficiency); Sanfilippo syndrome type D (mucopolysaccharidosis type IIID (MPS IIID); N-acetylglucosamine-6-sulfate sulfatase deficiency); Schindler/Kanzaki disease (alpha-N-acetylgalactosaminidase deficiency); sialidosis (sialidase deficiency); Sly syndrome (mucopolysaccharidosis type VII (MPS VII); β-glucuronidase deficiency); and Tay-Sachs disease (β-hexosaminidase A deficiency).

In particular variations, an mRNA encoding an ornithine transcarbamylase (OTC) protein is delivered in accordance with the present methods to treat ornithine transcarbamylase deficiency (OTCD). OTCD is a urea cycle disorder that can trigger hyperammonemia, a life-threatening illness that leads to brain damage, coma or even death. This is due to deficiency in the activity of OTC, a key enzyme in the urea cycle, which primarily takes place in the liver and is responsible for removal of excess nitrogen in the body. Ammonium nitrogen is produced from protein intake as well as protein breakdown in the body. In the liver, this ammonium nitrogen is converted into urea by enzymes in the urea cycle. Urea is non-toxic and cleared easily through the kidneys in urine, normally. However, when the OTC enzyme is deficient, ammonia levels rise in blood and cause severe brain damage. Patients with severe OTC deficiency are most often identified 2-3 days after birth where the patient has significantly elevated blood ammonia levels and ends up in a coma. Patients with milder OTC deficiency can have crises during times of stress resulting in elevated ammonia levels that can also lead to coma. Current therapies include ammonia scavenger drugs (Buphenyl, Ravicti) for use in patients with hyperammonemia.

The OTC gene is X-linked. The disease is present in males with one mutant allele and in females either homozygous or heterozygous with mutant alleles. Male patients are typically those with the severest OTC deficiency found right after birth. In addition to elevation in blood ammonia levels, urinary orotic acid levels are also elevated. In patients with severe OTC deficiency, OTC enzyme activity is <20% of normal levels. In patients with milder OTC deficiency, OTC enzyme activity is up to 30% of normal levels.

A method for treating OTCD with a lipid nanoparticle comprising an OTC-encoding mRNA and a membrane-destabilizing polymer generally includes administering to a subject having OTCD an effective amount of the lipid nanoparticle and an effective amount of the membrane-destabilizing polymer, where at least one of the lipid nanoparticle and membrane-destabilizing polymer includes a targeting ligand that specifically binds to a molecule on the surface of liver cells within the subject, and whereby the OTC-encoding mRNA is delivered to liver cells and translated during protein synthesis to produce the OTC protein. The OTC-encoding mRNA may be an mRNA as set forth above with respect to a method for increasing OTC protein in a cell.

The efficacy of a composition or method for treating a disease can be evaluated in vivo in animal models of disease. Particularly suitable animal models for evaluating efficacy of a [lipid nanoparticle]/[membrane-destabilizing polymer] composition (or combination of LNP composition and polymer composition) for treatment of OTCD includes known mouse models having deficiencies of the OTC enzyme in the liver. One such mouse model, OTC-spf$^{ash}$ (sparse fur and abnormal skin and hair) mice, contain an R129H mutation resulting in reduced levels of OTC protein and have only 5-10% of the normal level of enzyme activity in liver (see Hodges et al., *Proc. Natl. Acad. Sci. USA* 86:4142-4146, 1989). Another model, OTC-spf mice, contain an H117N mutation which results in reduced levels of enzyme activity to 5-10% of normal levels (see Rosenberg et al., *Science* 222:426-428, 1983). Both of these mouse models have elevated urine orotic acid levels compared to their wild-type littermate mice. A third model for OTC deficiency is inducing hyperammonemia in OTC-spf or OTC-spf$^{ash}$ mice (Cunningham et al., *Mol Ther* 19: 854-859, 2011). These mice are treated with OTC siRNA or AAV2/8 vector/OTC shRNA to knockdown residual endogenous OTC expression and activity. Plasma ammonia levels are elevated and mice die within approximately 7-28 days.

In additional variations, an mRNA encoding an enzyme deficient in an organic acidemia is delivered in accordance with the present methods to treat the organic acidemia. Organic acidemia (also known as aciduria) (OA) is a group of disorders characterized by the excretion of non-amino organic acids in the urine. Most organic acidemias result from dysfunction of a specific step in amino acid catabolism, usually the result of deficient enzyme activity. The majority of organic acid disorders are caused by abnormal amino acid catabolism of branched-chain amino acids or lysine. They include propionic acidemia (PA), methylmalonic acidemia (MMA), maple syrup urine disease (MSUD), and others. These organic acidemias are inherited in an autosomal recessive manner. A neonate affected with an OA is usually well at birth and for the first few days of life. The usual clinical presentation is that of toxic encephalopathy and includes vomiting, poor feeding, neurologic symptoms such as seizures and abnormal tone, and lethargy progressing to coma. Outcome can be improved by diagnosis and treatment in the first ten days of life. In the older child or adolescent, variant forms of the OAs can present as loss of intellectual function, ataxia or other focal neurologic signs, Reye syndrome, recurrent ketoacidosis, or psychiatric symptoms.

Clinical laboratory findings indicate that organic acidemias include acidosis, ketosis, hyperammonemia, abnormal liver function, hypoglycemia, and neutropenia. First-line diagnosis in the organic acidemias is urine organic acid analysis using gas chromatography with mass spectrometry (GC/MS). The urinary organic acid profile is nearly always abnormal in the face of acute illness. Confirmatory testing involves assay of the activity of the deficient enzyme in lymphocytes or cultured fibroblasts and/or molecular genetic testing. Characteristics of the three primary disorders are summarized in Table 1.

the position of the metabolic block, and the effects of the toxic compounds. Treatment strategies include: (1) dietary restriction of the precursor amino acids and (2) use of adjunctive compounds to (a) dispose of toxic metabolites or (b) increase activity of deficient enzymes. Liver transplantation has been successful in a small number of affected individuals. Even with current clinical management approaches, individuals with organic acidemias have a greater risk of infection and a higher incidence of pancreatitis, which can be fatal.

Enzyme replacement therapy via specific mRNA delivery to the liver offers the most effective treatment of the organic acidemias. In certain embodiments of a method for treating an organic acidemia, an mRNA encoding a methylmalonyl CoA mutase (MUT) is delivered to a subject in accordance with the present methods to treat methylmalonic acidemia MMA. In other embodiments, an mRNA encoding a PCC subunit (PCCA or PCCB) is delivered to a subject in accordance with the present methods to treat propionic acidemia (PA). In yet other embodiments, an mRNA encoding a BCKDH subunit is delivered to a subject in accordance with the present methods to treat maple syrup urine disease (MSUD). A method for treating MMA, PA, or MSUD with a lipid nanoparticle comprising an Mut, Pcca/b, or BCKDH subunit mRNA and a membrane-destabilizing polymer generally includes administering to a subject having an organic acidemia of the specified type an effective amount of the lipid nanoparticle and an effective amount of the membrane-destabilizing polymer, where at least one of the lipid nanoparticle and membrane-destabilizing polymer includes a

TABLE 1

Metabolic Findings in Organic Acidemias Caused by Abnormal Amino Acid Catabolism

| Disorder | Amino Acid Pathway(s) Affected | Enzyme | Diagnostic Analytes by GC/MS and Quantitative Amino Acid Analysis |
| --- | --- | --- | --- |
| Propionic acidemia (PA) | Isoleucine, valine, methionine, threonine | Propionyl CoA carboxylase (PCC) (composed of three PCCA subunits and three PCCB subunits) | Propionic acid, 3-OH propionic acid, methyl citric acid, propionyl glycine in urine Propionyl carnitine, increased glycine in blood |
| Methylmalonic acidemia (MMA) | Isoleucine, valine, methionine, threonine | Methylmalonyl CoA mutase (MUT) | Methylmalonic acid in blood and urine Propionic acid, 3-OH propionic acid, methyl citrate in urine Acyl carnitines, increased glycine in blood |
| Maple syrup urine disease (MSUD) | Leucine, isoleucine, valine | Branched-chain ketoacid dehydrogenase (BCKDH) (composed of four different subunits) | Branched-chain ketoacids and hydroxyacids in urine Alloisoleucine in plasma |

Once the detection of specific analytes narrows the diagnostic possibilities, the activity of the deficient enzyme is assayed in lymphocytes or cultured fibroblasts as a confirmatory test. For many pathways, no single enzyme assay can establish the diagnosis. For others, tests such as complementation studies need to be done.

The goal of therapy is to restore biochemical and physiologic homeostasis. Neonates require emergency diagnosis and treatment depending on the specific biochemical lesion, targeting ligand that specifically binds to a molecule on the surface of liver cells within the subject, and whereby the Mut, Pcca/b, or BCKDH subunit mRNA is delivered to liver cells and translated during protein synthesis to produce the respective protein. A Mut or Pcca/b mRNA may be an mRNA as set forth above with respect to a method for increasing the respective protein in a cell.

The efficacy of a composition or method for treating an organic acidemia disease can be evaluated in vivo in animal models of disease. For example, particularly suitable animal models for evaluating efficacy of a mRNA/LNP and polymer composition (or combination of mRNA/LNP composition and polymer composition) for treatment of MMA and PA are as follows. Mut$^{-/-}$ neonatal mice with a severe form of MMA, which normally die within the first 21 days of life, have been successfully treated with hepatocyte-directed delivery of the methylmalonyl-CoA mutase (Mut) gene. Following an intrahepatic injection of adeno-associated virus expressing the murine Mut gene, Mut$^{-/-}$ mice were rescued and lived beyond 1 year of age (Carrillo-Carrasco et al., *Hum. Gene Ther.* 21:1147-1154, 2010). Another MMA disease model where mice survive into adulthood is Mut$^{-/-}$ mice with Mut cDNA expressed under the control of an insulated, muscle-specific promoter (Mut$^{-/-}$;Tg$^{INS-MCK-Mut}$) (Manoli et al., 2011, SIMD Abstract). These mice have elevated plasma methylmalonic acid levels and decreased oxidative capacity as measured by a $^{13}$C propionate oxidation/breathe assay. A mouse model of PA (Pcca$^{-/-}$ mice) succumbs to death 24-36 h after birth and is associated with fatal ketoacidosis (Miyazaki et al., *J. Biol. Chem.* 276: 35995-35999, 2001). Pcca gene transfer that provides a postnatal PCC activity of 10-20% in the liver of a transgenic mouse strain attenuates the fatal ketoacidosis in newborn mice (Miyazaki et al., 2001, supra). Recently, an intrahepatic adeno-associated virus mediated gene transfer for human Pcca was tested in neonatal Pcca$^{-/-}$ mice (Chandler et al., *Hum. Gene Ther.* 22:477-481, 2010). The authors found a sustained therapeutic effect as demonstrated in a survival rate of approximately 64% and reduction of disease-related metabolites (Chandler et al., 2010, supra). Another mouse disease model of PA is a hypomorphic model where Pcca$^{-/-}$ mice express a transgene bearing an A138T mutant of the PCCA protein. These mice have 2% of wild-type PCC activity, survive to adulthood and have elevations in disease-related metabolites (Guenzel et al., *Mol. Ther.* 21:1316-1323, 2013). Treatment of these mice with adeno-virus or AAV vector expressing human PCCA cDNA resulted in increased PCC enzyme activity and correction of disease marker levels (Guenzel et al., 2013, supra). Taken together, in murine models of MMA and PA gene transfer approaches rescue neonatal mice or restore enzyme activity and correct disease metabolite levels in adult disease models thereby permitting evaluation of mRNA delivery for restoration of the defective enzymes.

In additional variations, an mRNA encoding arginosuccinate lyase (ASL) or argininosuccinate synthetase (ASS1) is delivered in accordance with the present methods to treat argininosuccinate aciduria (ASA) or citrullinemia type I (CTLN I), respectively. Suitable animal models for evaluating efficacy of a mRNA/LNP and polymer for treatment of ASA and CTLN I are as follows. ASL hypomorphic mice have a neomycin gene inserted into intron 9 which leads to deficiency in the ASL enzyme (~10% of wild type levels of mRNA and protein) and elevations in argininosuccinate and citrulline plasma levels (Erez et al., *Nat Med.* 17:1619-1626, 2011) which is the signature of ASA. These mice if left untreated will die on their own starting around 3 weeks of age. Treatment of these mice with helper dependent adeno-viral vector expressing mouse ASL at 4 weeks of age led to improved survival, normalized ASL protein expression, and reduction in argininosuccinate and citrulline plasma levels (Nagamani et al., *Am J Hum Genet.* 90:836-846, 2012). ASS1 hypomorphic mice result from a spontaneous recessive mutation (T389I substitution) known as follicular dystrophy (fold). This mutation leads to unstable ASS1 protein structure and ~5-10% of normal enzyme activity. Homozygous fold/fold mice have elevated plasma citrulline and ammonia levels. These mice will also die on their own if untreated (Perez et al., *Am J Pathol.* 177:1958-1968, 2010). Treatment of these mice with AAV8 vector expressing human ASS1 led to improved survival and decreased plasma citrulline and ammonia levels (Chandler et al., *Gene Ther.* 20:1188-1191, 2013). Thus, in murine models of ASA and CTLN I hepatic gene transfer methods restore enzyme activity and correct the disease thereby permitting evaluation of mRNA delivery for restoration of the defective enzymes.

In certain other embodiments of a method of treating a disease associated with defective gene expression and/or activity, the gene is selected from a growth factor gene, a growth factor receptor gene, a gene encoding an enzyme (for example, a phosphatase or a kinase, e.g., a protein tyrosine, serine, or threonine kinase), an adaptor protein gene, a gene encoding a G protein superfamily molecule, or a gene encoding a transcription factor.

Further examples of suitable gene targets useful in the methods of treating a disease associated with defective gene expression and/or activity as described herein include the following genes or genes encoding the following proteins: MEX3, MMP2, ApoB, ERBB2, Vascular Endothelial Growth Factor (VEGF), Vascular Endothelial Growth Factor Receptor (VEGFR), Platelet Derived Growth Factor Receptor (PDGF), ABL, KITT, FMS-like tyrosine kinase 3 (FLT3), Cay-1, Epidermal Growth Factor Receptor (EGFR), H-Ras, K-Ras, N-Ras, Bcl-2, Survivin, FAK, STAT-3, HER-3, Beta-Catenin, ornithine transcarbamylase, alpha-1-antitrypsin, and Src.

Other examples of suitable gene targets useful in the methods of treating a disease associated with defective gene expression and/or activity as described herein include tumor suppressors, where loss of function of the mutated gene can be corrected by delivery of mRNA encoding the functional protein to treat cancer. Suitable tumor suppressor targets include Retinoblastoma protein (pRb), p53 tumor-suppressor protein, Phosphatase and tensin homolog (PTEN), Von Hippel-Lindau tumor suppressor (pVHL), Adenomatous polyposis coli (APC), FAS receptor (FasR), Suppression of tumorigenicity 5 (ST5), YPEL3, Suppressor of tumorigenicity protein 7 (ST7), and Suppressor of tumorigenicity 14 protein (ST14).

In certain embodiments, a membrane-destabilizing polymer and a lipid nanoparticle comprising a therapeutic agent as described herein is used in the preparation of a medicament or combination of medicaments for the treatment of a disease amenable to treatment with the therapeutic agent. In some such embodiments, the disease is a disease associated with defective gene expression and/or activity in a subject.

In some embodiments, a membrane-destabilizing polymer and a lipid nanoparticle comprising an mRNA encoding a functional protein as described herein is used in the preparation of a medicament or combination of medicaments for the treatment of a disease associated with deficiency in a functional protein.

The invention is further illustrated by the following non-limiting examples.

EXAMPLES

Throughout this description, various known acronyms and abbreviations are used to describe monomers or monomeric residues derived from polymerization of such monomers. Without limitation, unless otherwise noted: "BMA"

(or the letter "B" as equivalent shorthand notation) represents butyl methacrylate or monomeric residue derived therefrom; "DMAEMA" (or the letter "D" as equivalent shorthand notation) represents N,N-dimethylaminoethyl methacrylate or monomeric residue derived therefrom; "PAA" (or the letter "P" as equivalent shorthand notation) represents 2-propylacrylic acid or monomeric residue derived therefrom; "PEGMA$_n$", wherein n=8-9 or 4-5, refers to the pegylated methacrylic monomer, $CH_3O(CH_2CH_2O)_nC(O)C(CH_3)CH_2$ or monomeric residue derived therefrom; "PDSMA" represents 2-(pyridin-2-yldisulfanyl)ethyl methacrylate or monomeric residue derived therefrom; "TFPMA" represents 2,3,5,6-tetrafluorphenyl methacrylate or monomeric residue derived therefrom; "PFPMA" represents pentafluorophenyl methacrylate or monomeric residue derived therefrom. In each case, any such designation indicates the monomer (including all salts, or ionic analogs thereof), or a monomeric residue derived from polymerization of the monomer (including all salts or ionic analogs thereof), and the specific indicated form is evident by context to a person of skill in the art. Figures of polymers or macro CTAs in the following examples are not meant to describe any particular arrangement of the constitutional units within a particular block. "KDa" and "k" as used herein refer to molecular weight in kilodaltons.

The following figure is illustrative of the structures of the monomers used in the preparation of the polymers:

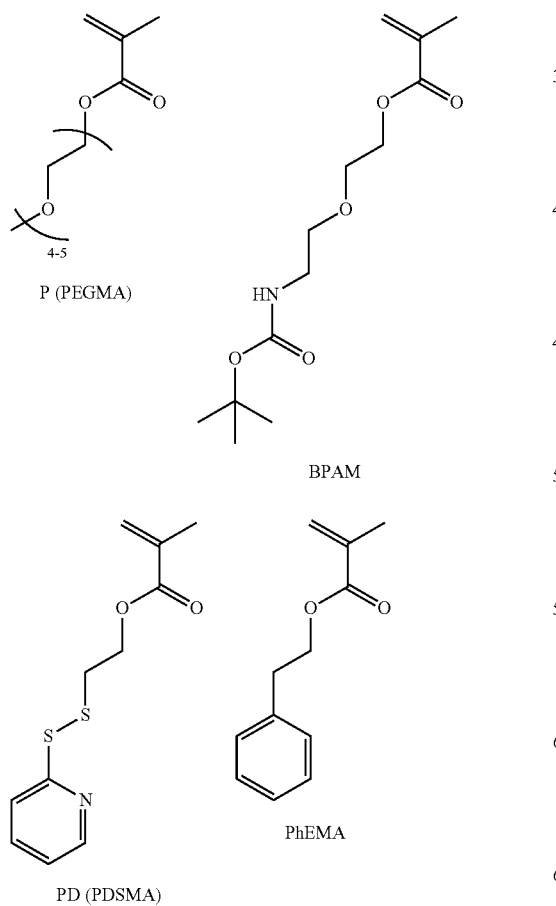

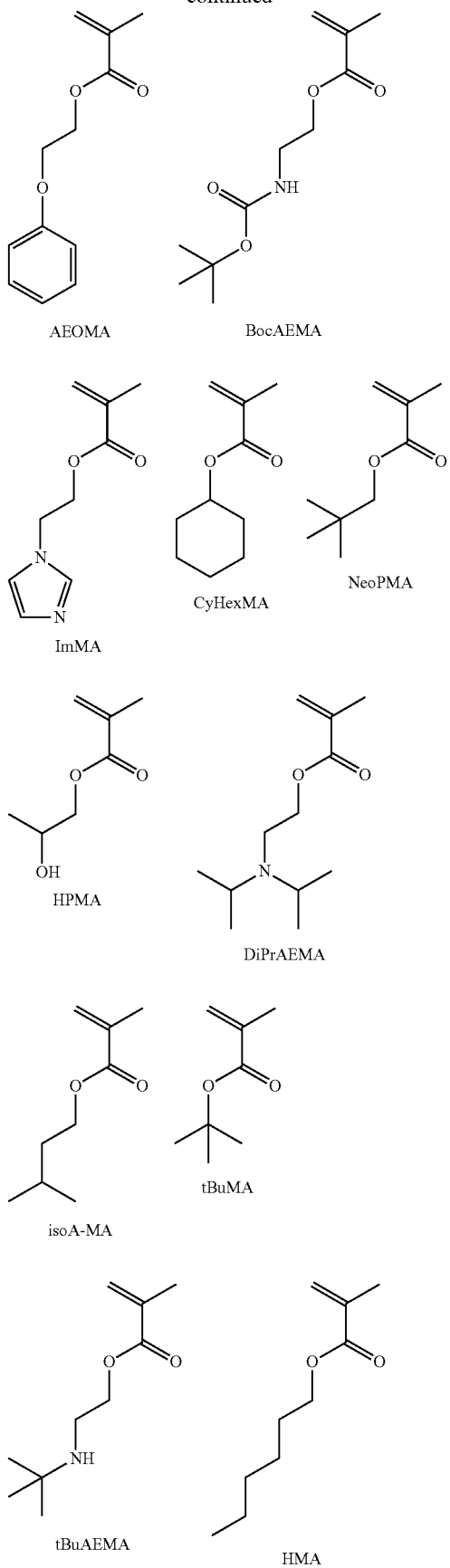

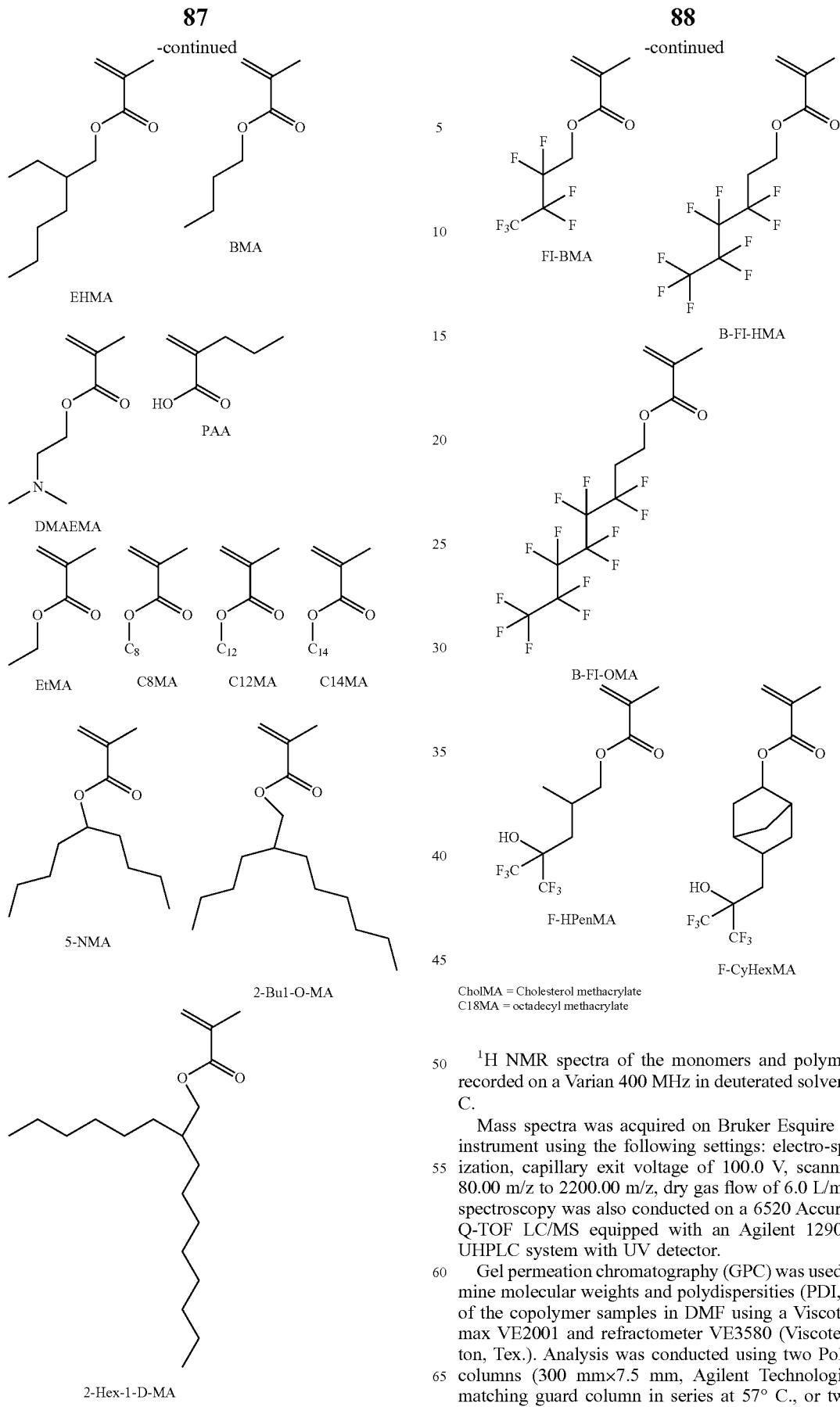

CholMA = Cholesterol methacrylate
C18MA = octadecyl methacrylate $^1$H NMR spectra of the monomers and polymers were recorded on a Varian 400 MHz in deuterated solvents at 25° C.

Mass spectra was acquired on Bruker Esquire Ion Trap instrument using the following settings: electro-spray ionization, capillary exit voltage of 100.0 V, scanning from 80.00 m/z to 2200.00 m/z, dry gas flow of 6.0 L/min. Mass spectroscopy was also conducted on a 6520 Accurate Mass Q-TOF LC/MS equipped with an Agilent 1290 Infinity UHPLC system with UV detector.

Gel permeation chromatography (GPC) was used to determine molecular weights and polydispersities (PDI, $M_w/M_n$) of the copolymer samples in DMF using a Viscotek GPC-max VE2001 and refractometer VE3580 (Viscotek, Houston, Tex.). Analysis was conducted using two PolarGel-M columns (300 mm×7.5 mm, Agilent Technologies) with matching guard column in series at 57° C., or two PolarGel-L columns (300 mm×7.5 mm, Agilent Technologies)

with matching guard column in series at 57° C., or two TSKgel G3000SW columns (300 mm×7.5 mm, 10 µm, Tosoh Biosciences LLC) in series at 57° C. HPLC-grade dimethylformamide (DMF) containing 1.0 wt % LiBr was used as the mobile phase.

UV/Vis spectroscopy was performed using a NanoDrop UV/Vis spectrometer (path length 0.1 cm).

Particle sizes of the polymers were measured by dynamic light scattering using a Malvern Zetasizer Nano ZS.

HPLC analysis was performed on Shimadzu LD-20AB with the variable-wavelength UV detector with a C18 analytical reverse phase column (ES Industries Chromega Columns, Sonoma C18 catalog number 155B21-SMA-C18(2), 100 Å, 25.0 cm×4.6 mm, column heated to 30° C., or a C18 Phenomenex 5µ 100 Å 250×4.6 mm×5 micron (Part #00G-4252-E0) Luna column with guard column heated to 30° C.).

All reagents were from commercial sources, unless indicated otherwise, and the monomers were purified from traces of stabilizing agents prior to use in the polymerization reactions. Cyano-4-(ethylsulfanylthiocarbonyl) sulfanylpentanoic acid (ECT) was obtained from Omm Scientific. Azobisisobutyronitrile (AIBN) (Wako chemicals) was used as the radical initiator in all polymerization reactions, unless stated otherwise.

Example 1: Lipid mRNA Nanoparticle Formulation with Sequential Injection of a Polymer DOTAP (Corden Pharma, Boulder, Colo., USA; catalog number LP-R4-117) or DOTMA (Avanti Polar Lipid Alabaster, Ala., USA; catalog number 890898P) was solubilized at 200 mg/mL in 200 proof ethanol at room temperature for 15 minutes. The DMPE-PEG$_{2K}$ (Corden Pharma, Boulder, Colo., USA; catalog number LP-R4-123) was solubilized at 25 mg/mL in 200 proof ethanol at room temperature for 15 minutes. The cholesteryl hemisuccinate (CHEMS) (Avanti Polar Lipid Alabaster, Ala., USA; catalog number 850524P) and the Cholesterol (CHOL) (Corden Pharma, Boulder, Colo., USA; catalog number CH-0355) were individually solubilized at 25 mg/mL in 200 proof at 75° C. for 5 minutes. Typically, for a 2 mL preparation of a DOTAP:CHEMS:CHOL:DMPE-PEG$_{2K}$ (50:32:16:2 mol %) LNP at N:P ratio of 7, a lipid ethanolic mixture containing 22 µL of DOTAP at 200 mg/mL in 200 proof ethanol, 79 µL of CHEMS at 25 mg/mL in 200 proof ethanol, 31.4 µL of CHOL at 25 mg/mL in 200 proof ethanol, 27.4 µL of DMPE-PEG$_{2K}$ at 25 mg/mL in 200 proof ethanol and 506 µL of 200 proof ethanol was prepared for a final volume of 0.666 mL and a final lipid concentration of 11.83 mg/mL. The lipid nanoparticle (LNP) formulations were prepared at N:P (nitrogen to phosphate) ratios from 3.5 to 28 based on the DOTAP or DOTMA concentration. The DOTAP:CHEMS or DOTMA:CHEMS ratio was fixed at 1.6 at 50:32 mol % respectively at the various N:P ratios. DMPE-PEG$_{2K}$ was varied from 2 to 5 mol %. The CHOL mol % was adjusted to result in 100 mol % final lipid concentration.

The Fluc (firefly luciferase) mRNA stock solution at 1 mg/mL in 10 mM Tris-HCl (pH 7.5) (TriLink Biotechnologies, San Diego, Calif., USA; catalog number L-6107) was diluted to 0.225 mg/mL in 20 mM HEPES/5% glucose, pH 7.4 buffer (HEPES buffer). The mRNA/LNPs were assembled at N:P ratios from 3.5 to 28 by mixing the ethanolic lipid solution with 0.225 mg/mL mRNA in HEPES buffer at a 1:3 ratio (lipid mixture in ethanol, mRNA in HEPES buffer) using the microfluidic device from Precision NanoSystems Inc (Vancouver BC, Canada) at a 12 mL/minute flow rate. The mRNA/LNPs in 33% ethanol were then incubated at room temperature for 60 minutes prior to dialysis for 18 hours against 100 volumes (200 mL) of HEPES buffer.

The polymer used for the sequential injection, polymer P1435 (NAG-C$_5$N-PEG$_{0.6k}$-[PEGMA300$_{87.9\%}$-PDSMA$_{12.1\%}$]$_{3.9kDa}$-b-[DMAEMA$_{34.7\%}$-BMA$_{53.5\%}$-PAA$_{11.8\%}$]$_{6.1kDa}$), was solubilized at 20 mg/mL in HEPES buffer with agitation at 400 rpm for 1 hour and then stored overnight at 4° C. The polymer was diluted to 7.5 mg/mL in HEPES buffer prior injection.

If mRNA/LNP and polymer were co-injected, a 2× solution of each was prepared. Just prior to dosing, the solutions were mixed and injected immediately.

The formulation particle size was measured by adding 10 µL of formulation to 90 µL of HEPES buffer into a disposable micro-cuvette and analyzed using the Malvern Instrument ZETASIZER NANO-ZS. The LNPs showed a particle size of 52 nm (z-average). The formulation zeta-potential at pH 7.4 was measured by adding 10 µL of formulation to 740 µL of HEPES buffer into a disposable 1 mL cuvette. The formulation zeta-potential at pH 4 was measured by adding 10 µL of formulation to 740 µL of sucrose acetate buffer (pH 4) into a disposable 1 mL cuvette. The zeta dip cell was inserted into the 1 mL cuvette and the formulation was analyzed using the ZETASIZER NANO-ZS. Typically, the DOTMA LNPs had a zeta potential of +12 mV at pH 7 and +16 mV at pH 4.0. The ability of the LNP to compact the mRNA was measured in a 96 well plate using a SYBR Gold dye accessibility assay. Typically, 50 µL of the lipid formulation at 0.01 mg/mL mRNA was added to 150 µL of diluted SYBR Gold stock solution (1 µL of Stock SYBR Gold in 3 mL of HEPES buffer) and incubated for 15 minutes at room temperature with agitation (100 RPM). The fluorescence was read at an excitation wavelength of 495 nm and emission wavelength of 538 nm. The percent dye accessibility was calculated by dividing the fluorescence intensity of the formulated mRNA by the fluorescence intensity of the free mRNA×100. The DOTMA LNPs showed 2% dye accessibility when prepared in HEPES buffer. Table 2 below shows a characterization of an exemplary LNP formulation.

TABLE 2

| Sample # | RP450-2 |
| --- | --- |
| Polymer or Lipid | DOTMA:CHEMS:CHOL:DMPE-PEG2K (50:32:13:5) |
| N/P | 27 |
| Polymer or Lipid Concentration (mg/mL) | 10.0 |
| Visual Appearance | Opalescent (+) |
| % Dye Access HEPES pH 7.4 | 2% |
| Z-Ave (nm) | 52 |
| PDI | 0.200 |
| Number (nm) | 30 |
| Pk 1 Mean Int (nm) | 57 |
| Pk 2 Mean Int (nm) | 4191 |
| Pk 1 Area Int (%) | 97 |
| Pk 2 Area Int (%) | 4 |
| ZP pH 7.4 (mV) | 12 |
| ZP pH 4 (mV) | 16 |
| Sizing data quality | Good |

Example 2: In Vivo Expression of mRNA with Lipid-mRNA Formulations and Co-Injection or Sequential Injection of Polymer Female CD-1 mice (7-10 weeks old) were used for evaluating the Fluc mRNA/LNP+polymer formulations. The formulations were dosed intravenously at 1 mg/kg of mRNA and 13 to 103 mg/kg of lipid, with 5 mice injected per group.

Polymer P1435 alone at 75 mg/kg was injected intravenously either as a co-injection or sequentially at 1, 5, 10, 30, 60 or 120 minutes post the Fluc mRNA/LNP injection. Mice injected with HEPES buffer was used as control. For each injection mice were given a final dose volume of approximately 0.25 mL or 10 mL/kg based on individual body weights.

The in vivo expression of luciferase was evaluated by detecting luminescence in mice using the Xenogen IVIS Lumina II Imaging System (Caliper Life Sciences, now Perkin Elmer). The imaging was performed at 6 hours following dosing. 15 minutes prior to imaging, each mouse received 0.25 mL of D-luciferin (Perkin Elmer), a luciferase substrate, at 15 mg/mL (dissolved in PBS) by intra-peritoneal injection. A few minutes before imaging, mice were place in an isoflurane chamber to induce anesthesia (isoflurane concentration at ~3%). Subsequently, mice were moved into the IVIS imaging chamber, with the snout connected to an isoflurane-filled nose cone with the mouse's ventral side up. The luminescence images were acquired using Living Image software (Caliper Life Sciences) with the exposure time, binning and F/Stop remaining the same throughout the study. Mice were put back to the cage as soon as the imaging was finished and they recovered within 1-3 minutes.

After the image acquisition was finished for all mice, the luminescence results were analyzed using Living Image software. Briefly, the color scale of each image was first adjusted to display specific luminescence signal and eliminate background signal. Then a region of interest (ROI) for the liver was defined using the ROI tools, and ROI measure button was clicked to show the photon flux data. Total flux (photons/sec) of the ROI on each animal was used to represent the intensity of luminescence. Total flux was averaged from all 5 mice for each formulation group for comparison.

Table 3 displays luminescence values in the liver for animals treated with DOTMA:CHEMS:CHOL:DMPE-PEG2k+Fluc mRNA nanoparticle with or without sequential injection of polymer P1435 at 10 minutes following the first injection. Data was acquired at 6 hours post dose. Fluc mRNA/LNP alone showed little luminescence (only 3-fold above buffer) but with polymer P1435 sequential injection, a 100-fold improvement in luminescence signal was detected.

TABLE 3

| Lipid-mRNA Nanoparticle | Lipid Dose (mg/kg) | mRNA Dose (mg/kg) | Polymer | Polymer Dose (mg/kg) | Timing Between Injections | Total Flux (photons/sec) Geomean | STDEV |
| --- | --- | --- | --- | --- | --- | --- | --- |
| Buffer | 0 | 0 | None | 0 | NA | 3.38E+05 | 1.00E+00 |
| DOTMA:CHEMS:CHOL:DMPE-PEG2K (50:32:13:5) N:P 27 + Fluc mRNA | 100 | 1 | None | 0 | NA | 6.24E+05 | 2.66E+05 |
| | 100 | 1 | P1435 | 75 | 10 min | 6.97E+07 | 4.86E+07 |

Table 4 displays luminescence values in the liver for animals treated with DOTAP:CHEMS:CHOL:DMPE-PEG2k+Fluc mRNA nanoparticle with or without sequential injection of polymer P1435 or polymer P1299 at 10 minutes following the first injection. N:P ratios from 14 to 27 and 2-5 mol % DMPE-PEG2k variations were evaluated. Data was acquired at 6 hours post dose. Again the mRNA/LNP alone showed little luminescence but with polymer P1435 sequential injection, a 100-fold improvement in luminescence signal was detected. Reducing the N:P ratio from 27 to 14, and reducing the DMPE-PEG2k from 5 to 3.5 mol % further improved the luminescence signal by another 3-fold. Sequential injection of polymer P1299 (NAG-C$_5$N-PEG$_{0.6k}$-[PEGMA300$_{80\%}$-PDSMA$_{10\%}$-BPAM$_{10\%}$]$_{3.5kDa}$-b-[DMAEMA$_{34\%}$-BPAM$_{56\%}$-PAA$_{10\%}$]$_{6.3kDa}$) showed 5-fold improvement in luminescent signal compared to mRNA/LNP alone.

TABLE 4

| Lipid-mRNA Nanoparticle | N:P | DMPE-PEG2k mol % | Lipid Dose (mg/kg) | mRNA Dose (mg/kg) | Polymer | Timing Between Injections | Total Flux (photons/sec) Geomean | STDEV |
| --- | --- | --- | --- | --- | --- | --- | --- | --- |
| Buffer | NA | NA | 0 | 0 | None | NA | 2.58E+05 | NA |
| DOTAP:CHEMS:CHOL:DMPE-PEG2K (2-5%) (50:32:13:X mol %) + Fluc mRNA | 27 | 5 | 113 | 1 | None | NA | 1.70E+06 | 8.94E+05 |
| | 27 | 5 | 113 | 1 | P1435 75 mg/kg | 10 min | 1.38E+08 | 1.88E+08 |
| | 21 | 5 | 88 | 1 | | | 1.61E+08 | 9.48E+07 |
| | 14 | 5 | 59 | 1 | | | 2.51E+08 | 2.07E+08 |
| | 27 | 3.5 | 107 | 1 | | | 3.43E+08 | 9.68E+07 |
| | 14 | 3.5 | 56 | 1 | | | 3.80E+08 | 1.26E+08 |
| | 27 | 2 | 102 | 1 | | | 2.26E+08 | 2.24E+08 |
| | 27 | 5 | 113 | 1 | P1299 75 mg/kg | | 8.34E+06 | 1.22E+07 |

Table 5 displays luminescence values in the liver for animals treated with DOTAP:CHEMS:CHOL:DMPE-PEG2k+Fluc mRNA nanoparticle with or without sequential injection of polymer P1435 at 10 minutes following the first injection or co-injection. N:P ratios from 3.5 to 14 and were evaluated. Data was acquired at 6 hours post dose. Again the mRNA/LNP alone showed little luminescence but with polymer P1435 sequential injection, a 300-fold improvement in luminescence signal was detected. Reducing the N:P ratio from 14 to 7, and reducing the DMPE-PEG2k to 2 mol % resulted in nearly a 500-fold improvement in luminescence signal compared to mRNA/LNP alone. Further reducing the N:P ratio to 3.5 resulted in lower luminescence. Sequential injection of mRNA/LNP and polymer P1435 showed slightly better luminescence signal compared to co-injection.

TABLE 5

| Lipid-mRNA Nanoparticle | N:P | Lipid Dose (mg/kg) | mRNA Dose (mg/kg) | Polymer | Timing Between Injections | Total Flux (photons/sec) Geomean | STDEV |
|---|---|---|---|---|---|---|---|
| Buffer | NA | 0 | 0 | None | NA | 3.19E+05 | NA |
| DOTAP:CHEMS: CHOL:DMPE- PEG2K (50:32:14.5:2 mol %) + Fluc mRNA | 14 | 53 | 1 | None | NA | 1.07E+06 | 1.31E+05 |
| | 3.5 | 13 | 1 | P1435 75 mg/kg | 10 min | 5.82E+07 | 5.61E+07 |
| | 7 | 26 | 1 | | | 5.07E+08 | 6.21E+08 |
| | 14 | 53 | 1 | | | 3.58E+08 | 3.93E+08 |
| | 14 | 53 | 1 | | co-injection | 2.48E+08 | 3.69E+08 |

Table 6 displays luminescence values in the liver for animals treated with DOTAP:CHEMS:CHOL:DMPE-PEG2k+Fluc mRNA nanoparticle with sequential injection of polymer P1435 from 1 to 120 minutes following the first injection or co-injection. Data was acquired at 6 hours post dose. The luminescence signal was similar between 1 and 10 minutes and dropped from 30 to 120 minutes. Sequential injection of mRNA/LNP and polymer P1435 showed four-fold higher luminescence signal compared to co-injection.

TABLE 6

| Lipid-mRNA Nanoparticle | Polymer | Timing Between Injections | mRNA Dose (mg/kg) | Total Flux (photons/sec) Geomean | STDEV |
|---|---|---|---|---|---|
| Buffer | None | NA | 0 | 2.52E+05 | NA |
| DOTAP:CHEMS: CHOL:DMPE- PEG2K (50:32:16:2) N:P 7 26 mg/kg + Fluc mRNA | P1435 75 mg/kg | co-injection | 1 | 1.57E+08 | 1.38E+08 |
| | | 1 min | 1 | 6.09E+08 | 3.40E+08 |
| | | 5 min | 1 | 8.24E+07 | 2.28E+08 |
| | | 10 min | 1 | 3.22E+08 | 2.43E+08 |
| | | 30 min | 1 | 7.69E+07 | 5.23E+07 |
| | | 60 min | 1 | 1.57E+07 | 1.24E+07 |
| | | 120 min | 1 | 6.03E+06 | 1.30E+07 |

Table 7 displays luminescence values in the liver for animals treated with DOTAP:CHEMS:CHOL:DMPE-PEG2k+Fluc mRNA nanoparticles with sequential injection of polymer P1435 at 1 minute following the first injection. Data was acquired at 6 hours post dose. In this study, two different Fluc mRNAs were tested. Fluc 2 mRNA showed a 15-fold improvement in luminescence signal compared to Fluc 1 mRNA. Fluc 2 mRNA contains Pseudo U only, a Cap 1 structure obtained from enzymatic capping and a longer poly A tail (approximately double that of Fluc 1—~220 bases) compared to Fluc 1 which has an ARCA cap structure, Pseudo U/5-methyl-C modifications, and a poly A tail length of 120 bases.

TABLE 7

| Lipid-mRNA Nanoparticle | Polymer | Fluc mRNA | Timing Between Injections | mRNA Dose (mg/kg) | Total Flux (photons/sec) | |
|---|---|---|---|---|---|---|
| | | | | | Geomean | STDEV |
| Buffer | None | None | NA | 0 | 1.82E+05 | NA |
| DOTAP:CHEMS:CHOL:DMPE-PEG2K (50:32:16:2) N:P 7 26 mg/kg | P1435 75 mg/kg | Fluc 1 mRNA | 1 min | 1 | 2.10E+08 | 1.57E+08 |
| | | Fluc 2 mRNA | | 1 | 3.04E+09 | 2.12E+09 |

Example 3: Synthesis of $PEG_{0.6k}$-CTA (Compound 6)

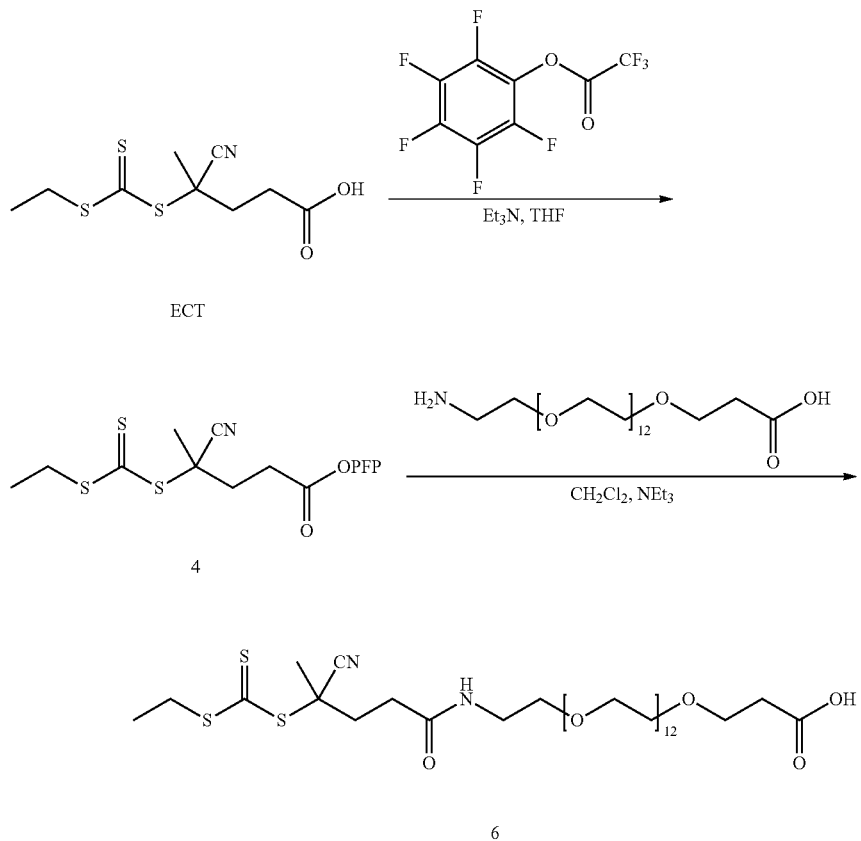

HOOC-$PEG_{0.6k}$-ECT (Compound 6). To a 100 mL one-neck round-bottom flask was added ECT (473 mg, 2.0 mmol, Omm Scientific) followed by anhydrous tetrahydrofuran (20 mL) and triethylamine (0.307 mL, 2.2 mmol). This mixture was stirred at 0° C. for 5 min before trifluoroacetic acid pentafluorophenyl ester (0.368 mL, 2.14 mmol) was added drop wise to the stirred reaction. The mixture was stirred at 0° C. for 5 min then warmed to room temperature.

After allowing to react for 20 min at room temperature, the reaction was diluted into EtOAc (100 mL) and extracted with saturated aqueous solution of $NaHCO_3$ (3×40 mL). The EtOAc layer was separated, dried over $Na_2SO_4$, filtered and then evaporated providing the crude PFP-ester 4 as yellow oil.

The crude ester 4 was dissolved in anhydrous $CH_2Cl_2$ (20 mL) and then cooled to 0° C. To the cooled stirred solution was added triethylamine (0.251 mL, 1.8 mmol) and Amino-dPEG12-acid (1.12 g, 1.8 mmol, Quanta Biodesign), and the mixture was warmed to room temperature. After stirring for 20 min at room temperature, the reaction mixture was evaporated using a rotary evaporator providing yellow oil. The yellow oil was dissolved in $CH_2Cl_2$ (approximately 2 mL) and the product was purified by flash chromatography ($SiO_2$, column size 5.0 cm ID×10.0 cm length; isocratic elution with 100% $CH_2Cl_2$ for 500 mL; then $CH_2Cl_2$/MeOH, 20:1 v/v for 500 mL; then $CH_2Cl_2$/MeOH, 10:1 v/v for 3.0 L). The product-containing fractions, as determined by TLC, were combined, and the solvent was removed by rotary evaporation providing 750 mg (48%) of the desired compound 6 as orange oil. H NMR (CD3OD): δ 1.35 (t, 3H, J=7.5 Hz, $CH_3$), 1.89 (s, 3H, $CH_3$), 2.38-2.57 (m, 6H), 3.32-3.41 (m, 4H), 3.50-3.75 (m, 48H).

Example 4: Synthesis of Na(OAc4)C5N-PEG$_{0.6K}$-CTA (Compound 8)

Step 1. Synthesis of Compound 3

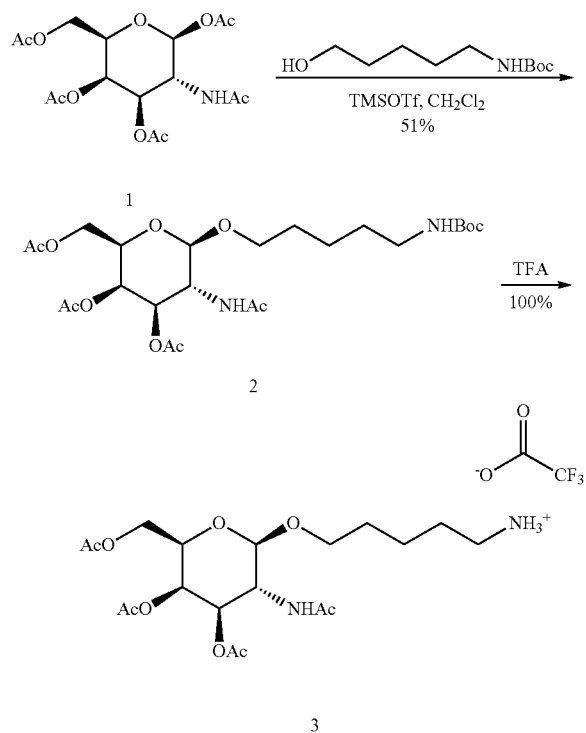

N-t-Boc-5-amino-1-pentanol. To a 1.0 L one-neck round-bottom flask containing a solution of 5-amino-1-pentanol (15.0 g, 145.4 mmol) in water (140 mL) and saturated aqueous NaHCO$_3$ (1.4 mL), a solution of di-tert-butyl dicarbonate (33.3 g, 152.7 mmol) in THF (280 mL) was added. The mixture was then stirred at room temperature overnight with the flask open to the atmosphere. The reaction mixture was diluted with saturated aqueous NaHCO$_3$ (90 mL) and extracted with EtOAc (400 mL). The organic layer was separated, dried over Na$_2$SO$_4$, filtered, and the solvent was evaporated providing 28.9 g (98%) of the final product as clear colorless oil. $^1$H NMR analysis showed the product was clean of impurities, and no further purification was attempted. Alternatively, N-t-Boc-5-amino-1-pentanol can be obtained from TCI America of Portland, Oreg.

Compound 2. Compound 2 was prepared by a procedure adopted from the literature (Westerlind, U. et al. *Glycoconj. J.* 2004, 21, 227-241). To a 500-mL one-neck round-bottom flask was added 2-acetamido-1,3,4,6-tetra-O-acetyl-2-deoxy-D-galactopyranose 1 (12.8 g, 32.8 mmol) followed by anhydrous CH$_2$Cl$_2$ (150 mL) and trimethylsilyl trifluoromethanesulfonate (14.3 mL, 79.2 mmol). This mixture was stirred at reflux overnight (ca. 18 h) under a flow of argon gas. The reaction mixture was cooled to 0° C. and treated with triethylamine (6.4 mL, 45.9 mmol) for 30 min before being warmed to room temperature, then washed with saturated aqueous NaHCO$_3$ (100 mL). The organic layer was separated and dried over Na$_2$SO$_4$, filtered and evaporated providing crude oxazoline intermediate. To the crude oxazoline product was added anhydrous CH$_2$Cl$_2$ (200 mL), N-t-Boc-5-amino-1-pentanol (10.0 g, 49.2 mmol) and 3 Å molecular sieves (18.0 g, dried at 150° C. for >24 h). This mixture was stirred at room temperature for 30 min under a blanket of argon gas. Trimethylsilyl trifluoromethanesulfonate (2.97 mL, 16.4 mmol) was added to the reaction mixture, and the solution was stirred at room temperature overnight. The solution was cooled to 0° C. and treated with triethylamine (3.2 mL, 23.07 mmol) for 30 min before being warmed to room temperature. After the reaction reached room temperature the mixture was filtered, and the mother liquor was evaporated providing the crude product as brown oil which was dissolved in anhydrous pyridine (100 mL) and treated with acetic anhydride (36 mL, 38.2 mmol). This mixture was stirred under an argon atmosphere at room temperature overnight, then evaporated under vacuum yielding a brown liquid, which was dissolved in CH$_2$Cl$_2$ (200 mL). The solution was vigorously stirred with a saturated aqueous NaHCO$_3$ solution (100 mL) and solid NaHCO$_3$ in an open flask at room temperature to quench remaining Ac$_2$O and the organic layer was separated. The aqueous layer was extracted with CH$_2$Cl$_2$ (1×200 mL) and all organic layers were combined. The organic layers were washed with saturated aqueous NaHCO$_3$ solution (1×100 mL), separated, dried over Na$_2$SO$_4$, filtered and evaporated providing the crude product as a brown oil which was then dissolved in CH$_2$Cl$_2$ (15 mL) and purified using column chromatography (SiO$_2$, column size 7.5 cm ID×16.0 cm length, EtOAc:Hexanes 1:3 v/v for 500 mL, EtOAc:Hexanes 4:1 v/v for 500 mL, 100% EtOAc for 1.0 L, 10% MeOH in EtOAc v/v for 3.0 L). Product-containing fractions were pooled and evaporated under vacuum to a white solid which was further purified by trituration with ether to yield the desired product as a white solid (5 g, 29%). ESI MS [M+H]$^+$ m/z 533.4.

Compound 3. To a 100 mL round bottom flask was added Compound 2 (3.14 g, 5.9 mmol) followed by trifluoroacetic acid (10 mL, TFA). The mixture was stirred until all of the carbohydrate was completely dissolved, then the TFA was evaporated under vacuum to yield light yellow oil. To the oily residue was added diethyl ether (10 mL), the mixture was sonicated for 2-5 min, and the supernatant was decanted. The trituration process was repeated (3×10 mL Et$_2$O), and the crude product was dried under vacuum to yield a white foam (3.2 g), which was used as described below.

Step 2

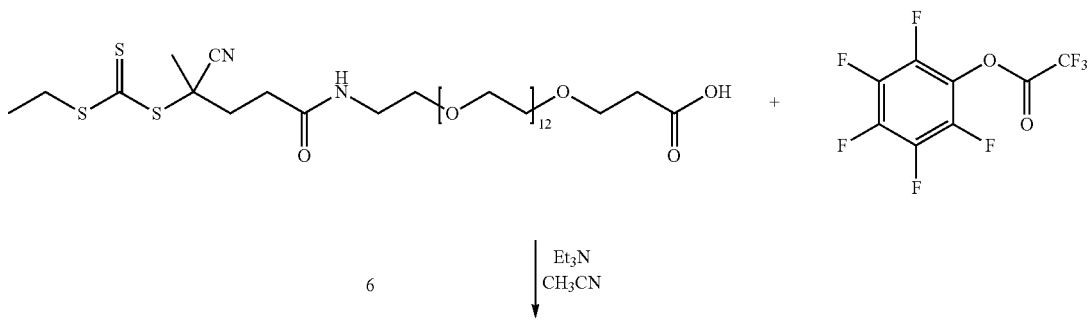

-continued

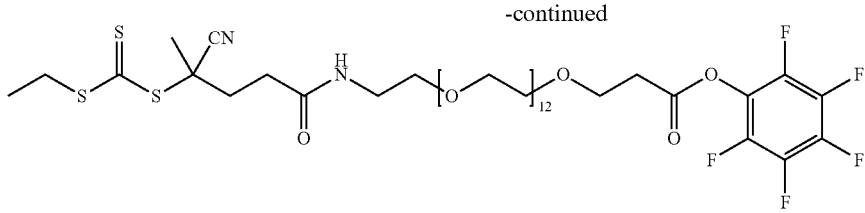

7

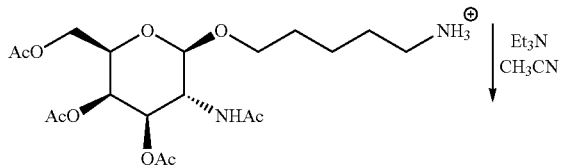

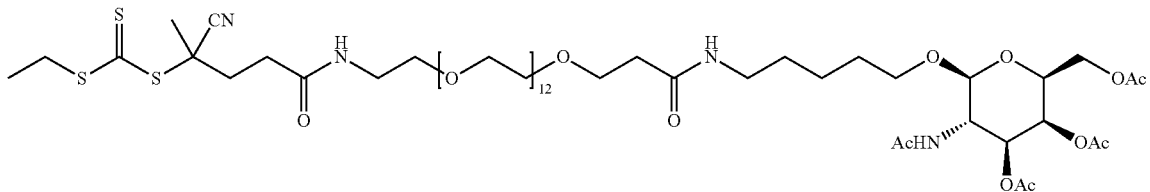

8

Compound 7. To a 250 mL one-neck round-bottom flask was added Compound 6 (3.37 g, 3.9 mmol, HPLC purified) followed by anhydrous $CH_2Cl_2$ (40.0 mL), and triethylamine (2.17 mL, 15.6 mmol). This solution was stirred at 0° C. under a low flow of argon gas for 5 min before trifluoroacetic acid pentafluorophenyl ester (737 µL, 4.29 mmol) as added dropwise to the reaction mixture. Then the mixture was warmed to room temperature and was stirred at room temperature for 30 min.

The reaction progress was followed by TLC ($SiO_2$, $CH_2Cl_2$ and MeOH, 9:1 v/v) by looking for the disappearance of the starting material ($R_f$=0.30) and the appearance of the PFP activated product ($R_f$=0.64). Once the starting material was consumed by TLC, the crude reaction was diluted with $CH_2Cl_2$ (300 mL) and the mixture was extracted using $NaHCO_3$ (3×50 mL). The organic layer was separated, dried over $Na_2SO_4$, filtered and evaporated providing 3.9 g (97%) of the final product as orange oil. All solvents and volatile reagents were thoroughly removed using high vacuum overnight before the crude product is carried on to the next synthetic step.

Compound 8. To a 100 mL one-neck round-bottom flask was added Compound 7 (3.6 g, 3.5 mmol) followed by anhydrous acetonitrile (7.5 mL) and triethylamine (1.46 mL, 10.5 mmol). The mixture was stirred under a flow of argon gas until all of the material was dissolved, then cooled to 0° C. with an ice bath. Deprotected amine 3 (1.81 g, 3.32 mmol) was dissolved in anhydrous acetonitrile (7.5 mL), and the resulting solution was added to the reaction mixture at 0° C. dropwise over 5 min. The reaction was allowed to warm to room temperature and was stirred at room temperature overnight. The solvents were evaporated using a rotary evaporator, and the crude product was dried under high vacuum. The reaction progress was followed by analytical HPLC by diluting the reaction mixture (5 µL) into $CH_3CN$ (695 µL) and 50 µL of the diluted mixture was analyzed by HPLC (10% $CH_3CN$ for 2 min, then linear gradient from 10% to 60% $CH_3CN$ over 20 min, total flow rate of 1.0 mL/min). The desired product had a retention time of 21.0 min.

The crude product was dissolved in MeOH (approximately 40 mL) and purified in 2-mL aliquots using preparative reverse phase HPLC (Phenomenex, Luna 5C18(2), 100 Å, 25.0 cm×21.2 mm, equipped with a SecurityGuard PREP Cartridge, C18 15×21.2 mm ID, $CH_3CN/H2O$, 30% $CH_3CN$ for 5 min, then linear gradient from 30% to 53% $CH_3CN$ over 20 min, total flow rate of 20.0 mL/min). The desired product eluted between 22.0 and 23.0 min. All the fractions containing the desired product were combined, and the solvent was completely removed using a rotary evaporator to yield 2.54 g (60%) of compound 8 after overnight drying under vacuum.

ESI MS: m/z 1277.6 ($[M+H]^{+1}$), 650.6 ($[M+Na+H]^{+2}$), 658.5 ($[M+K+H]^{+2}$), 661.7 ($[M+2Na]^{+2}$), 669.7 ($[M+Na+K]^{+2}$), 677.5 ($[M+2K]^{+2}$).

1H NMR (CD3OD): δ 1.35 (t, 3H, J=7.5 Hz), 1.33-1.62 (m, 6H), 1.88 (s, 3H), 1.93 (s, 3H), 1.95 (s, 3H), 2.03 (s, 3H), 2.15 (s, 3H), 2.32-2.56 (m, 6H), 3.15-3.25 (m, 2H), 3.25-3.42 (m, 6H), 3.50-3.70 (m, 44H), 3.97-4.20 (m, 4H), 4.55 (d, 1H, J=8.4 Hz), 5.05 (dd, 1H, $J_1$=11.4 Hz, $J_2$=3.4 Hz), 5.33 (dd, 1H, $J_1$=3.4 Hz, $J_2$=0.9 Hz).

Example 5: Preparation of Na(OH)C5N-PEG$_{0.6K}$-CTA (Compound 8a)

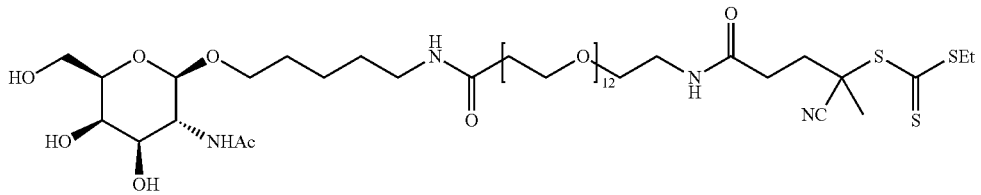

Compound 8a

Nag(OH)C5N-PEG$_{0.6K}$-CTA (Compound 8a) was prepared in a similar manner to the Nag(OAc4)C5N-PEG$_{0.6K}$-CTA in Example 4 (Compound 8) except that compound 3 in Example 4 is replaced by the unprotected sugar compound of compound 3a and the coupling reaction between compound 6 of Example 3 and compound 3 of Example 4 has been modified as shown below for compounds 6a and 3a.

Compound 3a is prepared as follows from compound 3b.

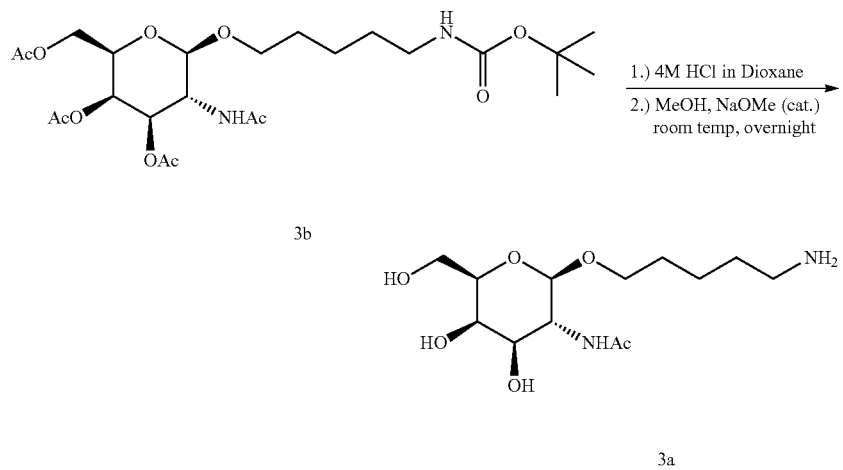

To a 250 mL one-neck round-bottom flask was added compound 3b (1.86 g, 3.5 mmol) followed by 4M HCl in dioxane (30 mL). This mixture was stirred and sonicated until all of the sugar was completely dissolved. Then the mixture was evaporated on a rotary evaporator providing an oily residue. To completely remove all HCl gas the compound was dissolved in dioxane (30 mL) and solvents removed by rotary evaporation. The solvent exchange process was performed a total of 3 times to completely remove all HCl. Then the flask was put under high vacuum for >30 min providing a white foam solid. The crude compound was dissolved in anhydrous MeOH (25 mL) and treated with 0.5 M sodium methoxide solution in MeOH (5.80 g, 7.175 mL, 3.59 mmol, 1.025 eq, measured by weight to ensure accuracy of addition). The first equivalent of NaOMe is used to de-protonate the quaternary amine salt liberating the free amine. Only a slight excess of NaOMe beyond one equivalent (i.e., 0.025 eq, 0.09 mmol) is needed to facilitate the acetyl deprotection. Once NaOMe is added the mixture is then stirred under a flow of argon overnight at room temperature. Reaction progress was monitored by LCMS using Agilent Q-TOF Liquid Chromatography Mass Spectrometer by dissolving the product in MeOH at ca. 1.0 μg/mL. The LC used a C18 UPLC column (Agilent Eclipse Plus C18, catalog number 959757-902, 1.8 m, 2.1 mm×50 mm, column at room temperature, CH$_3$CN/H$_2$O containing 0.1% formic acid, isocratic gradient at 5% CH$_3$CN for 1 min, then linear gradient from 5% to 90% CH$_3$CN over 4 min, total flow rate of 0.4 mL/min). The desired product elutes between 0.4-0.5 min using the above HPLC conditions while the crude intermediate product (i.e., Boc removed with acetyls still present) elutes between 2.0-2.2 min. Once the sugar was fully de-protected the catalytic NaOMe (0.09 mmol) is quenched by adding a slight excess of acetic acid (10 μL, 0.175 mmol) to the reaction mixture. Then all solvents are removed by evaporating on a rotary evaporator. This process yielded 1.1 g (100%) of the final product as a white solid. The final product was characterized using a 400 MHz 1H NMR with CD$_3$OD as solvent and all spectra were consistent with the desired product compound 3a.

Nag(OH)C5N-PEG$_{0.6K}$-CTA (Nag(OH)C5N-PEG$_{12}$-CTA; Compound 8a) was prepared as follows. Compound 6a was prepared as in Example 3 (Compound 6).

Figure 1B:
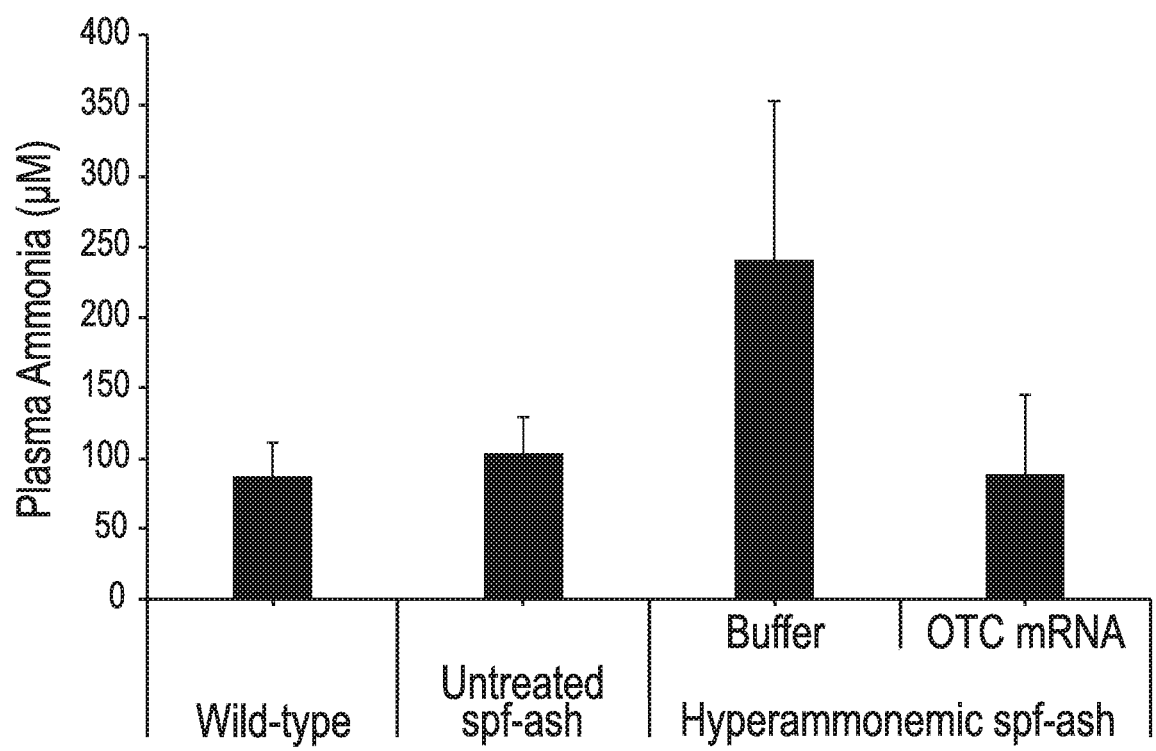
Figure 2A:
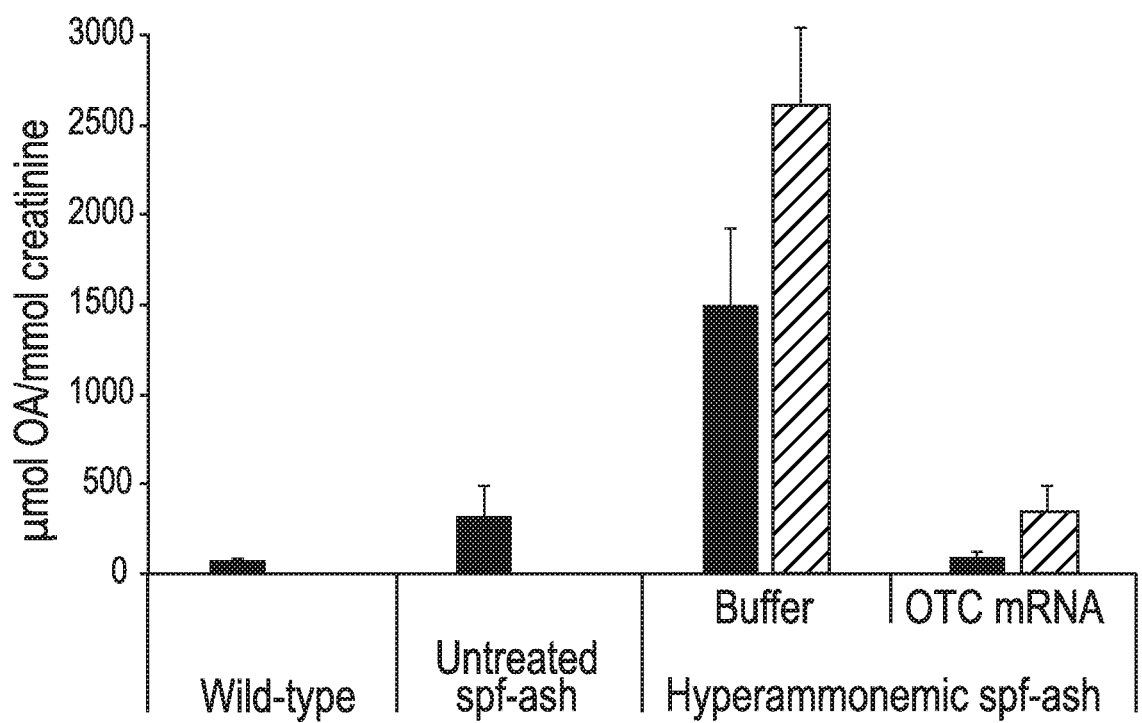
FIGS. 2A and 2B show reduction in orotic acid (OA) and plasma ammonia levels in hyperammonemic OTC-spf$^{ash}$ mice treated with mRNA encoding ornithine transcarbamylase (OTC). Hyperammonemia was induced in OTC-spf$^{ash}$ mice by treatment with AAV2/8 vector/OTC shRNA, and four days after AAV dosing, mice were treated twice per week with 1 mg/kg of OTC mRNA formulated in DOTAP:CHEMS:CHOL:DSPE-PEG$_{2k}$ (50:32:8:10) at N:P 7+co-injection of 35 mg/kg P82. See Example 21. Urine collected at day 6 and day 13 (post-AAV treatment) was analyzed for OA levels that were normalized to creatine levels, and plasma collected at day 13 was analyzed for ammonia levels. Orotic acid levels are shown in FIG. 2A (black fill=day 6; crosshatch fill=day 13). Plasma ammonia levels are shown in FIG. 2B.
Figure 2B:
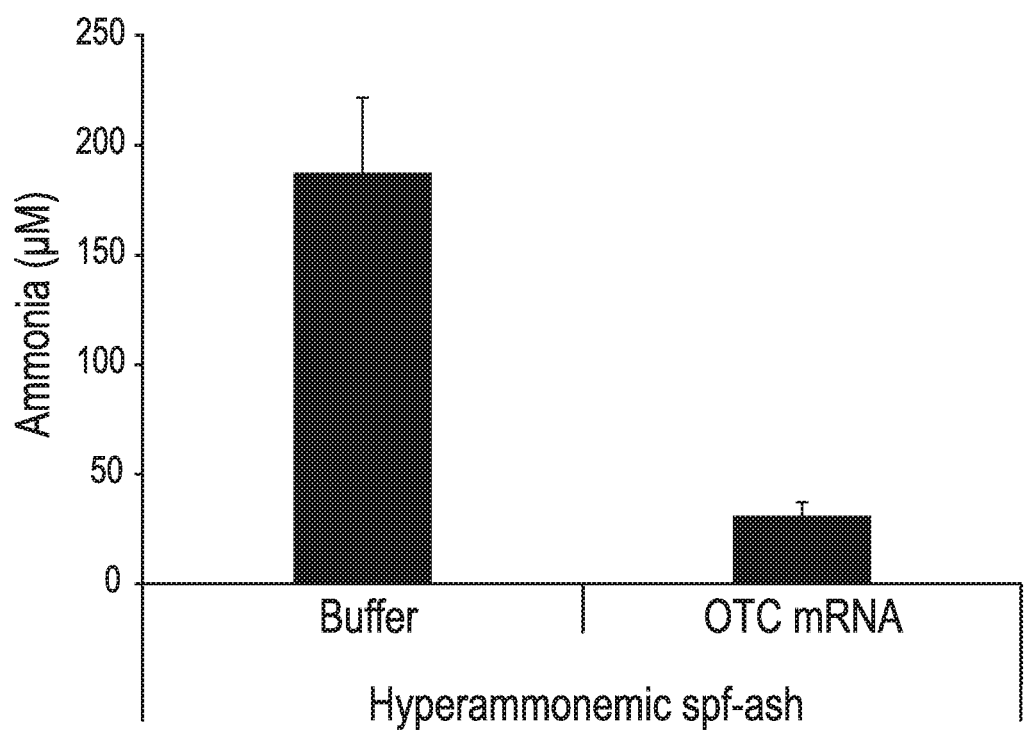
Figure 3:
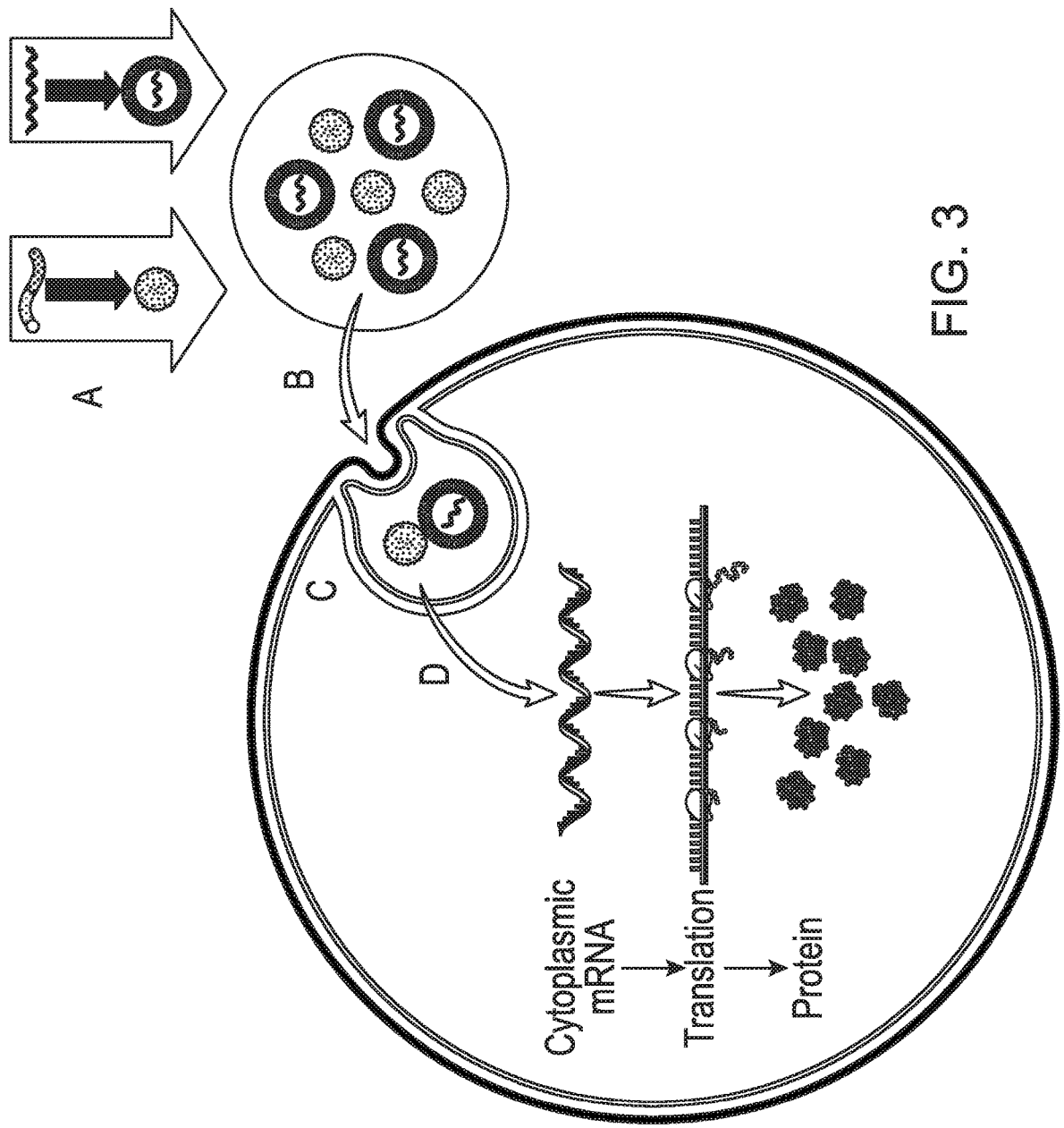
FIG. 3 schematically depicts a proposed mechanism of action for delivery of an mRNA to the cytosol of a target cell using a membrane-destabilizing polymer and an LNP carrier in accordance with an embodiment of the present disclosure. (A) Two separate nanoparticle solutions are prepared: one nanoparticle containing the membrane-destabilizing polymer and a second nanoparticle that is the LNP comprising the mRNA. (B) The two nanoparticle solutions are then mixed immediately prior to in vivo administration. (C) While not intending to be bound by theory, it is believed that the polymer and mRNA/LNP nanoparticles co-localize within the same intracellular vesicle (e.g., endosome) of the target cell, where (D) the membrane-destabilizing polymer triggers release of the mRNA into the cytosol for translation into protein.

To a 250 mL one-neck round-bottom flask was added compound 6a (3.17 g, 3.68 mmol) followed by anhydrous acetonitrile (10 mL). In a separate flasks the compound 3a (1.07 g, 3.5 mmol) was dissolved in anhydrous DMF (10 mL). Once compound 3a was partially dissolved as a milky white suspension the solution was transferred to a 100 mL addition funnel. In another flask was added PyBOP (2.0 g, 3.85 mmol) and anhydrous DMF (10 mL). The PyBOP/DMF solution was taken up into a 20 mL syringe. Then all 3 solutions (compound 6a/CH$_3$CN, compound 3a/DMF, and PyBOB/DMF) were combined simultaneously and as fast as possible while the reaction solution was vigorously stirred. Once the additions were complete the reaction was treated with N,N-diisopropylethylamine (1.22 mL, 7.0 mmol) and the solution was stirred at room temperature under a flow of argon gas for 30 min. The reaction progress was determined using Agilent Q-TOF Liquid Chromatography Mass Spectrometer by dissolving the crude reaction (1.0 µL) into MeOH (1.0 mL) and injecting 1.0 µL (FIGS. 1-2). The LC used a C18 UPLC column (Agilent Eclipse Plus C18, catalog number 959757-902, 1.8 µm, 2.1 mm×50 mm, column at room temperature, CH$_3$CN/H$_2$O containing 0.1% formic acid, isocratic gradient at 5% CH$_3$CN for 1 min, then linear gradient from 5% to 90% CH$_3$CN over 4 min, total flow rate of 0.4 mL/min). The desired product elutes between 3.0-3.1 min using the above HPLC conditions. The sugar starting material (i.e., compound 3a) was not detected on the mass spec analysis after the reaction was stirred at room temperature for 30 min. Mass spec analysis confirms the presence of compound 8a [M+Na]$^{+1}$=1173.5207 m/z; [M+H]$^{+1}$=1151.5397 m/z).

After reacting for 30 min the crude reaction mixture of compound 8a was diluted by the addition of H$_2$O (25 mL) and purified using C18 preparative reverse phase HPLC by Shimadzu (Phenomenex, Luna 5C18(2), part number 00G-4252-P0-AX, 100 Å, 25.0 cm×21.2 mm, with a Security-Guard PREP Cartridge, C18 15×21.2 mm ID, part number AJ0-7839, CH$_3$CN/H2O with 0.01% TFA, isocratic gradient at 5% CH$_3$CN for 5 min, then linear gradient from 5% to 50% CH$_3$CN over 17 min, then 50% to 53% CH3CN over 3 min, total flow rate of 20.0 mL/min, column at room temperature). 2.0 mL of the crude compound dissolved in DMF/H$_2$O (ca. 75 mg/mL) were injected each HPLC run. Using the HPLC purification conditions above the desired product compound 8a eluted between 21.5 and 22.5 min. All the fractions containing the desired product were combined and the water/CH3CN solvent was completely removed using a rotary evaporator then high vacuum overnight. The combined yield of the final product after HPLC purification and overnight high vacuum produced 3.05 g (76%) of the desired product as a bright orange solid. $^1$H NMR analysis was consistent with the presence of the desired product compound 8a.

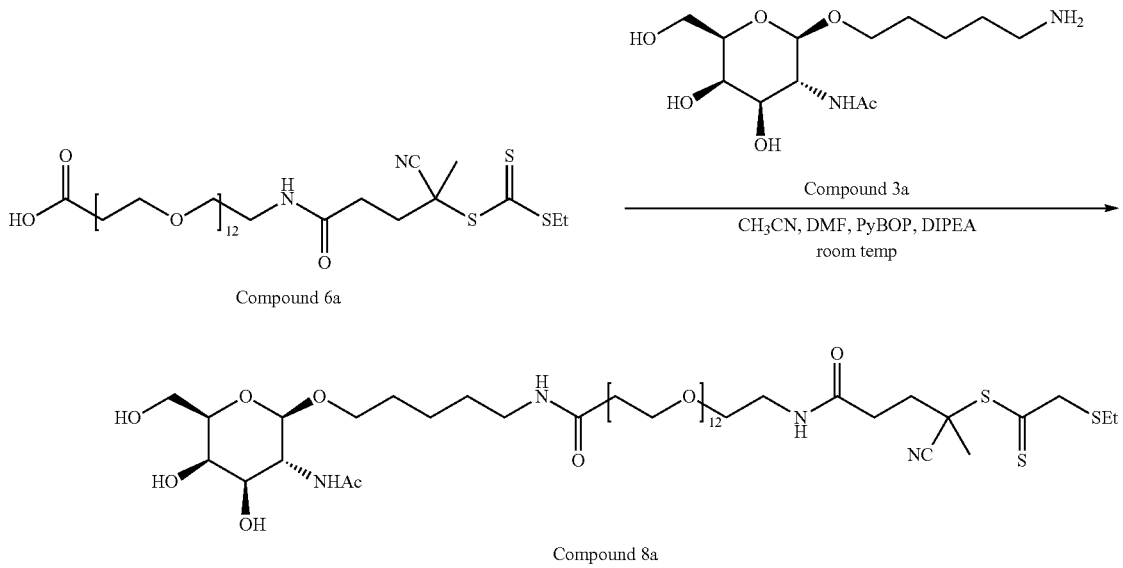

Compound 8a

Example 6: General Procedure for Polymer Synthesis

First block synthesis general procedure: The first block polymer is prepared using the following approximate ratios: [Monomer/CTA/Initiator]=[15-20/1/0.5] at approximately 1.3 M in DMF. Following oxygen purge with Nitrogen or Argon, the polymerization reaction is heated to 60-68° C. for a particular amount of time (generally 1 h 15 min-3 h) until the desired molecular weight is reached. The polymerization reaction is stopped by placing in an ice bath and opening the reaction to air. The desired polymer is purified by dialysis against methanol (3-7 days) using 2 KDa MWCO dialysis tubing. The resulting polymer is isolated by removing solvent under reduced atmosphere.

Second block synthesis general procedure: The second block polymer is prepared using the following approximate ratios: [Monomer/CTA/Initiator]=[100-130/1/0.5] at approximately 2-3 M in DMF. Following oxygen purge with Nitrogen or Argon, the polymerization reaction is heated to 60-68° C. for a particular amount of time (generally 3-6 h) until the desired molecular weight is reached. The polymerization reaction is stopped by placing in an ice bath and opening the reaction to air. The desired polymer is purified by precipitation into diethylether/hexanes and/or dialysis against methanol (3-5 days) using 2 KDa MWCO dialysis tubing. The resulting polymer can be isolated by removing solvent under reduced atmosphere, or dialysis against water using 2 KDa MWCO dialysis tubing, followed by lyophilization.

Example 7: Determining Monomer Incorporation within Individual Blocks of a Polymer During Polymer Synthesis The amount of a given monomer within a given polymer block, typically the first or hydrophilic polymer block, of the polymers exemplified and claimed herein has been determined by the following procedure. Samples taken before and after the polymerization reaction (i.e., $T_0$ (time zero) and $T_f$ (time final)) are analyzed by analytical HPLC to determine the extent of monomer consumption and/or monomer incorporation.

The initial monomer amounts in the polymerization reaction (time 0, $T_0$) are determined by sampling the polymerization reaction solution prior to nitrogen or argon purge. A (20 µL) sample of the reaction solution is withdrawn from the reaction solution and diluted into 180 µL of Methanol (MeOH). A portion of the resulting solution (10 µL) is further diluted into 590 µL MeOH, to afford a test sample with an overall dilution of 1:600 (from the polymerization reaction) for analysis by analytical HPLC.

Upon completion of the polymerization reaction a time final ($T_f$) sample is prepared analogous to the $T_0$ sample described above.

Analytical HPLC analysis of the $T_0$ and $T_f$ samples are performed using a C18 Phenomenex 5µ 100 Å 250×4.6 mm×5 micron (Part #00G-4252-E0) Luna column with guard column heated to 30° C. Three independent dilutions for each time point (i.e., $T_0$, and $T_f$) are prepared and analyzed for each time point. A 10 µl of sample is injected onto the column and eluted with the following gradient. Hold an isocratic eluent of 5% acetonitrile/water with 0.1% TFA for 2 minutes. Switch to a linear gradient from 5% to 95% acetonitrile over 25 minutes. Hold an isocratic eluent of 95% acetonitrile for 5 minutes. Return to 5% acetonitrile over 0.01 minutes. Hold the isocratic eluent of 5% acetonitrile/water with 0.1% TFA for 5 minutes. At least three independent sample preparations for both $T_0$ and $T_f$ were used for the calculation of monomer incorporation within the block.

The following methodology is used to calculate the % incorporation of a given monomer:
 a. Calculate the average $T_0$, and $T_f$ monomer peak areas from the three independent sample preparations
 b. Calculate the consumption of individual monomers in the reaction (monomer % consumption):
    =(1−($T_{f-avg}$ monomer peak area/$T_{0-avg}$ monomer peak area)×100.
 c. Calculate the molar fraction consumed of the individual monomers based on monomer input percent
    =(Monomer % conversion (calculated in step (b) above)×0.01)×monomer feed %.
 d. Total monomer consumption in the polymerization reaction and overall percent conversion:
    i. Total monomer consumption=sum of molar fraction consumed for the individual monomers calculated in step (c) above.
    ii. Overall % conversion=Total monomer consumption (calculated in step (d)(i) above)×100.
 e. Calculate the percent monomer incorporation for each monomer in the polymer
    i. =(Monomer molar fraction consumed (step (c) above)/total monomer consumed (step (d)(i) above)×100.

Example 8: Determining Monomer Incorporation within Individual Blocks of a Polymer During Polymer Synthesis The amount of a given monomer within a given polymer block, typically the second polymer block or the polymer block containing PAA, BMA and DMAEAMA, of the polymers exemplified and claimed herein has been determined by the following procedure. Samples taken before and after the polymerization reaction (i.e., $T_0$ (time zero) and $T_f$ (time final)) are analyzed by analytical HPLC to determine the extent of monomer consumption and/or monomer incorporation.

The initial monomer amounts in the polymerization reaction (time 0, $T_0$) are determined by sampling the polymerization reaction solution prior to nitrogen purge. A (20 µL) sample of the reaction solution is withdrawn and diluted into 180 µL of 1,1,1,3,3,3-hexafluoro-2-propanol (HFIP)/Methanol (MeOH)/Nano-pure water ($H_2O$) (2:1:1, v/v) containing 0.1% TFA. A portion of the resulting solution (10 µL) is further diluted into 590 µL of HFIP/MeOH/$H_2O$ (2:1:1, v/v) containing 0.1% TFA, to afford a test sample with an overall dilution of 1:600 (from the polymerization reaction) for analysis by analytical HPLC.

Upon completion of the polymerization reaction a time final ($T_f$) sample is prepared analogous to the $T_0$ sample described above. A (20 µL) sample of the reaction solution is withdrawn and diluted into 180 µL of 1,1,1,3,3,3-hexafluoro-2-propanol (HFIP)/Methanol (MeOH)/Nano-pure water ($H_2O$) (2:1:1, v/v) containing 0.1% TFA. A portion of the resulting solution (10 µL) is further diluted into 590 µL of HFIP/MeOH/$H_2O$ (2:1:1, v/v) containing 0.1% TFA, to afford a test sample with an overall dilution of 1:600 (from the polymerization reaction) for analysis by analytical HPLC.

Analytical HPLC analysis of the $T_0$, and $T_f$ samples are performed using a C18 Phenomenex 5µ 100 Å 250×4.6 mm×5 micron (Part #00G-4252-E0) Luna column with guard column heated to 30° C. Three independent dilutions for each time point (i.e., To, and $T_f$) are to be prepared and analyzed. A 10 µl of sample is injected onto the column and eluted with the following gradient. Hold an isocratic eluent of 5% acetonitrile/water with 0.1% TFA for 10 minutes. Switch to a linear gradient from 5% to 15% acetonitrile over 10 minutes. Switch to a linear gradient from 15% to 95% acetonitrile over 20 minutes. Hold an isocratic eluent of 95% eluent acetonitrile for 5 minutes. Return to 5% acetonitrile over 0.01 minutes. Hold the isocratic eluent of 5% acetonitrile/water with 0.1% TFA for 5 minutes. At least three independent sample preparations for both $T_0$, and $T_f$ were used for the calculation of monomer incorporation within the block.

The following methodology is used to calculate the % incorporation of a given monomer:
 a. Calculate the average $T_0$, and $T_f$ monomer peak areas from the three independent sample preparations
 b. Calculate the consumption of individual monomers in the reaction (monomer % consumption):
    =(1−($T_{f-avg}$ monomer peak area/$T_{0-avg}$ monomer peak area)×100
 c. Calculate the molar fraction consumed of the individual monomers based on monomer input percent
    =(Monomer % conversion (calculated in step b)×0.01)×monomer feed % (for example, DMAEMA=0.25, PAA=0.25, BMA=0.50)
 d. Total monomer consumption in the polymerization reaction and overall percent conversion:
    i. Total monomer consumption=sum of molar fraction consumed for the individual monomers calculated in (c).
    ii. Overall % conversion=Total monomer consumption (calculated in (d)(i)×100
 e. Calculate the percent monomer incorporation for each monomer in the polymer
    i. =(Monomer molar fraction consumed (calculated in (c) above)/total monomer consumed (calculated in (d)(i)))×100

Example 9: Synthesis of Polymer NagC5N-PEG$_{0.6}$-[PEGMA4-5$_{80}$-PDSMA$_{10}$-BPAM$_{10}$]$_{6.4}$-b-[D$_{25}$-B$_{50}$-P$_{25}$]$_{6.3}$ (P1)

Example 9.1: Synthesis of Macro-CTA C1

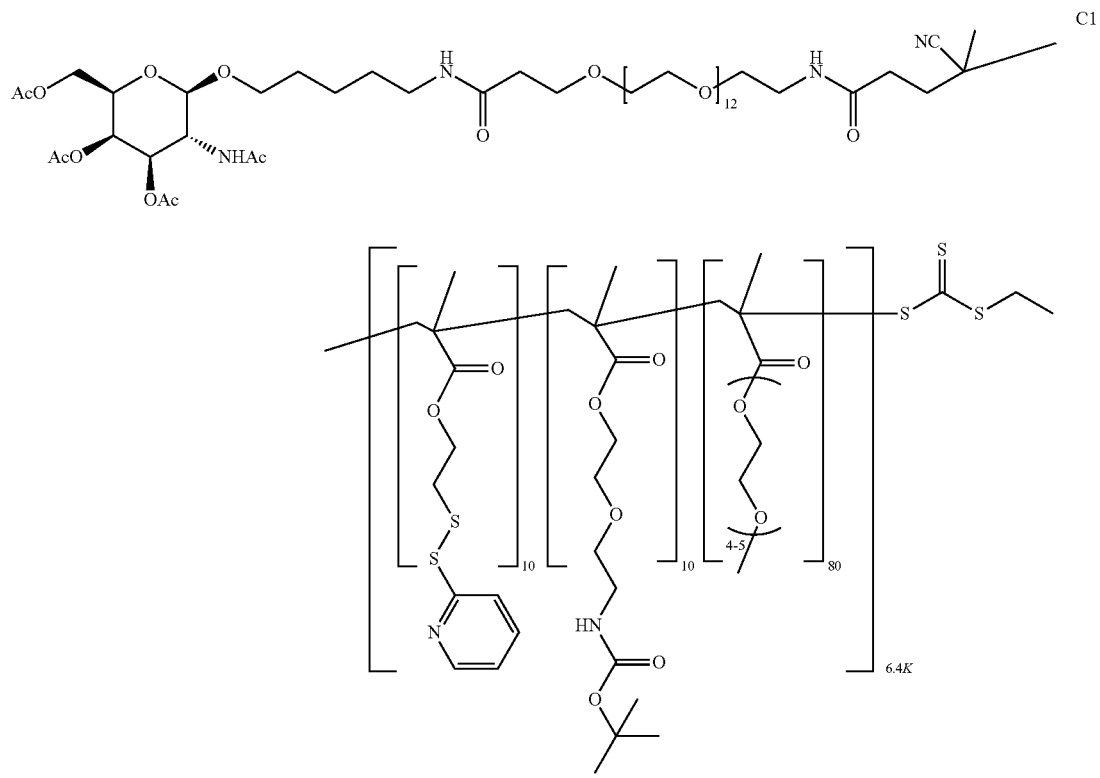

PEGMA4-5 (0.675 g, 2.25 mmol), PDSMA (0.072 g, 0.282 mmol), BPAM (0.077 g, 0.282 mmol), Nag(OAc4)-C5N-PEG$_{0.6K}$-CTA (Compound 8) (0.090 g, 0.0704 mmol; 1:40CTA:Monomers), AIBN (0.578 mg, 0.00252 mmol; CTA:AIBN 20:1) and DMF (1.65 g) were introduced under nitrogen in a sealed vial. The mixture was degassed by bubbling nitrogen for 30 minutes, and the reaction was allowed to proceed at 68° C. with rapid stirring for 2 hours. The reaction was stopped by placing the vial in ice and exposing the mixture to air. The polymer was purified by dialysis against methanol for 24 hours (Spectrum Labs, Spectra/Por Dialysis Membrane MWCO: 2000), followed by removal of solvents under vacuum. The resulting Macro-CTA was dried under vacuum for 6 hours. The structure and composition of the purified polymer were verified by $^1$H NMR, which also confirmed the absence of signals corresponding to vinyl groups of un-incorporated monomers. Purity of the polymer was confirmed by GPC analysis. $M_{n,GPC}$=7.7 kDa, dn/dc=0.05700, PDI=1.28.

Example 9.2: Synthesis of Polymer P1

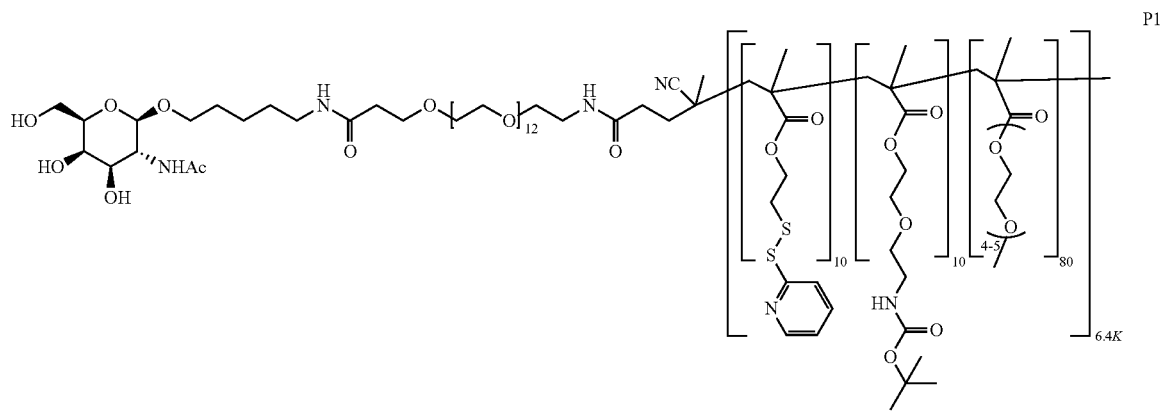

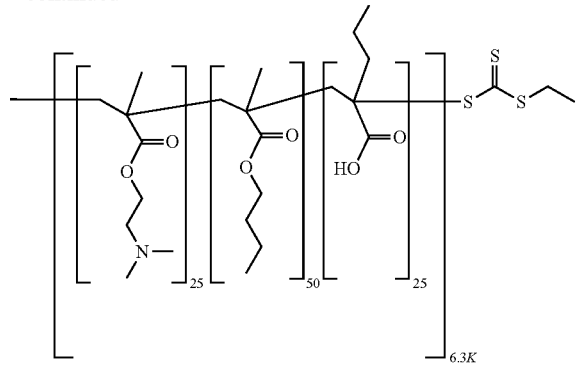

BMA (0.246 g, 1.73 mmol), PAA (0.099 g, 0.87 mmol), DMAEMA (0.136 g, 0.87 mmol), MacroCTA C1 (0.113 g, 0.0147 mmol; 1:236CTA:Monomers), AIBN (0.241 mg, 0.00147 mmol; CTA:AIBN 10:1) and DMF (0.615 g) were introduced in a vial. The mixture was degassed by bubbling nitrogen into the mixture for 30 minutes, and then allowed to react for 10 hr at 67-68° C. The reaction was stopped by placing the vial in ice and exposing the mixture to air. The polymer was purified by dialysis from acetone/DMF 1:1 into hexane/ether 75/25 (three times). The resulting polymer was dried under vacuum for at least 8 hours. The structure and composition of the purified polymer were verified by $^1$H NMR, which also confirmed the absence of signals corresponding to vinyl groups from un-incorporated monomers. GPC analysis: $M_n$=13.996 kDa, dn/dc=0.056505, PDI=1.26.

The acetyl groups were removed by treatment of the polymer with sodium methoxide (6 equivalents) in anhydrous methanol/chloroform under an atmosphere of argon at room temperature for 1.0 hour. The polymer was capped with 2,2'-dipyridyl disulfide (2 equivalents relative to pyridyl disulfide residues in the polymer) at room temperature for 1.0 hour under a flow of argon gas. After the capping the reaction was diluted with MeOH and filtered. The filtrate was transferred to a dialysis membrane with a 2000 g/mol molecular weight cut off (Spectrum Labs, Spectra/Por Dialysis Membrane MWCO: 2000) and dialyzed against MeOH over 24 hours followed by dialysis against water. The solvent was evaporated, and the polymer was dried under vacuum.

Example 10: Synthesis of Polymer NagC5N-PEG$_{0.6}$-[PEGMA4-5$_{80}$-PDSMA$_{10}$-BPAM$_{10}$]$_{7.2}$-b-[D$_{25}$-B$_{50}$-P$_{25}$]$_{6.1}$ (P2)

Example 10.1: Preparation of MacroCTA C2

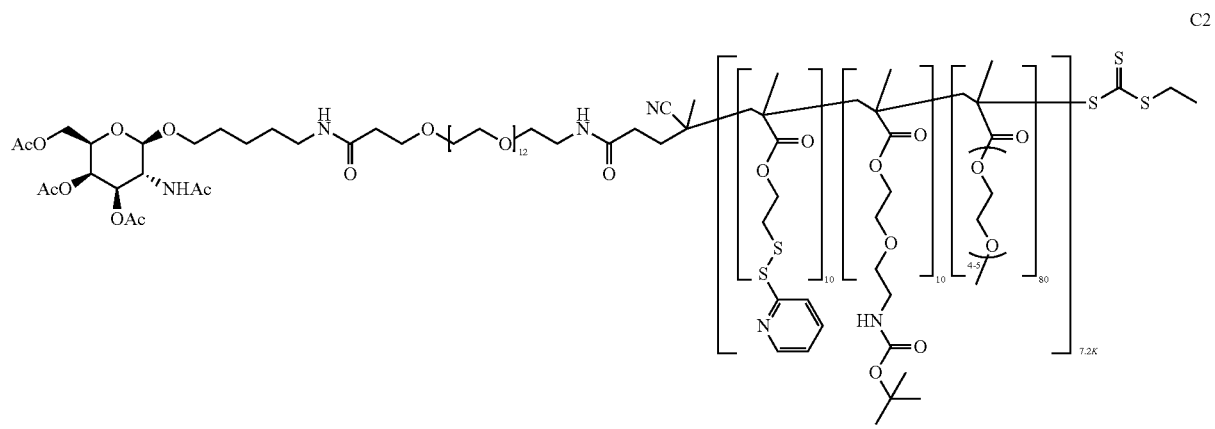

MacroCTA C2 was prepared as described in Example 9.1 starting from PEGMA4-5 (8.083 g, 27.0 mmol), PDSMA (0.860 g, 3.37 mmol), BPAM (0.921 g, 3.37 mmol), Nag(OAc4)C5N-PEG$_{0.6K}$-CTA (Compound 8) (1.076 g, 0.842 mmol; 1:40CTA:Monomers), AIBN (6.914 mg, 0.0421 mmol; CTA:AIBN 20:1) and DMF (19.73 g). Polymerization time was 2 hr 55 min. GPC: $M_n$=8.500 kDa; PDI~1.23; dn/dc=0.5780.

Example 10.2: Preparation of Polymer P2

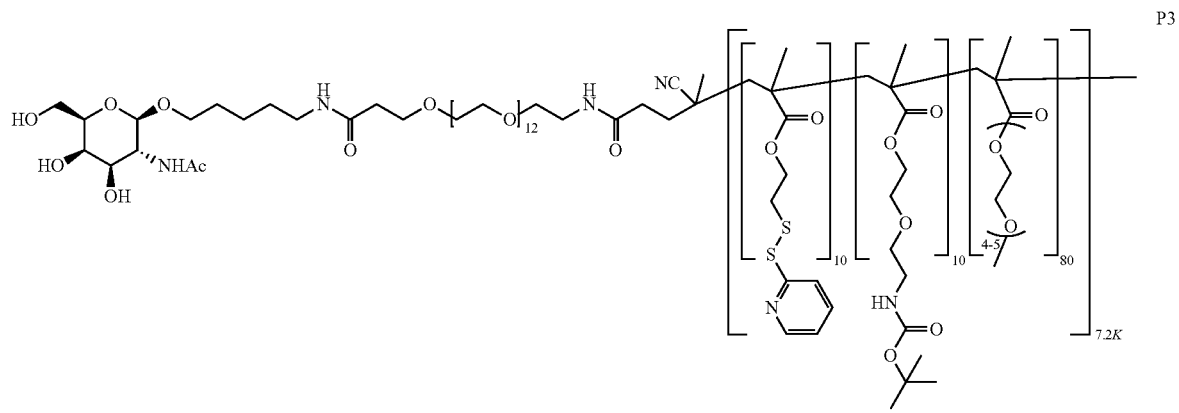

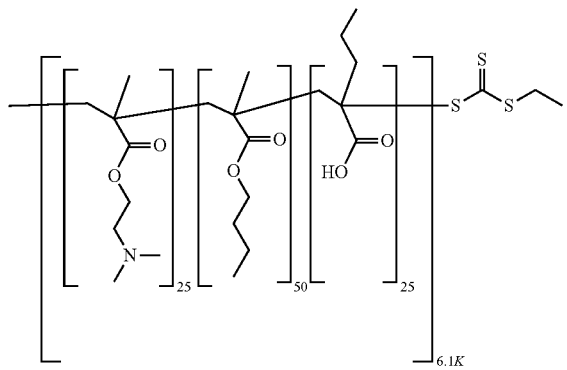

Extension of MacroCTA C2 by RAFT polymerization was carried out as described in Example 10.1 using BMA (0.553 g, 3.89 mmol), PAA (0.226 g, 1.98 mmol), DMAEMA (0.311 g, 1.98 mmol), MacroCTA C2 (0.560 g, 0.0659 mmol; 1:118CTA:Monomers), AIBN (1.082 mg, 0.00659 mmol; CTA:AIBN 10:1) and DMF (1.37 g+0.69 g). Polymerization was stopped after 5 hours, and the product was purified by dialysis from Acetone/DMF 1:1 into hexane/ether 75/25 (three times). GPC: dn/dc=0.053188; $M_n$=14.7 kDa; PDI=1.31. The acetyl groups were removed with NaOMe as described in Example 9.2.

Example 11: Synthesis of Polymer NagC5N-PEG$_{0.6}$-[PEGMA4-5$_{80}$-PDSMA$_{10}$-BPAM$_{10}$]$_{7.2}$-b-[D$_{25}$-B$_{50}$-P$_{25}$]$_{10.8}$ (P3)

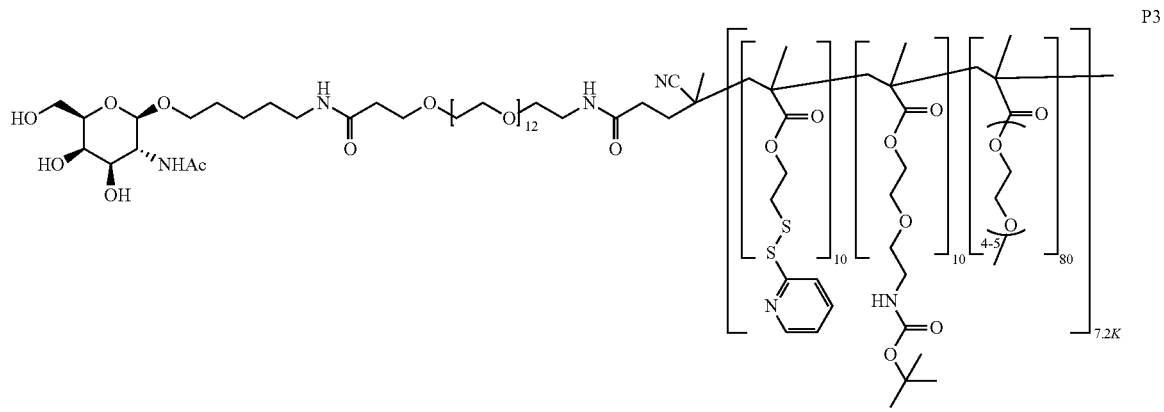

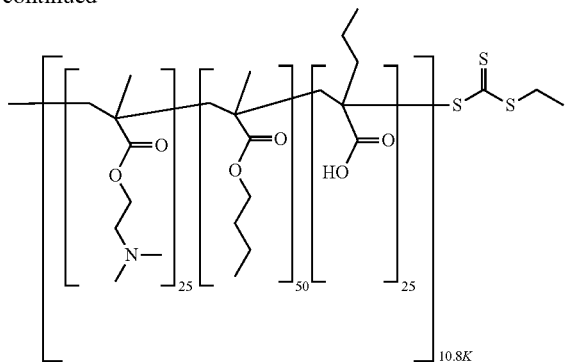

MacroCTA C2 (Example 10) was extended by RAFT polymerization as described in Example 10.2 using BMA (0.197 g, 1.39 mmol), PAA (0.079 g, 0.69 mmol), DMAEMA (0.109 g, 0.69 mmol), Macro-CTA (0.100 g, 0.0118 mmol; 1:236CTA:Monomers), AIBN (0.193 mg, 0.00118 mmol; CTA:AIBN 10:1) and DMF (0.492 g) for 4.5 hours, and the product was purified by dialysis from Acetone/DMF 1:1 into hexane/ether 75/25 (three times). GPC: dn/dc=0.053160; Mn=19.3 kDa; PDI=1.39. The acetyl groups were removed with NaOMe as described in Example 10.2.

Example 12: Synthesis of Polymer $PEG_{0.6}$-$[PEGMA4-5_{80}$-$PDSMA_{10}$-$BPAM_{10}]_{6.7}$-b-$[D_{25}$-$B_{50}$-$P_{25}]_{6.2}$ (P4)

Example 12.1: Preparation of MacroCTA C4

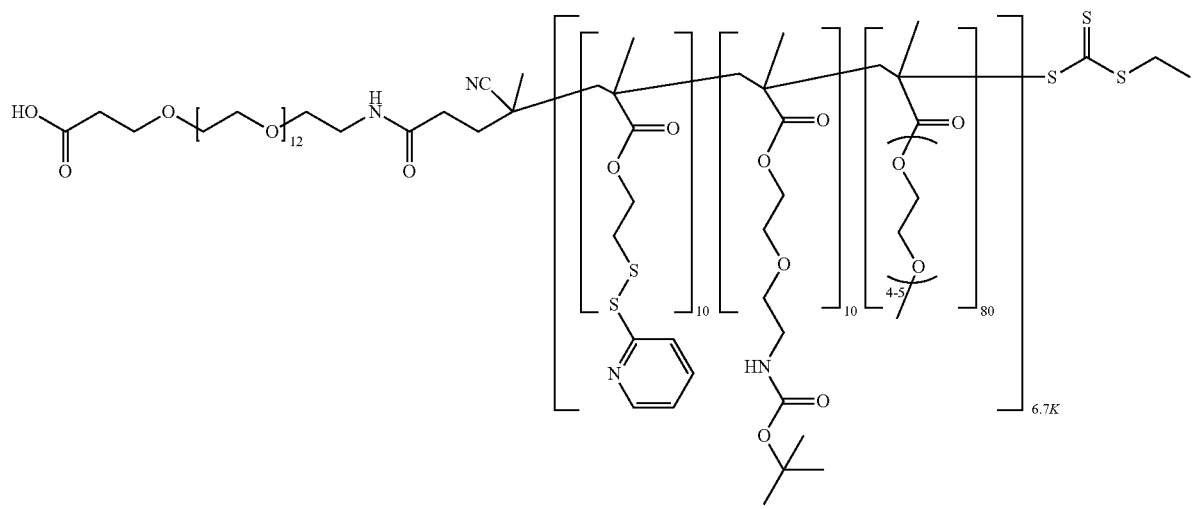

Macro-CTA C4 was prepared as described in Example 9 starting with PEGMA4-5 (5.128 g, 17.1 mmol), PDSMA (0.546 g, 2.14 mmol), BPAM (0.584 g, 2.14 mmol), $PEG_{0.6K}$-CTA (Compound 6) (0.461 g, 0.534 mmol; 1:40CTA:Monomers), AIBN (4.385 mg, 0.0267 mmol; CTA: AIBN 20:1) and DMF (12.52 g); reaction time was 1 hr 40 min. GPC: Mn=7.50 kDa; PDI~1.20; dn/dc=0.053910.

Example 12.2: Preparation of Polymer P4

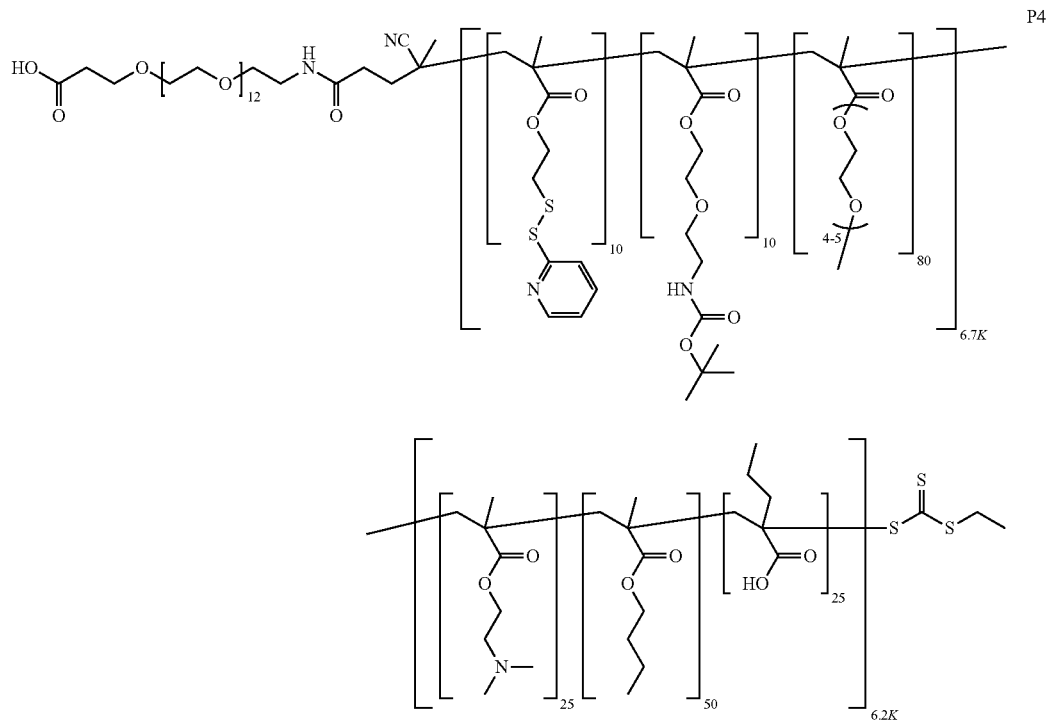

Synthesis and purification of Polymer P4 was carried out as described in Example 8.2 using BMA (1.656 g, 11.6 mmol), PAA (0.676 g, 5.92 mmol), DMAEMA (0.931 g, 5.92 mmol), MacroCTA C4 (1.5 g, 0.197 mmol; 1:118CTA: Monomers), AIBN (3.241 mg, 0.0197 mmol; CTA:AIBN 10:1) and DMF (4.16 g+2.08 g). GPC: dn/dc=0.050; $M_n$=13.8 kDa; PDI=1.1.

Example 13: Synthesis of Polymer NagC5N-PEG$_{0.6}$-[PEGMA4-5$_{80}$-PDSMA$_{10}$-BPAM$_{10}$]$_{6.6}$-b-[D$_{25}$-B$_{50}$-P$_{25}$]$_{14.7}$ (P5)

Example 13.1: Preparation of MacroCTA C5

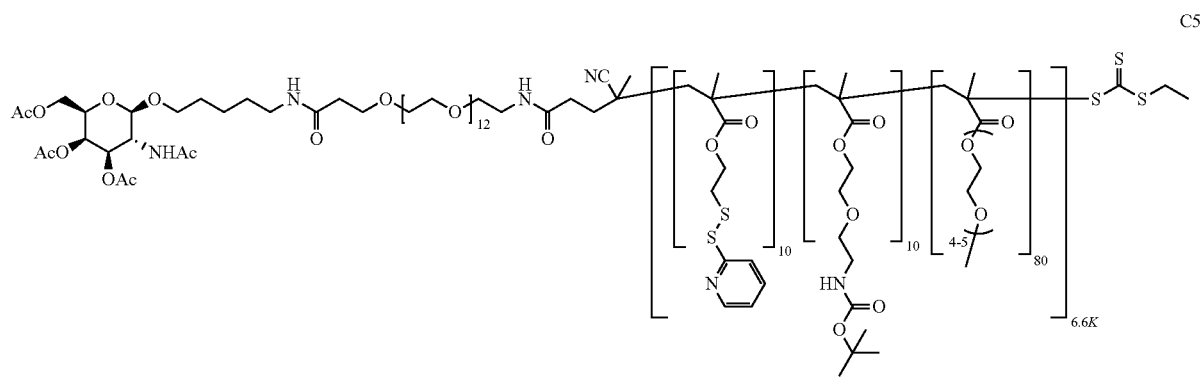

MacroCTA C5 was synthesized as described in Example 9.1 starting from PEGMA4-5 (0.5 g, 1.67 mmol), PDSMA (0.053 g, 0.208 mmol), BPAM (0.057 g, 0.208 mmol), Nag(OAc4)C5N-PEG$_{0.6K}$-CTA (Compound 8) (0.0665 g, 0.0521 mmol; 1:40CTA:Monomers), AIBN (0.428 mg, 0.0026 mmol; CTA:AIBN 20:1) and DMF (1.22 g). Polymerization time was 2 hr 30 min. GPC: Mn=7.85 kDa; PDI=1.18; dn/dc=0.066.

Example 13.2: Preparation of Polymer P5

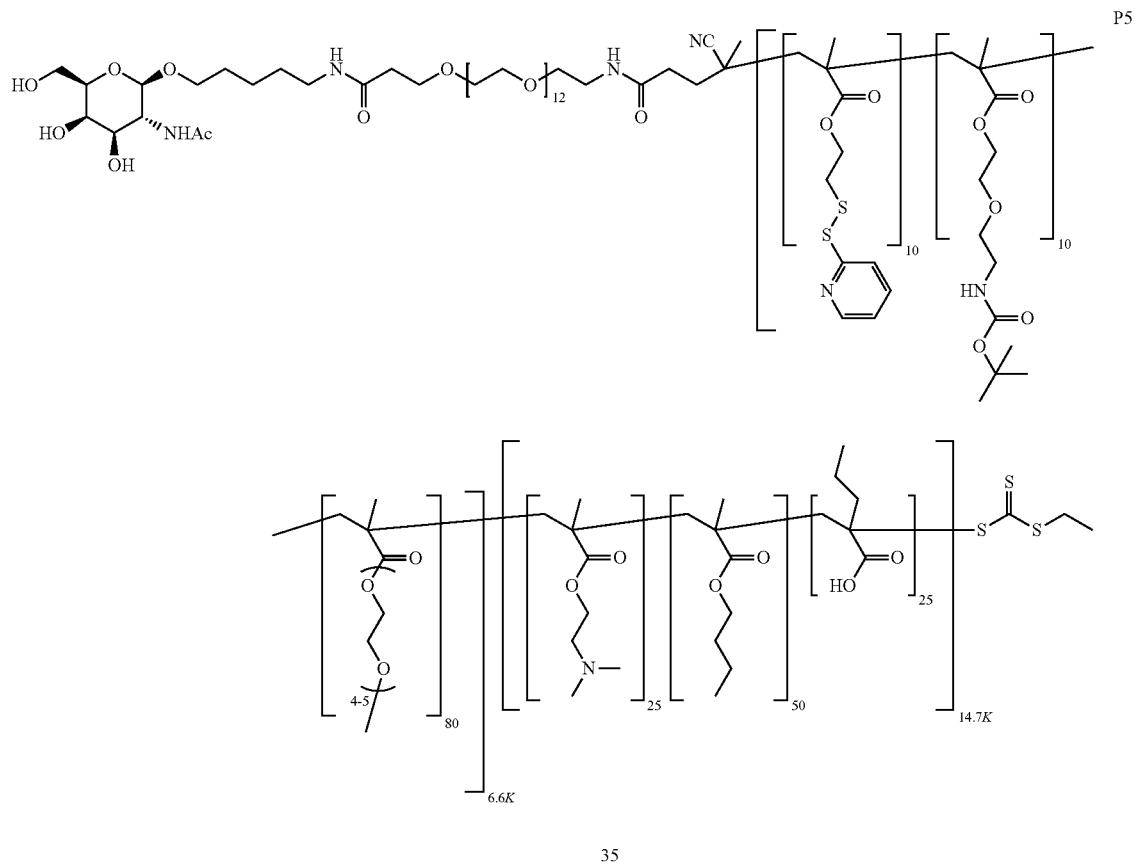

Synthesis and purification of Polymer P5 was carried out as described in Example 9.2 using BMA (0.62 g, 4.36 mmol), PAA (0.249 g, 2.18 mmol), DMAEMA (0.342 g, 2.18 mmol), MacroCTA C5 (0.189 g, 0.0242 mmol; 1:360CTA:Monomers), AIBN (0.398 mg, 0.00242 mmol; CTA:AIBN 10:1) and DMF (1.55 g). Polymerization was allowed to proceed for 10 hrs. GPC: dn/dc=0.063851; $M_n$=22.5 kDa; PDI=1.41. Deprotection was carried out as described in Example 9.2.

Example 14: Synthesis of Polymer NagC5N-PEG$_{0.6}$-[PEGMA4-5$_{80}$-PDSMA$_{10}$-BPAM$_{10}$]$_{3.5}$-b-[D$_{25}$-B$_{50}$-P$_{25}$]$_{6.3}$ (P6)

Example 14.1: Preparation of MacroCTA C6

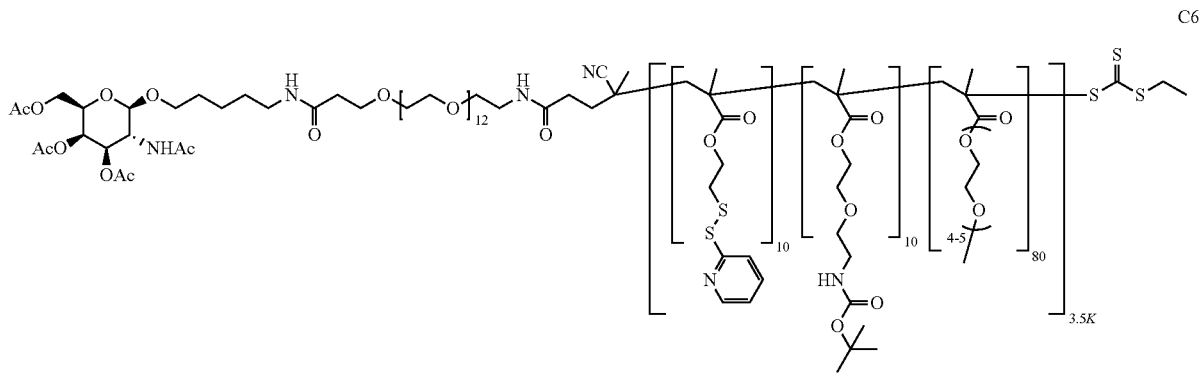

Macro-CTA C6 was synthesized as described in Example 9.1 starting from PEGMA4-5 (1.503 g, 5.00 mmol), PDSMA (0.160 g, 0.626 mmol), BPAM (0.171 g, 0.626 mmol), Nag(OAc4)C5N-PEG$_{0.6K}$-CTA (Compound 8) (0.500 g, 0.391 mmol; 1:40CTA:Monomers), AIBN (3.213 mg, 0.0196 mmol; CTA:AIBN 20:1) and DMF (3.668 g); reaction time was 1 hr 45 min. GPC: $M_n$=4.8 kDa; PDI=1.19; dn/dc=0.061481.

Example 14.2: Preparation of Polymer P6

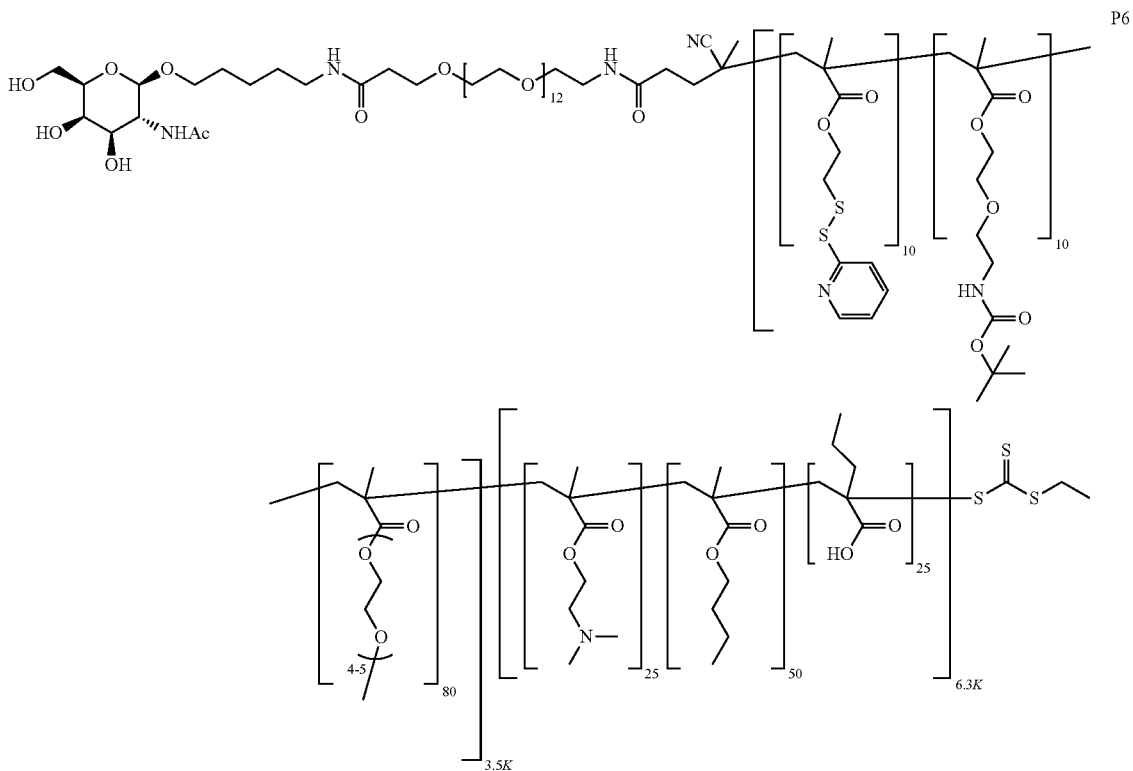

Synthesis and purification of Polymer P6 was carried out as described in Example 9.2 using BMA (0.218 g, 1.54 mmol), PAA (0.089 g, 0.781 mmol), DMAEMA (0.123 g, 0.781 mmol), MacroCTA C6 (0.125 g, 0.0260 mmol; 1:118CTA:Monomers), AIBN (0.428 mg, 0.00260 mmol; CTA:AIBN 10:1) and DMF (0.830 g). Polymerization was allowed to proceed for 4 hrs and 50 min. GPC: dn/dc=0.05812; $M_n$=11.1 kDa; PDI=1.38. Deprotection was carried out as described in Example 9.2.

Example 15: Synthesis of Polymer NagC5N-PEG$_{0.6}$-[PEGMA4-5$_{86}$-PDSMA$_{14}$]$_{3.82KDa}$-[BMA$_{45}$-PAA$_{15}$-DMAEMA$_{40}$]$_{5.98KDa}$ (P7)

Example 15.1: Preparation of MacroCTA C7

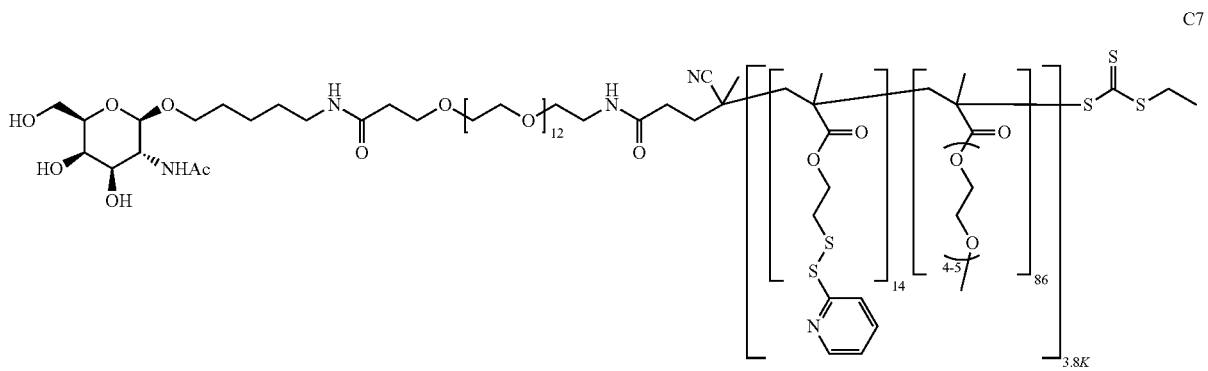

AIBN/DMF (21.93 g of 1.05603 mg/g ABIN in DMF) was added to Nag(OH)C5N-PEG$_{0.6K}$-CTA (synthesized as described in Example 5 compound 8a) (3.075 g; 2.6705 mmol) in a 40 ml reaction vessel and mixed to dissolve the CTA. DMF was then added until the total weight of DMF was 24.9627 g. To the resulting solution was added PEGMA (11.18 g, 37.2621 mmol, filtered through aluminum oxide (activated, basic, Brockmann I) and PDSMA (1.1211 g, 4.1393 mmol). The resulting solution was mixed and then transferred to a sealed 50 mL round bottom flask equipped with a magnetic stir bar. The resulting solution was de-oxygenated by bubbling nitrogen into the solution for 50 min on ice. The flask was moved to room temperature for 4 min and then placed in an oil bath pre-heated to 68° C. for 1 hour 42 minutes (stir speed was set at 350 rpm). The reaction was stopped by placing the vial in ice and exposing the mixture to air. The reaction solution was diluted with MeOH, transferred to dialysis membranes (Spectrum Labs, Spectrum Spectra/Por 6 Dialysis Membrane Tubing MWCO: 2000) and dialyzed against MeOH (6×4000 mL) for 6 days. Samples were taken for LC-MS, GPC and $^1$H NMR analyses. After dialysis, the solvent was removed under reduced atmosphere followed by high vacuum to afford 2.45 g of polymer. LC-MS analysis indicated no residual CTA peak. $^1$H NMR, which also confirmed the absence of signals corresponding to vinyl groups of un-incorporated monomers. Purity of the polymer was confirmed by GPC analysis. $M_{n,GPC}$=4.97 KDa, PDI=1.12, dn/dc=0.06469, PDI=1.12.

Example 15.2: Synthesis of Polymer P7

AIBN/DMF solution (7.0225 g; 1.10468 mg/g AIBN in DMF) was added to macro-CTA C7 (2.350 g) in a 40 mL reaction vessel; the sample was mixed to dissolve the macro-CTA. DMF was then added until the total weight of DMF was 15.05 g. BMA (3.967 g, filtered through aluminum oxide (activated, basic, Brockmann I), PAA (1.6217 g) and DMAEMA (2.237 g, filtered through aluminum oxide [activated, basic, Brockmann I]) were added to the resulting solution and the solution was mixed. The mixture was vortexed for several minutes to give a homogeneous stock solution and transferred to a sealed 50 mL round bottom flask equipped with a magnetic stir bar. The mixture was then cooled to 0° C. using an ice bath and maintained at 0° C. while degassed by vigorously bubbling nitrogen inside the solution for 55 minutes. The flask septa was placed into an oil bath pre-heated to 61° C. (stirring speed was 350) and allowed to stir for 4 hours 30 minutes. The reaction was stopped by placing the vial in ice and exposing the mixture to air. The reaction was then diluted with acetone (roughly the same volume of acetone as the DMF used in the reaction vial) and precipitated into a stirred mixture of ether/hexanes (1:3 v/v) in a 50 mL centrifuge tube once and then into a large beaker with 600 mL ether/hexanes (1:3 v/v). The polymer precipitate was isolated and dissolved with MeOH, transferred to three individual dialysis membranes (Spectrum Labs, Spectrum Spectra/Por 6 Dialysis Membrane Tubing MWCO: 2,000) and dialyzed against methanol (5×4000 mL) for 4 days. After the dialysis against methanol, it was dialyzed against nanopure water using the same membrane (×6, water changed every hour). When the dialysis was complete, the solution was transferred to tared vials and treated with liquid nitrogen before being lyophilized for 5 days to afford 3.46 g of the final product. The final product was analyzed by UV/vis, NMR, GPC and HPLC equipped with RI detector (for batch dn/dc). Analysis of the polymer

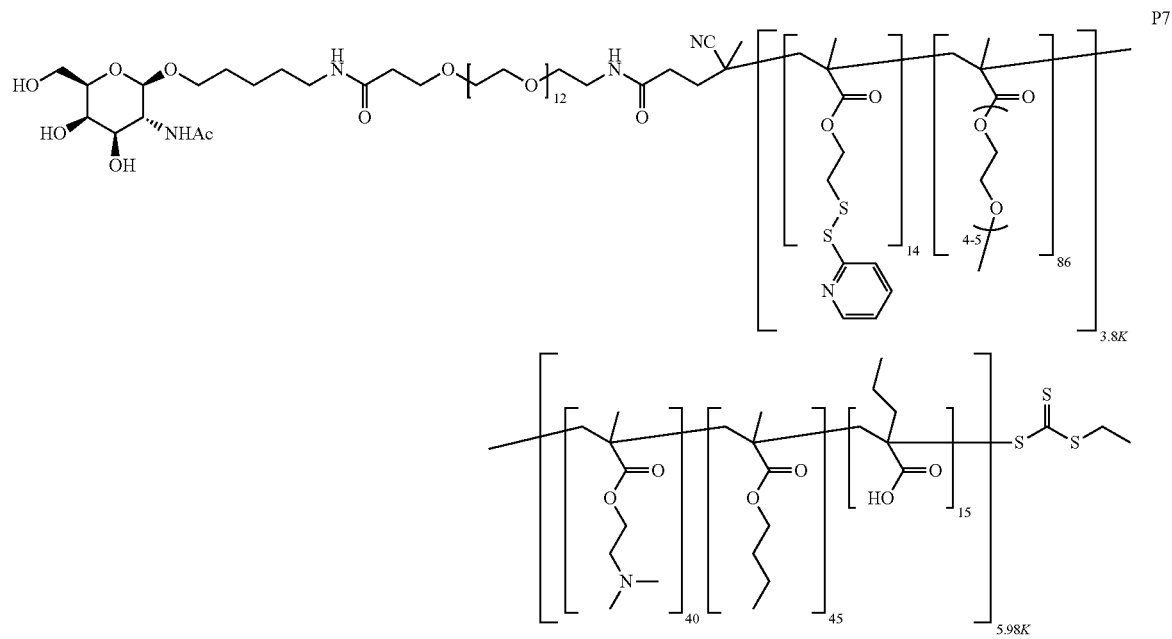

by $^1$H-NMR indicated a polymer with no vinyl groups remaining and the presence of PDSMA. The NMR is consistent for proposed structure. GPC results: Mn=10.936 KDa, PDI=1.30, dn/dc=0.057867.

Example 16: Synthesis of Polymer NAG-PEG$_{0.6}$-[PEGMA$_{100}$]$_{3.5k}$-[BMA$_{49}$-PAA$_{10}$-DMAEMA$_{33}$-PDSMA$_8$]$_{7.1k}$ (P8)

Example 16.1: Preparation of MacroCTA C8

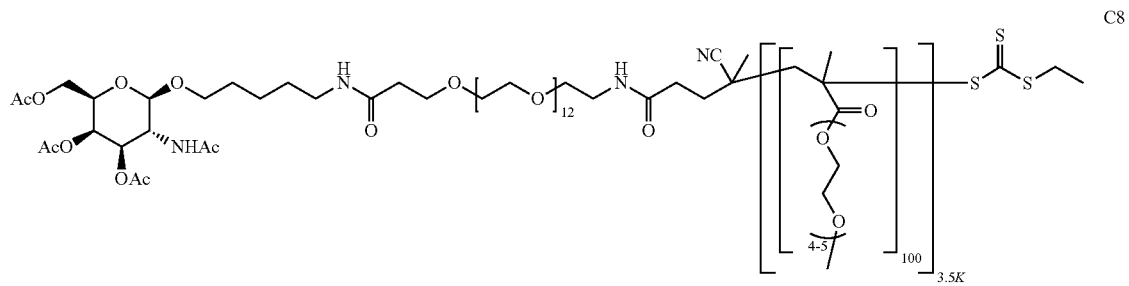

To a 20 mL reaction vial was added to Nag(OH)C5N-PEG$_{0.6K}$-CTA (synthesized as described in Example 5, compound 8a) (794.6 mg, 0.6922 mmol, CTA) followed by a solution of AIBN (5.0438 g solution dissolved in DMF at a concentration of 1.1268 mg/g, 5.68 mg AIBN, 0.03461 mmol, 2,2'-azobis(2-methylpropionitrile), compound recrystallized from MeOH) then an additional amount of DMF (432.2 mg) was added bringing the total amount of DMF used in this reaction to 5.4760 g. This solution was mixed and vortexed for several minutes until all of the CTA was completely dissolved. Once all the CTA was completely dissolved PEGMA (3219.3 mg, 10.730 mmol, poly(ethylene glycol) methyl ether methacrylate with average M$_n$ =300 g/mol, inhibited with 100 ppm MEHQ and 300 ppm of BHT inhibitors, Aldrich part number 447935-500 mL, inhibitors removed by passing the neat monomer through a plug of Al$_2$O$_3$, was added to the reaction vial. This mixture was stirred for several minutes. The reaction vial was partially sealed and cooled to 0° C. using an ice bath while the mixture was degassed by vigorously bubbling nitrogen for 30 minutes with magnetic stirring of the reaction solution. Then the vial was completely sealed and placed into a heater block. The stirring speed was set at 300 rpm, the thermometer was set at 68° C. and was maintained at this temperature during the entire process. The reaction was left to stir at 68° C. for 1 hours and 47 minutes. After the reaction is complete it was quenched by opening the vial and then placing the reaction vial in ice exposing the mixture to air. The reaction vial was diluted with MeOH (10 mL) and transferred to a dialysis membrane with a 2000 g/mol molecular weight cut off (Spectrum Labs, Spectrum Spectra/Por 6 Dialysis Membrane Tubing MWCO: 2000) and dialyzed against MeOH (3×4000 mL) for 4 days. The dialysis solution was changed every day for 3 iterations total. The polymer in the dialysis bag was analyzed according to the following procedure: A small aliquot of the dialysis solution (ca. 500-1000 µL) was withdrawn from the dialysis tubing and placed into a tared vial. The solution was then evaporated using a rotary evaporator. Once the solvents are removed the vial was transferred to a high vacuum line and placed under high vacuum. The compound is dried for <15 min. Once the vial weight is constant then the compound was dissolved immediately in DMF with 1% weight LiBr solution. The final concentration of the polymer was approximately 8 mg/mL in DMF with 1% wt LiBr (DMF measured by weight then converted to volume). A 20 kDa polystyrene standard (Fluka, part number 81407-1G) dissolved in DMF with 1% wt LiBr at a concentration of roughly 3 mg/mL (DMF measured by weight then converted to volume) is then injected (100 µL) on the GPC followed by the polymer sample of interest (60, 80, 100, and 120 µL). Once the final GPC analysis is determined then the dialysis solution was transferred to a 40 mL reaction vial then the solvents were removed using a rotary evaporator. Then the material was place on a high vacuum line (pressure <0.5 torr) for >24 hours. This process provided 682.9 mg of the final product. The final product is then analyzed by NMR and GPC. The final product was stored at room temperature under high vacuum. The NMR is consistent for proposed structure. GPC results: Mn=4.600, dn/dc=0.053354.

Example 16.2. Synthesis of Polymer P8

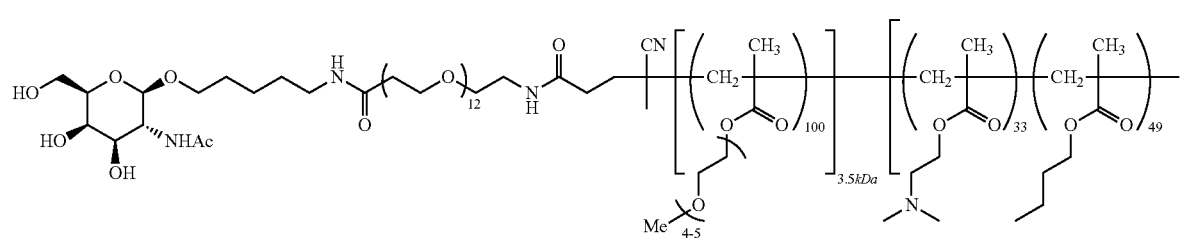

-continued

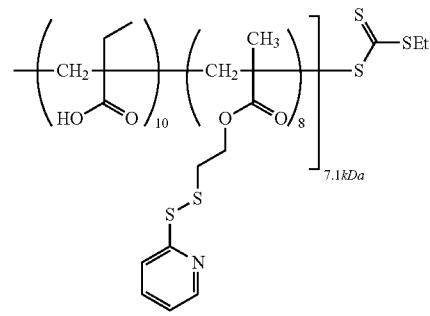

To a 40 mL reaction vial was added macro-CTA C8 (682.1 mg, 0.148 mmol) followed by a solution of AIBN (2.2338 g solution dissolved in DMF at a concentration of 1.0927 mg/g, (2.44 mg AIBN, 0.0148 mmol, 2,2'-azobis(2-methyl-propionitrile), compound recrystallized from MeOH) then an additional amount of DMF (2.6163 g) was added bringing the total amount of DMF used in this reaction to 4.8501 g. This solution was mixed and vortexed for several minutes until all of the CTA was completely dissolved. Once all the CTA was completely dissolved then BMA (1.1849 g, 8.314 mmol, purified by passing the neat monomer through a plug of $Al_2O_3$, butyl methacrylate, d—0.894 g/mL), PAA (488.0 mg, 4.231 mmol, unpurified 2-propylacrylic acid, d—0.951 g/mL), DMAEMA (661.8 mg, 4.231 mmol, purified by passing the neat monomer through a plug of $Al_2O_3$, 2-(di-methylamino)ethyl methacrylate, d—0.933 g/mL), and PDSMA (227.0 mg, 0891 mmol). This mixture was mixed for several minutes. The reaction mixture was then transferred to a brand new 20 mL reaction vial containing a magnetic stir bar. The reaction vial was partially sealed and cooled to 0° C. using an ice bath while the mixture was degassed by vigorously bubbling nitrogen for 30 minutes with magnetic stirring of the reaction solution. The vial was then completely sealed and placed into a heater block. The stirring speed was set at 300, the thermometer was set at 62° C. The reaction was left to stir at 62° C. for 5 hours and 50 minutes. After the reaction is complete it was quenched by opening the vial and then placing the reaction vial in ice exposing the mixture to air. The reaction solution was then diluted with acetone (~5 mL, roughly the same volume of acetone as the DMF used in the reaction vial) and precipitated into a stirred mixture of $Et_2O$/hexanes (1000 mL, 1:4 v/v) in a glass beaker. After the polymer had settled to the bottom (ca. 15 min) the solvents were decanted off. The precipitated polymer dissolved in MeOH was transferred into dialysis membranes with a 2000 g/mol molecular weight cut off (Spectrum Labs, Spectrum Spectra/Por 6 Dialysis Membrane Tubing MWCO: 2000) and dialyzed against MeOH (3×4000 mL) for 3 days (72 h). The dialysis solution was changed every day for 3 iterations total. After 3 days (72 h) dialysis against MeOH the dialysis solution is changed to nanopure $H_2O$ and dialyzed against $H_2O$ (5×4000 mL) for 5 hr. The dialysis solution was changed roughly every hour for 5 iterations total. Upon completion of dialysis the solutions were transferred to tared vials and frozen solid using a bucket of dry ice. Then the material was placed into the lyophilizer for >4 days total drying time. This process provided 1.0325 g of the final product. The final product was then analyzed by NMR and GPC. Analysis of the polymer by $^1$H-NMR indicated a polymer with no vinyl groups remaining and the presence of PDSMA. The NMR is consistent for proposed structure. GPC results: Mn=11.7 kDa, dn/dc=0.058046. The final product was stored in glass vials with rubber septum that were purged with argon and sealed with parafilm. The vials were stored at −20° C.

Example 17: Polymer Synthesis

By similar methods, the following polymers were synthesized according to the following conditions shown in Tables 8-67, below.

A. P67: NAG-PEG12-[PEGMA(300, 79.1%)-BPAM (10.0%)-PDSMA(10.9%)]3.56 KDa-b-[DMAEMA (34.7%)-BMA(54.7%)-PAA(10.5%)]4.71 KDa

TABLE 8

| P67 | Block 1 | Block 2 |
| --- | --- | --- |
| [M/CTA/I] | [12.8:1.6:1.6/1/0.05] | [30:59:30/1/0.1] |
| [concentration] | 1.17M | 2.61M |
| Time | 1 h 45 m | 5 h 35 m |
| Temperature | 67° C. | 61° C. |

CTA = Nag(OH)C5N-PEG$_{12}$-CTA; I = AIBN

B. P68: NAG-PEG12-[PEGMA(300; 89.8%)-PhEMA (10.2%)]3.23 KDa-b-[DMAEMA(33%)-BMA(57%)-PAA(10%)]6.0 KDa

TABLE 9

| P68 | Block 1 | Block 2 |
| --- | --- | --- |
| [M/CTA/I] | [13.95:1.55/1/0.05] | [30:59:30/1/0.1] |
| [concentration] | 1.2M | 2.3M |
| Time | 1 h 30 m | 4 h 30 m |
| Temperature | 67° C. | 65° C. |

CTA = Nag(OH)C5N-PEG$_{12}$-CTA; I = AIBN

C. P69: NAG-PEG12-[PEGMA(300;78.7%)-PhEMA (21.3%)]3.25 KDa-b-[DMAEMA(32.9%)-BMA (54.8%)-PAA(12.3%)]5.4 KDa

TABLE 10

| P69 | Block 1 | Block 2 |
| --- | --- | --- |
| [M/CTA/I] | [12.4:3.1/1/0.05] | [30:59:30/1/0.1] |
| [concentration] | 1.2M | 2.3M |
| Time | 1 h 30 m | 4 h 30 m |
| Temperature | 67° C. | 65° C. |

CTA = Nag(OH)C5N-PEG$_{12}$-CTA; I = AIBN

D. P70: NAG-PEG12-[PEGMA(300,88.6)-PhEMA(11.4%)]3.02 KDa-b-[DMAEMA(36.8%)-BMA(56.3%)-PAA(6.9%)]4.39 KDa

TABLE 11

| P70 | Block 1 | Block 2 |
|---|---|---|
| [M/CTA/I] | [12.4:3.1/1/0.05] | [30:59:30/1/0.1] |
| [concentration] | 1.2M | 2.3M |
| Time | 1 h 30 m | 4 h 30 m |
| Temperature | 67° C. | 65° C. |

CTA = Nag(OH)C5N-PEG$_{12}$-CTA; I = AIBN

E. P71: NAG-PEG12-[PEGMA(300, 69.5%)-BPAM(19.2%)-PDSMA (11.3%)]3.59 KDa-b-[DMAEMA(35.2%)-BMA (53.9%)-PAA (10.9%)]5.27 Kda

TABLE 12

| P71 | Block 1 | Block 2 |
|---|---|---|
| [M/CTA/I] | [12.8:3.2:1.65/1/0.05] | [30:59:30/1/0.1] |
| [concentration] | 1.22M | 2.62M |
| Time | 1 h 45 m | 5 h 35 m |
| Temperature | 67° C. | 61° C. |

CTA = Nag(OH)C5N-PEG$_{12}$-CTA; I = AIBN

F. P72: NAG-PEG12-[PEGMA(300, 80.3%)-ImMA(19.7)]3.7 KDa-b-[DMAEMA(35.9%)-BMA(53.9%)-PAA(10.2%)]4.7 KDa

TABLE 13

| P72 | Block 1 | Block 2 |
|---|---|---|
| [M/CTA/I] | [13:4.1/1/0.05] | [30:59:30/1/0.1] |
| [concentration] | 1.2M | 2.3M |
| Time | 1 h 30 m | 5 h |
| Temperature | 67° C. | 65° C. |

CTA = Nag(OH)C5N-PEG$_{12}$-CTA; I = AIBN

G. P73: NAG-PEG12-[PEGMA(300, 73.1%)-BMA(14.4%)-PhEMA(12.5%)]3.8 KDa-b-[DMAEMA(37.6%)-BMA(52.3%)-PAA(10.1%)]4.2 KDa

TABLE 14

| P73 | Block 1 | Block 2 |
|---|---|---|
| [M/CTA/I] | [12.8:1.6:1.6/1/0.05] | [30:59:30/1/0.1] |
| [concentration] | 1.2M | 2.3M |
| Time | 1 h 30 m | 5 h |
| Temperature | 67° C. | 61° C. |

CTA = Nag(OH)C5N-PEG$_{12}$-CTA; I = AIBN

H. P74: NAG-PEG12-[PEGMA(300, 80.3%)-BMA(23.3%)]3.8 KDa-b-[DMAEMA(38.2%)-BMA(51.5%)-PAA(10.3%)]3.5 KDa

TABLE 15

| P74 | Block 1 | Block 2 |
|---|---|---|
| [M/CTA/I] | [12.8:3.2/1/0.05] | [30:59:30/1/0.1] |
| [concentration] | 1.2M | 2.3M |
| Time | 1 h 30 m | 5 h |
| Temperature | 67° C. | 61° C. |

CTA = Nag(OH)C5N-PEG$_{12}$-CTA; I = AIBN

I. P75: NAG-PEG12-[PEGMA(300, 75.8%)-isoA-MA(11.8%)-PhEMA(12.4%)]3.3 KDa-b-[DMAEMA(39.3%)-BMA(51.6%)-PAA(9%)]4.95 KDa

TABLE 16

| P75 | Block 1 | Block 2 |
|---|---|---|
| [M/CTA/I] | [12.8:1.6:1.6/1/0.05] | [30:59:30/1/0.1] |
| [concentration] | 1.2M | 2.3M |
| Time | 1 h 40 m | 5 h |
| Temperature | 67° C. | 61° C. |

CTA = Nag(OH)C5N-PEG$_{12}$-CTA; I = AIBN

J. P76: NAG-PEG12-[PEGMA(300, 74.9%)-isoA-MA(25.1%)]2.9 KDa-b-[DMAEMA(38%)-BMA(53%)-PAA(9.1%)]5.2 KDa

TABLE 17

| P76 | Block 1 | Block 2 |
|---|---|---|
| [M/CTA/I] | [12.8:3.2/1/0.05] | [30:59:30/1/0.1] |
| [concentration] | 1.2M | 2.3M |
| Time | 1 h 40 m | 5 h |
| Temperature | 67° C. | 61° C. |

CTA = Nag(OH)C5N-PEG$_{12}$-CTA; I = AIBN

K. P77: NAG-PEG12-[PEGMA (300, 86%)-CyHexMA (14%)]2.98 KDa-b-[DMAEMA (36.2%)-BMA (51.7%)-PAA (12.2%)]4.66 KDa

TABLE 18

| P77 | Block 1 | Block 2 |
|---|---|---|
| [M/CTA/I] | [12.8:2.2/1/0.05] | [30:59:30/1/0.1] |
| [concentration] | 1.21M | 2.6M |
| Time | 2 h 35 m | 5 h |
| Temperature | 67° C. | 61° C. |

CTA = Nag(OH)C5N-PEG$_{12}$-CTA; I = AIBN

L. P78: NAG-PEG12-[PEGMA(300, 72.5%)-BPAM(27.5%)]3.8 KDa-b-[DMAEMA(25.6%)-BMA(64.8%)-PAA(9.6%)]5.5 KDa

TABLE 19

| P78 | Block 1 | Block 2 |
|---|---|---|
| [M/CTA/I] | [12.8:5/1/0.05] | [30:59:30/1/0.1] |
| [concentration] | 1.2M | 2.3M |
| Time | 1 h 45 m | 5 h 15 m |
| Temperature | 67° C. | 61° C. |

CTA = Nag(OH)C5N-PEG$_{12}$-CTA; I = AIBN

M. P79: NAG-PEG12-[PEGMA (300, 69.9%)-HMA (30.1%)]2.93 KDa-b-[DMAEMA (34.4%)-BMA (536%)-PAA (12%)]4.43 Kda

TABLE 20

| P79 | Block 1 | Block 2 |
|---|---|---|
| [M/CTA/I] | [10.8:5.2/1/0.05] | [30:59:30/1/0.1] |
| [concentration] | 1.21M | 2.96M |
| Time | 1 h 50 m | 4 h 40 m |
| Temperature | 68° C. | 61° C. |

CTA = Nag(OH)C5N-PEG$_{12}$-CTA; I = AIBN

N. P80: NAG-PEG12-[PEGMA (300, 85.4%)-EHMA (14.6%)]3.36 KDa-b-[DMAEMA (36.5%)-BMA (53.7%)-PAA (9.7%)]4.18 KDa

TABLE 21

| P80 | Block 1 | Block 2 |
|---|---|---|
| [M/CTA/I] | [16/1/0.05] | [30:59:30/1/0.1] |
| [concentration] | 1.21M | 2.62M |
| Time | 2 h | 5 h |
| Temperature | 68° C. | 61° C. |

CTA = Nag(OH)C5N-PEG$_{12}$-CTA; I = AIBN

O. P81: NAG-PEG12-[PEGMA(300, 72%)-Fl-BMA (28%)]3.75 KDa-b-[DMAEMA(30.7%)-BMA (56.7%)-PAA(12.6%)]5.7 KDa

TABLE 22

| P81 | Block 1 | Block 2 |
|---|---|---|
| [M/CTA/I] | [12.8:3.5/1/0.05] | [26:51:26/1/0.1] |
| [concentration] | 1.2M | 2.3M |
| Time | 1 h 35 m | 5 h 15 m |
| Temperature | 67° C. | 61° C. |

CTA = Nag(OH)C5N-PEG$_{12}$-CTA; I = AIBN

P. P82: NAG-PEG12-[PEGMA(300, 71.9%)-Fl-BMA (28.1%)]3.55 KDa-b-[DMAEMA(29.9%)-BMA (571.6%)-PAA(12.4%)]5.3 KDa

TABLE 23

| P82 | Block 1 | Block 2 |
|---|---|---|
| [M/CTA/I] | [12.8:3.5/1/0.05] | [26:51:26/1/0.1] |
| [concentration] | 1.2M | 2.3M |
| Time | 1 h 35 m | 5 h 15 m |
| Temperature | 67° C. | 61° C. |

CTA = Nag(OH)C5N-PEG$_{12}$-CTA; I = AIBN

Q. P83: NAG-PEG12-[PEGMA(300, 78.9%)-F-Cy-HexMA(21.1%)]4.56 KDa-b-[DMAEMA(33.2%)-BMA(55.4%)-PAA(11.4%)]5.3 KDa

TABLE 24

| P83 | Block 1 | Block 2 |
|---|---|---|
| [M/CTA/I] | [12.8:3.5/1/0.05] | [30:59:30/1/0.1] |
| [concentration] | 1.2M | 2.3M |
| Time | 1 h 35 m | 5 h 15 m |
| Temperature | 67° C. | 61° C. |

CTA = Nag(OH)C5N-PEG$_{12}$-CTA; I = AIBN

R. P84: NAG-PEG12-[PEGMA(300, 77.9%)-F-HPenMA (22.1%)]3.26 KDa-b-[DMAEMA(30.9%)-BMA (57.4%)-PAA(11.6%)]6.5 KDa

TABLE 25

| P84 | Block 1 | Block 2 |
|---|---|---|
| [M/CTA/I] | [12.8:4/1/0.05] | [30:59:30/1/0.1] |
| [concentration] | 1.2M | 2.3M |
| Time | 1 h 35 m | 5 h 15 m |
| Temperature | 67° C. | 61° C. |

CTA = Nag(OH)C5N-PEG$_{12}$-CTA; I = AIBN

S. P85: NAG-PEG12-[PEGMA(300, 79%)-BMA(21%)] 2.9 KDa-b-[DMAEMA(29.3%)-BMA(26.6%)-Fl-BMA(34.6%)-PAA(9.5%)]5.8 KDa

TABLE 26

| P85 | Block 1 | Block 2 |
|---|---|---|
| [M/CTA/I] | [12.8:3.2/1/0.05] | [30:59:30/1/0.1] |
| [concentration] | 1.2M | 2.3M |
| Time | 1 h 40 m | 5 h 15 m |
| Temperature | 67° C. | 61° C. |

CTA = Nag(OH)C5N-PEG$_{12}$-CTA; I = AIBN

T. P86: NAG-PEG12-[PEGMA (300, 78.1%)-C12MA (21.9%)]3.67 KDa-b-[DMAEMA (32.1%)-BMA (53.7%)-PAA (142%)]472 KDa

TABLE 27

| P86 | Block 1 | Block 2 |
|---|---|---|
| [M/CTA/I] | [12.8:3.2/1/0.05] | [30:59:30/1/0.1] |
| [concentration] | 1.21M | 2.38M |
| Time | 2 h 35 m | 5 h 30 m |
| Temperature | 68° C. | 61° C. |

CTA = Nag(OH)C5N-PEG$_{12}$-CTA; I = AIBN

U. P87: NAG-PEG12-[PEGMA (300, 69.7%)-EHMA (30.3%)]3.9 KDa-b-[DMAEMA (31.1%)-BMA (56.7%)-PAA (12.1%)]51 KDa

TABLE 28

| P87 | Block 1 | Block 2 |
|---|---|---|
| [M/CTA/I] | [15.1:6.3/1/0.05] | [30:59:30/1/0.1] |
| [concentration] | 1.24M | 2.96M |
| Time | 2 h 15 m | 6 h |
| Temperature | 68° C. | 62° C. |

CTA = Nag(OH)C5N-PEG$_{12}$-CTA; I = AIBN

V. P88: NAG-PEG12-[PEGMA (300, 76%)-5-NMA (24%)]3.0 KDa-b-[DMAEMA (34.4%)-BMA (54%)-PAA (11.6%)]5.6 KDa

TABLE 29

| P88 | Block 1 | Block 2 |
|---|---|---|
| [M/CTA/I] | [13.5:4.5/1/0.05] | [30:59:30/1/0.1] |
| [concentration] | 1.21M | 2.6M |
| Time | 2 h | 6 h |
| Temperature | 67° C. | 61.5° C. |

CTA = Nag(OH)C5N-PEG$_{12}$-CTA; I = AIBN

W. P89: NAG-PEG12-[PEGMA (300,73.8%)-BMA (26.2%)]3.5 KDa-b-[DMAEMA (30.7%)-BMA (58.9%)-PAA (10.4%)]4.9 KDa

TABLE 30

| P89 | Block 1 | Block 2 |
|---|---|---|
| [M/CTA/I] | [13.5:4.5/1/0.05] | [30:59:30/1/0.1] |
| [concentration] | 1.29M | 2.61M |
| Time | 2 h 5 m | 5 h 45 m |
| Temperature | 69° C. | 61° C. |

CTA = Nag(OH)C5N-PEG$_{12}$-CTA; I = AIBN

X. P90: NAG-PEG12-[PEGMA (300, 72.6%)-HMA (27.4%)]3.58 KDa-b-[DMAEMA (30.6%)-BMA (56.2%)-PAA (13.3%)]5.6 KDa

TABLE 31

| P90 | Block 1 | Block 2 |
| --- | --- | --- |
| [M/CTA/I] | [13:4.5/1/0.05] | [30:59:30/1/0.1] |
| [concentration] | 1.3M | 2.72M |
| Time | 2 h 30 m | 5 h 48 m |
| Temperature | 69° C. | 61° C. |

CTA Nag(OH)C5N-PEG$_{12}$-CTA; I = AIBN

Y. P91: CH3O-PEG12-[PEGMA (300, 92.8%)-PDSMA (7.2%)]3.6 KDa-b-[DMAEMA(34.2%)-BMA(54.7%)-PAA (11%)]6.5 KDa

TABLE 32

| P91 | Block 1 | Block 2 |
| --- | --- | --- |
| [M/CTA/I] | [14:1.55/1/0.05] | [30:59:30/1/0.1] |
| [concentration] | 1.21M | 2.35M |
| Time | 1 h 45 m | 5 h |
| Temperature | 67° C. | 65.5° C. |

CTA CH3O-PEG$_{12}$-CTA; I = AIBN

Z. P92: NAG-PEG12-[PEGMA (300, 83.2%)-AEOMA (16.8%)]3.0 KDa-b-[DMAEMA (36.2%)-BMA (52.2%)-PAA (11.6%)]5.6 KDa

TABLE 33

| P92 | Block 1 | Block 2 |
| --- | --- | --- |
| [M/CTA/I] | [12.8:2.2/1/0.05] | [30:59:30/1/0.1] |
| [concentration] | 1.21M | 2.5M |
| Time | 1 h 50 m | 5 h 20 m |
| Temperature | 67° C. | 61° C. |

CTA Nag(OH)C5N-PEG$_{12}$-CTA; I = AIBN

AA. P93: NAG-PEG12-[PEGMA (300, 77.6%)-CyHexMA (22.4%)]2.64 KDa-b-[DMAEMA (32.1%)-BMA(43.1%)-PAA (12.6%)-CyHexMA(12.3%)]4.67 KDa

TABLE 34

| P93 | Block 1 | Block 2 |
| --- | --- | --- |
| [M/CTA/I] | [8.4:2.3/1/0.05] | [30:45:30:10/1/0.1] |
| [concentration] | 1.21M | 2.3M |
| Time | 1 h 55 m | 4 h |
| Temperature | 68° C. | 61° C. |

CTA Nag(OH)C5N-PEG$_{12}$-CTA; I = AIBN

BB. P94: NAG-PEG12-[PEGMA (300, 72.2%)-B-Fl-HMA (27.8%)]4.2 KDa-b-[DMAEMA (35.7%)-BMA (54.4%)-PAA (9.9%)]4.7 KDa

TABLE 35

| P94 | | |
| --- | --- | --- |
| | Block 1 | Block 2 |
| [M/CTA/I] | [13:4.5/1/0.05] | [30:59:30/1/0.1] |
| [concentration] | 1.2M | 2.3M |
| Time | 1 h 35 m | 5 h 15 m |
| Temperature | 67° C. | 61° C. |

CTA Nag(OH)C5N-PEG$_{12}$-CTA; I = AIBN

CC. P95: NAG-PEG12-[PEGMA(300, 71.2%)-Fl-BMA (28.8%)]3.55 KDa-b-[DMAEMA(34.2%)-BMA (57.9%)-PAA(7.9%)]4.9 KDa

TABLE 36

| P95 | Block 1 | Block 2 |
| --- | --- | --- |
| [M/CTA/I] | [12.8:3.5/1/0.05] | [26:51:26/1/0.1] |
| [concentration] | 1.2M | 2.3M |
| Time | 1 h 35 m | 5 h 15 m |
| Temperature | 67° C. | 61° C. |

CTA Nag(OH)C5N-PEG$_{12}$-CTA; I = AIBN

DD. P96: NAG-PEG12-[PEGMA(300, 72.6%)-Fl-BMA (27.4%)]3.55 KDa-b-[DMAEMA(30.7%)-BMA (561%)-PAA(13.2%)]4.9 KDa

TABLE 37

| P96 | Block 1 | Block 2 |
| --- | --- | --- |
| [M/CTA/I] | [12.8:3.5/1/0.05] | [26:51:26/1/0.1] |
| [concentration] | 1.2M | 2.3M |
| Time | 1 h 35 m | 5 h 15 m |
| Temperature | 67° C. | 61° C. |

CTA Nag(OH)C5N-PEG$_{12}$-CTA; I = AIBN

EE. P97: NAG-PEG12-[PEGMA(300, 70.0%)-Fl-BMA (30.0%)]3.55 KDa-b-[DMAEMA(31.3%)-BMA (60.7%)-PAA(8.0%)]5.1 KDa

TABLE 38

| P97 | Block 1 | Block 2 |
| --- | --- | --- |
| [M/CTA/I] | [12.8:3.5/1/0.05] | [26:51:26/1/0.1] |
| [concentration] | 1.2M | 2.3M |
| Time | 1 h 35 m | 5 h 15 m |
| Temperature | 67° C. | 61° C. |

CTA Nag(OH)C5N-PEG$_{12}$-CTA; I = AIBN

FF. P98: NAG-PEG12-[PEGMA(300, 75%)-2-Bu1-OMA(25%]4.26 KDa-b-[DMAEMA(32.1%)-BMA (55.7%)-PAA(12.2%)]5.69 KDa

TABLE 39

| P98 | Block 1 | Block 2 |
| --- | --- | --- |
| [M/CTA/I] | [15:6.1/1/0.05] | [30:59.5:30/1/0.1] |
| [concentration] | 1.3M | 2.97M |
| Time | 2 h 30 m | 5 h 45 m |
| Temperature | 70° C. | 62° C. |

CTA Nag(OH)C5N-PEG$_{12}$-CTA; I = AIBN

GG. P99: NAG-PEG12-[PEGMA(300, 73.3%)-5-NMA (26.7%)]4.05 KDa-b-[DMAEMA(31.5%)-BMA (55.2%)-PAA(13.3%)]5.20 KDa

TABLE 40

| P99 | Block 1 | Block 2 |
| --- | --- | --- |
| [M/CTA/I] | [15:6.1/1/0.05] | [30:59:30/1/0.1] |
| [concentration] | 1.3M | 2.76M |
| Time | 2 h 30 m | 5 h 40 m |
| Temperature | 70° C. | 62° C. |

CTA Nag(OH)C5N-PEG$_{12}$-CTA; I = AIBN

HH. P100: NAG-PEG12-[PEGMA(300, 74.1%)-Fl-BMA (25.9%)]3.79 KDa-b-[DMAEMA(29.9%)-BMA(56.2%)-PAA(13.9%)]5.44 KDa

TABLE 41

| P100 | Block 1 | Block 2 |
|---|---|---|
| [M/CTA/I] | [13:3.5/1/0.05] | [30:59:30/1/0.1] |
| [concentration] | 1.22M | 2.52M |
| Time | 2 h 5 m | 5 h 35 m |
| Temperature | 68° C. | 62° C. |

CTA Nag(OH)C5N-PEG$_{12}$-CTA; I = AIBN

II. P101: NAG-PEG12-[PEGMA(300, 72.2%)-B-Fl-OMA(27.8%)]4.2 KDa-b-[DMAEMA(35.7%)-BMA(54.4%)-PAA(9.9%)]5.6 KDa

TABLE 42

| P101 | Block 1 | Block 2 |
|---|---|---|
| [M/CTA/I] | [13:5/1/0.05] | [30:59:30/1/0.1] |
| [concentration] | 1.2M | 2.3M |
| Time | 1 h 35 m | 5 h 15 m |
| Temperature | 67° C. | 61° C. |

CTA Nag(OH)C5N-PEG$_{12}$-CTA; I = AIBN

JJ. P102: NAG-PEG12-[PEGMA(300, 71.9%)-F-BMA (28.1%)]3.55 KDa-b-[DMAEMA(27.3%)-BMA(60.9%)-PAA(11.9%)]4.55 KDa

TABLE 43

| P102 | Block 1 | Block 2 |
|---|---|---|
| [M/CTA/I] | [12.8:3.5/1/0.05] | [26:51:26/1/0.1] |
| [concentration] | 1.2M | 2.3M |
| Time | 1 h 35 m | 5 h 15 m |
| Temperature | 67° C. | 61° C. |

CTA Nag(OH)C5N-PEG$_{12}$-CTA; I = AIBN

KK. P106: NAG-PEG12-[PEGMA(300, 74%)-HMA (26%)]4.1 KDa-b-[DMAEMA(31%)-BMA(56%)-PAA(13%)]*5 KDa

TABLE 44

| P# | Block 1 | Block 2 |
|---|---|---|
| [M/CTA/I] | [15.5:4.5/1/0.05] | [30:59:30/1/0.1] |
| [concentration] | 1.35M | 2.3M |
| Time | 3 h 15 min | 5 h 30 m |
| Temperature | 69° C. | 61° C. |

CTA Nag(OH)C5N-PEG$_{12}$-CTA; I = AIBN
*Monomer incorporation for block is estimated based on historical incorporation levels LL. P107: NAG-PEG12-[PEGMA(300, 74%)-HMA (26%)]*4.1 KDa-b-[DMAEMA(31%)-BMA(56%)-PAA(13%)]*4.2 KDa

TABLE 45

| P# | Block 1 | Block 2 |
|---|---|---|
| [M/CTA/I] | [15.5:4.5/1/0.05] | [27:51:36.5/1/0.1] |
| [concentration] | 1.35M | 2.3M |
| Time | 3 h 15 m | 5 h 30 m |
| Temperature | 69° C. | 61° C. |

CTA Nag(OH)C5N-PEG$_{12}$-CTA; I = AIBN
*Monomer incorporation for block is estimated based on historical incorporation levels MM. P108: NAG-PEG12-[PEGMA(300, 80%)-HMA (20%)]*4.96 KDa-b-[DMAEMA(31%)-BMA(56%)-PAA(13%)]*5.5 KDa

TABLE 46

| P# | Block 1 | Block 2 |
|---|---|---|
| [M/CTA/I] | [19.5:4.5/1/0.05] | [30:59:30/1/0.1] |
| [concentration] | 1.5M | 2.3M |
| Time | 3 h 10 m | 6 h 10 m |
| Temperature | 69° C. | 61° C. |

CTA Nag(OH)C5N-PEG$_{12}$-CTA; I = AIBN
*Monomer incorporation for block is estimated based on historical incorporation levels NN. P109: NAG-PEG12-[PEGMA(300, 80%)-HMA (20%)]*4.96 KDa-b-[DMAEMA(31%)-BMA(56%)-PAA(13%)]*6.5 KDa

TABLE 47

| P# | Block 1 | Block 2 |
|---|---|---|
| [M/CTA/I] | [19.5:4.5/1/0.05] | [30:59:30/1/0.1] |
| [concentration] | 1.5M | 2.9M |
| Time | 3 h 10 m | 7 h |
| Temperature | 69° C. | 62° C. |

CTA Nag(OH)C5N-PEG$_{12}$-CTA; I = AIBN
*Monomer incorporation for block is estimated based on historical incorporation levels OO. P110: NAG-PEG12-[PEGMA(300, 77.7%)-EHMA (22.3%)]4.37 KDa-b-[DMAEMA(31%)-BMA(56%)-PAA(13%)]*6 KDa

TABLE 48

| P# | Block 1 | Block 2 |
|---|---|---|
| [M/CTA/I] | [16:5/1/0.05] | [30:59:30/1/0.1] |
| [concentration] | 1.3M | 3M |
| Time | 3 h | 6 h 30 m |
| Temperature | 68° C. | 62° C. |

CTA Nag(OH)C5N-PEG$_{12}$-CTA; I = AIBN
*Monomer incorporation for block is estimated based on historical incorporation levels PP. P111: NAG-PEG12-[PEGMA(300, 77%)-Fl-BMA (23%)]5.80 KDa-b-[DMAEMA(27.3%)-BMA(60.9%)-PAA(11-9%)]*5.74 KDa

TABLE 49

| P# | Block 1 | Block 2 |
|---|---|---|
| [M/CTA/I] | [20:4.3/1/0.05] | [30:59:30/1/0.1] |
| [concentration] | 1.5M | 2.3M |
| Time | 3 h | 6 h 20 m |
| Temperature | 68° C. | 61° C. |

CTA Nag(OH)C5N-PEG$_{12}$-CTA; I = AIBN
*Monomer incorporation for block is estimated based on historical incorporation levels QQ. P112: NAG-PEG12-[PEGMA(300, 77%)-Fl-BMA (23%)]5.80 KDa-b-[DMAEMA(27.3%)-BMA(60.9%)-PAA(11.9%)]*6.10 KDa

TABLE 50

| P# | Block 1 | Block 2 |
|---|---|---|
| [M/CTA/I] | [20:4.3/1/0.05] | [30:59:30/1/0.1] |
| [concentration] | 1.5M | 2.3M |
| Time | 3 h | 7 h 20 m |
| Temperature | 68° C. | 61° C. |

CTA Nag(OH)C5N-PEG$_{12}$-CTA; I = AIBN
*Monomer incorporation for block is estimated based on historical incorporation levels RR. P113: NAG-PEG12-[PEGMA(300, 84.9%)-Chol-MA(15.1%)]*3.5 KDa-b-[DMAEMA(31%)-BMA(56%)-PAA(13%)]*4.67 KDa

TABLE 51

| P# | Block 1 | Block 2 |
|---|---|---|
| [M/CTA/I] | [12.8:2.2/1/0.05] | [26:51:26/1/0.1] |
| [concentration] | 0.97M | 2.3M |
| Time | 2 h 15 m | 5 h |
| Temperature | 67° C. | 63° C. |

CTA Nag(OH)C5N-PEG$_{12}$-CTA; I = AIBN
*Monomer incorporation for block is estimated based on historical incorporation levels SS. P114: NAG-PEG12-[PEGMA(300, 67%)-HMA(33%)]*5.7 KDa-b-[DMAEMA(31%)-BMA(56%)-PAA(13%)]*6.15 KDa

TABLE 52

| P# | Block 1 | Block 2 |
|---|---|---|
| [M/CTA/I] | [20:7.5/1/0.05] | [30:59/30/1/0.1] |
| [concentration] | 1.55M | 2.89M |
| Time | 4 h | 5 h 45 m |
| Temperature | 68° C. | 62° C. |

CTA Nag(OH)C5N-PEG$_{12}$-CTA; I = AIBN
*Monomer incorporation for block is estimated based on historical incorporation levels TT. P115: NAG-PEG12-[PEGMA(300, 67%)-HMA(33%)]*5.7 KDa-b-[DMAEMA(31%)-BMA(56%)-PAA(13%)]*6 KDa

TABLE 53

| P# | Block 1 | Block 2 |
|---|---|---|
| [M/CTA/I] | [20:7.5/1/0.05] | [30:59/30/1/0.1] |
| [concentration] | 1.55M | 2.89M |
| Time | 4 h | 7 h |
| Temperature | 68° C. | 62° C. |

CTA Nag(OH)C5N-PEG$_{12}$-CTA; I = AIBN
*Monomer incorporation for block is estimated based on historical incorporation levels UU. P116: NAG-PEG12-[PEGMA(300, 73%)-Fl-BMA(27%)]*+6.3 KDa-b-[DMAEMA(27.3%)-BMA(60.9%)-PAA(11.9%)]*+5.9 KDa

TABLE 54

| P# | Block 1 | Block 2 |
|---|---|---|
| [M/CTA/I] | [20:6.5/1/0.05] | [30:59/30/1/0.1] |
| [concentration] | 1.5M | 2.3M |
| Time | 3 h | 7 h |
| Temperature | 68° C. | 61° C. |

CTA Nag(OH)C5N-PEG$_{12}$-CTA; I = AIBN
*Monomer incorporation for block is estimated based on historical incorporation levels
+Molecular weight of block is estimated based on trace overlays with polymers of known molecular weight

VV. P117:

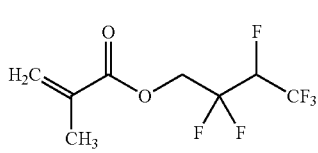

PF-BMA

NAG-PEG 12-[PEGMA(300, 72%)-PF-BMA(28%)]*+3.7 KDa-b-[DMAEMA(27.3%)-BMA(60.9%)-PAA(11.9%)]*5.0 KDa

TABLE 55

| P# | Block 1 | Block 2 |
|---|---|---|
| [M/CTA/I] | [12.8:3.5/1/0.05] | [26:51:26/1/0.1] |
| [concentration] | 1.5M | 2.3M |
| Time | 1 h 45 min | 5 h 20 min |
| Temperature | 68° C. | 61° C. |

CTA Nag(OH)C5N-PEG$_{12}$-CTA; I = AIBN
*Monomer incorporation for block is estimated based on historical incorporation levels
+Molecular weight of block is estimated based on trace overlays with polymers of known molecular weight WW. P118: NAG-PEG12-[PEGMA(300, 70%)-HMA(30%)]*5.2 KDa-b-[DMAEMA(31%)-BMA(56%)-PAA(13%)]*5.7 KDa

TABLE 56

| P# | Block 1 | Block 2 |
|---|---|---|
| [M/CTA/I] | [20:7/1/0.05] | [30.7:60:30.7/1/0.1] |
| [concentration] | 1.5M | 2.3M |
| Time | 3 h 15 m | 5 h 45 m |
| Temperature | 69° C. | 61° C. |

CTA Nag(OH)C5N-PEG$_{12}$-CTA; I = AIBN
*Monomer incorporation for block is estimated based on historical incorporation levels XX. P119: NAG-PEG12-[PEGMA(300, 70%)-HMA(30%)]*5.2 KDa-b-[DMAEMA(31%)-BMA(56%)-PAA(13%)]*5 KDa

TABLE 57

| P# | Block 1 | Block 2 |
|---|---|---|
| [M/CTA/I] | [20:7/1/0.05] | [26:52:26/1/0.1] |
| [concentration] | 1.5M | 2.3M |
| Time | 3 h 15 m | 5 h 25 m |
| Temperature | 69° C. | 61° C. |

CTA Nag(OH)C5N-PEG$_{12}$-CTA; I = AIBN
*Monomer incorporation for block is estimated based on historical incorporation levels YY. P120: NAG-PEG12-[PEGMA(300, 75%)-Cy-HexMA(25%)]*4 KDa-b-[DMAEMA(31%)-BMA(56%)-PAA(13%)]*5.2 KDa

TABLE 58

| P# | Block 1 | Block 2 |
|---|---|---|
| [M/CTA/I] | [15.5:4.5/1/0.05] | [30.7:60:30.7/1/0.1] |
| [concentration] | 1.3M | 2.3M |
| Time | 3 h | 5 h 40 m |
| Temperature | 69° C. | 61° C. |

CTA Nag(OH)C5N-PEG$_{12}$-CTA; I = AIBN
*Monomer incorporation for block is estimated based on historical incorporation levels ZZ. P121: NAG-PEG12-[PEGMA(300, 75%)-Me-Cy-HexMA(25%)]*4.3 KDa-b-[DMAEMA(31%)-BMA(56%)-PAA(139c)]*5.1 KDa

TABLE 59

| P# | Block 1 | Block 2 |
|---|---|---|
| [M/CTA/I] | [16:4/1/0.05] | [30.7:60:30.7/1/0.1] |
| [concentration] | 1.3M | 2.3M |
| Time | 3 h | 5 h 35 m |
| Temperature | 69° C. | 61° C. |

CTA Nag(OH)C5N-PEG$_{12}$-CTA; I = AIBN
*Monomer incorporation for block is estimated based on historical incorporation levels AAA P122: NAG-PEG12-[PEGMA(300, 73%)-Fl-BMA (27%)]*+6.3 KDa-b-[DMAEMA(27.3%)-BMA (60.9%)-PAA(11.9%)]*+6.9 KDa

TABLE 60

| P# | Block 1 | Block 2 |
|---|---|---|
| [M/CTA/I] | [20:6.5/1/0.05] | [30:59:30/1/0.1] |
| [concentration] | 1.5M | 2.6M |
| Time | 3 h | 9 h |
| Temperature | 68° C. | 61° C. |

CTA Nag(OH)C5N-PEG$_{12}$-CTA; I = AIBN
*Monomer incorporation for block is estimated based on historical incorporation levels
+Molecular weight of block is estimated based on trace overlays with polymers of known molecular weight BBB. P123: NAG-PEG12-[PEGMA(300, 79%)-Bu1-O-MA(21%)]*4.88 KDa-b-[DMAEMA(31%)-BMA (56%)-PAA(13%)]*4.6 KDa

TABLE 61

| P# | Block 1 | Block 2 |
|---|---|---|
| [M/CTA/I] | [16:4/1/0.05] | [30.7:60:30.7/1/0.1] |
| [concentration] | 1.3M | 2.3M |
| Time | 3 h 30 m | 5 h 20 m |
| Temperature | 69° C. | 61° C. |

CTA Nag(OH)C5N-PEG$_{12}$-CTA; I = AIBN
*Monomer incorporation for block is estimated based on historical incorporation levels CCC. P124: NAG-PEG12-[PEGMA(300, 74%)-HMA (26%)]*4.15 KDa-b-[DMAEMA(31%)-BMA(56%)-PAA(13%)]*5 KDa

TABLE 62

| P# | Block 1 | Block 2 |
|---|---|---|
| [M/CTA/I] | [15.5:4.5/1/0.05] | [30:59:30/1/0.1] |
| [concentration] | 1.35M | 2.3M |
| Time | 3 h 15 min | 5 h 30 m |
| Temperature | 69° C. | 61° C. |

CTA Nag(OH)C5N-PEG$_{12}$-CTA; I = AIBN
*Monomer incorporation for block is estimated based on historical incorporation levels DDD P125: NAG-PEG12-[PEGMA(300, 74%)-HMA (26%)]*4.15 KDa-b-[DMAEMA(31%)-BMA(56%)-PAA(13%)]*5 KDa

TABLE 63

| P# | Block 1 | Block 2 |
|---|---|---|
| [M/CTA/I] | [15.5:4.5/1/0.05] | [30:59:30/1/0.1] |
| [concentration] | 1.35M | 2.3M |
| Time | 3 h 15 min | 5 h 30 m |
| Temperature | 69° C. | 61° C. |

CTA Nag(OH)C5N-PEG$_{12}$-CTA; I = AIBN
*Monomer incorporation for block is estimated based on historical incorporation levels EEE. P103: NAG-PEG12-[PEGMA(300, 70.3%)-Fl-BMA(29.7%)]3.6 KDa-b-[DMAEMA(32.2%)-BMA (57.6%)-PAA(10.2%)]5 KDa

TABLE 64

| P# | Block 1 | Block 2 |
|---|---|---|
| [M/CTA/I] | [12.8:3.5/1/0.05] | [26:52:26/1/0.1] |
| [concentration] | 1.2M | 2.3M |
| Time | 1 h 42 m | 5 h 30 m |
| Temperature | 68° C. | 61° C. |

CTA Nag(OH)C5N-PEG$_{12}$-CTA; I = AIBN

FFF. P104: NAG-PEG12-[PEGMA(300, 68%)-Fl-BMA (32%)]*3.7 KDa-b-[DMAEMA(31%)-BMA(56%)-PAA(13%)]*5.3 KDa

TABLE 65

| P# | Block 1 | Block 2 |
|---|---|---|
| [M/CTA/I] | [12.8:3.5/1/0.05] | [26:51:26/1/0.1] |
| [concentration] | 1.2M | 2.3M |
| Time | 1 h 40 min | 5 h 30 m |
| Temperature | 67° C. | 61° C. |

CTA Nag(OH)C5N-PEG$_{12}$-CTA; I = AIBN
*Monomer incorporation for block is estimated based on historical incorporation levels GGG P105: NAG-PEG12-[PEGMA(300, 73%)-Fl-BMA (27%)]*+4.3 KDa-b-[DMAEMA(31%)-BMA(56%)-PAA(13%)]*5.3 KDa

TABLE 66

| P# | Block 1 | Block 2 |
|---|---|---|
| [M/CTA/I] | [12.8:3.5/1/0.05] | [26:51:26/1/0.1] |
| [concentration] | 1.2M | 2.3M |
| Time | 1 h 40 min | 5 h 30 m |
| Temperature | 67° C. | 61° C. |

CTA Nag(OH)C5N-PEG$_{12}$-CTA; I = AIBN
*Monomer incorporation for block is estimated based on historical incorporation levels
+Molecular weight of block is estimated based on trace overlays with polymers of known molecular weight HHH P106: NAG-PEG12-[PEGMA(300, 73%)-Fl-BMA (27%)]*+4.3 KDa-b-[DMAEMA(31%)-BMA(56%)-PAA(13%)]*+5.3 KDa

TABLE 67

| P# | Block 1 | Block 2 |
|---|---|---|
| [M/CTA/I] | [12.8:3.5/1/0.05] | [26:51:26/1/0.1] |
| [concentration] | 1.2M | 2.3M |
| Time | 1 h 40 min | 5 h 30 m |
| Temperature | 67° C. | 61° C. |

CTA Nag(OH)C5N-PEG$_{12}$-CTA; I = AIBN
*Monomer incorporation for block is estimated based on historical incorporation levels
+Molecular weight of block is estimated based on trace overlays with polymers of known molecular weight Example 18: In Vivo Expression of mRNA with Lipid-mRNA Formulations and Co-Injection or Sequential Injection of Additional Polymers Additional polymers were tested with sequential or co-injection with mRNA/LNP using the same methods as described in Example 2.

Table 68 displays luminescence values in the liver for animals treated with DOTAP:CHEMS:CHOL:DMPE-PEG2k+Fluc mRNA nanoparticles with sequential injection of polymer P1435, P1299, or P67 at 1 minute following the first injection. Data was acquired at 6 hours post dose. mRNA/LNP+polymer P67 showed 5-fold and 8-fold improvement in luminescent signal compared to polymers P1435 or P1299, respectively.

TABLE 68

| Lipid-mRNA Nanoparticle | Polymer | Fluc mRNA | Timing Between Injections | mRNA Dose (mg/kg) | Total Flux (photons/sec) Geomean | STDEV |
|---|---|---|---|---|---|---|
| Buffer | None | None | NA | 0 | 1.83E+05 | NA |
| DOTAP:CHEMS:CHOL:DMPE-PEG2K (50:32:16:2) N:P 7 26 mg/kg | P1435 75 mg/kg | Fluc 3 mRNA | 1 min | 1 | 1.23E+09 | 1.15E+09 |
| | P1299 75 mg/kg | Fluc 3 mRNA | | 1 | 7.80E+08 | 2.19E+09 |
| | P67 75 mg/kg | Fluc 3 mRNA | | 1 | 6.23E+09 | 7.28E+09 |

Table 69 displays luminescence values in the liver for animals treated with DOTAP:CHEMS:CHOL:DMPE-PEG2k+Fluc mRNA nanoparticles with sequential injection of polymer P67 at 1 minute following the first injection. Data was acquired at 6 hours post dose. In this study, two different Fluc mRNAs were tested. Fluc 2 mRNA showed a 21-fold improvement in luminescence signal compared to Fluc 1 mRNA. Modifications of Fluc 1 and Fluc 2 mRNAs are described above in Example 2.

TABLE 69

| Lipid-mRNA Nanoparticle | Polymer | Fluc mRNA | Timing Between Injections | mRNA Dose (mg/kg) | Total Flux (photons/sec) Geomean | STDEV |
|---|---|---|---|---|---|---|
| Buffer | None | None | NA | 0 | 2.81E+05 | NA |
| DOTAP:CHEMS:CHOL:DMPE-PEG2K (50:32:16:2) N:P 7 26 mg/kg | P67 75 mg/kg | Fluc 1 mRNA | 1 min | 1 | 4.20E+08 | 1.82E+08 |
| | | Fluc 2 mRNA | | 1 | 8.85E+09 | 3.90E+09 |

Table 70 displays luminescence values in the liver for animals treated with DOTAP:CHEMS:CHOL:DMPE-PEG2k+Fluc mRNA nanoparticles with co-injection of NAG targeted polymer P67 compared to non-targeted polymer P91. mRNA/LNP+polymer were mixed at a 1:1 ratio and injected immediately into mice. Data was acquired at 6 hours post dose. mRNA/LNP+NAG targeted polymer P67 showed 130-fold improvement in luminescent signal compared to non-targeted polymer P91.

TABLE 70

| Lipid-mRNA Nanoparticle | Polymer | Fluc mRNA | Timing Between Injections | mRNA Dose (mg/kg) | Total Flux (photons/sec) Geomean | STDEV |
|---|---|---|---|---|---|---|
| Buffer | None | None | NA | 0 | 2.03E+05 | |
| DOTAP:CHEMS:CHOL:DMPE-PEG2K (50:32:16:2) N:P 7 26 mg/kg | P67 75 mg/kg | Fluc 2 mRNA | co-injection | 1 | 4.03E+09 | 7.04E+09 |
| | P91 75 mg/kg | Fluc 2 mRNA | | 1 | 3.07E+07 | 9.45E+06 |

Example 19: DOTAP:CHEMS:Cholesterol:DSPE-PEG$_{2k}$ and DOTAP:CHEMS:Cholesterol:DSPE-PEG$_{2k}$-NAG mRNA Nanoparticle Formulation with Sequential or Co-Injection of a Polymer: Formulation Characteristics DOTAP (Corden Pharma, Boulder, Colo., USA; catalog number LP-R4-117) was solubilized at 50 mg/mL in 200 proof ethanol at room temperature for 15 minutes. The DSPE-PEG$_{2K}$(Corden Pharma, Boulder, Colo., USA; catalog number LP-R4-039) or the DSPE-PEG-NAG (PhaseRx Inc.) was solubilized at 50 mg/mL in 200 proof ethanol at room temperature for 15 minutes. The cholesteryl hemisuccinate (CHEMS) (Avanti Polar Lipid Alabaster, Ala., USA; catalog number 850524P) and the Cholesterol (CHOL) (Corden Pharma, Boulder, Colo., USA; catalog number CH-0355) were individually solubilized at 25 mg/mL in 200 proof at 75° C. for 5 minutes. Typically, for a 2 mL preparation of DOTAP:CHEMS:CHOL:DSPE-PEG$_{2K}$ (50:32:8:10 mol %) LNP at a N:P ratio of 7, a lipid ethanolic mixture containing 178 µL of DOTAP at 50 mg/mL in 200 proof ethanol, 158 µL of CHEMS at 25 mg/mL in 200 proof ethanol, 31 µL of CHOL at 25 mg/mL in 200 proof ethanol, 143 µL of DSPE-PEG$_{2K}$ at 50 mg/mL in 200 proof ethanol and 156 µL of 200 proof ethanol was prepared for a final volume of 0.666 mL and a total lipid concentration of 31 mg/mL. For 2 mL preparation of DOTAP:CHEMS:CHOL:DSPE-PEG$_{2K}$-NAG (50:32:8:10 mol %) LNP at a N:P ratio of 7, the lipid ethanolic mixture containing 178 µL of DOTAP at 50 mg/mL in 200 proof ethanol, 158 µL of CHEMS at 25 mg/mL in 200 proof ethanol, 31 µL of CHOL at 25 mg/mL in 200 proof ethanol, 160 µL of DSPE-PEG$_{2K}$-NAG at 50 mg/mL in 200 proof ethanol and 161 µL of 200 proof ethanol was prepared for a final volume of 0.666 mL and a total lipid concentration of 32.5 mg/mL.

The lipid nanoparticle (LNP) formulations were prepared at N:P (nitrogen to phosphate) ratios from 1.75 to 14 based on the DOTAP concentration. The DOTAP:CHEMS ratio was fixed at 1.6 at 50:32 mol % respectively at the various N:P ratios. DSPE-PEG$_{2K}$ or DSPE-PEG$_{2K}$-NAG were varied from 1 to 15 mol %. The CHOL mol % was adjusted to result in 100 mol % final lipid concentration.

The Fluc (firefly luciferase) mRNA stock solution at 1 mg/mL in 10 mM Tris-HCl (pH 7.5) was diluted to 0.45 mg/mL in 300 mM sucrose 20 mM phosphate, pH 7.4 buffer (SUP buffer). The mRNA/LNPs were assembled at N:P ratios from 1.75 to 14 by mixing the ethanolic lipid solution with 0.45 mg/mL mRNA in SUP buffer at a 1:2 ratio (lipid ethanolic mixture:mRNA in SUP buffer) using the microfluidic device from Precision NanoSystems Inc (Vancouver BC, Canada) at a 12 mL/minute flow rate. The mRNA/LNPs in 33% ethanol were then incubated at room temperature for 60 minutes prior to dialysis for 18 hours against 100 volumes (200 mL) of SUP buffer.

The polymers used for sequential injection or co-injection were solubilized at 20 mg/mL in SUP buffer with agitation at 400 rpm for 1 hour and then stored overnight at 4° C. The polymers were diluted to 5-10 mg/mL in SUP buffer prior to injection.

If mRNA/LNP and polymer were co-injected, a 2× solution of each was prepared. Just prior to dosing, the solutions were mixed and injected immediately.

The formulation particle size was measured by adding 10 µL of formulation to 90 µL of SUP buffer into a disposable micro-cuvette and analyzed using the Malvern Instrument ZETASIZER NANO-ZS. The LNPs showed a particle size of 85 nm (Z-average). The formulation zeta-potential at pH 7.4 was measured by adding 10 µL of formulation to 740 µL of SUP buffer into a disposable 1 mL cuvette. The formulation zeta-potential at pH 4 was measured by adding 10 µL of formulation to 740 µL of sucrose acetate buffer (pH 4) into a disposable 1 mL cuvette. The zeta dip cell was inserted into the 1 mL cuvette and the formulation was analyzed using the ZETASIZER NANO-ZS. Typically, the DOTAP LNPs had a zeta potential of +1.6 mV at pH 7 and +10 mV at pH 4.0. The ability of the LNP to compact the mRNA was measured in a 96 well plate using a SYBR Gold dye accessibility assay. Typically, 50 µL of the lipid formulation at 0.01 mg/mL mRNA was added to 150 µL of diluted SYBR Gold stock solution (1 µL of Stock SYBR Gold in 3 mL of SUP buffer) and incubated for 15 minutes at room temperature with agitation (100 RPM). The fluorescence was read at an excitation wavelength of 495 nm and emission wavelength of 538 nm. The percent dye accessibility was calculated by dividing the fluorescence intensity of the formulated mRNA by the fluorescence intensity of the free mRNA×100.

The DOTAP LNPs showed 8% dye accessibility when prepared in SUP buffer. Table 71 below shows characterization of exemplary LNP formulations.

TABLE 71

LNPs Characteristics

| Sample # | RP600-1 | RP495-13 |
| --- | --- | --- |
| Lipid | DOTAP:CHEMS:CHOL:DSPE-PEG2K (50:32:8:10) | DOTAP:CHEMS:CHOL:DSPE-PEG2K-NAG (50:32:8:10) |
| N/P | 7 | 7 |
| Lipid Concentration (mg/mL) | 9.5 | 10.8 |
| Visual Appearance | Opalescent (+) | Opalescent (+) |
| % Dye access SUP pH 7.4 | 8% | 8% |
| Z-Ave (nm) | 85 | 98 |
| PDI | 0.242 | 0.312 |
| Number (nm) | 38 | 37 |
| Pk 1 Mean Int (nm) | 105 | 232 |
| Pk 2 Mean Int (nm) | 4536 | 63 |
| Pk 1 Area Int (%) | 97 | 57 |
| Pk 2 Area Int (%) | 3 | 43 |
| ZP pH 7.4 (mV) | 1.6 | −5 |
| ZP pH 4 (mV) | 10 | 8 |
| Sizing data quality | Good | Good |

Example 20: In Vivo Expression of mRNA with DOTAP:CHEMS:Cholesterol:DSPE-PEG$_{2k}$ and DOTAP:CHEMS:Cholesterol:DSPE-PEG$_{2k}$-NAG mRNA Formulations and Co-Injection or Sequential Injection of Polymer Additional LNPs described in Example 19 were tested with various polymers using sequential or co-injection and the same methods as described in Example 2.

Table 72 displays luminescence values in the liver for animals treated with DOTAP:CHEMS:CHOL:DMPE-PEG2k, DOTAP:CHEMS:CHOL:DSPE-PEG2k, or DOTAP:CHEMS:CHOL:DSPE-PEG2k-NAG+Fluc mRNA nanoparticles with co-injection of polymer P67. mRNA/LNP+polymer were mixed at a 1:1 ratio and injected immediately into mice. Data was acquired at 6, 24, and 48 hours post dose. Both DOTAP:CHEMS:CHOL:DSPE-PEG2k-NAG and DOTAP:CHEMS:CHOL:DSPE-PEG2k LNP showed longer duration of expression with 8.7-fold and 2.6-fold greater luminescent signal in area under the curve (AUC) values compared to DOTAP:CHEMS:CHOL:DMPE-PEG2k LNP respectively.

TABLE 72

| Lipid-mRNA Nanoparticle | Polymer | Fluc 2 mRNA Dose (mg/kg) | Imaging Time Point | Total Flux (photons/sec) Geomean | STDEV | AUC | Fold Change to DMPE-PEG2K LNP |
| --- | --- | --- | --- | --- | --- | --- | --- |
| Buffer | None | 0 | 6 h | 3.34E+05 | | | |
| DOTAP:CHEMS:CHOL:DMPE-PEG2K (50:32:16:2) N:P 7 26 mg/kg | P67 75 mg/kg | 1 | 6 h | 3.61E+09 | 7.87E+08 | 4.02E+10 | 1.0 |
| | | | 24 h | 3.17E+08 | 1.23E+08 | | |
| | | | 48 h | 1.11E+07 | 3.07E+06 | | |

TABLE 72-continued

| Lipid-mRNA Nanoparticle | Polymer | Fluc 2 mRNA Dose (mg/kg) | Imaging Time Point | Total Flux (photons/sec) Geomean | STDEV | AUC | Fold Change to DMPE-PEG2K LNP |
|---|---|---|---|---|---|---|---|
| DOTAP:CHEMS: CHOL:DSPE-PEG2K (50:32:8:10) N:P 7 35 mg/kg | P67 75 mg/kg | 1 | 6 h 24 h 48 h | 7.23E+09 1.16E+09 2.15E+08 | 3.87E+09 1.08E+09 9.83E+07 | 1.05E+11 | 2.6 |
| DOTAP:CHEMS: CHOL:DSPE-PEG2K-NAG (50:32:8:10) N:P 7 36 mg/kg | P67 75 mg/kg | 1 | 6 h 24 h 48 h | 1.51E+10 4.14E+09 1.19E+08 | 2.15E+10 6.19E+09 2.03E+08 | 3.49E+11 | 8.7 |

Table 73 displays luminescence values in the liver for animals treated with DOTAP:CHEMS:CHOL:DSPE-PEG2k or DOTAP:CHEMS:CHOL:DSPE-PEG2k-NAG+ Fluc mRNA nanoparticles with co-injection of polymer P71 or P81. mRNA/LNP+polymer were mixed at a 1:1 ratio and injected immediately into mice. Data was acquired at 6, 24, 48, 72, and 96 hours post dose. DOTAP:CHEMS:CHOL: DSPE-PEG2k and DOTAP:CHEMS:CHOL:DSPE-PEG2k-NAG LNPs+P81 showed 7-fold and 2.8-fold greater luminescent signal in area under the curve (AUC) values compared to either LNP+P71 respectively.

TABLE 73

| Lipid-mRNA Nanoparticle | Polymer | Fluc 2 mRNA Dose (mg/kg) | Imaging Time Point | Total Flux (photons/sec) Geomean | STDEV | AUC |
|---|---|---|---|---|---|---|
| Buffer | None | 0 | 6 h | 1.35E+05 | | |
| DOTAP:CHEMS:CHOL: DSPE-PEG2K (50:32:8:10) N:P 7 35 mg/kg | P71 50 mg/kg | 1 | 6 h 24 h 48 h 72 h 96 h | 1.19E+10 5.45E+09 9.81E+07 6.66E+06 1.86E+06 | 9.52E+09 3.96E+09 8.21E+07 4.99E+06 1.17E+06 | 2.88E+11 |
| DOTAP:CHEMS:CHOL: DSPE-PEG2K (50:32:8:10) N:P 7 35 mg/kg | P81 45 mg/kg | 1 | 6 h 24 h 48 h 72 h 96 h | 9.40E+10 3.26E+10 6.91E+08 4.28E+07 1.05E+07 | 5.40E+10 3.23E+10 7.29E+08 4.38E+07 9.19E+06 | 2.01E+12 |
| DOTAP:CHEMS:CHOL: DSPE-PEG2K-NAG (50:32:8:10) N:P 7 36 mg/kg | P71 50 mg/kg | 0.5 | 6 h 24 h 48 h 72 h 96 h | 2.17E+10 5.84E+09 8.88E+07 7.06E+06 2.10E+06 | 1.88E+10 4.45E+09 9.94E+07 6.69E+06 2.09E+06 | 3.95E+11 |
| DOTAP:CHEMS:CHOL: DSPE-PEG2K-NAG (50:32:8:10) N:P 7 36 mg/kg | P81 35 mg/kg | 0.5 | 6 h 24 h 48 h 72 h 96 h | 6.06E+10 9.87E+09 1.60E+08 1.21E+07 3.91E+06 | 1.16E+10 6.23E+09 1.33E+08 7.43E+06 2.24E+06 | 7.95E+11 |

Table 74 displays luminescence values in the liver for animals treated with DOTAP:CHEMS:CHOL:DSPE-PEG2k+Fluc 2 mRNA nanoparticles with co-injection of polymer P71 or P92. mRNA/LNP+polymer were mixed at a 1:1 ratio and injected immediately into mice. Data was acquired at 6 hours post dose. Fluc mRNA/DOTAP: CHEMS:CHOL:DSPE-PEG2k LNP+P71 showed 4 to 13-fold greater luminescent signal compared to P92.

TABLE 74

| Lipid-mRNA Nanoparticle | Fluc mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: DSPE-PEG2K (50:32:8:10) N:P 7 35 mg/kg | 1 1 1 | P71 P92 P92 | 50 25 50 | 5.97E+09 4.71E+08 1.37E+09 | 8.09E+09 7.35E+08 1.62E+09 |

Table 75 displays luminescence values in the liver for animals treated with DOTAP:CHEMS:CHOL:DSPE-PEG2k+Fluc 2 mRNA nanoparticles with co-injection of polymer P71, P93, P79, or P80. mRNA/LNP+polymer were mixed at a 1:1 ratio and injected immediately into mice. Data was acquired at 6 hours post dose. Flue mRNA/DOTAP:CHEMS:CHOL:DSPE-PEG2k LNP+P80 or P79 showed 5-fold or 2-fold greater luminescent signal compared to P71 respectively. P93 showed similar activity to P71.

TABLE 75

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.1 | P71 | 50 | 4.74E+08 | 3.69E+08 |
| DSPE-PEG2K | 0.1 | P93 | 25 | 2.04E+08 | 2.05E+08 |
| (50:32:8:10) | 0.1 | P93 | 50 | 3.41E+08 | 3.65E+08 |
| N:P 7 3.5 mg/kg | 0.1 | P79 | 25 | 1.12E+09 | 4.36E+08 |
|  | 0.1 | P80 | 25 | 2.37E+09 | 1.93E+09 |

Table 76 displays luminescence values in the liver for animals treated with DOTAP:CHEMS:CHOL:DSPE-PEG2k+Fluc 2 mRNA nanoparticles with co-injection of polymer P71, P82, P94, or P86. mRNA/LNP+polymer were mixed at a 1:1 ratio and injected immediately into mice. Data was acquired at 6 hours post dose. Flue mRNA/DOTAP:CHEMS:CHOL:DSPE-PEG2k LNP+P82, P94, or P86 showed 6 to 13-fold greater luminescent signal compared to P71.

TABLE 76

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.5 | P71 | 50 | 1.61E+09 | 1.75E+09 |
| DSPE-PEG2K | 1 | P82 | 30 | 1.62E+10 | 6.45E+09 |
| (50:32:8:10) | 1 | P82 | 40 | 1.53E+10 | 1.80E+10 |
| N:P 7 35 mg/kg | 1 | P94 | 40 | 2.01E+10 | 7.91E+09 |
|  | 1 | P86 | 40 | 1.00E+10 | 1.21E+10 |

Table 77 displays luminescence values in the liver for animals treated with DOTAP:CHEMS:CHOL:DSPE-PEG2k+Fluc 2 mRNA nanoparticles with co-injection of polymer P71, P87, P88, or P89. mRNA/LNP+polymer were mixed at a 1:1 ratio and injected immediately into mice. Data was acquired at 6 hours post dose. Flue mRNA/DOTAP:CHEMS:CHOL:DSPE-PEG2k LNP+P87, P88, or P89 showed 3 to 18-fold greater luminescent signal compared to P71.

TABLE 77

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.1 | P71 | 50 | 1.54E+08 | 1.23E+08 |
| DSPE-PEG2K | 0.1 | P87 | 25 | 4.05E+08 | 7.71E+08 |
| (50:32:8:10) | 0.1 | P87 | 35 | 2.85E+09 | 3.22E+09 |
| N:P 7 3.5 mg/kg | 0.1 | P88 | 25 | 1.26E+09 | 1.87E+09 |
|  | 0.1 | P89 | 25 | 3.89E+08 | 2.19E+08 |
|  | 0.1 | P89 | 35 | 6.06E+08 | 6.54E+08 |
|  | 0.1 | P89 | 50 | 1.11E+09 | 9.00E+08 |

Table 78 displays luminescence values in the liver for animals treated with DOTAP:CHEMS:CHOL:DSPE-PEG2k+Fluc 2 mRNA nanoparticles with co-injection of polymer P95, P90, P96, or P87. mRNA/LNP+polymer were mixed at a 1:1 ratio and injected immediately into mice. Data was acquired at 6 hours post dose. Fluc mRNA/DOTAP:CHEMS:CHOL:DSPE-PEG2k LNP+P90, P96, or P87 showed similar luminescent signal as P95.

TABLE 78

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 1 | P95 | 30 | 1.17E+10 | 1.34E+10 |
| DSPE-PEG2K | 1 | P95 | 40 | 4.18E+10 | 2.54E+10 |
| (50:32:8:10) | 1 | P96 | 35 | 2.09E+10 | 2.35E+10 |
| N:P 7 35 mg/kg | 1 | P90 | 30 | 1.59E+10 | 1.78E+10 |
|  | 1 | P87 | 35 | 3.27E+10 | 1.39E+10 |

Table 79 displays luminescence values in the liver for animals treated with DOTAP:CHEMS:CHOL:DSPE-PEG2k+FLuc 2 mRNA nanoparticles with co-injection of polymer P71, P77, or P78. mRNA/LNP+polymer were mixed at a 1:1 ratio and injected immediately into mice. Data was acquired at 6 hours post dose. Fluc mRNA/DOTAP:CHEMS:CHOL:DSPE-PEG2k LNP+P77 or P78 showed 3 to 8-fold greater luminescent signal compared to P71.

TABLE 79

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.5 | P71 | 50 | 1.10E+09 | 1.02E+09 |
| DSPE-PEG2K | 0.5 | P77 | 25 | 1.90E+09 | 1.01E+09 |
| (50:32:8:10) | 0.5 | P77 | 50 | 1.12E+09 | 2.37E+09 |
| N:P 7 17 mg/kg | 0.5 | P77 | 75 | 9.02E+09 | 1.00E+10 |
|  | 0.5 | P78 | 25 | 3.46E+08 | 3.56E+08 |
|  | 0.5 | P78 | 50 | 3.78E+09 | 1.85E+09 |

Table 80 displays luminescence values in the liver for animals treated with DOTAP:CHEMS:CHOL:DSPE-PEG2k+FLuc 2 mRNA nanoparticles with co-injection of polymer P96, P98, P99, or P100. mRNA/LNP+polymer were mixed at a 1:1 ratio and injected immediately into mice. Data was acquired at 6 hours post dose. Flue mRNA/DOTAP:CHEMS:CHOL:DSPE-PEG2k LNP+P98, P99, or P100 showed 3 to 5-fold greater luminescent signal compared to P96.

TABLE 80

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.1 | P96 | 35 | 1.30E+09 | 1.17E+09 |
| DSPE-PEG2K | 0.1 | P98 | 25 | 1.23E+09 | 2.46E+09 |
| (50:32:8:10) | 0.1 | P98 | 35 | 4.62E+09 | 2.14E+09 |
| N:P 7 3.5 mg/kg | 0.1 | P99 | 25 | 5.80E+09 | 1.54E+09 |
|  | 0.1 | P100 | 25 | 1.22E+09 | 2.18E+09 |
|  | 0.1 | P100 | 35 | 3.24E+09 | 5.98E+09 |

Table 81 displays luminescence values in the liver for animals treated with DOTAP:CHEMS:CHOL:DSPE-PEG2k+FLuc 2 mRNA nanoparticles with co-injection of polymer P82, P90, P106, or P107. mRNA/LNP+polymer were mixed at a 1:1 ratio and injected immediately into mice. Data was acquired at 6 hours post dose. Flue mRNA/DOTAP:CHEMS:CHOL:DSPE-PEG2k LNP+P90, P106, or P107 showed 3 to 10-fold greater luminescent signal compared to P82.

TABLE 81

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.5 | P82 | 30 | 3.78E+09 | 9.23E+09 |
| DSPE-PEG2K | 0.5 | P90 | 25 | 7.12E+09 | 3.69E+09 |
| (50:32:8:10) | 0.5 | P90 | 35 | 2.74E+10 | 8.39E+09 |
| N:P 7 17.5 mg/kg | 0.5 | P106 | 25 | 1.85E+10 | 1.43E+10 |
| | 0.5 | P106 | 35 | 4.12E+10 | 1.26E+10 |
| | 0.5 | P106 | 45 | 1.65E+10 | 3.47E+10 |
| | 0.5 | P107 | 25 | 7.93E+09 | 4.97E+09 |
| | 0.5 | P107 | 35 | 1.47E+10 | 9.46E+09 |
| | 0.5 | P107 | 45 | 1.35E+10 | 1.34E+10 |

Table 82 displays luminescence values in the liver for animals treated with DOTAP:CHEMS:CHOL:DSPE-PEG2k+FLuc 2 mRNA nanoparticles with co-injection of polymer P97, P104, P108, or P109. mRNA/LNP+polymer were mixed at a 1:1 ratio and injected immediately into mice. Data was acquired at 6 hours post dose. Flue mRNA/DOTAP:CHEMS:CHOL:DSPE-PEG2k LNP+P104, P108, or P109 showed up to 2-fold greater luminescent signal compared to P97.

TABLE 82

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.5 | P97 | 30 | 1.08E+10 | 5.89E+09 |
| DSPE-PEG2K | 0.5 | P104 | 25 | 4.49E+09 | 9.32E+08 |
| (50:32:8:10) | 0.5 | P104 | 30 | 6.82E+09 | 2.69E+10 |
| N:P 7 17.5 mg/kg | 0.5 | P104 | 35 | 2.58E+10 | 3.59E+09 |
| | 0.5 | P108 | 25 | 1.37E+10 | 1.40E+10 |
| | 0.5 | P108 | 35 | 1.36E+10 | 1.58E+10 |
| | 0.5 | P108 | 45 | 2.37E+10 | 2.28E+10 |
| | 0.5 | P109 | 25 | 8.33E+09 | 1.25E+10 |
| | 0.5 | P109 | 35 | 2.07E+10 | 2.31E+10 |

Table 83 displays luminescence values in the liver for animals treated with DOTAP:CHEMS:CHOL:DSPE-PEG2k+FLuc 2 mRNA nanoparticles with co-injection of polymer P103, P90, P106, or P108. mRNA/LNP+polymer were mixed at a 1:1 ratio and injected immediately into mice. Data was acquired at 6 hours post dose. Flue mRNA/DOTAP:CHEMS:CHOL:DSPE-PEG2k LNP+P90, P106, or P108 showed up to 2-fold greater luminescent signal compared to P103.

TABLE 83

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.5 | P103 | 30 | 5.94E+10 | 3.36E+10 |
| DSPE-PEG2K | 0.5 | P103 | 35 | 7.11E+10 | 4.71E+10 |
| (50:32:8:10) | 0.5 | P90 | 30 | 1.52E+10 | 2.78E+10 |
| N:P 7 17.5 mg/kg | 0.5 | P90 | 35 | 7.65E+09 | 2.03E+10 |
| | 0.5 | P106 | 30 | 1.18E+11 | 2.23E+10 |
| | 0.5 | P106 | 35 | 4.94E+10 | 4.68E+10 |
| | 0.5 | P108 | 30 | 9.45E+10 | 2.12E+10 |
| | 0.5 | P108 | 35 | 4.99E+10 | 5.03E+10 |

Table 84 displays luminescence values in the liver for animals treated with DOTAP:CHEMS:CHOL:DSPE-PEG2k+FLuc 2 mRNA nanoparticles with co-injection of polymer P95, P111, or P112. mRNA/LNP+polymer were mixed at a 1:1 ratio and injected immediately into mice. Data was acquired at 6 hours post dose. Fluc mRNA/DOTAP:CHEMS:CHOL:DSPE-PEG2k LNP+P111 or P112 showed up to 4-fold greater luminescent signal compared to P95.

TABLE 84

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.5 | P95 | 30 | 6.19E+09 | 1.71E+10 |
| DSPE-PEG2K | 0.5 | P111 | 25 | 4.12E+09 | 6.41E+09 |
| (50:32:8:10) | 0.5 | P111 | 35 | 1.90E+10 | 3.63E+09 |
| N:P 7 17.5 mg/kg | 0.5 | P112 | 25 | 7.28E+09 | 1.15E+10 |
| | 0.5 | P112 | 35 | 1.98E+10 | 1.49E+10 |
| | 0.5 | P112 | 45 | 2.66E+10 | 1.46E+10 |

Table 85 displays luminescence values in the liver for animals treated with DOTAP:CHEMS:CHOL:DSPE-PEG2k+FLuc 2 mRNA nanoparticles with co-injection of polymer P103, P106, P114 or P115. mRNA/LNP+polymer were mixed at a 1:1 ratio and injected immediately into mice. Data was acquired at 6 hours post dose. Fluc mRNA/DOTAP:CHEMS:CHOL:DSPE-PEG2k LNP+P106, P114, or P115 showed up to 7-fold greater luminescent signal compared to P103.

TABLE 85

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.5 | P103 | 30 | 3.54E+09 | 5.27E+09 |
| DSPE-PEG2K | 0.5 | P106 | 20 | 6.96E+09 | 4.36E+09 |
| (50:32:8:10) | 0.5 | P106 | 25 | 1.19E+10 | 1.10E+10 |
| N:P 7 17.5 mg/kg | 0.5 | P114 | 25 | 2.46E+10 | 1.16E+10 |
| | 0.5 | P115 | 25 | 8.28E+09 | 1.93E+10 |

Table 86 displays luminescence values in the liver for animals treated with DOTAP:CHEMS:CHOL:DSPE-PEG2k+FLuc 2 mRNA nanoparticles with co-injection of polymer P103, P116 or P117. mRNA/LNP+polymer were mixed at a 1:1 ratio and injected immediately into mice. Data was acquired at 6 hours post dose. Flue mRNA/DOTAP:CHEMS:CHOL:DSPE-PEG2k LNP+P116 or P117 showed lower luminescent signal compared to P103.

TABLE 86

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.5 | P103 | 30 | 2.72E+10 | 1.13E+10 |
| DSPE-PEG2K | 0.5 | P116 | 25 | 5.31E+09 | 3.32E+09 |
| (50:32:8:10) | 0.5 | P116 | 35 | 1.20E+10 | 9.23E+09 |
| N:P 7 17.5 mg/kg | 0.5 | P117 | 25 | 5.53E+08 | 5.10E+08 |
| | 0.5 | P117 | 35 | 1.35E+09 | 1.44E+09 |

Table 87 displays luminescence values in the liver for animals treated with DOTAP:CHEMS:CHOL:DSPE-PEG2k+FLuc 2 mRNA nanoparticles with co-injection of polymer P105, P98 or P123. mRNA/LNP+polymer were mixed at a 1:1 ratio and injected immediately into mice. Data was acquired at 6 hours post dose. Flue mRNA/DOTAP:CHEMS:CHOL:DSPE-PEG2k LNP+P98 or P123 showed similar luminescent signal compared to P105.

TABLE 87

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.5 | P105 | 30 | 2.11E+10 | 2.54E+10 |
| DSPE-PEG2K | 0.5 | P98 | 20 | 1.85E+10 | 1.60E+10 |
| (50:32:8:10) | 0.5 | P98 | 30 | 7.79E+09 | 1.93E+10 |
| N:P 7 17.5 mg/kg | 0.5 | P98 | 40 | 2.07E+10 | 3.92E+10 |
| | 0.5 | P123 | 20 | 3.21E+10 | 1.56E+10 |
| | 0.5 | P123 | 30 | 2.77E+10 | 3.78E+10 |
| | 0.5 | P123 | 40 | 3.50E+10 | 3.16E+10 |

Table 88 displays luminescence values in the liver for animals treated with DOTAP:CHEMS:CHOL:DSPE-PEG2k+FLuc 2 mRNA nanoparticles with co-injection of polymer P105, P106, P124 or P125. mRNA/LNP+polymer were mixed at a 1:1 ratio and injected immediately into mice. Data was acquired at 6 hours post dose. Flue mRNA/DOTAP:CHEMS:CHOL:DSPE-PEG2k LNP+P106, P124 or P125 showed up to 2-fold greater luminescent signal compared to P105.

TABLE 88

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.5 | P105 | 30 | 1.80E+10 | 1.00E+10 |
| DSPE-PEG2K | 0.5 | P106 | 25 | 6.46E+09 | 1.85E+10 |
| (50:32:8:10) | 0.5 | P124 | 15 | 1.34E+10 | 2.10E+09 |
| N:P 7 17.5 mg/kg | 0.5 | P124 | 25 | 4.16E+10 | 2.27E+10 |
| | 0.5 | P125 | 15 | 6.31E+09 | 9.98E+09 |
| | 0.5 | P125 | 25 | 3.79E+10 | 2.02E+10 |

Table 89 displays luminescence values in the liver for animals treated with DOTAP:CHEMS:CHOL:DSPE-PEG2k+FLuc 2 mRNA nanoparticles with co-injection of polymer P105, P118, P119 or P110. mRNA/LNP+polymer were mixed at a 1:1 ratio and injected immediately into mice. Data was acquired at 6 hours post dose. Flue mRNA/DOTAP:CHEMS:CHOL:DSPE-PEG2k LNP+P118, P119 or P110 showed similar luminescent signal compared to P105.

TABLE 89

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: | 0.5 | P105 | 30 | 2.78E+10 | 1.32E+10 |
| DSPE-PEG2K | 0.5 | P118 | 20 | 1.99E+10 | 6.98E+09 |
| (50:32:8:10) | 0.5 | P118 | 30 | 2.86E+10 | 1.66E+10 |
| N:P 7 17.5 mg/kg | 0.5 | P119 | 20 | 2.36E+10 | 8.30E+09 |
| | 0.5 | P119 | 30 | 2.42E+10 | 1.07E+10 |
| | 0.5 | P110 | 20 | 9.48E+09 | 1.10E+10 |
| | 0.5 | P110 | 30 | 2.22E+10 | 1.95E+10 |

Example 21: Therapeutic Efficacy of mRNA with Lipid-mRNA Formulations and Co-Injection of Polymer in Ornithine Transcarbamylase Deficient Mice Hyperammonemia was induced in OTC-spf$^{ash}$ mice that were treated with AAV2/8 vector/OTC shRNA to knock-down residual endogenous OTC expression and activity (Cunningham et al., *Mol Ther* 19: 854-859, 2011). Plasma ammonia levels and orotic acid levels were elevated in these mice. Four (4) days after AAV dosing, 1 mg/kg of OTC mRNA formulated in DOTAP:CHEMS:CHOL:DMPE-PEG$_{2k}$ (50:32:16:2) at N:P 7+co-injection of 50 mg/kg P67 was dosed into these mice twice a week. Urine was collected on day 6 (post single mRNA dose) and day 13 (post 3 repeat mRNA doses) following AAV treatment and analyzed for orotic acid levels that were normalized to creatinine levels. Significant reduction of orotic acid was seen following OTC mRNA treatment to near normal levels (see FIG. 1A). Plasma was collected on day 13 (post 3 repeat mRNA doses) following AAV treatment and analyzed for ammonia levels. Plasma ammonia in OTC mRNA treated mice were at normal levels similar to that in wild type and untreated OTC-spf$^{ash}$ mice compared to hyperammonemic buffer treated mice (see FIG. 1B).

In a separate hyperammonemia study in OTC-spf$^{ash}$ mice similar to that above, 1 mg/kg of OTC mRNA formulated in DOTAP:CHEMS:CHOL:DSPE-PEG$_{2k}$ (50:32:8:10) at N:P 7+co-injection of 35 mg/kg P82 was dosed into these mice twice a week. Urine was collected on day 6 (post single mRNA dose) and day 13 (post 3 repeat mRNA doses) following AAV treatment and analyzed for orotic acid levels that were normalized to creatinine levels. Significant reduction of orotic acid was seen following OTC mRNA treatment to normal levels (see FIG. 2A). Plasma was collected on day 13 (post 3 repeat mRNA doses) following AAV treatment and analyzed for ammonia levels. Plasma ammonia in OTC mRNA treated mice were normalized compared to hyperammonemic buffer treated mice (see FIG. 2B).

Example 22: Preparation of DSPE-PEG$_{2K}$-NAG

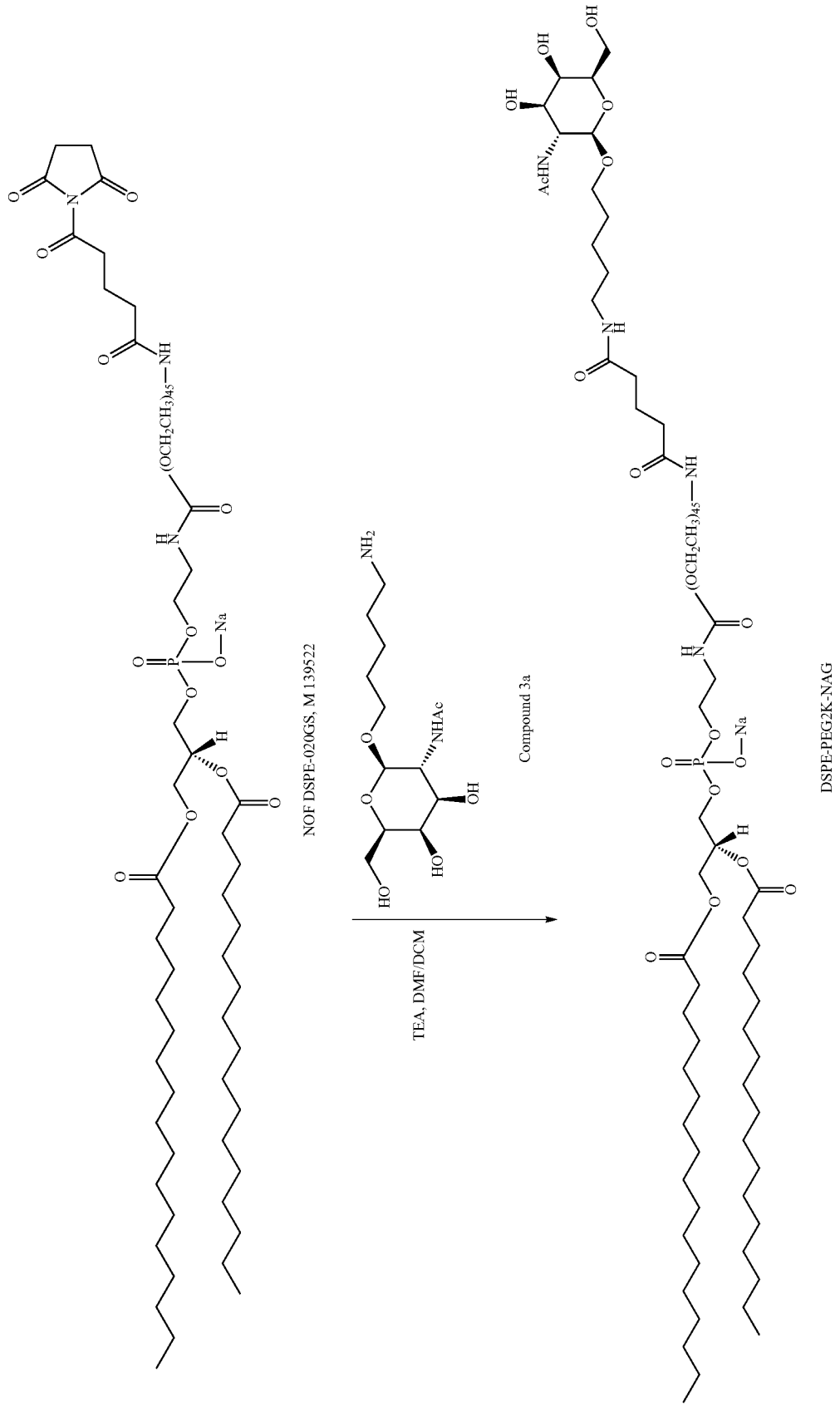

To compound 3a (204 mg, 0.665 mmol, 2 eq) was added DMF (1.5 mL), and the solution was stirred for 25 min. To the resulting solution was added trimethylamine (TEA, 185 µL, 1.33 mmol, 4 eq). After 5 min, DSPE-020GS (NOF, 1.00 g, 0.332 mmol, 1 eq) was added, followed by dichloromethane (DCM, 2.0 mL) and additional DMF (0.5 mL), and the resulting solution was stirred at ambient temperature. After 5 h, solvent was removed under reduced atmosphere, and the residue was taken up in DCM (100 mL). The DCM layer was washed with saturated $NaHCO_3$ (30 mL). The resulting $NaHCO_3$ layer was washed with DCM (50 mL). The combined organic layer was dried ($Na_2SO_4$), and concentrated under reduced atmosphere. The resulting residue was purified by silica gel chromatography (2.5×7.5 cm, eluent=10% MeOH/DCM (300 mL), then 15% MeOH/DCM (400 mL), then 20% MeOH/DCM (600 mL), fraction size=18×150 mm test tubes, fractions collected after 125 mL eluent eluded from column). Fractions 11-40 were concentrated under reduced atmosphere to afford DSPE-$PEG_2$K-NAG (439 mg, 41% yield).

Example 23: In Vivo Expression of mRNA with Repeat Doses of DOTAP:CHEMS:Cholesterol: DMPE-PEG2k and DOTAP:CHEMS:Cholesterol: DSPE-$PEG_{2k}$ mRNA Formulations and Co-Injection of Polymer LNP formulations co-injected with polymer were tested for mRNA expression using a repeat dosing regime. Co-injections of mRNA/LNP+polymer and evaluation of in vivo luciferase expression were performed using the same methods as described in Example 2.

Table 90 displays luminescence values in the liver for animals treated with DOTAP:CHEMS:CHOL:DMPE-PEG2k or DOTAP:CHEMS:CHOL:DSPE-PEG2k+Fluc mRNA nanoparticles with co-injection of polymer P103. mRNA/LNP+polymer were mixed at a 1:1 ratio and injected immediately into mice. Data was acquired at 6 hours post each dose. Formulations were repeat dosed by IV administration once a week for 10 weeks in CD-1 mice. Repeat administration with LNP containing an exchangeable PEG lipid, DMPE-PEG2K, resulted in similar luminescent signal at each weekly dose out to 10 weeks. In contrast, repeat administration with LNP containing a stable PEG lipid, DSPE-PEG2K, resulted in a significant 20-fold drop in activity starting at week 3. This decrease ranged from 4 to 30-fold drop in activity over the subsequent 8 repeat doses compared to week 1 activity.

TABLE 90

| Lipid-mRNA Nanoparticle | Fluc 2 mRNA Dose (mg/kg) | Polymer | Repeat dosing time point | Total Flux (photons/sec) | | Fold Reduction from Week 1 Activity |
|---|---|---|---|---|---|---|
| | | | | Geomean | STDEV | |
| DOTAP:CHEMS: CHOL:DMPE-PEG2K (50:32:16:2) N:P 7 13 mg/kg | 0.5 | 30 mg/kg P103 | Week 1 | 3.07E+10 | 1.70E+10 | 1 |
| | | | Week 2 | 3.02E+10 | 2.79E+10 | 1.0 |
| | | | Week 3 | 4.35E+10 | 2.16E+10 | 0.7 |
| | | | Week 4 | 1.95E+10 | 1.16E+10 | 1.6 |
| | | | Week 5 | 8.85E+09 | 5.78E+09 | 3.5 |
| | | | Week 6 | 3.05E+10 | 1.24E+10 | 1.0 |
| | | | Week 7 | 2.57E+10 | 1.21E+10 | 1.2 |
| | | | Week 8 | 1.55E+10 | 1.07E+10 | 2.0 |
| | | | Week 9 | 2.72E+10 | 1.49E+10 | 1.1 |
| | | | Week 10 | 1.41E+10 | 5.50E+09 | 2.2 |
| DOTAP:CHEMS: CHOL:DSPE-PEG2K (50:32:8:10) N:P 7 17 mg/kg | 0.5 | 30 mg/kg P103 | Week 1 | 1.45E+10 | 9.30E+09 | 1 |
| | | | Week 2 | 8.83E+09 | 7.23E+09 | 1.6 |
| | | | Week 3 | 7.03E+08 | 1.15E+09 | 20.6 |
| | | | Week 4 | 7.49E+08 | 7.48E+08 | 19.4 |
| | | | Week 5 | 4.72E+08 | 3.54E+08 | 30.7 |
| | | | Week 6 | 3.39E+09 | 3.53E+09 | 4.3 |
| | | | Week 7 | 9.52E+08 | 9.55E+08 | 15.2 |
| | | | Week 8 | 1.39E+09 | 1.16E+09 | 10.4 |
| | | | Week 9 | 2.67E+09 | 2.32E+09 | 5.4 |
| | | | Week 10 | 1.75E+09 | 1.89E+09 | 8.3 |

Example 24: Treatment of Argininosuccinic Aciduria with mRNA Formulations in a Hypomorphic Argininosuccinic Lyase (ASL) Mouse Model Groups of 5-10 hypomorphic $Asl^{Neo/Neo}$ mice are treated by intravenous route of administration with mRNA encoding argininosuccinic lyase (ASL) formulated in a lipid nanoparticle, either co-injected or sequentially injected with a membrane-destabilizing polymer that targets hepatocytes in the liver as described herein, thereby achieving expression and activity of ASL. Mice are treated with vehicle control or Asl mRNA from 0.1-5 mg/kg. Either single or repeat dosing is performed with a variety of dosing intervals (e.g., daily, every 2 days, biweekly, etc.). Blood is collected to examine plasma amino acids (argininosuccinic acid, citrulline, arginine), plasma ammonia, and serum transaminases at different time points ranging from 3 hours to 72 hours post final dose on the short term or up to 2 weeks post dose for duration of effect. At these time points, mice are sacrificed and livers collected and sampled to measure ASL enzyme activity, ASL protein expression by western analysis and immunofluorescence of liver tissue sections. Body weights are measured if longer term studies are carried out to monitor growth and survival as the $Asl^{Neo/Neo}$ mice have significant growth restrictions and mice die within 6 to 14 weeks of life despite ongoing treatment with triple therapy (sodium benzoate, sodium nitrite, L-arginine) (Erez et al., *Nat Med* 2011. 17:1619-1626).

Results are compared to vehicle-treated mice as well as to wild-type littermate mice that have normal levels of ASL protein expression, plasma amino acid levels, plasma ammonia, and serum transaminases. Efficacy is shown by detectable levels of ASL protein expression evaluated by western and immunofluorescence that is above the level detected in vehicle treated mice. Plasma argininosuccinc acid (ASA) levels are normally not detectable and plasma citrulline levels are ~70 µM in wild-type littermate mice whereas $Asl^{Neo/Neo}$ mice have ~100 µM ASA and ~200 µM citrulline levels. Plasma ammonia levels in wild-type littermate mice are normal, ~50 µM, whereas in $Asl^{Neo/Neo}$ mice levels are elevated in the range of 100-500 µM. Efficacy by plasma amino acid and plasma ammonia levels is a correction towards levels seen in wild-type littermate mice. In longer term studies efficacy is shown by increased growth and survival in comparison to vehicle treated mice.

Example 25: Treatment of Citrullinemia Type 1 (CTLN1) with mRNA Formulations in a Argininosuccinic Synthetase (ASS1) Deficient Murine Model of CTLN1 (Fold/Fold)

Groups of 5-10 $Ass1^{fold/fold}$ mice are treated by intravenous route of administration with mRNA encoding argininosuccinic synthetase (ASS1) formulated in a lipid nanoparticle, either co-injected or sequentially injected with a membrane-destabilizing polymer that targets hepatocytes in the liver as described herein, thereby achieving expression and activity of ASS1. Mice are treated with vehicle control or Ass1 mRNA from 0.1-5 mg/kg. Either single or repeat dosing is performed with a variety of dosing intervals (e.g., daily, every 2 days, biweekly, etc.). Blood is collected to examine plasma amino acids (citrulline, arginine) and plasma ammonia levels at different time points ranging from 3 hours to 72 hours post final dose on the short term or up to 2 weeks post dose for duration of effect. At these time points, mice are sacrificed and livers collected and sampled to measure ASS1 enzyme activity, ASS1 protein expression by western analysis and immunofluorescence of liver tissue sections. Body weights are measured if longer term studies are carried out to monitor growth and survival as the $Ass1^{fold/fold}$ mice have growth restrictions and die within the first 3 weeks of life if not treated with sodium benzoate and L-arginine (Perez et al., *Am J Pathol.* 177:1958-1968, 2010).

Results are compared to vehicle-treated mice as well as to wild-type littermate mice that have normal levels of ASS1 enzyme activity, plasma amino acid and plasma ammonia levels. Efficacy is shown by correction of ASS1 enzyme activity that is above the level detected in vehicle treated mice. Plasma citrulline levels are ~70 µM in wild-type littermate mice whereas $Ass1^{fold/fold}$ mice have significantly elevated citrulline levels, ~2000-3000 µM. Plasma ammonia levels in wild-type littermate mice are normal, ~50 µM, whereas $Ass1^{fold/fold}$ mice have elevations in the range of 100-500 µM. Levels are high if mice are not treated with sodium benzoate and L-arginine. Efficacy by plasma amino acid and plasma ammonia levels is a correction towards levels seen in wild-type littermate mice. In longer term studies efficacy is shown by increased growth and survival in comparison to vehicle treated mice if mice are taken off sodium benzoate and L-arginine treatment.

Example 26: DOTAPen:CHEMS:Cholesterol: DMPE-PEG$_{2k}$ mRNA Nanoparticle Formulation with Sequential or Co-Injection of a Polymer: Formulation Characteristics (R)-N,N,N-trimethyl-4,5-bis(oleoyloxy)pentan-1-aminium chloride (DOTAPen) was synthesized as described in Example 34 and solubilized at 50 mg/mL in 200 proof ethanol at room temperature for 15 minutes. The DMPE-PEG$_{2K}$ (Corden Pharma, Boulder, Colo., USA; catalog number LP-R4-123) was solubilized at 50 mg/mL in 200 proof ethanol at room temperature for 15 minutes. The cholesteryl hemisuccinate (CHEMS) (Avanti Polar Lipid Alabaster, Ala., USA; catalog number 850524P) and the Cholesterol (CHOL) (Corden Pharma, Boulder, Colo., USA; catalog number CH-0355) were individually solubilized at 25 mg/mL in 200 proof at 75° C. for 5 minutes. For a 2 mL preparation of DOTAPen:CHEMS:CHOL:DMPE-PEG$_{2K}$ (50:32:16:2 mol %) LNP at a N:P ratio of 7, a lipid ethanolic mixture containing 92 µL of DOTAPen at 50 mg/mL in 200 proof ethanol, 79 µL of CHEMS at 25 mg/mL in 200 proof ethanol, 32 µL of CHOL at 25 mg/mL in 200 proof ethanol, 14 µL of DMPE-PEG$_{2K}$ at 50 mg/mL in 200 proof ethanol and 450 µL of 200 proof ethanol was prepared for a final volume of 0.666 mL and a total lipid concentration of 27 mg/mL.

The lipid nanoparticle (LNP) formulations were prepared at N:P (nitrogen to phosphate) ratios from 7 to 10 based on the DOTAPen concentration. The DOTAPen:CHEMS ratio was fixed at 1.6 at 50:32 mol % respectively at the various N:P ratios.

The Fluc (firefly luciferase) mRNA stock solution at 1 mg/mL in 10 mM Tris-HCl (pH 7.5) was diluted to 0.225 mg/mL in 300 mM sucrose 20 mM phosphate, pH 7.4 buffer (SUP buffer). The mRNA/LNPs were assembled at N:P ratios from 7 or 10 by mixing the ethanolic lipid solution with 0.225 mg/mL mRNA in SUP buffer at a 1:2 ratio (lipid ethanolic mixture:mRNA in SUP buffer) using the microfluidic device from Precision NanoSystems Inc (Vancouver BC, Canada) at a 12 mL/minute flow rate. The mRNA/LNPs in 33% ethanol were then incubated at room temperature for 60 minutes prior to dialysis for 18 hours against 100 volumes (200 mL) of SUP buffer.

The polymers used for co-injection were solubilized at 20 mg/mL in SUP buffer with agitation at 400 rpm for 1 hour and then stored overnight at 4° C. The polymers were diluted to 6 mg/mL in SUP buffer prior to injection.

Since the mRNA/LNP and polymer were co-injected, a 2× solution of each was prepared. Just prior to dosing, the solutions were mixed and injected immediately.

The formulation particle size was measured by adding 10 µL of formulation to 90 µL of SUP buffer into a disposable micro-cuvette and analyzed using the Malvern Instrument ZETASIZER NANO-ZS. The LNPs showed a particle size of 88 nm (Z-average). The formulation zeta-potential at pH 7.4 was measured by adding 10 µL of formulation to 740 µL of SUP buffer into a disposable 1 mL cuvette. The formulation zeta-potential at pH 4 was measured by adding 10 µL of formulation to 740 µL of sucrose acetate buffer (pH 4) into a disposable 1 mL cuvette. The zeta dip cell was inserted into the 1 mL cuvette and the formulation was analyzed using the ZETASIZER NANO-ZS. The DOTAPen LNPs had a zeta potential of −4 mV at pH 7 and +12 mV at pH 4. The ability of the LNP to compact the mRNA was measured in a 96-well plate using a RiboGreen dye accessibility assay. 100 µL of nanoparticles diluted 1:64 in SUP for the dye accessible mRNA measurement or 100 µL of nanoparticles diluted 1:200 in SUP for total mRNA measurement was loaded in a 96-well plate. To this, 100 µL of a 1:200 dilution of RiboGreen reagent in SUP buffer for the dye accessible measurement or 100 µL of a 1:200 dilution of RiboGreen reagent in 0.2% Triton X-100/SUP buffer for the total mRNA measurement, was added to each well, respectively. The plate was incubated at room temperature in the dark for 5 minutes. The fluorescence was read using a Molecular Devices SpectraMax M5 with excitation at 480 nm and emission at 520 nm. Finally, the percent dye accessibility was calculated by subtracting the µM concentration of dye accessible mRNA from the µM concentration of the total mRNA, dividing that value by the µM concentration of total mRNA, and then multiplying by 100.

injection of polymer. mRNA/LNP+polymer were mixed at a 1:1 ratio and injected immediately into mice. Data was acquired at 6 hours post dose. Fluc mRNA/DOTAPen: CHEMS:CHOL:DSPE-PEG2k LNP+P105 showed 3 to 6-fold lower luminescent signal compared to Fluc mRNA/DOTAP:CHEMS:CHOL:DSPE-PEG2k LNP+P105.

TABLE 92

| Lipid-mRNA Nanoparticle | Fluc 2 mRNA Dose (mg/kg) | Polymer | Polymer Dose (mg/kg) | Total Flux (photons/sec) Geomean | STDEV |
|---|---|---|---|---|---|
| DOTAP:CHEMS:CHOL: DSPE-PEG2K (50:32:8:10) N:P 7 17.5 mg/kg | 0.5 | P105 | 30 | 1.80E+10 | 1.00E+10 |
| DOTAPen:CHEMS:CHOL: DMPE-PEG2K (50:32:16:2) N:P 10 17.5 mg/kg | 0.5 | P105 | 30 | 5.16E+09 | 5.74E+09 |
| DOTAPen:CHEMS:CHOL: DMPE-PEG2K (50:32:16:2) N:P 7 17.5 mg/kg | 0.5 | P105 | 30 | 2.93E+09 | 3.45E+09 |

The DOTAPen LNPs showed 28% dye accessibility when prepared in SUP buffer. Table 91 below shows characterization of exemplary LNP formulations.

TABLE 91

| LNPs Characteristics | | |
|---|---|---|
| | Sample # | |
| | RP659-1 | RP659-2 |
| Lipid | DOTAPen:CHEMS:CHOL: DMPE-PEG2K (50:32:16:2) | |
| N/P | 10 | 7 |
| Lipid Concentration (mg/mL) | 3.9 | 2.7 |
| Visual Appearance | Opalescent (+) | Opalescent (+) |
| % Dye access SUP pH 7.4 | 50% | 28% |
| Z-Ave (nm) | 83 | 88 |
| PDI | 0.051 | 0.070 |
| Number (nm) | 64 | 63 |
| Pk 1 Mean Int (nm) | 88 | 95 |
| Pk 2 Mean Int (nm) | 0 | 0 |
| Pk 1 Area Int (%) | 100 | 100 |
| Pk 2 Area Int (%) | 0 | 0 |
| ZP pH 7.4 (mV) | −6 | −4 |
| ZP pH 4 (mV) | 10 | 12 |
| Sizing data quality | GOOD | GOOD |

Example 27: In Vivo Expression of mRNA with DOTAPen:CHEMS:Cholesterol:DMPE-PEG$_{2k}$ mRNA Formulations and Co-Injection of Polymer DOTAPen-containing LNPs described in Example 26 were tested with P105 using co-injection and the same methods as described in Example 2.

Table 92 displays luminescence values in the liver for animals treated with DOTAPen:CHEMS:CHOL:DMPE-PEG2k+Fluc mRNA nanoparticles at N:P ratio of 7 or 10 with co-injection of polymer P105. Activity of DOTAPen-containing LNPs was compared to DOTAP:CHEMS:CHOL:DSPE-PEG2k+Fluc mRNA nanoparticles with co- Example 28: In Vivo Expression of hEPO mRNA with DOTAP:CHEMS:Cholesterol:DSPE-PEG$_{2k}$ mRNA Formulations and Co-Injection of Polymer Female CD-1 mice (7-10 weeks old) were used for evaluating hEPO mRNA formulated in DOTAP:CHEMS:Cholesterol:DSPE-PEG2k LNP with co-injection of P96 polymer. The formulation was dosed intravenously at 1 mg/kg of mRNA, 35 mg/kg of lipid, and 35 mg/kg of polymer with 5 mice injected per group. Mice injected with sucrose phosphate buffer were used as control. For each injection mice were given a final dose volume of approximately 0.25 mL or 10 mL/kg based on individual body weights.

The in vivo expression of hEPO mRNA was evaluated in mouse serum collected at 6 hours post dose. Blood was taken by retro-orbital sampling and collected in serum separator tubes. Serum was isolated by centrifugation and stored frozen at −20° C. until assayed. For ELISA assay the serum was diluted in PBS and then run using Human Epo Quantikine IVD ELISA (R&D Systems #DEPOO) according to manufacturer's protocol. Briefly, 100 µL of diluted sample was mixed with 100 µL Epo assay diluent in an ELISA plate and shaken at 500 RPM for 1 hour. The solution was removed and replaced with 200 µL of antibody conjugate and shaken for an additional hour. The plate was then washed and developed using a two component HRP/TMB system and read at 450 nm.

Table 93 displays hEPO serum levels for animals treated with buffer or with hEPO mRNA/LNP with co-injection of polymer P96. No detectable levels of hEPO were seen in buffer treated mice in comparison to 2.98×10$^6$ µg/mL of hEPO detected with 1 mg/kg of hEPO mRNA.

TABLE 93

| Lipid-mRNA Nanoparticle | hEPO mRNA Dose (mg/kg) | Polymer | Polymer Dose (mg/kg) | hEPO serum levels (pg/mL) Average | STDEV |
|---|---|---|---|---|---|
| None | 0 | none | none | <2.5 | |
| DOTAP:CHEMS:CHOL:DSPE-PEG2K (50:32:8:10) N:P 7 35 mg/kg | 1 | P96 | 35 | 2.98E+06 | 1.24E+06 |

Example 29: In Vivo Cytokine Analysis of HPLC-Purified and Non-Purified mRNAs with DOTAP:CHEMS:Cholesterol:DSPE-PEG$_{2k}$ mRNA Formulations and Co-Injection of Polymer Female CD-1 mice (7-10 weeks old) were used for evaluating HPLC-purified or non-purified Fluc mRNA formulated in DOTAP:CHEMS:Cholesterol:DSPE-PEG2k LNP with co-injection of P95 polymer. The formulation was dosed intravenously at 1 mg/kg of mRNA, 35 mg/kg of lipid, and 30 mg/kg of polymer with 5 mice injected per group. Mice injected with sucrose phosphate buffer were used as control. For each injection mice were given a final dose volume of approximately 0.25 mL or 10 mL/kg based on individual body weights.

Mouse IP-10 cytokine levels were quantified using R&D systems Mouse CXCL10/IP-10/CRG-2 Quantikine ELISA kit (#SMCX100). Blood was taken by retro-orbital sampling at 3 hours post dose and collected in serum separator tubes. Serum was isolated by centrifugation and stored frozen at −20° C. until assayed. For ELISA the serum was diluted in PBS and then run according to manufacturer's protocol. Briefly, 50 µL of diluted sample was mixed with 50 µL assay diluent in an ELISA plate and incubated at RT for two hours. The solution was removed and replaced with 200 µL of antibody conjugate and incubated at RT for two hours. The plate was then washed and developed using a two component HRP/TMB system and read at 450 nm.

Table 94 displays IP-10 serum levels for animals treated with buffer or with HPLC-purified or non-purified Fluc mRNA formulated in LNP with co-injection of polymer P95. IP-10 cytokine levels at 3 hours post dose were significantly reduced with HPLC-purified Fluc mRNA in comparison to high IP-10 cytokine levels induced with non-purified Fluc mRNA.

TABLE 94

| Lipid-mRNA Nanoparticle | mRNA | Polymer | Polymer Dose (mg/kg) | Mouse IP-10 serum levels (pg/mL) Average | STDEV |
|---|---|---|---|---|---|
| None | 0 | none | none | <30 | |
| DOTAP:CHEMS:CHOL:DSPE-PEG2K (50:32:16:2) N:P 7 17 or 35 mg/kg | 0.5 mg/kg Non-Purified Fluc 2 mRNA | P95 | 30 | 10293 | 4524 |
| | 1 mg/kg Non-Purified Fluc 2 mRNA | P95 | 30 | 14827 | 2824 |
| | 0.5 mg/kg HPLC-Purified Fluc 2 mRNA | P95 | 30 | 644 | 639 |
| | 1 mg/kg HPLC-Purified Fluc 2 mRNA | P95 | 30 | 2377 | 3175 |

Example 30: In Vivo Expression of HPLC-Purified or Non-Purified Flue mRNA with DOTAP:CHEMS:Cholesterol:DSPE-PEG$_{2k}$ and Co-Injection of Polymer Following Repeat Dosing HPLC-purified Fluc 2 mRNA and non-purified Fluc 2 mRNA formulated in DOTAP:CHEMS:CHOL:DSPE-PEG2k LNPs with P95 using co-injection were repeat dosed in CD-1 mice using the same methods described in Example 2.

Table 95 displays luminescence values in the liver for animals treated with DOTAP:CHEMS:CHOL:DSPE-PEG2k+HPLC-purified or non-purified Fluc 2 mRNA nanoparticles with co-injection of polymer P95. mRNA/LNP+polymer were mixed at a 1:1 ratio and injected immediately into mice. Data was acquired at 6 hours post each dose. Formulations were repeat dosed by IV administration once a week for 5 weeks in CD-1 mice. Repeat administration with HPLC-purified Fluc mRNA resulted in little reduction in luminescent signal (up to 8-fold) at each weekly dose out to 5 weeks. In contrast, repeat administration with non-purified Fluc mRNA resulted in up to 76-fold reduction in luminescent signal at each weekly dose out to 5 weeks.

TABLE 95

| Lipid-mRNA Nanoparticle | mRNA Dose | Polymer | Repeat dosing time point | Total Flux (photons/sec) Geomean | STDEV | Fold Reduction from Week 1 Activity |
|---|---|---|---|---|---|---|
| DOTAP:CHEMS: CHOL:DMPE- PEG2K (50:32:16:2) N:P 7 17.5 mg/kg | 0.5 mg/kg of Non-Purified Fluc 2 mRNA | 30 mg/kg P95 | Week 1 | 8.02E+09 | 5.83E+09 | 1 |
| | | | Week 2 | 1.50E+09 | 3.16E+09 | 5.3 |
| | | | Week 3 | 1.79E+08 | 2.32E+08 | 44.9 |
| | | | Week 4 | 1.05E+08 | 4.96E+07 | 76.6 |
| | | | Week 5 | 3.10E+08 | 9.54E+08 | 25.9 |
| | 0.5 mg/kg of HPLC-Purified Fluc2 mRNA | 30 mg/kg P95 | Week 1 | 1.09E+10 | 1.12E+10 | 1 |
| | | | Week 2 | 4.82E+09 | 2.03E+09 | 2.3 |
| | | | Week 3 | 1.30E+09 | 8.92E+09 | 8.4 |
| | | | Week 4 | 1.82E+09 | 4.61E+09 | 6.0 |
| | | | Week 5 | 5.29E+09 | 1.20E+10 | 2.1 |

Example 31: In Vivo Cytokine Analysis of HPLC-Purified and Non-Purified mRNAs with DOTAP:CHEMS:Cholesterol:DMPE-PEG$_{2k}$ mRNA Formulations and Co-Injection of Polymer Male OTC-spf$^{ash}$ mice (8-12 weeks old) were used for evaluating HPLC purified or non-purified hOTC or untranslatable hOTC control mRNA (AUG start codon was mutated to AAG) formulated in DOTAP:CHEMS:Cholesterol:DMPE-PEG2k LNP with co-injection of P103 polymer. The formulation was dosed intravenously at 1 mg/kg of mRNA, 27 mg/kg of lipid, and 30 mg/kg of polymer with 5 mice injected per group. Mice injected with sucrose phosphate buffer were used as control. For each injection mice were given a final dose volume of approximately 0.25 mL or 10 mL/kg based on individual body weights.

Mouse IP-10 cytokine levels were quantified using R&D systems Mouse CXCL10/IP-10/CRG-2 Quantikine ELISA kit (#SMCX100). Blood was taken by retro-orbital sampling at 3 hours post dose and collected in serum separator tubes. Serum was isolated by centrifugation and stored frozen at −20° C. until assayed. For ELISA the serum was diluted in PBS and then run according to manufacturer's protocol. Briefly, 50 μL of diluted sample was mixed with 50 μL assay diluent in an ELISA plate and incubated at RT for two hours. The solution was removed and replaced with 200 μL of antibody conjugate and incubated at RT for two hours. The plate was then washed and developed using a two component HRP/TMB system and read at 450 nm.

Table 96 displays IP-10 serum levels for animals treated with buffer or with HPLC-purified or non-purified hOTC mRNA or untranslatable hOTC control mRNA formulated in LNP with co-injection of polymer P103. No induction of IP-10 cytokine levels at 3 hours post dose was observed with HPLC-purified mRNA in comparison to high IP-10 cytokine levels induced with non-purified mRNA.

TABLE 96

| Lipid-mRNA Nanoparticle | mRNA | Polymer | Polymer Dose (mg/kg) | Mouse IP-10 serum levels (pg/mL) | |
|---|---|---|---|---|---|
| | | | | Average | STDEV |
| None - Buffer | 0 | none | none | <30 | |
| DOTAP:CHEMS:CHOL: DMPE-PEG2K (50:32:16:2) N:P 7 27 mg/kg | 1 mg/kg HPLC-Purified hOTC | P103 | 30 | <30 | |
| | 1 mg/kg Non-Purified hOTC | P103 | 30 | 8337 | 506 |
| | 1 mg/kg HPLC-Purified untranslatable hOTC control | P103 | 30 | <30 | |
| | 1 mg/kg Non-Purified untranslatable hOTC control | P103 | 30 | 5622 | 1330 |

Example 32: Therapeutic Efficacy of HPLC-Purified mRNA with Lipid-mRNA Formulations and Co-Injection of Polymer in Ornithine Transcarbamylase Deficient Mice Hyperammonemia was induced in OTC-spf$^{ash}$ mice as described in Example 21. Four (4) days after AAV dosing, 1 mg/kg of HPLC-purified OTC mRNA or 1 mg/kg of HPLC-purified untranslatable OTC control mRNA formulated in DOTAP:CHEMS:CHOL:DMPE-PEG$_{2k}$(50:32:16:2) at N:P 7+co-injection of 30 mg/kg polymer P103 was administered every 3 to 4 days for a total of 3 repeat doses. Urine was collected 48 h post the second mRNA dose (on day 9 following AAV treatment) and analyzed for orotic acid levels that were normalized to creatinine levels. Orotic acid (OA) levels were reduced following OTC mRNA treatment (336±166 μmol OA/mmol creatinine) in comparison to buffer treatment (999±192 μmol OA/mmol creatinine) or untranslatable control mRNA treatment (882±192 μmol OA/mmol creatinine). Plasma was collected on day 12 (24 h post 3rd repeat mRNA dose) following AAV treatment and analyzed for ammonia levels. Plasma ammonia levels were reduced to normal levels (43±29 μM ammonia) following treatment with OTC mRNA in comparison to hyperammonemic mice treated with untranslatable control mRNA (217±119 μM ammonia) or buffer treatment (110±24 μM ammonia). To examine whether any cytokine induction was observed following administration of HPLC-purified OTC or untranslatable control mRNA, serum was collected at 3 h post the first mRNA dose and examined for IP-10 levels. IP-10 levels were below the level of quantitation (<30 μg/mL) in both HPLC-purified OTC mRNA and untranslatable control mRNA treated mice, similar to buffer treated mice. In contrast, unpurified Fluc 2 mRNA control showed high induction of IP-10 serum levels (13,009±4932 μg/mL).

Example 33: Expression of OTC mRNA with Lipid-mRNA Formulations and Co-Injection of Polymer in Ornithine Transcarbamylase Deficient Mice OTC-spf$^{ash}$ mice were administered a single IV dose of 3 mg/kg of OTC mRNA, 3 mg/kg of untranslatable OTC control mRNA, or buffer. Each mRNA was formulated in DOTAP:CHEMS:CHOL:DSPE-PEG$_{2k}$ (50:32:18:10) at N:P 7+co-injection of 30 mg/kg polymer P105. Mice were sacrificed at 6, 24, or 48 h post dose and liver tissue samples were collected for OTC western analysis. To prepare protein extracts from liver tissue, 400-600 μl of freshly prepared Pierce T-PER tissue lysis buffer (1 Pierce protease and phosphatase inhibitor cocktail tablet for 10 ml of lysis buffer) was added into each sample tube containing approximately 200 mg of liver tissue. Tubes were then loaded onto MP Bio Fastprep-24 Instrument (Cat #116004500) to homogenize tissue for 20 seconds at a speed of 6 m/s. Each tissue homogenate was centrifuged at 4° C., 13,000 rpm for 15 minutes, and the supernatant was transferred to a new Eppendorf tube. This whole cell lysate was further analyzed for total protein concentration by BCA assay (Thermo Scientific, Cat #23225). 25 μg of each sample was loaded per lane on 4-12% SDS-PAGE gels (Bio-Rad, Cat #345-0124) after mixing protein extract with 4× sample buffer (Bio-Rad, Cat #161-0791) and 20×XT Reducing Reagent (Bio-Rad, Cat #161-0792) for a final protein concentration of 5 μg/l. Samples were then heated at 95° C. for 5 minutes prior to running on gel. Following electrophoresis, blotting was performed by transferring proteins from gels to PVDF membranes (Bio-Rad, Cat #170-4157) under Bio-Rad Transfer-Blot Turbo system (Cat #170-4155). Subsequently, the blots were blocked in Odyssey Blocking Buffer (LI-COR, Cat #927-40000) at room temperature for 1 hour, followed by incubation with OTC (Sigma, Cat #HPA000243, 1:2000 dilution) or HSP90 (Origene, Cat #TA500494, 1:8000 dilution) primary antibodies at 4° C. overnight. After several washes in TBST buffer, the blots were incubated with HRP-conjugated secondary antibody (Cell Signaling, Cat #7076S, 1:2000) at room temperature for 1 hour. To visualize protein bands, the washed blots were incubated with luminescence-based HRP substrate (Millipore, Cat #WBLUF0500) and then imaged under Bio-Rad ChemiDoc XRS system (Cat #170-8265). The quantification of westerns was performed using Bio-Rad Image Lab Software (Cat #170-9690) linked to the ChemiDoc system. To quantitate OTC expression levels in treated OTC-spf$^{ash}$ samples relative to wild-type littermate sample, the intensity of the OTC protein band was divided by that of loading control HSP90 in the same sample. This ratio was then divided by a similar ratio of a wild-type littermate sample. This was viewed as % OTC expression relative to wild-type.

Table 97 displays % OTC expression relative to wild-type littermate mouse for OTC-spf$^{ash}$ mice treated with 3 mg/kg of OTC mRNA, 3 mg/kg untranslatable control mRNA, or buffer. At 24 and 48 h post dose, OTC mRNA treatment in OTC-spf$^{ash}$ mice showed approximately 40% of wild-type OTC expression levels. No OTC expression was detectable from untranslatable control mRNA above the level seen with buffer treatment.

TABLE 97

| Lipid-mRNA Nanoparticle | Treatment | Polymer Dose (mg/kg) | Time Point (h) | % OTC Expression Relative to Wild-Type AVG | STDEV |
|---|---|---|---|---|---|
| DOTAP:CHEMS:CHOL: DSPE-PEG2K (50:32:8:10) N:P 7 105 mg/kg | Buffer | none | 6 h | 10.4% | 2% |
| | 3 mg/kg OTC mRNA | 30 mg/kg | 6 h | 13.4% | 4.2% |
| | | | 24 h | 41.1% | 13.1% |
| | | | 48 h | 41.6% | 10.1% |
| | 3 mg/kg untranslatable control mRNA | 30 mg/kg | 6 h | 10.1% | 1% |
| | | | 24 h | 9.9% | 1.2% |

Example 34: Synthesis of Cationic Lipids

Part 1: Synthesis of (R)-5-(dimethylamino)pentane-1,2-diyl dioleate hydrochloride (DODAPen-Cl)

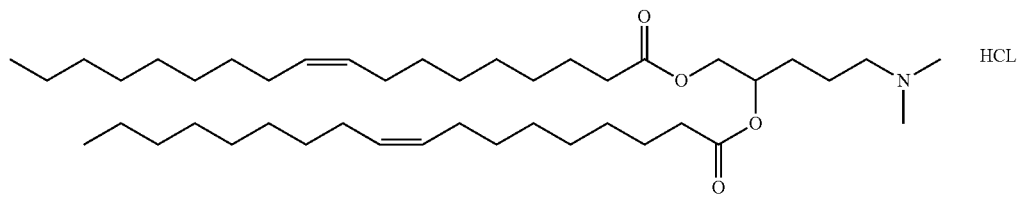

(R)-5-bromopentane-1,2-diyl dioleate (1.66 g, 2.33 mmol) was dissolved in anhydrous acetonitrile (50.0 mL) in a 100 mL round bottom flask equipped with a magnetic stirring bar. Dimethylamine hydrochloride (0.951 g, 11.7 mmol) and diisopropylethylamine (2.03 mL, 11.7 mmol) were added successively to the suspension and the mixture was heated to 60° C. in an oil bath for 16 h. The now-clear solution was cooled to RT (upon which it turned cloudy) and the solvent was removed under reduced pressure on the rotovap to afford a brown oily residue. The crude residue was purified by silica gel chromatography using a gradient of dichloromethane:methanol (0 to 10%) to afford the clean product as a light brown semi-solid (1.20 g, 1.77 mmol. Yield: 76%). The hydrochloride salt was obtained by adding concentrated hydrochloric acid to the oily product and concentrating the mixture to dryness on the rotovap and subsequently under high vacuum. The final product was obtained as a waxy off-white. The final product was characterized by NMR (400 MHz 1H NMR with CD$_3$OD as solvent) and all spectra were consistent with the desired.

Part 2: Synthesis of (R)-5-guanidinopentane-1,2-diyl dioleate hydrochloride (DOPen-G)

Part 2A: Synthesis of (R)-5-((tert-butoxycarbonyl)amino)pentane-1,2-diyl dioleate (R)-tert-butyl-(4,5-dihydroxypentyl)carbamate (2.10 g, 9.58 mmol) was dissolved in anhydrous dichloromethane (50.0 mL) in a 250 mL round bottom flask equipped with a magnetic stirring bar. Oleic acid (5.70 g, 20.2 mmol) was added to the mixture and the stirring solution was cooled to 0° C. in an ice bath. Dicyclohexylcarbodiimide (4.94 g, 23.9 mmol) and dimethylaminopyridine (1.17 g, 9.58 mmol) were added to the cold solution and the reaction was warmed to RT over 16 h. The solid dicyclohexyl urea precipitate was filtered out on a Buchner funnel and washed with dichloromethane (4×25 mL). The dichloromethane filtrate was concentrated under reduced pressure on a rotovap to obtain an oily residue. The resulting residue was purified by silica gel chromatography using a gradient of hexane:ethyl acetate (0 to 10%). The pure product was obtained as a colorless oil (6.89 g, 9.21 mmol). Yield: 96%. The product was characterized by NMR (400 MHz 1H NMR with CD$_3$OD as solvent) and all spectra were consistent with (R)-5-((tert-butoxycarbonyl)amino)pentane-1,2-diyl dioleate.

Part 2B: Synthesis of (R)-5-aminopentane-1,2-diyl dioleate hydrochloride (R)-5-((tert-butoxycarbonyl)amino)pentane-1,2-diyl dioleate (6.87 g, 9.18 mmol) was dissolved in anhydrous 1,4-dioxane (50.0 mL) in a 250 mL round bottom flask equipped with a magnetic stirring bar. 4N hydrochloric acid in 1,4-dioxane was added (46.0 mL, 184 mmol) and the solution was stirred at RT for 4 h. The solvent was removed under reduced pressure on a rotovap and the product was dried under high vacuum for 16 h. The pure product was obtained as a viscous colorless oil (6.29 g, 9.18 mmol) in quantitative yield. The product was characterized by NMR (400 MHz 1H NMR with CD$_3$OD as solvent) and all spectra were consistent with (R)-5-aminopentane-1,2-diyl dioleate hydrochloride.

Part 2C: Synthesis of (R)-5-(2,3-bis(tert-butoxycarbonyl)guanidino)pentane-1,2-diyl dioleate (R)-5-aminopentane-1,2-diyl dioleate hydrochloride (2.46 g, 3.59 mmol) was dissolved in anhydrous dichloromethane (50.0 mL) in a 250 mL round bottom flask equipped with a magnetic stirring bar. Triethylamine (1.00 mL, 7.17 mmol) and 1,3-Di-Boc-2-(trifluoromethylsulfonyl)guanidine (1.55 g, 3.96 mmol) were added successively and the mixture was stirred at ambient temperature for 22 h.

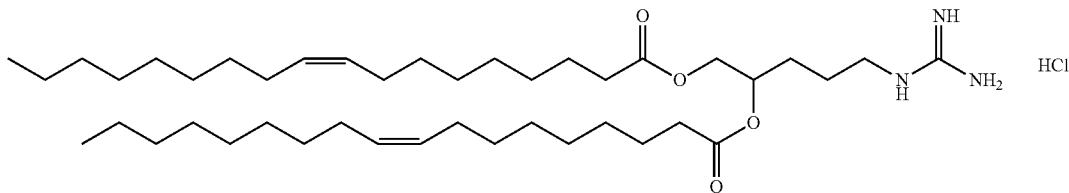 [SMILES: CCCCCCCC/C=C\CCCCCCCC(=O)OCC(CCCNC(=N)N)OC(=O)CCCCCCC/C=C\CCCCCCCC ; Cl]

The solution was concentrated under reduced pressure on a rotovap to afford an oily residue. The resulting residue was purified by silica gel chromatography using a gradient of hexane:ethyl acetate (0 to 10%). The pure product was obtained as a colorless oil (3.00 g, 3.37 mmol). Yield: 94%. The product was characterized by NMR (400 MHz 1H NMR with CDCl$_3$ as solvent) and all spectra were consistent with (R)-5-(2,3-bis(tert-butoxycarbonyl)guanidino)pentane-1,2-diyl dioleate.

Part D: Synthesis of (R)-5-guanidinopentane-1,2-diyl dioleate hydrochloride (DOPen-G)

(R)-5-(2,3-bis(tert-butoxycarbonyl)guanidino)pentane-1,2-diyl dioleate (1.81 g, 2.03 mmol) was dissolved in anhydrous 1,4-dioxane (20.0 mL) in a 250 mL round bottom flask equipped with a magnetic stirring bar. 4N hydrochloric acid in 1,4-dioxane was added (30.2 mL, 121 mmol) and the solution was stirred at RT for 48 h. The solvent was removed under reduced pressure on a rotovap to afford an oily residue. The resulting residue was purified on silica gel chromatography using a gradient of dichloromethane:methanol (0t o100%). The pure product was dried under high vacuum for 20 h to yield an off-white semi-solid (1.00 g, 1.38 mmol). Yield: 68%. The product was characterized by NMR (400 MHz 1H NMR with CD$_3$OD as solvent) and all spectra were consistent with DOPen-G.

Part 3: Synthesis of (R)-N,N,N-trimethyl-4,5-bis(oleoyloxy)pentan-1-aminium chloride (DOTAPen)

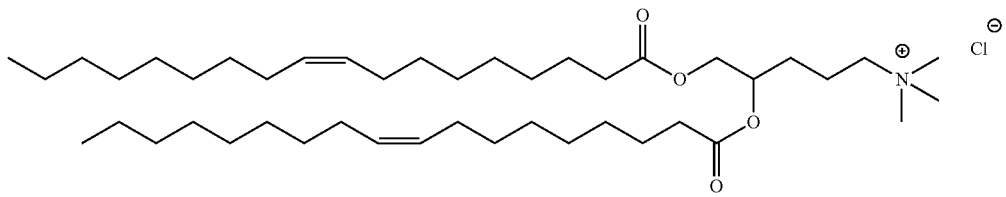 [SMILES: CCCCCCCC/C=C\CCCCCCCC(=O)OCC(CCC[N+](C)(C)C)OC(=O)CCCCCCC/C=C\CCCCCCCC ; [Cl-]]

(R)-5-(dimethylamino)pentane-1,2-diyl dioleate (DODA-Pen, 0.700 g, 1.04 mmol) was dissolved in anhydrous acetonitrile (10.0 mL) in a 100 mL round bottom flask equipped with a magnetic stirring bar. Diisopropylethylamine (1.80 mL, 10.3 mmol) and iodomethane (1.93 mL, 31.0 mmol) were added successively and the solution was refluxed at 85° C. for 20 h. The solution was cooled to RT and diluted with diethyl ether (300 mL) upon which a precipitate of diisopropylethylaminium iodide salt formed. The solid precipitate was filtered out and the combined organic phase was concentrated under reduced pressure on a rotovap. The crude residue was passed through a short silica gel column using a mixture of dichloromethane and methanol (10%). The pure product (iodide salt) was obtained as a brown-red semi-solid (780 mg). The product was then passed through an Amberlite IRA 400 chloride ion-exchange resin column and eluted with a mixture of dichloromethane:methanol (33%). The column procedure was repeated 10 times to obtain the desired product as the chloride salt. After drying under high vacuum, the pure product was obtained as a light brown waxy solid (430 mg, 0.592 mmol). Yield: 57%. The product was characterized by NMR (400 MHz 1H NMR with $CD_3OD$ as solvent) and all spectra were consistent with DOTAPen.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

---

What is claimed is:

1. A pH-sensitive, membrane-destabilizing polymer of formula V:

$$T1\text{-}L\text{-}[PEGMA_m\text{-}M2_n]_v\text{-}[DMAEMA_q\text{-}PAA_r\text{-}BMA_s]_w \quad \quad V$$

wherein
PEGMA is polyethyleneglycol methacrylate residue with 2-20 ethylene glycol units;
M2 is butyl methacrylate residue or hexyl methacrylate residue;
BMA is butyl methacrylate residue;
PAA is propyl acrylic acid residue;
DMAEMA is dimethylaminoethyl methacrylate residue;
m and n are each a mole fraction greater than 0, wherein m is greater than n and m+n=1;
q is a mole fraction of 0.2 to 0.75;
r is a mole fraction of 0.05 to 0.6;
s is a mole fraction of 0.2 to 0.75;
q+r+s=1;
v is 1 to 25 kDa;
w is 1 to 25 kDa;
T1 is a first targeting ligand comprising an N-acetylgalactosamine (NAG) residue; and
L is a linking moiety comprising a polyethylene glycol (PEG) moiety.

2. The polymer of claim 1, wherein M2 is hexyl methacrylate residue.

3. The polymer of claim 1, wherein PEGMA is polyethyleneglycol methacrylate residue having 4-5 ethylene glycol units or 7-8 ethylene glycol units.

4. The polymer of claim 1, wherein the linking moiety L comprises a polyethylene glycol (PEG) moiety having 2-20 ethylene glycol units.

5. The polymer of claim 1, wherein the polymer of formula V is $$NAG\text{-}PEG_{12}\text{-}[PEGMA300_m\text{-}HMA_n]_v\text{-}[D_q\text{-}P_r\text{-}B_s]_w \qquad Vi,$$

wherein
- $PEG_{12}$ is a linking moiety comprising a polyethylene glycol having 12 ethylene glycol units;
- HMA is hexyl methacrylate residue;
- B is a butyl methacrylate residue (BMA);
- P is a propyl acrylic acid residue (PAA); and
- D is a dimethylaminoethyl methacrylate residue (DMAEMA).

6. The polymer of claim 5, wherein m is 0.7 to 0.85.
7. The polymer of claim 5, wherein n is 0.15 to 0.3.
8. The polymer of claim 5, wherein s is 0.5 to 0.65.
9. The polymer of claim 5, wherein v is 2.5 to 7 kDa.
10. The polymer of claim 5, wherein w is 4 to 7 kDa.
11. The polymer of claim 5, wherein q is 0.25 to 0.4.
12. The polymer of claim 5, wherein r is 0.07 to 0.15.

* * * * *

SEQUENCE LISTING

```
<160> NUMBER OF SEQ ID NOS: 51

<210> SEQ ID NO 1
<211> LENGTH: 354
<212> TYPE: PRT
<213> ORGANISM: Homo sapiens
<220> FEATURE:
<221> NAME/KEY: TRANSIT
<222> LOCATION: (1)..(34)
<223> OTHER INFORMATION: native mitochondrial leader seqeuence

<400> SEQUENCE: 1

Met Leu Phe Asn Leu Arg Ile Leu Leu Asn Asn Ala Ala Phe Arg Asn
1               5                   10                  15

Gly His Asn Phe Met Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
    130                 135                 140
```

```
Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu
    210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
            260                 265                 270

Glu Lys Lys Lys Arg Leu Gln Ala Phe Gln Gly Tyr Gln Val Thr Met
        275                 280                 285

Lys Thr Ala Lys Val Ala Ala Ser Asp Trp Thr Phe Leu His Cys Leu
    290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
            340                 345                 350

Lys Phe

<210> SEQ ID NO 2
<211> LENGTH: 354
<212> TYPE: PRT
<213> ORGANISM: Artificial
<220> FEATURE:
<223> OTHER INFORMATION: Human ornithine transcarbamylase with mouse
      mitochondrial leader sequence
<220> FEATURE:
<221> NAME/KEY: TRANSIT
<222> LOCATION: (1)..(34)
<223> OTHER INFORMATION: mouse mitochondrial leader sequence

<400> SEQUENCE: 2

Met Leu Ser Asn Leu Arg Ile Leu Leu Asn Asn Ala Ala Leu Arg Lys
1               5                   10                  15

Gly His Thr Ser Val Val Arg His Phe Trp Cys Gly Lys Pro Val Gln
            20                  25                  30

Ser Gln Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125
```

```
Arg Val Leu Ser Ser Met Ala Asp Ala Val Leu Ala Arg Val Tyr Lys
    130                 135                 140

Gln Ser Asp Leu Asp Thr Leu Ala Lys Glu Ala Ser Ile Pro Ile Ile
145                 150                 155                 160

Asn Gly Leu Ser Asp Leu Tyr His Pro Ile Gln Ile Leu Ala Asp Tyr
                165                 170                 175

Leu Thr Leu Gln Glu His Tyr Ser Ser Leu Lys Gly Leu Thr Leu Ser
            180                 185                 190

Trp Ile Gly Asp Gly Asn Asn Ile Leu His Ser Ile Met Met Ser Ala
        195                 200                 205

Ala Lys Phe Gly Met His Leu Gln Ala Ala Thr Pro Lys Gly Tyr Glu
    210                 215                 220

Pro Asp Ala Ser Val Thr Lys Leu Ala Glu Gln Tyr Ala Lys Glu Asn
225                 230                 235                 240

Gly Thr Lys Leu Leu Leu Thr Asn Asp Pro Leu Glu Ala Ala His Gly
                245                 250                 255

Gly Asn Val Leu Ile Thr Asp Thr Trp Ile Ser Met Gly Gln Glu Glu
            260                 265                 270

Glu Lys Lys Lys Arg Leu Gln Ala Phe Gln Gly Tyr Gln Val Thr Met
        275                 280                 285

Lys Thr Ala Lys Val Ala Ala Ser Asp Trp Thr Phe Leu His Cys Leu
    290                 295                 300

Pro Arg Lys Pro Glu Glu Val Asp Asp Glu Val Phe Tyr Ser Pro Arg
305                 310                 315                 320

Ser Leu Val Phe Pro Glu Ala Glu Asn Arg Lys Trp Thr Ile Met Ala
                325                 330                 335

Val Met Val Ser Leu Leu Thr Asp Tyr Ser Pro Gln Leu Gln Lys Pro
            340                 345                 350

Lys Phe

<210> SEQ ID NO 3
<211> LENGTH: 1262
<212> TYPE: DNA
<213> ORGANISM: Artificial
<220> FEATURE:
<223> OTHER INFORMATION: cDNA encoding human ornithine transcarbamylase,
      codon-optimized for mouse expression
<220> FEATURE:
<221> NAME/KEY: promoter
<222> LOCATION: (1)..(20)
<223> OTHER INFORMATION: T7 promoter

<400> SEQUENCE: 3
taatacgact cactataggg aaataagaga gaaaagaaga gtaagaagaa atataagagc      60
caccatgctg ttcaacctca gaatcctcct caataacgcc gcctttagaa acggtcataa    120
cttcatggtc agaaacttta gatgtggtca gcctctccag aacaaagtgc agctcaaggg    180
gcgggacctg ctcacccctga aaatttcac aggcgaggaa atcaagtaca tgctctggct    240
gtctgccgat ctgaagttca ggatcaagca aagggcgaa tatctcccac tgctccaggg    300
gaaaagtctg gtatgatct tcgaaaagcg gagtactagg accagactgt caacagagac    360
tggattcgct ctgctcggag acacccatg ctttctgacc acacaggaca ttcatctcgg    420
tgtgaacgag tcactgaccg acacagctcg agtcctcagc tccatggcag atgccgtgct    480
ggcaagggtc tacaaacaga gtgacctcga taccctggct aaggaagcaa gcatccccat    540
cattaatgga ctctccgacc tgtatcaccc tatccagatt ctggccgatt acctcaccct    600
```

```
gcaggagcat tattctagtc tgaaagggct cacactgagc tggattggcg acggaaacaa      660
tatcctgcac tccattatga tgtctgccgc taagtttggc atgcatctgc aggcagccac      720
accaaaagga tacgaacccg atgcttccgt gactaagctg ccgaacagt  atgctaaaga      780 gaacggaact aagctgctcc tgaccaatga ccccctggag gctgcacacg ggggtaacgt      840
cctgatcact gatacctgga tttccatggg ccaggaggaa gagaagaaaa agcgcctgca      900
ggcattccag ggataccagg tgacaatgaa aactgccaag gtcgccgctt ctgattggac      960
ttttctccat tgtctgcccc gaaagcctga agaggtggac gatgaggtct tctattcacc     1020
tcggagcctg gtgtttccag aagccgagaa tcgcaagtgg acaatcatgg cagtgatggt     1080
gtccctcctc acagactatt ccccacagct ccagaagccc aagttttgag cggccgctta     1140
attaagctgc cttctgcggg gcttgccttc tggccatgcc cttcttctct cccttgcacc     1200
tgtacctctt ggtctttgaa taaagcctga gtaggaagtc tagagtttaa acatttaaat     1260
ct                                                                     1262
```

<210> SEQ ID NO 4
<211> LENGTH: 1262
<212> TYPE: DNA
<213> ORGANISM: Artificial
<220> FEATURE:
<223> OTHER INFORMATION: cDNA encoding human ornithine transcarbamylase with mouse mitochondrial leader sequence, codon-optimized for mouse expression
<220> FEATURE:
<221> NAME/KEY: promoter
<222> LOCATION: (1)..(20)
<223> OTHER INFORMATION: T7 promoter

<400> SEQUENCE: 4

```
taatacgact cactataggg aaataagaga gaaaagaaga gtaagaagaa atataagagc       60
caccatgctc tctaacctca ggattctgct caacaacgct gctctgcgga aaggccatac      120
ctctgtcgtc aggcacttct ggtgtgggaa acccgtgcag agccaggtgc agctcaaggg      180
gcgggacctg ctcacccctga aaaatttcac aggcgaggaa atcaagtaca tgctctggct      240
gtctgccgat ctgaagttca ggatcaagca gaagggcgaa tatctcccac tgctccaggg      300
gaaaagtctg ggtatgatct tcgaaaagcg gagtactagg accagactgt caacagagac      360
tggattcgct ctgctcggag gacacccatg ctttctgacc acacaggaca ttcatctcgg      420
tgtgaacgag tcactgaccg acacagctcg agtcctcagc tccatggcag atgccgtgct      480
ggcaagggtc tacaaacaga gtgacctcga taccctggct aaggaagcaa gcatccccat      540
cattaatgga ctctccgacc tgtatcaccc tatccagatt ctggccgatt acctcacccT      600
gcaggagcat tattctagtc tgaaagggct cacactgagc tggattggcg acggaaacaa      660
tatcctgcac tccattatga tgtctgccgc taagtttggc atgcatctgc aggcagccac      720
accaaaagga tacgaacccg atgcttccgt gactaagctg ccgaacagt  atgctaaaga      780 gaacggaact aagctgctcc tgaccaatga ccccctggag gctgcacacg ggggtaacgt      840
cctgatcact gatacctgga tttccatggg ccaggaggaa gagaagaaaa agcgcctgca      900
ggcattccag ggataccagg tgacaatgaa aactgccaag gtcgccgctt ctgattggac      960
ttttctccat tgtctgcccc gaaagcctga agaggtggac gatgaggtct tctattcacc     1020
tcggagcctg gtgtttccag aagccgagaa tcgcaagtgg acaatcatgg cagtgatggt     1080
gtccctcctc acagactatt ccccacagct ccagaagccc aagttttgag cggccgctta     1140
attaagctgc cttctgcggg gcttgccttc tggccatgcc cttcttctct cccttgcacc     1200
```

| tgtacctctt ggtctttgaa taaagcctga gtaggaagtc tagagtttaa acatttaaat | 1260 |
| ct | 1262 |

<210> SEQ ID NO 5
<211> LENGTH: 1262
<212> TYPE: DNA
<213> ORGANISM: Artificial
<220> FEATURE:
<223> OTHER INFORMATION: cDNA encoding human ornithine transcarbamylase,
      codon-optimized for human expression
<220> FEATURE:
<221> NAME/KEY: promoter
<222> LOCATION: (1)..(20)
<223> OTHER INFORMATION: T7 promoter

<400> SEQUENCE: 5

| taatacgact cactataggg aaataagaga gaaaagaaga gtaagaagaa atataagagc | 60 |
| caccatgctg tttaacctga ggattctgct gaacaacgct gcttttcgga acggccacaa | 120 |
| ctttatggtg cggaactttc ggtgcggaca gccactgcag aacaaagtgc agctgaaggg | 180 |
| gagggacctg ctgaccctga aaaatttcac aggagaggaa atcaagtaca tgctgtggct | 240 |
| gtctgccgat ctgaagttcc ggatcaagca gaagggcgaa tatctgccac tgctgcaggg | 300 |
| caaaagtctg gggatgatct tcgaaaagag gagtactcgg accagactgt caacagagac | 360 |
| tggattcgct ctgctgggag acacccatg ctttctgacc acacaggaca ttcatctggg | 420 |
| cgtgaacgag tcactgaccg acacagctcg agtcctgagc tccatggcag atgccgtgct | 480 |
| ggcacgggtc tacaaacaga gcgacctgga taccctggct aaggaagcaa gcatccccat | 540 |
| cattaatggg ctgtccgacc tgtatcaccc tatccagatt ctggccgatt acctgacccT | 600 |
| gcaggagcat tattctagtc tgaaaggcct gacactgagc tggattgggg acggaaacaa | 660 |
| tatcctgcac tccattatga tgtctgccgc taagtttgga atgcatctgc aggcagccac | 720 |
| accaaaaggc tacgaacccg atgccagtgt gactaagctg ccgaacagt atgctaaaga | 780 |
| gaacggcact aagctgctgc tgaccaatga ccctctggag gctgcacacg aggcaacgt | 840 |
| cctgatcact gatacctgga tttccatggg ccaggaggaa gagaagaaaa agcgcctgca | 900 |
| ggcattccag gggtaccagg tgacaatgaa aactgccaag gtcgccgctt ctgattggac | 960 |
| ttttctgcat tgtctgcccc gaaaacctga gaggtggac gatgaggtct tctattcacc | 1020 |
| taggagcctg gtgtttccag aagccgagaa tcgcaagtgg acaatcatgg ctgtgatggt | 1080 |
| gtccctgctg actgattatt cccccagct gcagaaacct aagttctgag cggccgctta | 1140 |
| attaagctgc cttctgcggg gcttgccttc tggccatgcc cttcttctct cccttgcacc | 1200 |
| tgtacctctt ggtctttgaa taaagcctga gtaggaagtc tagagtttaa acatttaaat | 1260 |
| ct | 1262 |

<210> SEQ ID NO 6
<211> LENGTH: 1221
<212> TYPE: RNA
<213> ORGANISM: Artificial
<220> FEATURE:
<223> OTHER INFORMATION: mRNA encoding human ornithine transcarbamylase,
      codon-optimized for mouse expression

<400> SEQUENCE: 6

| gggaaauaag agagaaaaga gaguaagaa gaaauauaag agccaccaug cguucaaccc | 60 |
| ucagaauccu ccucaauaac gccgccuuua gaaacgguca uaacuucaug gucagaaacu | 120 |
| uuagauguogg ucagccucuc cagaacaaag ugcagcucaa ggggcgggac cugcucaccc | 180 |

| | |
|---|---|
| ugaaaaauuu cacaggcgag gaaaucaagu acaugcucug cugucugcc gaucugaagu | 240 |
| ucaggaucaa gcagaagggc gaauaucucc cacugcucca ggggaaaagu cuggguauga | 300 |
| ucuucgaaaa gcggaguacu aggaccagac ugucaacaga acuggauuc gcucugcucg | 360 |
| gaggacaccc augcuuucug accacacagg acauucaucu cggugugaac gagucacuga | 420 |
| ccgacacagc ucgagccuc agcuccaugg cagaugccgu gcuggcaagg gucuacaaac | 480 |
| agagugaccu cgauacccug gcuaaggaag caagcauccc caucauuaau ggacucuccg | 540 |
| accuguauca cccuauccag auucuggccg auuaccucac ccugcaggag cauuauucua | 600 |
| gucugaaagg gcucacacug agcuggauug gcgacggaaa caauauccug cacuccauua | 660 |
| ugaugucugc cgcuaaguuu ggcaugcauc ugcaggcagc cacaccaaaa ggaucgaac | 720 |
| ccgaugcuuc cgugacuaag cuggccgaac aguaugcuaa agagaacgga acuaagcugc | 780 |
| uccugaccaa ugacccccug gaggcugcac acggggguaa cguccugauc acugauaccu | 840 |
| ggauuuccau gggccaggag gaagagaaga aaaagcgccu gcaggcauuc cagggauacc | 900 |
| aggugacaau gaaaacugcc aaggucgccg cuucugauug gacuuuucuc cauugucugc | 960 |
| cccgaaagcc ugaagaggug gacgaugagu cuucuauuc accucggagc ugguguuuc | 1020 |
| cagaagccga gaaucgcaag uggacaauca uggcagugau gguguccucu cucacagacu | 1080 |
| auucccaca gcuccagaag cccaaguuuu gagcggccgc uuaauuaagc ugccuucgc | 1140 |
| gggggcuugcc uucuggccau gcccuucuuc ucccuugc accguaccu cuuggucuuu | 1200 |
| gaauaaagcc ugaguaggaa g | 1221 |

<210> SEQ ID NO 7
<211> LENGTH: 1221
<212> TYPE: RNA
<213> ORGANISM: Artificial
<220> FEATURE:
<223> OTHER INFORMATION: mRNA encoding human ornithine transcarbamylase
      with mouse mitochondrial leader sequence, codon-optimized for
      mouse expression

<400> SEQUENCE: 7

| | |
|---|---|
| gggaaauaag agagaaaaga agaguaagaa gaaauauaag agccaccaug cucucuaacc | 60 |
| ucaggauucu gcucaacaac gcugcucugc ggaaaggcca uaccucuguc gucaggcacu | 120 |
| ucuggugugg gaaacccgug cagagccagg ugcagcucaa ggggcgggac cugcucaccc | 180 |
| ugaaaaauuu cacaggcgag gaaaucaagu acaugcucug cugucugcc gaucugaagu | 240 |
| ucaggaucaa gcagaagggc gaauaucucc cacugcucca ggggaaaagu cuggguauga | 300 |
| ucuucgaaaa gcggaguacu aggaccagac ugucaacaga acuggauuc gcucugcucg | 360 |
| gaggacaccc augcuuucug accacacagg acauucaucu cggugugaac gagucacuga | 420 |
| ccgacacagc ucgagccuc agcuccaugg cagaugccgu gcuggcaagg gucuacaaac | 480 |
| agagugaccu cgauacccug gcuaaggaag caagcauccc caucauuaau ggacucuccg | 540 |
| accuguauca cccuauccag auucuggccg auuaccucac ccugcaggag cauuauucua | 600 |
| gucugaaagg gcucacacug agcuggauug gcgacggaaa caauauccug cacuccauua | 660 |
| ugaugucugc cgcuaaguuu ggcaugcauc ugcaggcagc cacaccaaaa ggaucgaac | 720 |
| ccgaugcuuc cgugacuaag cuggccgaac aguaugcuaa agagaacgga acuaagcugc | 780 |
| uccugaccaa ugacccccug gaggcugcac acggggguaa cguccugauc acugauaccu | 840 |
| ggauuuccau gggccaggag gaagagaaga aaaagcgccu gcaggcauuc cagggauacc | 900 |
| aggugacaau gaaaacugcc aaggucgccg cuucugauug gacuuuucuc cauugucugc | 960 |

```
cccgaaagcc ugaagaggug gacgaugagg ucuucuauuc accucggagc cuggugoouc   1020 cagaagccga gaaucgcaag uggacaauca uggcagugau ggugucccuc cucacagacu   1080
auuccccaca gcuccagaag cccaaguuuu gagcggccgc uuaauuaagc ugccuucugc   1140
ggggcuugcc uucuggccau gcccuucuuc ucucccuugc accuguaccu cuuggucuuu   1200
gaauaaagcc ugaguaggaa g                                            1221

<210> SEQ ID NO 8
<211> LENGTH: 1221
<212> TYPE: RNA
<213> ORGANISM: Artificial
<220> FEATURE:
<223> OTHER INFORMATION: mRNA encoding human ornithine transcarbamylase,
      codon-optimized for human expression

<400> SEQUENCE: 8
gggaauuaag agagaaaaga agaguaagaa gaaauauaag agccaccaug cuguuuaacc     60
ugaggauucu gcugaacaac gcugcuuuuc ggaacggcca caacuuuaug gugcggaacu    120
uucggugcgg acagccacug cagaacaaag ugcagcugaa ggggagggac cugcugaccc    180
ugaaaaauuu cacaggagag gaaaucaagu acaugcugug gcugucugcc gaucugaagu    240
uccggaucaa gcagaagggc gaauaucugc cacugcugca gggcaaaagu cuggggauga    300
ucuucgaaaa gaggaguacu cggaccagac ugucaacaga gacuggauuc gcucugcugg    360
gaggacaccc augcuuucug accacacagg acauucaucu gggcgugaac gagucacuga    420
ccgacacagc ucgaguccug agcuccaugg cagaugccgu gcuggcacgg gucuacaaac    480
agagcgaccu ggauacccug gcuaaggaag caagcauccc caucauuaau gggcuguccg    540
accuguauca cccuauccag auucuggccg auuaccugac ccugcaggag cauuauucua    600
gucugaaagg ccugacacug agcuggauug gggacggaaa caauauccug cacuccauua    660
ugaugucugc cgcuaaguuu ggaaugcauc ugcaggcagc cacaccaaaa ggcuacgaac    720
ccgaugccag ugugacuaag cuggccgaac aguaugcuaa agagaacggc acuaagcugc    780
ugcugaccaa ugacccucug gaggcugcac acggaggcaa cguccugauc acugauaccu    840
ggauuuccau gggccaggag gaagagaaga aaaagcgccu gcaggcauuc cagggguacc    900
aggugacaau gaaaacugcc aaggucgccg cuucugauug gacuuucugc cauugucugc    960
cccgaaaacc ugaagaggug gacgaugagg ucuucuauuc accuaggagc cuggugouuc   1020 cagaagccga gaaucgcaag uggacaauca uggcugugau ggugucccug cugacugauu   1080
auccccccca gcugcagaaa ccuaaguucu gagcggccgc uuaauuaagc ugccuucugc   1140
ggggcuugcc uucuggccau gcccuucuuc ucucccuugc accuguaccu cuuggucuuu   1200
gaauaaagcc ugaguaggaa g                                            1221

<210> SEQ ID NO 9
<211> LENGTH: 750
<212> TYPE: PRT
<213> ORGANISM: Homo sapiens
<220> FEATURE:
<221> NAME/KEY: TRANSIT
<222> LOCATION: (1)..(32)
<223> OTHER INFORMATION: native mitochondrial leader sequence
```

<400> SEQUENCE: 9

```
Met Leu Arg Ala Lys Asn Gln Leu Phe Leu Ser Pro His Tyr Leu
1               5                   10                  15

Arg Gln Val Lys Glu Ser Ser Gly Ser Arg Leu Ile Gln Gln Arg Leu
            20                  25                  30

Leu His Gln Gln Gln Pro Leu His Pro Glu Trp Ala Ala Leu Ala Lys
        35                  40                  45

Lys Gln Leu Lys Gly Lys Asn Pro Glu Asp Leu Ile Trp His Thr Pro
    50                  55                  60

Glu Gly Ile Ser Ile Lys Pro Leu Tyr Ser Lys Arg Asp Thr Met Asp
65                  70                  75                  80

Leu Pro Glu Glu Leu Pro Gly Val Lys Pro Phe Thr Arg Gly Pro Tyr
                85                  90                  95

Pro Thr Met Tyr Thr Phe Arg Pro Trp Thr Ile Arg Gln Tyr Ala Gly
            100                 105                 110

Phe Ser Thr Val Glu Glu Ser Asn Lys Phe Tyr Lys Asp Asn Ile Lys
        115                 120                 125

Ala Gly Gln Gln Gly Leu Ser Val Ala Phe Asp Leu Ala Thr His Arg
    130                 135                 140

Gly Tyr Asp Ser Asp Asn Pro Arg Val Arg Gly Asp Val Gly Met Ala
145                 150                 155                 160

Gly Val Ala Ile Asp Thr Val Glu Asp Thr Lys Ile Leu Phe Asp Gly
                165                 170                 175

Ile Pro Leu Glu Lys Met Ser Val Ser Met Thr Met Asn Gly Ala Val
            180                 185                 190

Ile Pro Val Leu Ala Asn Phe Ile Val Thr Gly Glu Glu Gln Gly Val
        195                 200                 205

Pro Lys Glu Lys Leu Thr Gly Thr Ile Gln Asn Asp Ile Leu Lys Glu
    210                 215                 220

Phe Met Val Arg Asn Thr Tyr Ile Phe Pro Pro Glu Pro Ser Met Lys
225                 230                 235                 240

Ile Ile Ala Asp Ile Phe Glu Tyr Thr Ala Lys His Met Pro Lys Phe
                245                 250                 255

Asn Ser Ile Ser Ile Ser Gly Tyr His Met Gln Glu Ala Gly Ala Asp
            260                 265                 270

Ala Ile Leu Glu Leu Ala Tyr Thr Leu Ala Asp Gly Leu Glu Tyr Ser
        275                 280                 285

Arg Thr Gly Leu Gln Ala Gly Leu Thr Ile Asp Glu Phe Ala Pro Arg
    290                 295                 300

Leu Ser Phe Phe Trp Gly Ile Gly Met Asn Phe Tyr Met Glu Ile Ala
305                 310                 315                 320

Lys Met Arg Ala Gly Arg Arg Leu Trp Ala His Leu Ile Glu Lys Met
                325                 330                 335

Phe Gln Pro Lys Asn Ser Lys Ser Leu Leu Leu Arg Ala His Cys Gln
            340                 345                 350

Thr Ser Gly Trp Ser Leu Thr Glu Gln Asp Pro Tyr Asn Asn Ile Val
        355                 360                 365

Arg Thr Ala Ile Glu Ala Met Ala Ala Val Phe Gly Gly Thr Gln Ser
    370                 375                 380

Leu His Thr Asn Ser Phe Asp Glu Ala Leu Gly Leu Pro Thr Val Lys
385                 390                 395                 400

Ser Ala Arg Ile Ala Arg Asn Thr Gln Ile Ile Gln Glu Glu Ser
                405                 410                 415
```

Gly Ile Pro Lys Val Ala Asp Pro Trp Gly Ser Tyr Met Met Glu
           420                 425                 430

Cys Leu Thr Asn Asp Val Tyr Asp Ala Ala Leu Lys Leu Ile Asn Glu
       435                 440                 445

Ile Glu Glu Met Gly Gly Met Ala Lys Ala Val Ala Glu Gly Ile Pro
   450                 455                 460

Lys Leu Arg Ile Glu Glu Cys Ala Ala Arg Arg Gln Ala Arg Ile Asp
465                 470                 475                 480

Ser Gly Ser Glu Val Ile Gly Val Asn Lys Tyr Gln Leu Glu Lys
               485                 490                 495

Glu Asp Ala Val Glu Val Leu Ala Ile Asp Asn Thr Ser Val Arg Asn
               500                 505                 510

Arg Gln Ile Glu Lys Leu Lys Lys Ile Lys Ser Ser Arg Asp Gln Ala
           515                 520                 525

Leu Ala Glu Arg Cys Leu Ala Ala Leu Thr Glu Cys Ala Ala Ser Gly
           530                 535                 540

Asp Gly Asn Ile Leu Ala Leu Ala Val Asp Ala Ser Arg Ala Arg Cys
545                 550                 555                 560

Thr Val Gly Glu Ile Thr Asp Ala Leu Lys Lys Val Phe Gly Glu His
               565                 570                 575

Lys Ala Asn Asp Arg Met Val Ser Gly Ala Tyr Arg Gln Glu Phe Gly
           580                 585                 590

Glu Ser Lys Glu Ile Thr Ser Ala Ile Lys Arg Val His Lys Phe Met
       595                 600                 605

Glu Arg Glu Gly Arg Arg Pro Arg Leu Leu Val Ala Lys Met Gly Gln
   610                 615                 620

Asp Gly His Asp Arg Gly Ala Lys Val Ile Ala Thr Gly Phe Ala Asp
625                 630                 635                 640

Leu Gly Phe Asp Val Asp Ile Gly Pro Leu Phe Gln Thr Pro Arg Glu
               645                 650                 655

Val Ala Gln Gln Ala Val Asp Ala Asp Val His Ala Val Gly Ile Ser
           660                 665                 670

Thr Leu Ala Ala Gly His Lys Thr Leu Val Pro Glu Leu Ile Lys Glu
       675                 680                 685

Leu Asn Ser Leu Gly Arg Pro Asp Ile Leu Val Met Cys Gly Gly Val
   690                 695                 700

Ile Pro Pro Gln Asp Tyr Glu Phe Leu Phe Glu Val Gly Val Ser Asn
705                 710                 715                 720

Val Phe Gly Pro Gly Thr Arg Ile Pro Lys Ala Ala Val Gln Val Leu
               725                 730                 735

Asp Asp Ile Glu Lys Cys Leu Glu Lys Lys Gln Gln Ser Val
           740                 745                 750

<210> SEQ ID NO 10
<211> LENGTH: 2409
<212> TYPE: RNA
<213> ORGANISM: Artificial
<220> FEATURE:
<223> OTHER INFORMATION: mRNA encoding human methylmalonyl-coenzyme A
      mutase

<400> SEQUENCE: 10
gggaauuaag agagaaaaga agaguaagaa gaaauauaag agccaccaug uuaagagcua    60
agaaucagcu uuuuuacuu ucaccucauu accugaggca gguaaaagaa ucaucaggcu    120
ccaggcucau acagcaacga cuucuacacc agcaacagcc ccuucaccca gaaugggcug    180

```
cccuggcuaa aaagcagcug aaaggcaaaa acccagaaga ccuaauaugg cacaccccgg    240
aagggaucuc uauaaaaccc uuguauucca agagagauac uauggacuua ccugaagaac    300
uuccaggagu gaagccauuc acacuggac cauauccuac cauguauacc uuuaggcccu    360
ggaccauccg ccaguaugcu gguuuuagua cuguggaaga aagcaauaag uucuauaagg    420
acaacauuaa ggcuggucag cagggauuau caguugccuu ugaucggcg acacaucgug    480 gcuaugauuc agacaacccu cgaguucgug gugauguugg aauggcugga guugcuauug    540
acacugugga agauaccaaa auucuuuuug auggaauucc uuuagaaaaa augucaguuu    600
ccaugacuau gaauggagca guuauuccag uucuugcaaa uuuuauagua acuggagaag    660
aacaaggugu accuaaagag aagcuuacug guaccaucca aaaugauaua cuaaaggaau    720
uuaugguucg aaauacauac auuuuuccuc cagaaccauc caugaaaauu auugcugaca    780
uauugaauua uacagcaaag cacaugccaa aauuuaauuc aauucaauu agguggauacc    840 auaugcagga agcaggggcu gaugccauuc uggagcuggc cuauacuuua gcagauggau    900
uggaguacuc uagaacugga cuccaggcug ccugacaau ugaugaauuu gcaccaaggu    960
ugucuuucuu cuggggaauu ggaaugaauu ucuauaugga aauagcaaag augagagcug    1020
guagaagacu cugggcucac uuaauagaga aaauguuuca gccuaaaaac ucaaaaucuc    1080
uucuucuaag agcacacugu cagacaucug gauggucacu acugagcag gaucccuaca    1140 auaauauugu ccguacugca auagaagcaa uggcagcagu auuuggaggg acucagucuu    1200
ugcacacaaa uucuuuugau gaagcuuugg guuugccaac ugugaaaagu gcucgaauug    1260
ccaggaacac acaaaucauc auucaagaag aaucuggau ucccaaagug gcugauccuu    1320
ggggagguuc uuacaugaug gaaugucuca caaaugaugu uuaugaugcu gcuuuaaagc    1380
ucauuaauga aauugaagaa augggguggaa uggccaaagc uguagcugag gaauaccua    1440 aacuucgaau ugaagaaugu gcugcccgaa gacaagcuag aauagauucu gguucugaag    1500
uaauuguugg aguaaauaag uaccaguugg aaaaagaaga cgcuguagaa guucuggcaa    1560
uugauaauac uucagugcga acaggcaga uugaaaaacu aagaagauc aaauccagca    1620 gggaucaagc uuuggcugaa cguugucuug cugcacuaac cgaaugugcu gcuagcggag    1680
auggaaauau ccuggcucuu gcaguggaug caucucgggc aagauguaca gugggagaaa    1740
ucacagaugc ccugaaaaag guauuuggug aacauaaagc gaaugaucga auggugagug    1800
gagcauaucg ccaggaauuu ggagaaguaa aagagauaac aucgcuauc aagagggguc    1860 auaaauuau ggaacgugaa ggucgcagac cucgucuucu cuguagcaaaa augggacaag    1920 auggccauga cagaggagca aaaguuauug cuacaggauu ugcugaucuu gguuuugaug    1980
uggacauagg cccucuuuuc cagacucccc gugaaguggc ccagcaggcu gggaugcgg    2040 augugcaugc ugugggcaua agcacccucg cugcugguca uaaaccccua guccugaac    2100 ucaucaaaga acuuaacucc cuuggacggc cagauauucu ugucaugugu ggagggguga    2160
uaccaccuca ggauuaugaa uucuguuug aaguggugu uuccaaugua uuugguccgg    2220
ggacucgaau uccaaaggcu gccguucagg ugcuugauga uauugagaag uguuuggaaa    2280
agaagcagca aucuguauaa gcggccgcuu aauuaagcug ccuucugcgg ggcuugccuu    2340
cuggccaugc ccuucuucuc ucccuugcac cuguaccucu uggucuuuga auaaagccug    2400
aguaggaag                                                             2409
```

-continued

```
<210> SEQ ID NO 11
<211> LENGTH: 728
<212> TYPE: PRT
<213> ORGANISM: Homo sapiens
<220> FEATURE:
<221> NAME/KEY: TRANSIT
<222> LOCATION: (1)..(52)
<223> OTHER INFORMATION: native mitochondrial leader sequence

<400> SEQUENCE: 11

Met Ala Gly Phe Trp Val Gly Thr Ala Pro Leu Val Ala Ala Gly Arg
1               5                   10                  15

Arg Gly Arg Trp Pro Pro Gln Gln Leu Met Leu Ser Ala Ala Leu Arg
            20                  25                  30

Thr Leu Lys His Val Leu Tyr Tyr Ser Arg Gln Cys Leu Met Val Ser
        35                  40                  45

Arg Asn Leu Gly Ser Val Gly Tyr Asp Pro Asn Glu Lys Thr Phe Asp
50                  55                  60

Lys Ile Leu Val Ala Asn Arg Gly Glu Ile Ala Cys Arg Val Ile Arg
65                  70                  75                  80

Thr Cys Lys Lys Met Gly Ile Lys Thr Val Ala Ile His Ser Asp Val
                85                  90                  95

Asp Ala Ser Ser Val His Val Lys Met Ala Asp Glu Ala Val Cys Val
            100                 105                 110

Gly Pro Ala Pro Thr Ser Lys Ser Tyr Leu Asn Met Asp Ala Ile Met
        115                 120                 125

Glu Ala Ile Lys Lys Thr Arg Ala Gln Ala Val His Pro Gly Tyr Gly
    130                 135                 140

Phe Leu Ser Glu Asn Lys Glu Phe Ala Arg Cys Leu Ala Ala Glu Asp
145                 150                 155                 160

Val Val Phe Ile Gly Pro Asp Thr His Ala Ile Gln Ala Met Gly Asp
                165                 170                 175

Lys Ile Glu Ser Lys Leu Leu Ala Lys Lys Ala Glu Val Asn Thr Ile
            180                 185                 190

Pro Gly Phe Asp Gly Val Val Lys Asp Ala Glu Glu Ala Val Arg Ile
        195                 200                 205

Ala Arg Glu Ile Gly Tyr Pro Val Met Ile Lys Ala Ser Ala Gly Gly
    210                 215                 220

Gly Gly Lys Gly Met Arg Ile Ala Trp Asp Asp Glu Glu Thr Arg Asp
225                 230                 235                 240

Gly Phe Arg Leu Ser Ser Gln Glu Ala Ala Ser Ser Phe Gly Asp Asp
                245                 250                 255

Arg Leu Leu Ile Glu Lys Phe Ile Asp Asn Pro Arg His Ile Glu Ile
            260                 265                 270

Gln Val Leu Gly Asp Lys His Gly Asn Ala Leu Trp Leu Asn Glu Arg
        275                 280                 285

Glu Cys Ser Ile Gln Arg Arg Asn Gln Lys Val Val Glu Glu Ala Pro
    290                 295                 300

Ser Ile Phe Leu Asp Ala Glu Thr Arg Arg Ala Met Gly Glu Gln Ala
305                 310                 315                 320

Val Ala Leu Ala Arg Ala Val Lys Tyr Ser Ser Ala Gly Thr Val Glu
                325                 330                 335

Phe Leu Val Asp Ser Lys Lys Asn Phe Tyr Phe Leu Glu Met Asn Thr
            340                 345                 350

Arg Leu Gln Val Glu His Pro Val Thr Glu Cys Ile Thr Gly Leu Asp
        355                 360                 365
```

Leu Val Gln Glu Met Ile Arg Val Ala Lys Gly Tyr Pro Leu Arg His
370                 375                 380

Lys Gln Ala Asp Ile Arg Ile Asn Gly Trp Ala Val Glu Cys Arg Val
385                 390                 395                 400

Tyr Ala Glu Asp Pro Tyr Lys Ser Phe Gly Leu Pro Ser Ile Gly Arg
                405                 410                 415

Leu Ser Gln Tyr Gln Glu Pro Leu His Leu Pro Gly Val Arg Val Asp
                420                 425                 430

Ser Gly Ile Gln Pro Gly Ser Asp Ile Ser Ile Tyr Tyr Asp Pro Met
                435                 440                 445

Ile Ser Lys Leu Ile Thr Tyr Gly Ser Asp Arg Thr Glu Ala Leu Lys
450                 455                 460

Arg Met Ala Asp Ala Leu Asp Asn Tyr Val Ile Arg Gly Val Thr His
465                 470                 475                 480

Asn Ile Ala Leu Leu Arg Glu Val Ile Ile Asn Ser Arg Phe Val Lys
                485                 490                 495

Gly Asp Ile Ser Thr Lys Phe Leu Ser Asp Val Tyr Pro Asp Gly Phe
                500                 505                 510

Lys Gly His Met Leu Thr Lys Ser Glu Lys Asn Gln Leu Leu Ala Ile
                515                 520                 525

Ala Ser Ser Leu Phe Val Ala Phe Gln Leu Arg Ala Gln His Phe Gln
530                 535                 540

Glu Asn Ser Arg Met Pro Val Ile Lys Pro Asp Ile Ala Asn Trp Glu
545                 550                 555                 560

Leu Ser Val Lys Leu His Asp Lys Val His Thr Val Val Ala Ser Asn
                565                 570                 575

Asn Gly Ser Val Phe Ser Val Glu Val Asp Gly Ser Lys Leu Asn Val
                580                 585                 590

Thr Ser Thr Trp Asn Leu Ala Ser Pro Leu Leu Ser Val Ser Val Asp
                595                 600                 605

Gly Thr Gln Arg Thr Val Gln Cys Leu Ser Arg Glu Ala Gly Gly Asn
                610                 615                 620

Met Ser Ile Gln Phe Leu Gly Thr Val Tyr Lys Val Asn Ile Leu Thr
625                 630                 635                 640

Arg Leu Ala Ala Glu Leu Asn Lys Phe Met Leu Glu Lys Val Thr Glu
                645                 650                 655

Asp Thr Ser Ser Val Leu Arg Ser Pro Met Pro Gly Val Val Val Ala
                660                 665                 670

Val Ser Val Lys Pro Gly Asp Ala Val Ala Glu Gly Gln Glu Ile Cys
                675                 680                 685

Val Ile Glu Ala Met Lys Met Gln Asn Ser Met Thr Ala Gly Lys Thr
                690                 695                 700

Gly Thr Val Lys Ser Val His Cys Gln Ala Gly Asp Thr Val Gly Glu
705                 710                 715                 720

Gly Asp Leu Leu Val Glu Leu Glu
                725

<210> SEQ ID NO 12
<211> LENGTH: 2343
<212> TYPE: RNA
<213> ORGANISM: Artificial
<220> FEATURE:
<223> OTHER INFORMATION: mRNA encoding human propionyl CoA carboxylase,
      alpha polypeptide (PCCA)

<400> SEQUENCE: 12

```
gggaaauaag agagaaaaga agaguaagaa gaaauauaag agccaccaug gcggggUucu    60
ggucggggac agcaccgcug gucgcugccg gacggcgugg gcgguggccg ccgcagcagc   120
ugaugcugga cgcggcgcug cggacccuga agcauguucu guacuauuca agacagugcu   180
uaauggaguc ccguaaucuu gguucagugg gauaugaucc uaaugaaaaa acuuuugaua   240
aaauucuugu ugcuaauaga ggagaaauug caugucgggu uauuagaacu ugcaagaaga   300
ugggcauuaa gacaguugcc auccacagug auguugaugc uaguucuguu caugugaaaa   360
uggcggauga ggcugucugu guuggccccag cucccaccag uaaaagcuac cucaacaugg   420
augccaucau ggaagccauu aagaaaacca gggcccaagc uguacaucca gguuauggau   480
uccuuucaga aaacaaagaa uuugccagau guuggcagc agaagaugc guuuucauug   540
gaccugacac acaugcuauu caagccaugg gcgacaagau ugaaagcaaa uuauuagcua   600
agaaagcaga gguuaauaca aucccugggcu uugauggagu agucaaggau gcagaagaag   660
cugucagaau ugcaagggaa auuggcuaccc cugucaugau caaggccuca gcagguggug   720
gugggaaagg caugcgcauu gcuugggaug augaagagag cagggauggu uuuagauugu   780
caucucaaga agcugcuucu aguuuggcg augauagacu acuaauagaa aaauuuauug   840
auaauccucg ucauauagaa auccagguuc uaggugauaa acaugggaau gcuuauggc   900
uuaaugaaag agagugcuca auucagaaa gaaaucagaa gguggggag gaagcaccaa   960
gcauuuuuuu ggaugcggag acucgaagag cgaugggaga acaagcugua gcucuugcca  1020
gagcaguaaa auuaucccucu gcugggaccg uggaguuccu uggacucu aagaagaauu  1080
uuuauuucuu ggaaaugaau acaagaucucc agguugagca uccugucaca gaaugccuua  1140
cuggcccuga ccuaguccag gaaaugacc guguugcaa gggcuacccu ucaggcaca  1200
aacaagcuga uacucgcauc aacgcgguggg caguugauag cgggguauau gcugaggacc  1260
ccuacaaguc uuuugguuua ccaucauuug ggagauugucc ucaguacaca gaaccguuac  1320
aucuaccugg uguccgaguug gacaguggca uccaaccagg aaguguauu agcauuuauu  1380
augauccuau gauuucaaaa cuaaucacau auggcucucga uagaacugag gcacugaaga  1440
gaauggcaga ugcacuggau aacuaguuua ucgagugu uacacauaau auugcauuac  1500
uucgagaggu gauaaucaac ucacgcuuug uaaaaggaga caucagcacu aaauucuccu  1560
ccgauguggua uccugaggc uucaaaggac acaugcuaac caagagugag aagaaccagu  1620
uauuggcaau agcaucauca uuguuuugg cauuccaguu aagagcacaa cauuucaag  1680
aaaauucaag aauugccuguu auuaaaccag acauagccaa cugggagcuc ucaguaaaau  1740
ugcaugauaa aguucauacc guaguagcau caaacaaugg ucaguguuc ucgguggaag  1800
uugauggguc gaaacuaaau gugaccagca cguggaaccu ggcuucgccc uauugucug  1860
ucagcguuga uggcacucag aggacugucc aguucuuuc ucgagaagca gguggaaaca  1920
ugagcauuca guucuugggu acaguguaca agugaauau cuuaaccaga cuugccgcag  1980
aauugaacaa auuuaugcug gaaaagugua cugaggacac aagcaguguu cugcguuccc  2040
cgaugcccgg aguggugg ccgucucug ucaagccugg agacgcggua gcagaagguc  2100
aagaaauuug ugugauugaa gccaugaaaa ugcagaauag uaugcagcu gggaaaaacug  2160
gcacggugaa aucugugcac ugucaagcug agacacagu uggagaaggg gaucugcucg  2220
uggagcugga augagcggcc gcuuaauuaa gcugccuucu gcggggcuug ccuucuggcc  2280
```

```
augcccuucu ucucucccuu gcaccuguac cucuuggucu uugaauaaag ccugaguagg    2340
aag                                                                 2343
```

<210> SEQ ID NO 13
<211> LENGTH: 539
<212> TYPE: PRT
<213> ORGANISM: Homo sapiens
<220> FEATURE:
<221> NAME/KEY: TRANSIT
<222> LOCATION: (1)..(28)
<223> OTHER INFORMATION: native mitochondrial leader sequence

<400> SEQUENCE: 13

```
Met Ala Ala Ala Leu Arg Val Ala Ala Val Gly Ala Arg Leu Ser Val
1               5                   10                  15

Leu Ala Ser Gly Leu Arg Ala Ala Val Arg Ser Leu Cys Ser Gln Ala
            20                  25                  30

Thr Ser Val Asn Glu Arg Ile Glu Asn Lys Arg Arg Thr Ala Leu Leu
        35                  40                  45

Gly Gly Gly Gln Arg Arg Ile Asp Ala Gln His Lys Arg Gly Lys Leu
    50                  55                  60

Thr Ala Arg Glu Arg Ile Ser Leu Leu Leu Asp Pro Gly Ser Phe Val
65                  70                  75                  80

Glu Ser Asp Met Phe Val Glu His Arg Cys Ala Asp Phe Gly Met Ala
                85                  90                  95

Ala Asp Lys Asn Lys Phe Pro Gly Asp Ser Val Val Thr Gly Arg Gly
            100                 105                 110

Arg Ile Asn Gly Arg Leu Val Tyr Val Phe Ser Gln Asp Phe Thr Val
        115                 120                 125

Phe Gly Gly Ser Leu Ser Gly Ala His Ala Gln Lys Ile Cys Lys Ile
    130                 135                 140

Met Asp Gln Ala Ile Thr Val Gly Ala Pro Val Ile Gly Leu Asn Asp
145                 150                 155                 160

Ser Gly Gly Ala Arg Ile Gln Glu Gly Val Glu Ser Leu Ala Gly Tyr
                165                 170                 175

Ala Asp Ile Phe Leu Arg Asn Val Thr Ala Ser Gly Val Ile Pro Gln
            180                 185                 190

Ile Ser Leu Ile Met Gly Pro Cys Ala Gly Gly Ala Val Tyr Ser Pro
        195                 200                 205

Ala Leu Thr Asp Phe Thr Phe Met Val Lys Asp Thr Ser Tyr Leu Phe
    210                 215                 220

Ile Thr Gly Pro Asp Val Val Lys Ser Val Thr Asn Glu Asp Val Thr
225                 230                 235                 240

Gln Glu Glu Leu Gly Gly Ala Lys Thr His Thr Thr Met Ser Gly Val
                245                 250                 255

Ala His Arg Ala Phe Glu Asn Asp Val Asp Ala Leu Cys Asn Leu Arg
            260                 265                 270

Asp Phe Phe Asn Tyr Leu Pro Leu Ser Ser Gln Asp Pro Ala Pro Val
        275                 280                 285

Arg Glu Cys His Asp Pro Ser Asp Arg Leu Val Pro Glu Leu Asp Thr
    290                 295                 300

Ile Val Pro Leu Glu Ser Thr Lys Ala Tyr Asn Met Val Asp Ile Ile
305                 310                 315                 320

His Ser Val Val Asp Glu Arg Glu Phe Phe Glu Ile Met Pro Asn Tyr
                325                 330                 335
```

Ala Lys Asn Ile Ile Val Gly Phe Ala Arg Met Asn Gly Arg Thr Val
                340                 345                 350

Gly Ile Val Gly Asn Gln Pro Lys Val Ala Ser Gly Cys Leu Asp Ile
            355                 360                 365

Asn Ser Ser Val Lys Gly Ala Arg Phe Val Arg Phe Cys Asp Ala Phe
370                 375                 380

Asn Ile Pro Leu Ile Thr Phe Val Asp Val Pro Gly Phe Leu Pro Gly
385                 390                 395                 400

Thr Ala Gln Glu Tyr Gly Gly Ile Ile Arg His Gly Ala Lys Leu Leu
                405                 410                 415

Tyr Ala Phe Ala Glu Ala Thr Val Pro Lys Val Thr Val Ile Thr Arg
            420                 425                 430

Lys Ala Tyr Gly Gly Ala Tyr Asp Val Met Ser Ser Lys His Leu Cys
            435                 440                 445

Gly Asp Thr Asn Tyr Ala Trp Pro Thr Ala Glu Ile Ala Val Met Gly
            450                 455                 460

Ala Lys Gly Ala Val Glu Ile Ile Phe Lys Gly His Glu Asn Val Glu
465                 470                 475                 480

Ala Ala Gln Ala Glu Tyr Ile Glu Lys Phe Ala Asn Pro Phe Pro Ala
                485                 490                 495

Ala Val Arg Gly Phe Val Asp Asp Ile Ile Gln Pro Ser Ser Thr Arg
            500                 505                 510

Ala Arg Ile Cys Cys Asp Leu Asp Val Leu Ala Ser Lys Lys Val Gln
            515                 520                 525

Arg Pro Trp Arg Lys His Ala Asn Ile Pro Leu
530                 535

<210> SEQ ID NO 14
<211> LENGTH: 1776
<212> TYPE: RNA
<213> ORGANISM: Artificial
<220> FEATURE:
<223> OTHER INFORMATION: mRNA encoding human propionyl CoA carboxylase,
      beta polypeptide (PCCB)

<400> SEQUENCE: 14
gggaaauaag agagaaaaga agaguaagaa gaaauauaag agccaccaug gcggcggcau      60
uacggguggc ggcggucggg gcaaggcuca gcguucuggc gagcggucuc cgcgccgcgg     120
uccgcagccu uugcagccag gccaccucug uuaacgaacg caucgaaaac aagcgccgga     180
ccgcgcugcu ggagggggc caacgccgua uugacgcgca gcacaagcga ggaaagcuaa     240
cagccaggga gaggaucagu ucuugcuggg acccuggcag cuuuguugag agcgacaugu     300
uuguggaaca cagaugugca gauuuuggaa uggcugcuga uaagaauaag uuuccuggag     360
acagcguggu cacuggacga ggccgaauca augguaaugu cguuuaugcu ucagucagg     420 auuuuacagu uuuuggaggc agucuggcag gagcacaugc ccaaaagauc ugcaaaauca     480
uggaccaggc cauaacgguu ggggcuccag ugauugggcu gaaugacucu ggggagcac     540 ggauccaaga aggaguggag ucuuuggcug gcuaugcaga cauccuuucug aggaauguua     600 cggcauccgg agucaucccu cagauuucuc ugaucaauggg cccauguqcu gguggggccq     660 ucuacucccc agcccuaaca gacuucacgu ucauggaaaa ggacaccucc uaccuguuca     720
ucacuggccc ugauguugug aagucuguca ccaaugagga guuaccccag gaggagcucg     780
guggugccaa gacccacacc accaugucag gugugggccca cagagcuuu gaaaaugaug     840 uugaugccuu uguuaaaucuc cggaauucu ucaacuaccu gccccugagc agucaggacc     900

```
cggcucccgu ccgugagugc cacgauccca gugaccgucu gguccugag cuugacacaa    960 uugucccuuu ggaaucaacc aaagccuaca acauggugga caucauacac ucuguuguug   1020
augagcguga auuuuugag aucaugccca auuaugccaa gaacaucauu guugguuug    1080 caagaaugaa ugggaggacu guuggaauug uuggcaacca accuaaggug gccucaggau   1140
gcuuggauau uaauucaucu gugaaagggg cucguuugu cagauucugu gaugcauuca    1200
auauuccacu caucacuuuu guugaugucc cuggcuuucu accuggcaca gcacaggaau   1260 acggggcau cauccggcau ggugccaagc uucucuacgc auuugcugag caacuguac     1320 ccaaagucac agucaucacc aggaaggccu auggaggugc cuaugaugc augagcucua    1380 agcaccuuug uggugauacc aacuaugccu ggcccaccgc agagauugca gucaugggag   1440
caaagggcgc ugggagauc aucuucaaag gcaugagaa uggaagcu gcucaggcag      1500 aguacaucga gaaguuugcc aacccuuucc cugcagcagu gcgagggu ugggaugaca    1560 ucauccaacc uucuuccaca cgugcccgaa ucugcuguga ccuggaugc uuggccagca   1620 agaagguaca acguccuugg agaaaacaug caaauauucc auuguaagcg gccgcuuaau   1680
uaagcugccu ucucgggggc uugccuucug gccaugcccu cuucucucc cuugcaccug    1740 uaccucuugg ucuuugaaua aagccugagu aggaag                             1776
```

```
<210> SEQ ID NO 15
<211> LENGTH: 30
<212> TYPE: PRT
<213> ORGANISM: Artificial
<220> FEATURE:
<223> OTHER INFORMATION: GALA peptide

<400> SEQUENCE: 15

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 16
<211> LENGTH: 18
<212> TYPE: PRT
<213> ORGANISM: Artificial
<220> FEATURE:
<223> OTHER INFORMATION: truncated GALA peptide

<400> SEQUENCE: 16

Cys Ala Glu Ala Leu Ala Glu Ala Leu Ala Glu Ala Leu Ala Glu Ala
1               5                   10                  15

Leu Ala

<210> SEQ ID NO 17
<211> LENGTH: 26
<212> TYPE: PRT
<213> ORGANISM: Apis mellifera

<400> SEQUENCE: 17

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

```
<210> SEQ ID NO 18
<211> LENGTH: 27
<212> TYPE: PRT
<213> ORGANISM: Artificial
<220> FEATURE:
<223> OTHER INFORMATION: Melittin peptide with N-terminal cysteine

<400> SEQUENCE: 18

Cys Gly Ile Gly Ala Val Leu Lys Val Leu Thr Thr Gly Leu Pro Ala
1               5                   10                  15

Leu Ile Ser Trp Ile Lys Arg Lys Arg Gln Gln
            20                  25

<210> SEQ ID NO 19
<211> LENGTH: 21
<212> TYPE: PRT
<213> ORGANISM: Artificial
<220> FEATURE:
<223> OTHER INFORMATION: HPH-1 peptide

<400> SEQUENCE: 19

Phe Ile Ile Asp Ile Ile Ala Phe Leu Leu Met Gly Gly Phe Ile Val
1               5                   10                  15

Tyr Val Lys Asn Leu
            20

<210> SEQ ID NO 20
<211> LENGTH: 24
<212> TYPE: PRT
<213> ORGANISM: Artificial
<220> FEATURE:
<223> OTHER INFORMATION: HPH-1 peptide with N-terminal Cys-Ala-Ala

<400> SEQUENCE: 20

Cys Ala Ala Phe Ile Ile Asp Ile Ile Ala Phe Leu Leu Met Gly Gly
1               5                   10                  15

Phe Ile Val Tyr Val Lys Asn Leu
            20

<210> SEQ ID NO 21
<211> LENGTH: 17
<212> TYPE: PRT
<213> ORGANISM: Artificial
<220> FEATURE:
<223> OTHER INFORMATION: sHGP peptide

<400> SEQUENCE: 21

Cys Ala Arg Gly Trp Glu Val Leu Lys Tyr Trp Trp Asn Leu Leu Gln
1               5                   10                  15

Tyr

<210> SEQ ID NO 22
<211> LENGTH: 30
<212> TYPE: PRT
<213> ORGANISM: Artificial
<220> FEATURE:
<223> OTHER INFORMATION: bPrPp peptide

<400> SEQUENCE: 22

Met Val Lys Ser Lys Ile Gly Ser Trp Ile Leu Val Leu Phe Val Ala
1               5                   10                  15

Met Trp Ser Asp Val Gly Leu Cys Lys Lys Arg Pro Lys Pro
            20                  25                  30
```

```
<210> SEQ ID NO 23
<211> LENGTH: 18
<212> TYPE: PRT
<213> ORGANISM: Artificial
<220> FEATURE:
<223> OTHER INFORMATION: MAP peptide

<400> SEQUENCE: 23

Lys Leu Ala Leu Lys Leu Ala Leu Lys Ala Leu Lys Ala Ala Leu Lys
1               5                   10                  15

Leu Ala

<210> SEQ ID NO 24
<211> LENGTH: 11
<212> TYPE: PRT
<213> ORGANISM: Artificial
<220> FEATURE:
<223> OTHER INFORMATION: PTD4 peptide

<400> SEQUENCE: 24

Tyr Ala Arg Ala Ala Ala Arg Gln Ala Arg Ala
1               5                   10

<210> SEQ ID NO 25
<211> LENGTH: 29
<212> TYPE: PRT
<213> ORGANISM: Artificial
<220> FEATURE:
<223> OTHER INFORMATION: Maurocalcine peptide

<400> SEQUENCE: 25

Gly Asp Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu
                20                  25

<210> SEQ ID NO 26
<211> LENGTH: 10
<212> TYPE: PRT
<213> ORGANISM: Artificial
<220> FEATURE:
<223> OTHER INFORMATION: SynB3 peptide

<400> SEQUENCE: 26

Arg Arg Leu Ser Tyr Ser Arg Arg Arg Phe
1               5                   10

<210> SEQ ID NO 27
<211> LENGTH: 18
<212> TYPE: PRT
<213> ORGANISM: Artificial
<220> FEATURE:
<223> OTHER INFORMATION: SynB1 peptide

<400> SEQUENCE: 27

Arg Gly Gly Arg Leu Ser Tyr Ser Arg Arg Arg Phe Ser Thr Ser Thr
1               5                   10                  15

Gly Arg

<210> SEQ ID NO 28
<211> LENGTH: 17
<212> TYPE: PRT
<213> ORGANISM: Artificial
<220> FEATURE:
<223> OTHER INFORMATION: YTA4 peptide
```

```
<400> SEQUENCE: 28

Ile Ala Trp Val Lys Ala Phe Ile Arg Lys Leu Arg Lys Gly Pro Leu
1               5                   10                  15

Gly

<210> SEQ ID NO 29
<211> LENGTH: 16
<212> TYPE: PRT
<213> ORGANISM: Artificial
<220> FEATURE:
<223> OTHER INFORMATION: YTA2 peptide

<400> SEQUENCE: 29

Tyr Thr Ala Ile Ala Trp Val Lys Ala Phe Ile Arg Lys Leu Arg Lys
1               5                   10                  15

<210> SEQ ID NO 30
<211> LENGTH: 20
<212> TYPE: PRT
<213> ORGANISM: Artificial
<220> FEATURE:
<223> OTHER INFORMATION: CADY peptide

<400> SEQUENCE: 30

Gly Leu Trp Arg Ala Leu Trp Arg Leu Leu Arg Ser Leu Trp Arg Leu
1               5                   10                  15

Leu Trp Arg Ala
            20

<210> SEQ ID NO 31
<211> LENGTH: 15
<212> TYPE: PRT
<213> ORGANISM: Artificial
<220> FEATURE:
<223> OTHER INFORMATION: Pep-3 peptide

<400> SEQUENCE: 31

Lys Trp Phe Glu Thr Trp Phe Thr Glu Trp Pro Lys Lys Arg Lys
1               5                   10                  15

<210> SEQ ID NO 32
<211> LENGTH: 21
<212> TYPE: PRT
<213> ORGANISM: Artificial
<220> FEATURE:
<223> OTHER INFORMATION: Pep-1 peptide

<400> SEQUENCE: 32

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 33
<211> LENGTH: 21
<212> TYPE: PRT
<213> ORGANISM: Artificial
<220> FEATURE:
<223> OTHER INFORMATION: PepFect peptide (amide linkage from epsilon
      amino group of Lys7)
```

```
<400> SEQUENCE: 33

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 34
<211> LENGTH: 21
<212> TYPE: PRT
<213> ORGANISM: Artificial
<220> FEATURE:
<223> OTHER INFORMATION: PepFect-3 peptide

<400> SEQUENCE: 34

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 35
<211> LENGTH: 16
<212> TYPE: PRT
<213> ORGANISM: Artificial
<220> FEATURE:
<223> OTHER INFORMATION: Penetratin peptide

<400> SEQUENCE: 35

Arg Gln Ile Lys Ile Trp Phe Gln Asn Arg Arg Met Lys Trp Lys Lys
1               5                   10                  15

<210> SEQ ID NO 36
<211> LENGTH: 30
<212> TYPE: PRT
<213> ORGANISM: Artificial
<220> FEATURE:
<223> OTHER INFORMATION: KALA peptide

<400> SEQUENCE: 36

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 37
<211> LENGTH: 18
<212> TYPE: PRT
<213> ORGANISM: Artificial
<220> FEATURE:
<223> OTHER INFORMATION: pVEC peptide

<400> SEQUENCE: 37

Leu Leu Ile Ile Leu Arg Arg Arg Ile Arg Lys Gln Ala His Ala His
1               5                   10                  15

Ser Lys

<210> SEQ ID NO 38
<211> LENGTH: 29
<212> TYPE: PRT
<213> ORGANISM: Artificial
<220> FEATURE:
<223> OTHER INFORMATION: RVG peptide
```

```
<400> SEQUENCE: 38

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 39
<211> LENGTH: 16
<212> TYPE: PRT
<213> ORGANISM: Artificial
<220> FEATURE:
<223> OTHER INFORMATION: MPS peptide

<400> SEQUENCE: 39

Ala Ala Val Ala Leu Leu Pro Ala Val Leu Leu Ala Leu Leu Ala Lys
1               5                   10                  15

<210> SEQ ID NO 40
<211> LENGTH: 27
<212> TYPE: PRT
<213> ORGANISM: Artificial
<220> FEATURE:
<223> OTHER INFORMATION: Transportan peptide

<400> SEQUENCE: 40

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 41
<211> LENGTH: 12
<212> TYPE: PRT
<213> ORGANISM: Artificial
<220> FEATURE:
<223> OTHER INFORMATION: TAT peptide

<400> SEQUENCE: 41

Gly Arg Lys Lys Arg Arg Gln Arg Arg Pro Pro Gln
1               5                   10

<210> SEQ ID NO 42
<211> LENGTH: 20
<212> TYPE: PRT
<213> ORGANISM: Artificial
<220> FEATURE:
<223> OTHER INFORMATION: BMV Gag-(7-25) peptide

<400> SEQUENCE: 42

Lys Met Thr Arg Ala Gln Arg Arg Ala Ala Ala Arg Arg Asn Arg Arg
1               5                   10                  15

Trp Thr Ala Arg
            20

<210> SEQ ID NO 43
<211> LENGTH: 28
<212> TYPE: PRT
<213> ORGANISM: Artificial
<220> FEATURE:
<223> OTHER INFORMATION: hCT(18-32)-k7 peptide (branched structure
      between Ala13 and Lys14)
```

<400> SEQUENCE: 43

Lys Lys Arg Lys Ala Pro Lys Lys Arg Lys Phe Ala Lys Phe His
1               5                   10                  15

Thr Phe Pro Gln Thr Ala Ile Gly Val Gly Ala Pro
            20                  25

<210> SEQ ID NO 44
<211> LENGTH: 22
<212> TYPE: PRT
<213> ORGANISM: Artificial
<220> FEATURE:
<223> OTHER INFORMATION: M1073 peptide

<400> SEQUENCE: 44

Met Val Thr Val Leu Phe Arg Arg Leu Arg Ile Arg Arg Ala Ser Gly
1               5                   10                  15

Pro Pro Arg Val Arg Val
            20

<210> SEQ ID NO 45
<211> LENGTH: 23
<212> TYPE: PRT
<213> ORGANISM: Artificial
<220> FEATURE:
<223> OTHER INFORMATION: EB1 peptide

<400> SEQUENCE: 45

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 46
<211> LENGTH: 27
<212> TYPE: PRT
<213> ORGANISM: Artificial
<220> FEATURE:
<223> OTHER INFORMATION: MPG-beta peptide

<400> SEQUENCE: 46

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 47
<211> LENGTH: 27
<212> TYPE: PRT
<213> ORGANISM: Artificial
<220> FEATURE:
<223> OTHER INFORMATION: MPG-beta peptide

<400> SEQUENCE: 47

Gly Ala Leu Phe Leu Ala Phe Leu Ala Ala Ala Leu Ser Leu Met Gly
1               5                   10                  15

Leu Trp Ser Gln Pro Lys Lys Lys Arg Lys Val
            20                  25

<210> SEQ ID NO 48
<211> LENGTH: 464
<212> TYPE: PRT
<213> ORGANISM: Homo sapiens

<400> SEQUENCE: 48

Met Ala Ser Glu Ser Gly Lys Leu Trp Gly Gly Arg Phe Val Gly Ala
1               5                   10                  15

Val Asp Pro Ile Met Glu Lys Phe Asn Ala Ser Ile Ala Tyr Asp Arg
            20                  25                  30

His Leu Trp Glu Val Asp Val Gln Gly Ser Lys Ala Tyr Ser Arg Gly
        35                  40                  45

Leu Glu Lys Ala Gly Leu Leu Thr Lys Ala Glu Met Asp Gln Ile Leu
    50                  55                  60

His Gly Leu Asp Lys Val Ala Glu Glu Trp Ala Gln Gly Thr Phe Lys
65                  70                  75                  80

Leu Asn Ser Asn Asp Glu Asp Ile His Thr Ala Asn Glu Arg Arg Leu
                85                  90                  95

Lys Glu Leu Ile Gly Ala Thr Ala Gly Lys Leu His Thr Gly Arg Ser
            100                 105                 110

Arg Asn Asp Gln Val Val Thr Asp Leu Arg Leu Trp Met Arg Gln Thr
        115                 120                 125

Cys Ser Thr Leu Ser Gly Leu Leu Trp Glu Leu Ile Arg Thr Met Val
    130                 135                 140

Asp Arg Ala Glu Ala Glu Arg Asp Val Leu Phe Pro Gly Tyr Thr His
145                 150                 155                 160

Leu Gln Arg Ala Gln Pro Ile Arg Trp Ser His Trp Ile Leu Ser His
                165                 170                 175

Ala Val Ala Leu Thr Arg Asp Ser Glu Arg Leu Leu Glu Val Arg Lys
            180                 185                 190

Arg Ile Asn Val Leu Pro Leu Gly Ser Gly Ala Ile Ala Gly Asn Pro
        195                 200                 205

Leu Gly Val Asp Arg Glu Leu Leu Arg Ala Glu Leu Asn Phe Gly Ala
    210                 215                 220

Ile Thr Leu Asn Ser Met Asp Ala Thr Ser Glu Arg Asp Phe Val Ala
225                 230                 235                 240

Glu Phe Leu Phe Trp Ala Ser Leu Cys Met Thr His Leu Ser Arg Met
                245                 250                 255

Ala Glu Asp Leu Ile Leu Tyr Cys Thr Lys Glu Phe Ser Phe Val Gln
            260                 265                 270

Leu Ser Asp Ala Tyr Ser Thr Gly Ser Ser Leu Met Pro Gln Lys Lys
        275                 280                 285

Asn Pro Asp Ser Leu Glu Leu Ile Arg Ser Lys Ala Gly Arg Val Phe
    290                 295                 300

Gly Arg Cys Ala Gly Leu Leu Met Thr Leu Lys Gly Leu Pro Ser Thr
305                 310                 315                 320

Tyr Asn Lys Asp Leu Gln Glu Asp Lys Glu Ala Val Phe Glu Val Ser
                325                 330                 335

Asp Thr Met Ser Ala Val Leu Gln Val Ala Thr Gly Val Ile Ser Thr
            340                 345                 350

Leu Gln Ile His Gln Glu Asn Met Gly Gln Ala Leu Ser Pro Asp Met
        355                 360                 365

Leu Ala Thr Asp Leu Ala Tyr Tyr Leu Val Arg Lys Gly Met Pro Phe
    370                 375                 380

Arg Gln Ala His Glu Ala Ser Gly Lys Ala Val Phe Met Ala Glu Thr
385                 390                 395                 400

Lys Gly Val Ala Leu Asn Gln Leu Ser Leu Gln Glu Leu Gln Thr Ile
                405                 410                 415

```
        Ser Pro Leu Phe Ser Gly Asp Val Ile Cys Val Trp Asp Tyr Gly His
                        420                 425                 430

Ser Val Glu Gln Tyr Gly Ala Leu Gly Gly Thr Ala Arg Ser Ser Val
                    435                 440                 445

Asp Trp Gln Ile Arg Gln Val Arg Ala Leu Leu Gln Ala Gln Gln Ala
                450                 455                 460

<210> SEQ ID NO 49
<211> LENGTH: 1551
<212> TYPE: RNA
<213> ORGANISM: Artificial
<220> FEATURE:
<223> OTHER INFORMATION: mRNA encoding human argininosuccinate lyase
      (ASL) isoform 1, codon-optimized for mouse expression

<400> SEQUENCE: 49
gggaauuaag agagaaaaga agaguaagaa gaaauauaag agccaccaug gcaucagaga      60
gcgguaaacu gugggguggg agauucgugg gugccgucga uccuauuaug agaaauuca     120 acgccagcau ugccuacgac agacaccugu ggaggugga cguccagggc ucaaaggccu     180
acagccgggg ucuggagaag gcaggccugc ucacaaaagc cgaaauggac cagauccugc     240
acggacucga uaaggugcu gaggaauggg cacaggggac auucaaacug aacucuaacg     300
acgaggauau ccacacugcu aacgagagga gacugaagga acucauuggc ccacagcug     360 gaaaacugca uacuggacgg agccgcaacg accagguggu cacagaucug agacucugga     420
ugcggcagac cugcucuaca cugaguggac ugcucuggga gcucauucga acuaugguuu     480
acagggcaga ggccgaaaga gacguccugu uccaggaua uacccaccug cagcgagcac     540
agccaaucag guggucucac uggauucuga gucacgcugu ggcacucacc cgcgauucug     600
agcgacugcu cgaagugcga aagaggauca acguccugcc ucucgggagu ggugccauug     660
cugggaaucc acuggugug acagggagc ugcucagagc ugaacugaac uucggcgcaa     720
ucacccugaa uucaauggac gccacaagcg agcgcgauuu ugucgccgaa uucuucuuuu     780 gggcuaguc ugcaugacc caucuccuca ggauggcuga ggaccugauc cucuacuga     840 caaaggaauu cagcuuugug cagcuguccg acgcauauuc uacggugagc ucccugaugc     900
cccagaagaa aaacccugac ucccuggagc ucauuagauc uaaggcagga cgaguguucg     960
gaaggugcgc agggcucguc augacucuga aaggccucc auccacuac aauaaggacc    1020 ugcaggagga uaagaagcc gvuuugaag ucagugacac aaugucagcu ugucuucagg    1080
ucgcaacugg ugugaucagc acccugcaga uucaccagga aaacauggga caggcucugu    1140
ccccagacau gcuggccacu gaucgcuu acuaucuggu gcgaaaggga augccuuca    1200 ggcaggcaca cgaggccagc ggcaaggcag uguuuauggc cgaaaccaaa ggcgucgccc    1260
ugaaucagcu gucccuccag gagcugcaga caaucagcc ccucuucccc ggggacguga    1320
uuugugucug ggauuacgga cacucugugg aacaguacgg ggccugggc ggaaccgcua    1380 gaagcagcgu cgauuggcag auuaggcagg uccgagcccu ccucaggca cagcaggccu    1440 gagcggccgc uuaauuaagc ugccuucgc ggggcuugcc uucuggccau gcccuucuuc    1500 ucuccuugc accuguaccu cuuggucuuu gaauaaagcc ugaguaggaa g              1551

<210> SEQ ID NO 50
<211> LENGTH: 412
<212> TYPE: PRT
<213> ORGANISM: Homo sapiens
```

<400> SEQUENCE: 50

```
Met Ser Ser Lys Gly Ser Val Val Leu Ala Tyr Ser Gly Gly Leu Asp
1               5                   10                  15

Thr Ser Cys Ile Leu Val Trp Leu Lys Glu Gln Gly Tyr Asp Val Ile
            20                  25                  30

Ala Tyr Leu Ala Asn Ile Gly Gln Lys Glu Asp Phe Glu Ala Arg
        35                  40                  45

Lys Lys Ala Leu Lys Leu Gly Ala Lys Val Phe Ile Glu Asp Val
    50                  55                  60

Ser Arg Glu Phe Val Glu Glu Phe Ile Trp Pro Ala Ile Gln Ser Ser
65                  70                  75                  80

Ala Leu Tyr Glu Asp Arg Tyr Leu Leu Gly Thr Ser Leu Ala Arg Pro
            85                  90                  95

Cys Ile Ala Arg Lys Gln Val Glu Ile Ala Gln Arg Glu Gly Ala Lys
            100                 105                 110

Tyr Val Ser His Gly Ala Thr Gly Lys Gly Asn Asp Gln Val Arg Phe
            115                 120                 125

Glu Leu Ser Cys Tyr Ser Leu Ala Pro Gln Ile Lys Val Ile Ala Pro
130                 135                 140

Trp Arg Met Pro Glu Phe Tyr Asn Arg Phe Lys Gly Arg Asn Asp Leu
145                 150                 155                 160

Met Glu Tyr Ala Lys Gln His Gly Ile Pro Ile Pro Val Thr Pro Lys
                165                 170                 175

Asn Pro Trp Ser Met Asp Glu Asn Leu Met His Ile Ser Tyr Glu Ala
            180                 185                 190

Gly Ile Leu Glu Asn Pro Lys Asn Gln Ala Pro Pro Gly Leu Tyr Thr
        195                 200                 205

Lys Thr Gln Asp Pro Ala Lys Ala Pro Asn Thr Pro Asp Ile Leu Glu
    210                 215                 220

Ile Glu Phe Lys Lys Gly Val Pro Val Lys Val Thr Asn Val Lys Asp
225                 230                 235                 240

Gly Thr Thr His Gln Thr Ser Leu Glu Leu Phe Met Tyr Leu Asn Glu
                245                 250                 255

Val Ala Gly Lys His Gly Val Gly Arg Ile Asp Ile Val Glu Asn Arg
            260                 265                 270

Phe Ile Gly Met Lys Ser Arg Gly Ile Tyr Glu Thr Pro Ala Gly Thr
        275                 280                 285

Ile Leu Tyr His Ala His Leu Asp Ile Glu Ala Phe Thr Met Asp Arg
    290                 295                 300

Glu Val Arg Lys Ile Lys Gln Gly Leu Gly Leu Lys Phe Ala Glu Leu
305                 310                 315                 320

Val Tyr Thr Gly Phe Trp His Ser Pro Glu Cys Glu Phe Val Arg His
                325                 330                 335

Cys Ile Ala Lys Ser Gln Glu Arg Val Glu Gly Lys Val Gln Val Ser
            340                 345                 350

Val Leu Lys Gly Gln Val Tyr Ile Leu Gly Arg Glu Ser Pro Leu Ser
        355                 360                 365

Leu Tyr Asn Glu Glu Leu Val Ser Met Asn Val Gln Gly Asp Tyr Glu
    370                 375                 380

Pro Thr Asp Ala Thr Gly Phe Ile Asn Ile Asn Ser Leu Arg Leu Lys
385                 390                 395                 400

Glu Tyr His Arg Leu Gln Ser Lys Val Thr Ala Lys
                405                 410
```

```
<210> SEQ ID NO 51
<211> LENGTH: 1395
<212> TYPE: RNA
<213> ORGANISM: Artificial
<220> FEATURE:
<223> OTHER INFORMATION: mRNA encoding human argininosuccinate
      synthetase (ASS1), codon-optimized for mouse expression

<400> SEQUENCE: 51
gggaaauaag agagaaaaga agaguaagaa gaaauauaag agccaccaug agcucaaagg        60
ggaguguggu gcuggccuau ucuggcgggc uggauaccuc uugcauucug guuggcuga       120
aggaacaggg uuacgacgug aucgcauacc uggccaacau ugggcagaag gaggauuuug       180
aggaagcuag aaagaaagca cugaaacucg gcgccaagaa aguguucauc gaggacgucu       240
cccgggaauu cguggaggaa uuuaucggc cagccauuca gagcuccgcu cuguacgagg       300
auagauaucu gcucggaacc agccucgcac gacccugcau cgccaggaag caggugagga       360
uugcucagcg cgaaggggca aaguacgucu cccacggugc cacaggcaaa ggaaacgacc       420
aggugcgauu ugagcugucu uguuauaguc ucgaccccca gaucaagguc auugcccccu       480
ggcgcaugcc cgaguucuac aaccgguuua agggccgcaa cgaccugaug gaauacgcua       540
aacagcacgg aauccaauu cccgugacuc uaagaaccc cugguccaug gaugagaauc       600
ugaugcauau cucuuacgag gcugggauuc ucgaaaaccc uaagaaucag gcacccccug       660
gucuguauac uaagacccag gacccagcca aagcucccaa cacaccugau auccuggaga       720
uugaauuuaa gaaaggggug ccugucaaag ugacuaacgu gaaagacggu accacacacc       780
agaccucucu ggagcucuuu auguaccuga acgaagucgc aggcaagcac ggggugggua       840
gaaucgauau ugucgagaau cgguucaucg ggaugaaaag ucgcgguauu uacgaaaccc       900
cugcuggaac aauccuguau cacgcccauc ucgacauuga ggcuucaca auggauagag       960
aagugagaaa gaucaaacag ggccugggac ucaaguucgc cgagcuggug uacacuggau      1020
uuuggcacuc uccagagugc gaauucgugc gacauuguau cgcuaagagu caggagaggg      1080
ucgaagggaa gguccaggug ucaguccuga aaggccaggu guacauucuc ggacgggagu      1140
caccccugag ccucuauaac gaggaacugg ugagcaugaa cguccagggc gacuacgaac      1200
cuacagacgc cacuggauuc aucaacauca acucacucag gcucaaggaa uaccacaggc      1260
uccagucaaa agucacagca aaguaggcgg ccgcuuaauu aagcugccuu cugcggggcu      1320
ugccuucugg ccaugcccuu cuucucuccc uugcaccugu accucuuggu cuuugaauaa      1380
agccugagua ggaag                                                      1395
```